United States Patent
Duvey et al.

(10) Patent No.: US 12,234,218 B2
(45) Date of Patent: *Feb. 25, 2025

(54) HETEROCYCLIC COMPOUNDS AS MODULATORS OF mGluR7

(71) Applicant: PRAGMA Therapeutics, Archamps (FR)

(72) Inventors: Guillaume Duvey, Thyez (FR); Sylvain Celanire, Reignier-Esery (FR)

(73) Assignee: PRAGMA Therapeutics, Archamps (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/810,922

(22) Filed: Jul. 6, 2022

(65) Prior Publication Data

US 2022/0363664 A1 Nov. 17, 2022

Related U.S. Application Data

(63) Continuation of application No. 16/650,817, filed as application No. PCT/EP2018/076080 on Sep. 26, 2018, now Pat. No. 11,414,395.

(30) Foreign Application Priority Data

Sep. 26, 2017 (EP) ..................................... 17306269

(51) Int. Cl.
| | |
|---|---|
| C07D 401/14 | (2006.01) |
| A61K 31/502 | (2006.01) |
| C07D 401/04 | (2006.01) |
| C07D 403/04 | (2006.01) |
| C07D 413/14 | (2006.01) |
| C07D 417/04 | (2006.01) |

(52) U.S. Cl.
CPC ......... *C07D 401/04* (2013.01); *C07D 401/14* (2013.01); *C07D 403/04* (2013.01); *C07D 413/14* (2013.01); *C07D 417/04* (2013.01); *C07B 2200/07* (2013.01)

(58) Field of Classification Search
CPC .. C07D 401/04; C07D 401/14; C07D 403/04; C07D 413/14; C07D 417/04; A61K 31/502
See application file for complete search history.

(56) References Cited

U.S. PATENT DOCUMENTS

2009/0062269 A1  3/2009 Subharekha et al.

FOREIGN PATENT DOCUMENTS

| RU | 2232017 | 7/2004 |
|---|---|---|
| WO | WO 2000/020001 | 4/2000 |
| WO | WO 2005/082887 | 9/2005 |
| WO | WO 2006/113498 | 10/2006 |
| WO | WO 2007/002701 | 1/2007 |
| WO | WO 2007/021308 | 2/2007 |
| WO | WO 2007/021309 | 2/2007 |
| WO | WO 2007/092364 | 8/2007 |
| WO | WO 2008/051403 | 5/2008 |
| WO | WO 2008/131439 | 10/2008 |
| WO | WO 2009/047255 | 4/2009 |
| WO | WO 2014/055548 | 4/2014 |
| WO | WO 2017/112678 | 6/2017 |

OTHER PUBLICATIONS

Extended European Search Report issued in European Application No. 17306299.6, dated Jan. 16, 2018.
Kalinichev et al., "ADX71743, a Potent and Selective Negative Allosteric Modulator of Metabotropic Glutamate Receptor 7: In Vitro and In Vivo Characterization," *Journal of Pharmacology and Experimental Therapeutics*, 344(3):624-636, 2013.
Koltunov et al., "Superacidic Activation of 1- and 3-Isoquinolinols and Their Electrophilic Reactions," *Journal of Organic Chemistry*, 67(25):8943-8951, 2002.
Nakamura et al., "Isoxazolopyridone derivatives as allosteric metabotropic glutamate receptor 7 antagonists," *Bioorganic & Medicinal Chemistry Letters*, 20(2):726-729, 2010.
Office Action and Search Report issued in Russian Application No. 2020114432, mailed Jan. 17, 2022.
PCT International Preliminary Report on Patentability issued in International Application No. PCT/EP2018/076080, dated Mar. 31, 2020.
PCT International Search Report and Written Opinion issued in International Application No. PCT/EP2018/076080, dated Nov. 22, 2018.
Palazzo et al., "Metabotropic Glutamate Receptor 7: From Synaptic Function to Therapeutic Implications", *Current Neuropharmacology*, 14:504-513, 2016.

*Primary Examiner* — Bruck Kifle
(74) *Attorney, Agent, or Firm* — Parker Highlander PLLC

(57) ABSTRACT

The present invention relates to novel heterocyclic compounds. The invention is also directed to compounds which are modulators of the metabotropic glutamate receptors (mGluR), preferably of the metabotropic glutamate receptor subtype 7 ("mGluR7"). The present invention also relates to pharmaceutical composition comprising such compounds and their use for the treatment or prevention of disorders associated with glutamate dysfunction or in which metabotropic glutamate receptor, preferably mGluR7 subtype of metabotropic glutamate receptors, is involved.

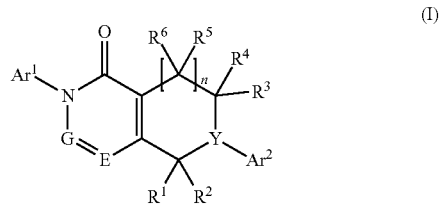

(I)

15 Claims, No Drawings

HETEROCYCLIC COMPOUNDS AS MODULATORS OF mGluR7

This application is a continuation of U.S. application Ser. No. 16/650,817, filed Mar. 25, 2020, which is a national phase application under 35 U.S.C. § 371 of International Application No. PCT/EP2018/076080, filed Sep. 26, 2018, which claims benefit of European Application No. 17306269.6, filed Sep. 26, 2017. The entire of contents of U.S. application Ser. No. 16/650,817 and International Application No. PCT/EP2018/076080 are hereby incorporated by reference.

SUMMARY OF THE INVENTION

The present invention relates to novel heterocyclic compounds. The invention is also directed to compounds which are modulators of the metabotropic glutamate receptors (mGluR), preferably of the metabotropic glutamate receptor subtype 7 ("mGluR7"). The invention is also directed to pharmaceutical compositions comprising such compounds, to processes for preparing such compounds and compositions, and to the use of such compounds and compositions for the prevention or treatment of disorders associated with glutamate dysfunction or in which metabotropic glutamate receptor, preferably mGluR7 subtype of metabotropic glutamate receptors, is involved.

BACKGROUND OF THE INVENTION

Glutamate is the major amino acid neurotransmitter in the mammalian central nervous system (CNS) and plays a major role in several physiological functions, such as learning and memory, sensory perception, development of synaptic plasticity and motor control. Furthermore, glutamate is at the centre of several neurological and psychiatric diseases, where there is an imbalance in glutamatergic neurotransmission.

Glutamate mediates synaptic neurotransmission through the activation of mGluR, belonging to class C G-protein coupled receptors (GPCRs), which have a modulatory role that contributes to the fine-tuning of synaptic efficacy (Schoepp et al. Neuropharmacology (1999), 38:1431). In particular the mGlu receptor subtype 7 (mGluR7) is widely distributed in the brain and has the highest degree of evolutionary conservation across species of all the mGlu receptors (Flor et al. Neuropharmacol. (1997), 36:153). More importantly, mGluR7 has the lowest affinity for glutamate, remaining inactive during normal state of neurotransmission, only becoming active in severe pathophysiological conditions or during times of excessive glutamate release (Ferraguti and Shigemoto, Cell Tissue Res. (2006), 326:483). MGluR7 is thought to act as a tonic break, inhibiting further glutamate release, along influencing other neurotransmitter release (e.g. GABA), and preventing glutamate excitotoxicity involved in many pathologies of the CNS and sensory disorders.

Specifically, modulators of the mGluR7, and preferably antagonists, inverse agonists and negative allosteric modulators (NAMs), are reported to hold potential for the treatment of neurological, psychiatric, mood disorders as well as pain and otic disorders, based on experimental studies on laboratory animals, deemed relevant to clinical syndromes.

Isoxazolopyridinone derivatives, including MMPIP (6-(4-methoxyphenyl)-5-methyl-3-(4-pyridinyl)-isoxazolo[4,5-c]pyridine-4(5H)-one hydrochloride) are described as mGluR7 NAMs (Nakamura et al., Bioorg. Med. Chem. Lett. (2010), 20:726; Suzuki et al., J. Pharmacol. Exp. Ther. (2007), 323:147), and showed context-dependency pharmacology with partial to full antagonism of the mGluR7 in vitro and in vivo (Niswender et al., Mol. Pharmacol. (2010), 77:459; Hikichi et al., Eur. J. Pharmacol. (2010), 10, 106). MMPIP exerts also inverse agonist activity due to constitutive activity of mGluR7 (Cieslik et al., Front. Mol. Neurosci., 20 Sep. 2018, doi:10.3389/fnmol.2018.00316).

Tetrahydrobenzoxazole derivatives, including (+)-6-(2,4-dimethylphenyl)-2-ethyl-6,7-dihydrobenzo[d]oxazol-4(5H)-one (ADX71743) and its racemic form are described as mGluR7 NAMs or inverse agonists, and have demonstrated anxiolytic and antipsychotic activity (Kalinichev et al., J. Pharmacol. Exp. Ther. (2013), 344:624; Cieslik et al., Front. Mol. Neurosci., 20 Sep. 2018, doi:10.3389/fnmol.2018.00316).

Chromenone derivatives, including 7-hydroxy-3-(4-iodophenoxy)-4H-chromen-4-one (XAP044) are described as weak mGluR7 allosteric antagonists, binding to the extracellular domain of the receptor. XAP044 has shown anxiolytic, antidepressant, anti-stress, and antipsychotic activity (Gee et al., J. Biol. Chem. (2014), 289:10975).

Combined expression of mGluR7 in brain regions and pharmacological manipulations of mGluR7 in genetically-modified mice and wild-type animals reveals an important role for mGluR7 in numerous CNS disorders, including depression, schizophrenia, anxiety, obsessive compulsive disorders and associated symptoms (reviewed by Pallazo et al., Curr. Neuropharmacol. (2016), 14(5): 504), and in particular in acute and chronic stress-related disorders (reviewed by Peterlik et al., Curr Neuropharmacol. (2016), 14(5): 514). Furthermore, mGluR7 represent a novel therapeutic approach for the treatment of psychostimulant (i.e. nicotine and cocaine) dependence (Li and Markou, CNS Neurol. Disord. Drug Targets (2015), 14(6):738; Li et al., Neuropharmacology (2013), 66:12). In addition, mGluR7 NAM MMPIP and allosteric antagonist XAP44 have shown to play a role in inhibiting pain responses, alleviating anxiety- and depression-like behavior, and improving cognitive performance in neuropathic pain mice models (Pallazzo et al., Pain (2015), 156(6):1060).

It has also been shown that mGluR7 is expressed in peripheral tissues such as colon mucosa and stomach (Julio-Pepper et al., Pharmacol. Rev. (2011), 63:35), suggesting a potential role for treating pathologies such as visceral pain, stress-associated gastrointestinal dysfunction such as diarrhoea or constipation in irritable bowel syndrom (IBS) or other related disorders.

Furthermore, mGluR7 is expressed in hair cells and spiral ganglion neurons of the inner ear (Friedman et al. (2008) WO2008/131439) along within the vestibular system (Zhou et al., Int J Mol. Sci. (2013) 14(11):22857; Horii et al., Exp. Brain Res. (2001) 139(2):188), suggesting a potential role for treating pathologies linked to the inner ear and auditory nervous system. such as age-related hearing loss (presbycusis), noise-induced hearing loss, acute and chronic hearing loss, tinnitus, Meniere's disease and vestibular disorders.

It has been shown that mGluR7 is expressed at the synaptic terminals of certain cone bipolar cells in the retina (Brandstatter et al., (1996) J. Neurosci., 16(15):4749-4756) suggesting mGluR7 modulators are of potential use in the acute and chronic treatment of glaucoma and other visual disorders.

Finally, numerous genome-wide human studies have also demonstrated the association of GRM7, the gene coding for the mGluR7, with severe diseases such as Age-Related Hearing Loss (ARHL; presbycusis), as reported by Friedman et al. (Hum. Mol. Genet. (2009), 18:785), Van Laer et al. (Eur. J. Hum. Genet. (2010), 18:685), Newman et al. (Hear. Res. (2012), 294:125), Luo et al. (Plos One (2013), 8(10):e77153) and more recently by Haider et al. (Front. Aging Neurosci. (2017), 9:346) and Matyas et al. (Pathol. Oncol. Res. (2018), doi: 10.1007/s12253-018-0388-6); Noise-Induced Hearing Loss, as reported by Lu et al. (BMC Med. Genet. (2018), 19(1):4); Tinnitus, as reported by Haider et al. (Front. Aging Neurosci. (2017), 9:346); schizophrenia, as reported by Niu et al. (Neurosci. Lett. (2015), 604:109); Attention-Deficit Hyperactivity Disorder (ADHD), as reported by Elia et al. (Nat. Genet. (2011), 44:78); major depressive disorder, as reported by Li et al. (Eur. Neuropsychopharmacol. (2015), doi: 10.1016/j.euroneuro.2015.05.004); bipolar disorders as reported by Kandaswamy et al. (Am. J. Med. Genet. B. Neuropsychiatr. Genet. (2015), 165B(4):365); alcohol-related addiction (Vadasz et al., Genomics (2007), 90(6):690) and autistic spectrum disorders, including autism (Liu et al., Am. J. Med. Genet. B. Neuropsychiatr. Genet. (2015), 168B(4):258).

Altogether, these pharmacological and genetic data strongly support the potential of mGluR7 modulators for the treatment of a wide range of disease and associated symptoms across psychiatric, neurological, neurodevelopmental, otic, pain, visual and gastrointestinal disorders.

It is an object of the invention to provide compounds having an activity on mGluR, preferably on mGluR7.

It is also an object of the invention to provide pharmaceutical composition comprising such compounds.

Another object of the invention is also to provide such compounds and/or pharmaceutical composition for the treatment of diseases related to mGluR, preferably mGluR7.

DESCRIPTION OF THE INVENTION

The invention relates to compounds of Formula (I),

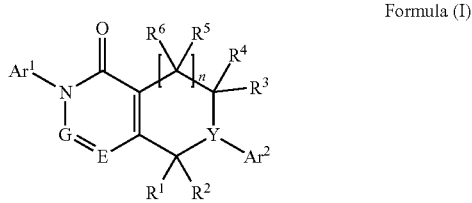

Formula (I)

wherein:
G is chosen among N or $CR^7$,
E is chosen among N or $CR^8$,
  provided that at least one of G or E is N
Y is $CR^9$,
$R^1$, $R^2$, $R^3$, $R^4$, $R^5$, $R^8$, $R^7$, $R^8$ and $R^9$, identical or different, are each independently selected in the group consisting of hydrogen, halogen, —CN, —$CF_3$—C(=O)$R^{10}$, —C(=O)O$R^{10}$, —C(=O)N$R^{10}R^{11}$, —O$R^{10}$, —OC(=O)$R^{10}$, —OC(=O)N$R^{10}R^{11}$, —S$R^{10}$, —S(O)$R^{10}$, —S(O)$_2R^{10}$, —S(O)$_2NR^{10}R^{11}$, —N$R^{10}R^{11}$, —N$R^{10}$C(=O)$R^{11}$, —N$R^{10}$C(=O)O$R^{11}$, —N$R^{10}$S(O)$_2R^{11}$, an optionally substituted radical chosen among: —($C_1$-$C_6$)alkyl, —($C_1$-$C_6$)haloalkyl, —($C_3$-$C_7$)cycloalkyl, —($C_1$-$C_6$)alkylene-($C_3$-$C_7$)cycloalkyl, or —($C_1$-$C_6$)cyanoalkyl,
any two radicals $R^1$ and $R^2$, $R^3$ and $R^4$, and $R^5$ and $R^8$ may be taken together to form an oxo (=O),
wherein $R^{10}$ and $R^{11}$ identical or different, are each independently selected from hydrogen, an optionally substituted radical chosen among: —($C_1$-$C_6$)alkyl, —($C_1$-$C_6$)haloalkyl, —($C_1$-$C_6$)cyanoalkyl, —($C_3$-$C_7$)cycloalkyl or —($C_1$-$C_6$)alkylene-($C_3$-$C_7$)cycloalkyl,
wherein optionally any two radicals selected from $R_1$, $R_2$, $R_3$, $R_4$, $R_5$, $R_6$, $R_9$, $R_{10}$ and $R_{11}$ may be taken together to form an optionally substituted 3 to 10-membered non-aromatic carbocyclic or heterocyclic ring or a 5 to 10-membered aromatic heterocyclic ring,
n is an integer selected from 0 or 1,
$Ar^1$ is an optionally substituted aryl or heteroaryl,
$Ar^2$ is an optionally substituted aryl or heteroaryl,
and the N-oxide forms thereof, the pharmaceutically acceptable salts and solvates thereof, or their optical isomers, racemates, diastereoisomers, enantiomers or tautomers thereof.

Surprisingly, the compounds of general Formula (I) demonstrate metabotropic glutamate receptor activity.

Preferably, in the compounds of Formula (I), $Ar^1$ represents an aryl or heteroaryl chosen among:

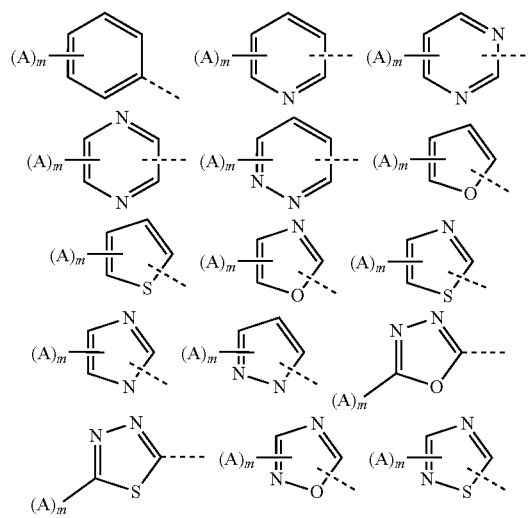

wherein m is the number of substituents A on the cycle and is an integer equal to 0, 1, 2, 3, 4 or 5.

Preferably, in the compounds of Formula (I), $Ar^2$ represents an aryl or heteroaryl chosen among:

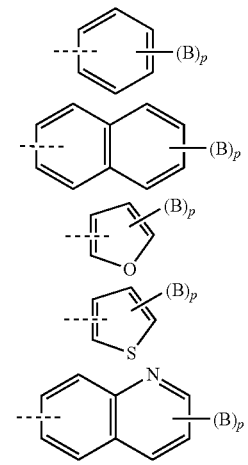

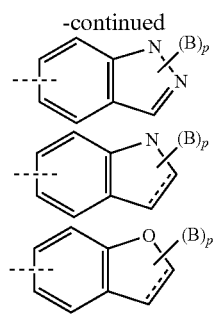

wherein p is the number of substituent B on the cycle and is an integer equal to 0, 1, 2, 3, 4 or 5. It should be understood that when $Ar^2$ is a bicycle, B may be on any of the two cycles.

A and B, as mentioned above, identical or different, are each independently selected from the group consisting of hydrogen, halogen, —CN, —NO$_2$, —OH, —NH$_2$, —CF$_3$, an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)alkylene-(C$_3$-C$_7$)cycloalkyl, —(C$_3$-C$_8$)cycloalkenyl, —(C$_1$-C$_6$)cyanoalkyl, —(C$_1$-C$_6$)alkylene-heteroaryl, —(C$_1$-C$_6$)alkylene-aryl, —(C$_1$-C$_6$)alkylene-heterocycle, aryl, heteroaryl, heterocycle, —OR$^{13}$, —(C$_1$-C$_6$)alkylene-OR$^{13}$, —O—(C$_2$-C$_6$)alkylene-OR$^{13}$, —NR$^{13}$(C$_2$-C$_6$)alkylene-OR$^{14}$, —(C$_2$-C$_6$)alkenylene-OR$^{13}$, —(C$_2$-C$_6$)alkynylene-OR$^{13}$, —NR$^{13}$R$^{14}$, —(C$_1$-C$_6$)alkylene-NR$^{13}$R$^{14}$, —O—(C$_2$-C$_6$)alkylene-NR$^{13}$R$^{14}$, —NR$^{13}$—(C$_2$-C$_6$)alkylene-NR$^{14}$R$^{15}$, —(C$_2$-C$_6$)alkenylene-NR$^{13}$R$^{14}$, —(C$_2$-C$_6$)alkynylene-NR$^{13}$R$^{14}$, —SR$^{13}$, —(C$_1$-C$_6$)alkylene-SR$^{13}$, —O—(C$_2$-C$_6$)alkylene-SR$^{13}$, —NR$^{13}$—(C$_2$-C$_6$)alkylene-SR$^{14}$, —S(=O)—R$^{13}$, —(C$_1$-C$_6$)alkylene-S(=O)—R$^{13}$, —O—(C$_1$-C$_6$)alkylene-S(=O)—R$^{13}$, —NR$^{13}$—(C$_1$-C$_6$)alkylene-S(=O)—R$^{14}$, —S(=O)$_2$—R$^{13}$, —(C$_1$-C$_6$)alkylene-S(=O)$_2$—R$^{13}$, —O—(C$_1$-C$_6$)alkylene-S(=O)$_2$—R$^{13}$, —NR$^{13}$—(C$_1$-C$_6$)alkylene-S(=O)$_2$—R$^{14}$, —S(=O)$_2$NR$^{13}$R$^{14}$, —(C$_1$-C$_6$)alkylene-S(=O)$_2$NR$^{13}$R$^{14}$, —O—(C$_1$-C$_6$)alkylene-S(=O)$_2$NR$^{13}$R$^{14}$, —NR$^{13}$—(C$_1$-C$_6$)alkylene-S(=O)$_2$NR$^{14}$R$^{15}$, —NR$^{13}$—S(=O)$_2$R$^{14}$, —(C$_1$-C$_6$)alkylene-NR$^{13}$—S(=O)$_2$R$^{14}$, —O—(C$_2$-C$_6$)alkylene-NR$^{13}$—S(=O)$_2$R$^{14}$, —NR$^{13}$—(C$_2$-C$_6$)alkylene-NR$^{14}$—S(=O)$_2$R$^{15}$, —C(=O)—NR$^{13}$R$^{14}$, —(C$_1$-C$_6$)alkylene-C(=O)—NR$^{13}$R$^{14}$, —O—(C$_1$-C$_6$)alkylene-C(=O)—NR$^{13}$R$^{14}$, —NR$^{13}$—(C$_1$-C$_6$)alkylene-C(=O)—NR$^{14}$R$^{15}$, —NR$^{13}$C(=O)—R$^{14}$, —(C$_1$-C$_6$)alkylene-NR$^{13}$C(=O)—R$^{14}$, —O—(C$_2$-C$_6$)alkylene-NR$^{13}$C(=O)—R$^{14}$, —NR$^{13}$—(C$_2$-C$_6$)alkylene-NR$^{14}$C(=O)—R$^{15}$, —C(=O)—R$^{13}$, —(C$_1$-C$_6$)alkylene-C(=O)—R$^{13}$, —O—(C$_1$-C$_6$)alkylene-C(=O)—R$^{13}$, —NR$^{13}$—(C$_1$-C$_6$)alkylene-C(=O)—R$^{14}$, —C(=O)—OR$^{13}$, —(C$_1$-C$_6$)alkylene-C(=O)—OR$^{13}$, —O—(C$_1$-C$_6$)alkylene-C(=O)—OR$^{13}$, —NR$^{13}$—(C$_1$-C$_6$)alkylene-C(=O)—OR$^{14}$, —OC(=O)—R$^{13}$, —(C$_1$-C$_6$)alkylene-OC(=O)—R$^{13}$, —O—(C$_2$-C$_6$)alkylene-OC(=O)—R$^{13}$, —NR$^{13}$—(C$_2$-C$_6$)alkylene-OC(=O)—R$^{14}$, —NR$^{13}$—C(=O)—NR$^{14}$R$^{15}$, —(C$_1$-C$_6$)alkylene-NR$^{13}$—C(=O)—NR$^{14}$R$^{15}$, —O—(C$_2$-C$_6$)alkylene-NR$^{13}$—C(=O)—NR$^{14}$R$^{15}$, —NR$^{13}$—(C$_2$-C$_6$)alkylene-NR$^{14}$—C(=O)—NR$^{15}$R$^{16}$, —NR$^{13}$—C(=O)—OR$^{14}$, —(C$_1$-C$_6$)alkylene-NR$^{13}$—C(=O)—OR$^{14}$, —O—(C$_2$-C$_6$)alkylene-NR$^{13}$—C(=O)—OR$^{14}$, —NR$^{13}$—(C$_2$-C$_6$)alkylene-NR$^{14}$—C(=O)—OR$^{15}$, —O—(C$_2$-C$_6$)alkylene-O—NR$^{13}$R$^{14}$, —(C$_1$-C$_6$)alkylene-O—C(=O)—NR$^{13}$R$^{14}$, —O—(C$_2$-C$_6$)alkylene-O—C(=O)—NR$^{13}$R$^{14}$, —NR$^{13}$—(C$_2$-C$_6$)alkylene-O—C(=O)—NR$^{14}$R$^{15}$, —C(=O)—(C$_1$-C$_6$)alkylene-NR$^{13}$R$^{14}$, —(C$_1$-C$_6$)alkylene-C(=O)—(C$_1$-C$_6$)alkylene-NR$^{13}$R$^{14}$, —C(=O)—(C$_1$-C$_6$)alkylene-OR$^{13}$, —(C$_1$-C$_6$)alkylene-C(=O)—(C$_1$-C$_6$)alkylene-OR$^{13}$, —NR$^{13}$—C(=S)—NR$^{14}$R$^{15}$, —(C$_1$-C$_6$)alkylene-NR$^{13}$—C(=S)—NR$^{14}$R$^{15}$, —NR$^{13}$—C(=NR$^{14}$)—NR$^{15}$R$^{16}$ or —(C$_1$-C$_6$)alkylene-NR$^{13}$—C(=NR$^{14}$)—NR$^{15}$R$^{16}$;

wherein R$^{13}$, R$^{14}$, R$^{15}$ and R$^{16}$ are each independently selected from hydrogen, an optionally substituted —(C$_1$-C$_6$)haloalkyl, —(C$_1$-C$_6$)alkyl, —(C$_1$-C$_6$)cyanoalkyl, —(C$_3$-C$_7$)cycloalkyl, —(C$_1$-C$_6$)alkylene-(C$_3$-C$_7$)cycloalkyl, heteroaryl, aryl, heterocycle, —(C$_1$-C$_6$)alkylene-heteroaryl, —(C$_1$-C$_6$)alkylene-heterocycle and —(C$_1$-C$_6$)alkylene-aryl;

wherein optionally any two radicals selected from R$^{13}$, R$^{14}$, R$^{15}$ or R$^{16}$ may be taken together to form a 3 to 10-membered carbocycle, heterocycle, aryl or heteroaryl ring; wherein each ring is optionally further substituted with 1 to 5 radicals independently selected from halogen, cyano, nitro, hydroxyl, amino, —(C$_1$-C$_6$)alkyl, —O—(C$_1$-C$_6$)alkyl and —N—((C$_1$-C$_6$)alkyl)$_2$;

wherein any two radicals A and any two radicals B may be combined with the intervening atoms to form a 3 to 10-membered carbocycle, heterocycle, aryl or heteroaryl ring; wherein each ring is optionally further substituted with 1 to 5 radicals independently selected from halogen, —CN, hydroxyl, amino, —(C$_1$-C$_6$)alkyl, —O—(C$_1$-C$_6$)alkyl and —N—((C$_1$-C$_6$)alkyl)$_2$, Preferably, in the compounds of Formula (I), substituents A, identical or different, are each independently selected from the group consisting of hydrogen, halogen, —CN, —CF$_3$, —OH, —NH$_2$, an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)alkylene-(C$_3$-C$_7$)cycloalkyl, —(C$_1$-C$_6$)alkylene-heterocycle, heterocycle, aryl, heteroaryl, —OR$^{13}$, —(C$_1$-C$_6$)alkylene-OR$^{13}$, —O—(C$_2$-C$_6$)alkylene-OR$^{13}$, —NR$^{13}$(C$_2$-C$_6$)alkylene-OR$^{14}$, —NR$^{13}$R$^{14}$, —(C$_1$-C$_6$)alkylene-NR$^{13}$R$^{14}$, —O—(C$_2$-C$_6$)alkylene-NR$^{13}$R$^{14}$, —NR$^{13}$—(C$_2$-C$_6$)alkylene-NR$^{14}$R$^{15}$, —SR$^{13}$, —(C$_1$-C$_6$)alkylene-SR$^{13}$, —O—(C$_2$-C$_6$)alkylene-SR$^{13}$, —NR$^{13}$—(C$_2$-C$_6$)alkylene-SR$^{14}$, —S(=O)—R$^{13}$, —S(=O)$_2$—R$^{13}$, —S(=O)$_2$NR$^{13}$R$^{14}$, —(C$_1$-C$_6$)alkylene-S(=O)$_2$NR$^{13}$R$^{14}$, —NR$^{13}$—S(=O)$_2$R$^{14}$, —(C$_1$-C$_6$)alkylene-S(=O)$_2$R$^{14}$, —O—(C$_2$-C$_6$)alkylene-NR$^{13}$—S(=O)$_2$R$^{14}$, —NR$^{13}$—(C$_2$-C$_6$)alkylene-NR$^{14}$—S(=O)$_2$R$^{15}$, —C(=O)—NR$^{13}$R$^{14}$, —(C$_1$-C$_6$)alkylene-C(=O)—NR$^{13}$R$^{14}$, —O—(C$_1$-C$_6$)alkylene-C(=O)—NR$^{13}$R$^{14}$, —NR$^{13}$—(C$_1$-C$_6$)alkylene-C(=O)—NR$^{14}$R$^{15}$, —NR$^{13}$C(=O)—R$^{14}$, —(C$_1$-C$_6$)alkylene-NR$^{13}$C(=O)—R$^{14}$, —O—(C$_2$-C$_6$)alkylene-NR$^{13}$C(=O)—R$^{14}$, —NR$^{13}$—(C$_2$-C$_6$)alkylene-NR$^{14}$C(=O)—R$^{15}$, —C(=O)—R$^{13}$, —C(=O)—OR$^{13}$, —(C$_1$-C$_6$)alkylene-C(=O)—OR$^{13}$, —O—(C$_1$-C$_6$)alkylene-C(=O)—OR$^{13}$, —NR$^{13}$—(C$_1$-C$_6$)alkylene-C(=O)—OR$^{14}$, —OC(=O)—R$^{13}$, —(C$_1$-C$_6$)alkylene-OC(=O)—R$^{13}$, —O—(C$_2$-C$_6$)alkylene-OC(=O)—R$^{13}$, —NR$^{13}$—(C$_2$-C$_6$)alkylene-OC(=O)—R$^{14}$ or —NR$^{13}$—C(=O)—OR$^{14}$;

wherein R$^{13}$, R$^{14}$ and R$^{15}$ are each independently selected from hydrogen, an optionally substituted —(C$_1$-C$_6$)alkyl, —(C$_3$-C$_7$)cycloalkyl, —(C$_1$-C$_6$)alkylene-(C$_3$-C$_7$)cycloalkyl, heteroaryl, aryl, heterocycle, —(C$_1$-C$_6$)alkylene-heteroaryl, —(C$_1$-C$_6$)alkylene-heterocycle and —(C$_1$-C$_6$)alkylene-aryl;

wherein optionally any two radicals selected from R$^{13}$, R$^{14}$ or R$^{15}$ on substituent A may be taken together to form a 3 to 10-membered carbocycle, heterocycle, aryl or heteroaryl ring; wherein each ring is optionally further substituted with 1 to 5 radicals independently selected from halogen, —CN, —NO$_2$, —OH, —NH$_2$, —(C$_1$-C$_6$)alkyl, —O—(C$_1$-C$_6$)alkyl and —N—((C$_1$-C$_6$)alkyl)$_2$;

wherein any two radicals A may be combined with the intervening atoms to form a 3 to 10-membered carbocycle, heterocycle, aryl or heteroaryl ring; wherein each ring is optionally further substituted with 1 to 5 radicals independently selected from halogen, —CN, —OH, —NH$_2$, —(C$_1$-C$_6$)alkyl, —O—(C$_1$-C$_6$)alkyl and —N—((C$_1$-C$_6$)alkyl)$_2$.

Preferably, in the compounds of Formula (I), substituents A, identical or different, are each independently selected from the group consisting of hydrogen, halogen, —CN, —CF$_3$, —OH, an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)alkylene-(C$_3$-C$_7$)cycloalkyl, —(C$_1$-C$_6$)alkylene-heterocycle, heterocycle, —OR$^{13}$, —(C$_1$-C$_6$)alkylene-OR$^{13}$, —O—(C$_2$-C$_6$)alkylene-OR$^{13}$, —NR$^{13}$(C$_2$-C$_6$)alkylene-OR$^{14}$, —O(C$_2$-C$_6$)alkylene-NR$^{13}$R$^{14}$, —NR$^{13}$—(C$_2$-C$_6$)alkylene-NR$^{14}$R$^{15}$, —NR$^{13}$R$^{14}$, —(C$_1$-C$_6$)alkylene-NR$^{13}$R$^{14}$, —NR$^{13}$C(=O)—R$^{14}$, —C(=O)—NR$^{13}$R$^{14}$, S(=O)$_2$NR$^{13}$R$^{14}$ or —NR$^{13}$—S(=O)$_2$R$^{14}$, wherein R$^{13}$ and R$^{14}$ are each independently selected from hydrogen, an optionally substituted —(C$_1$-C$_3$)alkyl, —(C$_3$-C$_7$)cycloalkyl, —(C$_1$-C$_6$)alkylene-(C$_3$-C$_7$)cycloalkyl, heterocycle and —(C$_1$-C$_6$)alkylene-heterocycle;

wherein optionally radicals R$^{13}$ and R$^{14}$ on substituent A may be taken together to form a 3 to 6-membered carbocycle, heterocycle, aryl or heteroaryl ring; wherein each ring is optionally further substituted with 1 to 5 radicals independently selected from halogen, —CN, —OH, —NH$_2$, —(C$_1$-C$_6$)alkyl, —O—(C$_1$-C$_6$)alkyl and —N—((C$_1$-C$_6$)alkyl)$_2$;

wherein any two radicals A may be combined with the intervening atoms to form a 3 to 10-membered carbocycle, heterocycle, aryl or heteroaryl ring; wherein each ring is optionally further substituted with 1 to 5 radicals independently selected from halogen, —CN, —(C$_1$-C$_6$)alkyl, —O—(C$_1$-C$_6$)alkyl and —N—((C$_1$-C$_6$)alkyl)$_2$.

Preferably, in the compounds of Formula (I), substituents A, identical or different, are each independently selected from the group consisting of hydrogen, halogen, —CN, —CF$_3$, —OH, an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)alkylene-(C$_3$-C$_7$)cycloalkyl, —(C$_1$-C$_6$)alkylene-heterocycle, heterocycle, —O—(C$_1$-C$_6$)alkyl, O—(C$_1$-C$_3$)alkyl-(C$_3$-C$_7$)cycloalkyl, —(C$_1$-C$_6$)alkylene-OR$^{13}$, —O—(C$_2$-C$_6$)alkylene-OR$^{13}$, —NR$^{13}$R$^{14}$, —(C$_1$-C$_6$)alkylene-NR$^{13}$R$^{14}$ or —NR$^{13}$C(=O)—R$^{14}$;

wherein R$^{13}$ and R$^{14}$ are each independently selected from hydrogen, an optionally substituted —(C$_1$-C$_3$)alkyl, —(C$_3$-C$_7$)cycloalkyl, —(C$_1$-C$_6$)alkylene-(C$_3$-C$_7$)cycloalkyl;

wherein optionally radicals R$^{13}$ and R$^{14}$ on substituent A may be taken together to form a 3 to 6-membered carbocycle or heterocycle, wherein each ring is optionally further substituted with 1 to 5 radicals independently selected from halogen, —CN, —OH, —NH$_2$, —(C$_1$-C$_6$)alkyl, —O—(C$_1$-C$_6$)alkyl and —N—((C$_1$-C$_6$)alkyl)$_2$;

wherein any two radicals A may be combined with the intervening atoms to form a 3 to 10-membered carbocycle, heterocycle, aryl or heteroaryl ring; wherein each ring is optionally further substituted with 1 to 5 radicals independently selected from halogen, —CN, —(C$_1$-C$_6$)alkyl, —O—(C$_1$-C$_6$)alkyl and —N—((C$_1$-C$_6$)alkyl)$_2$.

Preferably, in the compounds of Formula (I), substituents A identical or different, are each independently selected from the group consisting of hydrogen, methyl, ethyl, cyclopropyl, methoxy, ethoxy, hydroxy (—OH), cyclopropoxy, methoxymethyl, hydroxymethyl, 2-methoxyethoxy, 2-hydroxyethoxy, trifluoromethyl, chloro, fluoro, cyano, dimethylamino, azetidinyl, pyrrolidinyl, morpholino, morpholinomethyl, acetamido.

Preferably, in the compounds of Formula (I), substituents B identical or different, are each independently selected from the group consisting of hydrogen, halogen, —CN, —CF$_3$, an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)alkylene-(C$_3$-C$_7$)cycloalkyl, —(C$_1$-C$_6$)alkylene-heterocycle, —(C$_1$-C$_6$)alkylene-aryl, heterocycle, —OR$^{13}$, —(C$_1$-C$_6$)alkylene-OR$^{13}$, —O—(C$_2$-C$_6$)alkylene-OR$^{13}$, —NR$^{13}$(C$_2$-C$_6$)alkylene-OR$^{14}$, —NR$^{13}$R$^{14}$, —(C$_1$-C$_6$)alkylene-NR$^{13}$R$^{14}$, —O—(C$_2$-C$_6$)alkylene-NR$^{13}$R$^{14}$, —NR$^{13}$—(C$_2$-C$_6$)alkylene-NR$^{14}$R$^{15}$, —SR$^{13}$, —(C$_1$-C$_6$)alkylene-SR$^{13}$, —O—(C$_2$-C$_6$)alkylene-SR$^{13}$, —NR$^{13}$—(C$_2$-C$_6$)alkylene-SR$^{14}$, —S(=O)—R$^{13}$, —(C$_1$-C$_6$)alkylene-S(=O)—R$^{13}$, —O—(C$_1$-C$_6$)alkylene-S(=O)—R$^{13}$, —NR$^{13}$—(C$_1$-C$_6$)alkylene-S(=O)—R$^{14}$, —S(=O)$_2$—R$^{13}$, —(C$_1$-C$_6$)alkylene-S(=O)$_2$—R$^{13}$, —O—(C$_1$-C$_6$)alkylene-S(=O)$_2$—R$^{13}$, —NR$^{13}$—(C$_1$-C$_6$)alkylene-S(=O)$_2$—R$^{14}$, —S(=O)$_2$NR$^{13}$R$^{14}$, —(C$_1$-C$_6$)alkylene-S(=O)$_2$NR$^{13}$R$^{14}$, —O—(C$_1$-C$_6$)alkylene-S(=O)$_2$NR$^{13}$R$^{14}$, —NR$^{13}$—(C$_1$-C$_6$)alkylene-S(=O)$_2$NR$^{14}$R$^{15}$, —NR$^{13}$—S(=O)$_2$R$^{14}$, —(C$_1$-C$_6$)alkylene-NR$^{13}$—S(=O)$_2$R$^{14}$, —O—(C$_2$-C$_6$)alkylene-NR$^{13}$—S(=O)$_2$R$^{14}$, —NR$^{13}$—(C$_2$-C$_6$)alkylene-NR$^{14}$—S(=O)$_2$R$^{15}$, —C(=O)—NR$^{13}$R$^{14}$, —(C$_1$-C$_6$)alkylene-C(=O)—NR$^{13}$R$^{14}$, —O—(C$_1$-C$_6$)alkylene-C(=O)—NR$^{13}$R$^{14}$, —NR$^{13}$—(C$_1$-C$_6$)alkylene-C(=O)—NR$^{14}$R$^{15}$, —NR$^{13}$C(=O)—R$^{14}$, —(C$_1$-C$_6$)alkylene-NR$^{13}$C(=O)—R$^{14}$, —O—(C$_2$-C$_6$)alkylene-NR$^{13}$C(=O)—R$^{14}$, —NR$^{13}$—(C$_2$-C$_6$)alkylene-NR$^{14}$C(=O)—R$^{15}$, —C(=O)—R$^{13}$, —(C$_1$-C$_6$)alkylene-C(=O)—R$^{13}$, —O—(C$_1$-C$_6$)alkylene-C(=O)—R$^{13}$, —NR$^{13}$—(C$_1$-C$_6$)alkylene-C(=O)—R$^{14}$, —C(=O)—OR$^{13}$, —(C$_1$-C$_6$)alkylene-C(=O)—OR$^{13}$, —O—(C$_1$-C$_6$)alkylene-C(=O)—OR$^{13}$, —NR$^{13}$—(C$_1$-C$_6$)alkylene-C(=O)—OR$^{14}$, —OC(=O)—R$^{13}$, —(C$_1$-C$_6$)alkylene-OC(=O)—R$^{13}$, —O—(C$_2$-C$_6$)alkylene-OC(=O)—R$^{13}$, —NR$^{13}$—(C$_2$-C$_6$)alkylene-OC(=O)—R$^{14}$, —(C$_1$-C$_6$)alkylene-NR$^{13}$—C(=O)—NR$^{14}$R$^{15}$, —NR$^{13}$—C(=O)—OR$^{14}$, —(C$_1$-C$_6$)alkylene-NR$^{13}$—C(=O)—OR$^{14}$, —O—(C$_2$-C$_6$)alkylene-NR$^{13}$—C(=O)—OR$^{14}$, —NR$^{13}$—(C$_2$-C$_6$)alkylene-NR$^{14}$—C(=O)—OR$^{15}$, —O—C(=O)—NR$^{13}$R$^{14}$, —(C$_1$-C$_6$)alkylene-O—C(=O)—NR$^{13}$R$^{14}$, —O—(C$_2$-C$_6$)alkylene-O—C(=O)—NR$^{13}$R$^{14}$, —NR$^{13}$—(C$_2$-C$_6$)alkylene-O—C(=O)—NR$^{14}$R$^{15}$, —C(=O)—(C$_1$-C$_6$)alkylene-NR$^{13}$R$^{14}$, —C(=O)—(C$_1$-C$_6$)alkylene-OR$^{13}$;

wherein R$^{13}$, R$^{14}$ and R$^{15}$ are each independently selected from hydrogen, an optionally substituted —(C$_1$-C$_6$)haloalkyl, —(C$_1$-C$_6$)alkyl, —(C$_1$-C$_6$)cyanoalkyl, —(C$_3$-C$_7$)cycloalkyl, —(C$_1$-C$_6$)alkylene-(C$_3$-C$_7$)cycloalkyl, heteroaryl, aryl, heterocycle, —(C$_1$-C$_6$)alkylene-heteroaryl, —(C$_1$-C$_6$)alkylene-heterocycle and —(C$_1$-C$_6$)alkylene-aryl;

wherein optionally any two radicals selected from R$^{13}$, R$^{14}$ or R$^{15}$ on substituent B may be taken together to form a 3 to 10-membered carbocycle, heterocycle, aryl or heteroaryl ring; wherein each ring is optionally further substituted with 1 to 5 radicals independently selected from halogen, —CN, —NO$_2$, —OH, —NH$_2$, —(C$_1$-C$_6$)alkyl, —O—(C$_1$-C$_6$)alkyl and —N—((C$_1$-C$_6$)alkyl)$_2$;

wherein any two radicals B may be combined with the intervening atoms to form a 3 to 10-membered carbocycle, heterocycle, aryl or heteroaryl ring; wherein each ring is optionally further substituted with 1 to 5 radicals independently selected from halogen, —CN, —OH, —NH$_2$, —(C$_1$-C$_6$)alkyl, —O—(C$_1$-C$_6$)alkyl and —N—((C$_1$-C$_6$)alkyl)$_2$.

Preferably, in the compounds of Formula (I), substituents B identical or different, are each independently selected from the group consisting of hydrogen, halogen, —CF$_3$, —CN, an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)alkylene-(C$_3$-C$_7$)cycloalkyl, —(C$_1$-C$_6$)alkylene-aryl, heterocycle, —OR$^{13}$, —(C$_1$-C$_6$)alkylene-OR$^{13}$, —O—(C$_2$-C$_6$)alkylene-OR$^{13}$, —NR$^{13}$(C$_2$-C$_6$)alkylene-OR$^{14}$, —NR$^{13}$R$^{14}$, —SR$^{13}$, —(C$_1$-C$_6$)alkylene-SR$^{13}$, —S(=O)—R$^{13}$, —S(=O)$_2$—R$^{13}$, —NR$^{13}$C(=O)—R$^{14}$, —C(=O)—NR$^{13}$R$^{14}$, —C(=O)—OR$^{13}$, —OC(=O)—R$^{13}$, —C(=O)—(C$_1$-C$_6$)alkylene-OR$^{13}$ or —C(=O)—R$^{13}$;

wherein R$^{13}$ and R$^{14}$ are each independently selected from hydrogen, an optionally substituted —(C$_1$-C$_6$)alkyl, —(C$_3$-C$_7$)cycloalkyl, —(C$_1$-C$_6$)alkylene-(C$_3$-C$_7$)cycloalkyl, heteroaryl, aryl, heterocycle, —(C$_1$-C$_6$)alkylene-heteroaryl, —(C$_1$-C$_6$)alkylene-heterocycle and —(C$_1$-C$_6$)alkylene-aryl;

wherein optionally any two radicals selected from R$^{13}$ and R$^{14}$ on substituent B may be taken together to form a 3 to 10-membered carbocycle, heterocycle, aryl or heteroaryl ring; wherein each ring is optionally further substituted with 1 to 5 radicals independently selected from halogen, CN, —OH, —NH$_2$, —(C$_1$-C$_6$)alkyl, —O—(C$_1$-C$_6$)alkyl and —N—((C$_1$-C$_6$)alkyl)$_2$;

wherein any two radicals B may be combined with the intervening atoms to form a 3 to 10-membered carbocycle, heterocycle, aryl or heteroaryl ring; wherein each ring is optionally further substituted with 1 to 5 radicals independently selected from halogen, —CN, —OH, —NH$_2$, —(C$_1$-C$_6$)alkyl, —O—(C$_1$-C$_6$)alkyl and —N—((C$_1$-C$_6$)alkyl)$_2$.

Preferably, in the compounds of Formula (I), substituents B, identical or different, are each independently selected from the group consisting of hydrogen, halogen, —CF$_3$, an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)alkylene-(C$_3$-C$_7$)cycloalkyl, heterocycle, —O—(C$_1$-C$_6$)alkyl, —O—(C$_3$-C$_7$)cycloalkyl, —O—(C$_1$-C$_6$)alkylene-(C$_3$-C$_7$)cycloalkyl, —(C$_1$-C$_6$)alkylene-OR$^{13}$, —O—(C$_1$-C$_6$)alkylene-aryl, —O—(C$_2$-C$_6$)alkylene-O—(C$_1$-C$_6$)alkyl, —NR$^{13}$R$^{14}$ or —C(=O)—R$^{13}$;

wherein R$^{13}$ and R$^{14}$ are each independently selected from hydrogen, an optionally substituted —(C$_1$-C$_6$)alkyl, —(C$_3$-C$_7$)cycloalkyl, —(C$_1$-C$_6$)alkylene-(C$_3$-C$_7$)cycloalkyl, wherein optionally radicals R$^{13}$ and R$^{14}$ on substituent B may be taken together to form a 3 to 6-membered carbocycle, heterocycle, aryl or heteroaryl ring; wherein each ring is optionally further substituted with 1 to 5 radicals independently selected from halogen, —CN, —OH, —NH$_2$, —(C$_1$-C$_6$)alkyl, —O—(C$_1$-C$_6$)alkyl and —N—((C$_1$-C$_6$)alkyl)$_2$;

wherein any two radicals B may be combined with the intervening atoms to form a 3 to 10-membered carbocycle, heterocycle, aryl or heteroaryl ring; wherein each ring is optionally further substituted with 1 to 5 radicals independently selected from halogen, —CN, —(C$_1$-C$_6$)alkyl, —O—(C$_1$-C$_6$)alkyl and —N—((C$_1$-C$_6$)alkyl)$_2$.

Preferably, in the compounds of Formula (I), substituents B identical or different, are each independently selected from the group consisting of methyl, ethyl, cyclopropyl, methoxy, ethoxy, isopropoxy, cyclopropoxy, cyclopentyloxy, benzyloxy, cyclopropylmethoxy, methoxymethyl, 1-hydroxyethyl, 2-methoxyethoxy, 3-methoxypropoxy, trifluoromethyl, chloro, fluoro, dimethylamino, pyrrolidinyl, acetyl.

Preferably, in the compounds of Formula (I),
m is an integer equal to 0, 1 or 2; and/or
p is an integer equal to 1, 2 or 3.

Preferably, in the compounds of Formula (I), Ar$^1$ represents an aryl or heteroaryl chosen among:

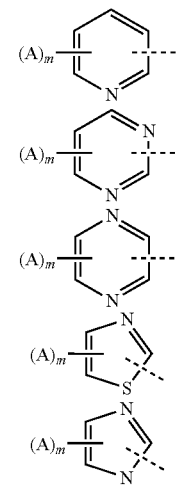

wherein A is defined above;
wherein m is the number of substituents A on the cycle and is an integer equal to 0, 1, 2, 3 or 4.

Preferably, in the compounds of Formula (I), Ar$^1$ represents an aryl or heteroaryl chosen among:
pyridin-2-yl, 3-chloropyridin-2-yl, 4-chloropyridin-2-yl, 5-chloropyridin-2-yl, 3-fluoropyridin-2-yl, 4-fluoropyridin-2-yl, 5-fluoropyridin-2-yl, 6-fluoropyridin-2-yl, 3-methoxypyridin-2-yl, 4-methoxypyridin-2-yl, 5-methoxypyridin-2-yl, 6-methoxypyridin-2-yl, 3-methylpyridin-2-yl, 5-methylpyridin-2-yl, 4-methylpyridin-2-yl, 6-methylpyridin-2-yl, 5-cyclopropylpyridin-2-yl, 5-hydroxypyridin-2-yl, 5-(methoxymethyl)pyridin-2-yl, 5-(hydroxymethyl)pyridin-2-yl, pyridin-3-yl, pyridin-4-yl, pyrazin-2-yl, pyrimidin-2-yl, pyrimidin-5-yl, 5-chloropyrimidin-2-yl, 5-fluoropyrimidin-2-yl, 5-methylpyrimidin-2-yl, 4-cyclopropylpyrimidin-2-yl, 5-cyclopropylpyrimidin-2-yl, 4,6-dimethylpyrimidin-2-yl, 5-(trifluoromethyl)pyrimidin-2-yl, 5-(morpholinomethyl)pyrimidin-2-yl, 4-methoxypyrimidin-2-yl, 5-methoxypyrimidin-2-yl, 4-methoxy-5-methylpyrimidin-2-yl, 5-(2-methoxyethoxy)pyrimidin-2-yl, 5-hydroxypyrimidin-2-yl, 5-(azetidin-1-yl)pyrimidin-2-yl, 5-(pyrrolidin-1-yl)pyrimidin-2-yl, 4-morpholinopyrimidin-2-yl, 5-morpholinopyrimidin-2-yl, thiazol-2-yl, thiazol-4-yl, 1-methyl-1H-imidazol-4-yl, 5-methoxypyrazin-2-yl.

Preferably, in the compounds of Formula (I), Ar$^2$ represents an aryl or heteroaryl chosen among:

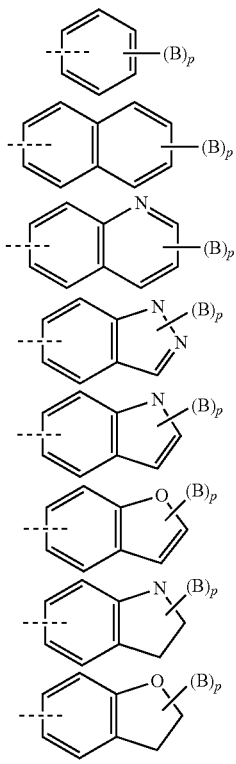

wherein B and p are as defined above.

Preferably, in the compounds of Formula (I), Ar² represents an aryl or heteroaryl chosen among:

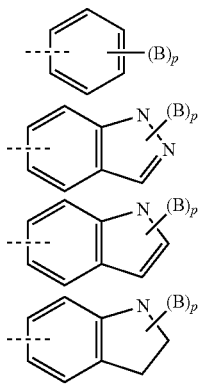

wherein B and p are as defined above.

Preferably, in the compounds of Formula (I), Ar² represents an aryl or heteroaryl chosen among:

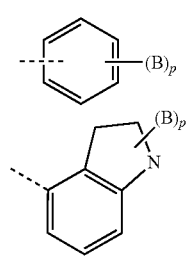

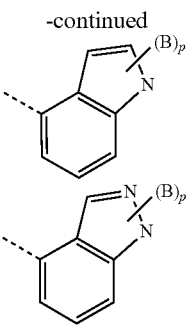

wherein B and p are as defined above.

Preferably, in the compounds of Formula (I), Ar² represents an aryl or heteroaryl chosen among:
2-methylphenyl, 2,4-dimethylphenyl, 2,4,6-trimethylphenyl, 3-methoxy-2-methylphenyl, 4-methoxy-2-methylphenyl, 5-methoxy-2-methylphenyl, 2-methoxy-3-methylphenyl, 3-methoxy-4-methylphenyl, 2-methoxy-4-methylphenyl, 2-methoxy-5-methylphenyl, 3-ethoxy-2-methylphenyl, 3-isopropoxy-2-methylphenyl, 3-cyclopropoxy-2-methylphenyl, 5-cyclopropoxy-2-methylphenyl, 3-(benzyloxy)-2-methylphenyl, 3-(3-methoxypropoxy)-2-methylphenyl, 3-(2-methoxyethoxy)-2-methylphenyl, 3-acetyl-2-methylphenyl, 4-acetyl-2-methylphenyl, 4-chloro-2-methylphenyl, 2-methyl-5-(pyrrolidin-1-yl)phenyl, 3-(dimethylamino)-2-methylphenyl, 5-methoxy-2,4-dimethylphenyl, 3-cyclopropylphenyl, 3-(methoxymethyl)phenyl, 3-(dimethylamino)phenyl, (1-hydroxyethyl)phenyl, 2-methoxyphenyl, 3-methoxyphenyl, 4-methoxyphenyl, 3-cyclopropoxyphenyl, 5-methoxy-2-(trifluoromethyl)phenyl, 3-(cyclopentyloxy)phenyl, 2,6-difluoro-3-methoxyphenyl, 2-chloro-3-methoxyphenyl, 2-fluoro-3-methoxyphenyl, 2-fluoro-5-methoxyphenyl, 2-chloro-5-methoxyphenyl, 1-methylindolin-4-yl, 1,5-dimethyl-1H-indazol-4-yl; 2-chloro-3-cyclopropoxyphenyl, 1-cyclopropylindolin-4-yl, 1-cyclopropyl-1H-indol-4-yl.

Preferably, in the compounds of Formula (I), $R^1$, $R^2$, $R^3$, $R^4$, $R^5$ and $R^6$ identical or different, are each independently selected from the group consisting of hydrogen, halogen, $-OR^{10}$, $-NR^{10}R^{11}$, an optionally substituted $-(C_1-C_3)$alkyl, $R^{10}$ and $R^{11}$ being as defined previously;
wherein any two radicals $R^1$ and $R^2$, $R^3$ and $R^4$, and $R^5$ and $R^6$ may be taken together to form an oxo;
wherein optionally any two radicals selected from $R^1$, $R^2$, $R^3$, $R^4$, $R^5$ and $R^6$ may be taken together to form an optionally substituted 3 to 10-membered non-aromatic carbocyclic or heterocyclic ring.

Preferably, in the compounds of Formula (I), $R^1$, $R^2$, $R^3$, $R^4$, $R^5$ and $R^6$ are hydrogen.

Preferably, in the compounds of Formula (I), $R^7$ and $R^8$ are selected from groups consisted of hydrogen, halogen, $-CN$, $-OR^{10}$, $-NR^{10}R^{11}$, $-CF_3$, an optionally substituted $-(C_1-C_3)$alkyl, wherein $R^{10}$ and $R^{11}$, identical or different, are each independently selected from hydrogen, $-(C_1-C_3)$alkyl or $-(C_3-C_7)$cycloalkyl, $R^{10}$ and $R^{11}$ being as defined previously;
wherein optionally the two radicals $R^{10}$ and $R^{11}$ may be taken together to form an optionally substituted 3 to 10-membered non-aromatic carbocyclic or heterocyclic ring.

Preferably, in the compounds of Formula (I), $R^7$ and $R^8$ are hydrogen.

Preferably, in the compounds of Formula (I), $R^9$ is selected from group consisting of hydrogen, halogen, —CN, —$OR^{10}$, —$NR^{10}R^{11}$, —$CF_3$, an optionally substituted —($C_1$-$C_3$)alkyl, wherein $R^{10}$ and $R^{11}$, identical or different, are each independently selected from hydrogen or —($C_1$-$C_3$)alkyl, wherein optionally the two radicals $R^{10}$ and $R^{11}$ may be taken together to form an optionally substituted 3 to 10-membered non-aromatic carbocyclic or heterocyclic ring.

Preferably, in the compounds of Formula (I), $R^9$ is hydrogen.

Preferably, in the compounds of Formula (I) according to the invention, only one of G or E is N.

In a first preferred aspect of Formula (I), the invention provides a compound according to Formula (II):

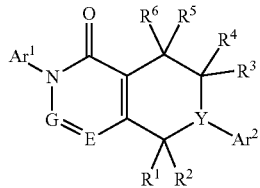

Formula (II)

wherein G, E, $Ar^1$, $Ar^2$, $R^1$, $R^2$, $R^3$, $R^4$, $R^5$, $R^6$ and Y are as defined above for compounds of Formula (I),
and the N-oxide forms thereof, the pharmaceutically acceptable salts and solvates thereof, or their optical isomers, racemates, diastereoisomers, enantiomers or tautomers thereof.

Preferably, in the compounds of Formula (II):

$Ar^1$ represents an aryl or heteroaryl chosen among:

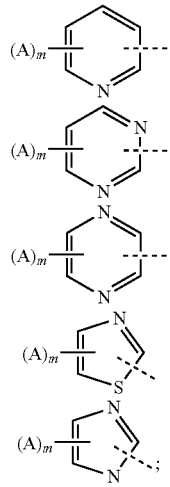

Wherein:
m is the number of substituents A on the cycle and is an integer equal to 0, 1, 2, 3 or 4, A, identical or different, are each independently selected from the group consisting of hydrogen, halogen, —CN, —$CF_3$, —OH, —$NH_2$, an optionally substituted radical selected from the group of —($C_1$-$C_6$)alkyl, —($C_1$-$C_6$)haloalkyl, —($C_3$-$C_7$)cycloalkyl, —($C_1$-$C_6$)alkylene-($C_3$-$C_7$)cycloalkyl, —($C_1$-$C_6$)alkylene-heterocycle, heterocycle, aryl, heteroaryl, —$OR^{13}$, —($C_1$-$C_6$)alkylene-$OR^{13}$, —O—($C_2$-$C_6$)alkylene-$OR^{13}$, —$NR^{13}$($C_2$-$C_6$)alkylene-$OR^{14}$, —$NR^{13}R^{14}$, —($C_1$-$C_6$)alkylene-$NR^{13}R^{14}$, —O—($C_2$-$C_6$)alkylene-$NR^{13}R^{14}$, —$NR^{13}$—($C_2$-$C_6$)alkylene-$NR^{14}R^{15}$, —$SR^{13}$, —($C_1$-$C_6$)alkylene-$SR^{13}$, —O—($C_2$-$C_6$)alkylene-$SR^{13}$, —$NR^{13}$—($C_2$-$C_6$)alkylene-$SR^{14}$, —S(=O)—$R^{13}$, —S(=O)$_2$—$R^{13}$, —S(=O)$_2NR^{13}R^{14}$, —($C_1$-$C_6$)alkylene-S(=O)$_2NR^{13}R^{14}$, —$NR^{13}$—S(=O)$_2R^{14}$, —($C_1$-$C_6$)alkylene-$NR^{13}$—S(=O)$_2R^{14}$, —O—($C_2$-$C_6$)alkylene-$NR^{13}$—S(=O)$_2R^{14}$, —$NR^{13}$—($C_2$-$C_6$)alkylene-$NR^{14}$—S(=O)$_2R^{15}$, —C(=O)—$NR^{13}R^{14}$, —($C_1$-$C_6$)alkylene-C(=O)—$NR^{13}R^{14}$, —O—($C_1$-$C_6$)alkylene-C(=O)—$NR^{13}R^{14}$, —$NR^{13}$—($C_1$-$C_6$)alkylene-C(=O)—$NR^{14}R^{15}$, —$NR^{13}C$(=O)—$R^{14}$, —($C_1$-$C_6$)alkylene-$NR^{13}C$(=O)—$R^{14}$, —O—($C_2$-$C_6$)alkylene-$NR^{13}C$(=O)—$R^{14}$, —$NR^{13}$—($C_2$-$C_6$)alkylene-$NR^{14}C$(=O)—$R^{15}$, —C(=O)—$R^{13}$, —C(=O)—$OR^{13}$, —($C_1$-$C_6$)alkylene-C(=O)—$OR^{13}$, —O—($C_1$-$C_6$)alkylene-C(=O)—$OR^{13}$, —$NR^{13}$—($C_1$-$C_6$)alkylene-C(=O)—$OR^{14}$, —OC(=O)—$R^{13}$, —($C_1$-$C_6$)alkylene-OC(=O)—$R^{13}$, —O—($C_2$-$C_6$)alkylene-OC(=O)—$R^{13}$, —$NR^{13}$—($C_2$-$C_6$)alkylene-OC(=O)—$R^{14}$ or —$NR^{13}$—C(=O)—$OR^{14}$;

wherein $R^{13}$, $R^{14}$ and $R^{15}$ are each independently selected from hydrogen, an optionally substituted —($C_1$-$C_6$)alkyl, —($C_3$-$C_7$)cycloalkyl, —($C_1$-$C_6$)alkylene-($C_3$-$C_7$)cycloalkyl, heteroaryl, aryl, heterocycle, —($C_1$-$C_6$)alkylene-heteroaryl, —($C_1$-$C_6$)alkylene-heterocycle and —($C_1$-$C_6$)alkylene-aryl;

wherein optionally any two radicals selected from $R^{13}$, $R^{14}$ or $R^{15}$ on substituent A may be taken together to form a 3 to 10-membered carbocycle, heterocycle, aryl or heteroaryl ring; wherein each ring is optionally further substituted with 1 to 5 radicals independently selected from halogen, —CN, —$NO_2$, —OH, —$NH_2$, —($C_1$-$C_6$)alkyl, —O—($C_1$-$C_6$)alkyl and —N—(($C_1$-$C_6$)alkyl)$_2$;

wherein any two radicals A may be combined with the intervening atoms to form a 3 to 10-membered carbocycle, heterocycle, aryl or heteroaryl ring; wherein each ring is optionally further substituted with 1 to 5 radicals independently selected from halogen, —CN, —OH, —$NH_2$, —($C_1$-$C_6$)alkyl, —O—($C_1$-$C_6$)alkyl and —N—(($C_1$-$C_6$)alkyl)$_2$;

and/or $Ar^2$ represents an aryl or heteroaryl chosen among:

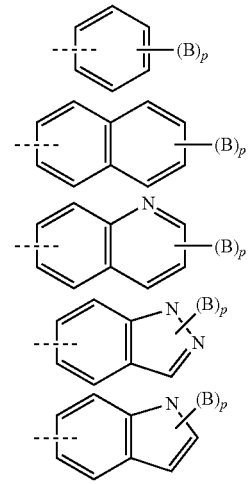

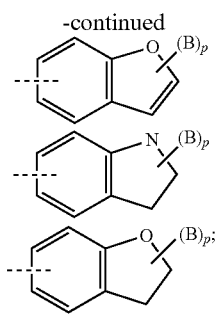

wherein
p is the number of substituent B on the cycle and is an integer equal to 0, 1, 2, 3, 4 or 5,
B, identical or different, are each independently selected from the group consisting of hydrogen, halogen, —CN, —CF$_3$, an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)alkylene-(C$_3$-C$_7$)cycloalkyl, —(C$_1$-C$_6$)alkylene-heterocycle, —(C$_1$-C$_6$)alkylene-aryl, heterocycle, —OR$^{13}$, —(C$_1$-C$_6$)alkylene-OR$^{13}$, —O—(C$_2$-C$_6$)alkylene-OR$^{13}$, —NR$^{13}$(C$_2$-C$_6$)alkylene-OR$^{14}$, —NR$^{13}$R$^{14}$, —(C$_1$-C$_6$)alkylene-NR$^{13}$R$^{14}$, —O—(C$_2$-C$_6$)alkylene-NR$^{13}$R$^{14}$, —NR$^{13}$—(C$_2$-C$_6$)alkylene-NR$^{14}$R$^{15}$, —SR$^{13}$, —(C$_1$-C$_6$)alkylene-SR$^{13}$, —O—(C$_2$-C$_6$)alkylene-SR$^{13}$, —NR$^{13}$—(C$_2$-C$_6$)alkylene-SR$^{14}$, —S(=O)—R$^{13}$, —(C$_1$-C$_6$)alkylene-S(=O)—R$^{13}$, —O—(C$_1$-C$_6$)alkylene-S(=O)—R$^{13}$, —NR$^{13}$—(C$_1$-C$_6$)alkylene-S(=O)—R$^{14}$, —S(=O)$_2$—R$^{13}$, —(C$_1$-C$_6$)alkylene-S(=O)$_2$—R$^{13}$, —O—(C$_1$-C$_6$)alkylene-S(=O)$_2$—R$^{13}$, —NR$^{13}$—(C$_1$-C$_6$)alkylene-S(=O)$_2$—R$^{14}$, —S(=O)$_2$NR$^{13}$R$^{14}$, —(C$_1$-C$_6$)alkylene-S(=O)$_2$NR$^{13}$R$^{14}$, —O—(C$_1$-C$_6$)alkylene-S(=O)$_2$NR$^{13}$R$^{14}$, —NR$^{13}$—(C$_1$-C$_6$)alkylene-S(=O)$_2$NR$^{14}$R$^{15}$, —NR$^{13}$—S(=O)$_2$R$^{14}$, —(C$_1$-C$_6$)alkylene-NR$^{13}$—S(=O)$_2$R$^{14}$, —O—(C$_2$-C$_6$)alkylene-NR$^{13}$—S(=O)$_2$R$^{14}$, —NR$^{13}$—(C$_2$-C$_6$)alkylene-NR$^{14}$—S(=O)$_2$R$^{15}$, —C(=O)—NR$^{13}$R$^{14}$, —(C$_1$-C$_6$)alkylene-C(=O)—NR$^{13}$R$^{14}$, —O—(C$_1$-C$_6$)alkylene-C(=O)—NR$^{13}$R$^{14}$, —NR$^{13}$—(C$_1$-C$_6$)alkylene-C(=O)—NR$^{14}$R$^{15}$, —NR$^{13}$C(=O)—R$^{14}$, —(C$_1$-C$_6$)alkylene-NR$^{13}$C(=O)—R$^{14}$, —O—(C$_2$-C$_6$)alkylene-NR$^{13}$C(=O)—R$^{14}$, —NR$^{13}$—(C$_2$-C$_6$)alkylene-NR$^{14}$C(=O)—R$^{15}$, —C(=O)—R$^{13}$, —(C$_1$-C$_6$)alkylene-C(=O)—R$^{13}$, —O—(C$_1$-C$_6$)alkylene-C(=O)—R$^{13}$, —NR$^{13}$—(C$_1$-C$_6$)alkylene-C(=O)—R$^{14}$, —C(=O)—OR$^{13}$, —(C$_1$-C$_6$)alkylene-C(=O)—OR$^{13}$, —O—(C$_1$-C$_6$)alkylene-C(=O)—OR$^{13}$, —NR$^{13}$—(C$_1$-C$_6$)alkylene-C(=O)—OR$^{14}$, —OC(=O)—R$^{13}$, —(C$_1$-C$_6$)alkylene-OC(=O)—R$^{13}$, —O—(C$_2$-C$_6$)alkylene-OC(=O)—R$^{13}$, —NR$^{13}$—(C$_2$-C$_6$)alkylene-OC(=O)—R$^{14}$, —(C$_1$-C$_6$)alkylene-NR$^{13}$—C(=O)—NR$^{14}$R$^{15}$, —NR$^{13}$—C(=O)—OR$^{14}$, —(C$_1$-C$_6$)alkylene-NR$^{13}$—C(=O)—OR$^{14}$, —O—(C$_2$-C$_6$)alkylene-NR$^{13}$—C(=O)—OR$^{14}$, —NR$^{13}$—(C$_2$-C$_6$)alkylene-NR$^{14}$—C(=O)—OR$^{15}$, —O—C(=O)—NR$^{13}$R$^{14}$, —(C$_1$-C$_6$)alkylene-O—C(=O)—NR$^{13}$R$^{14}$, —O—(C$_2$-C$_6$)alkylene-O—C(=O)—NR$^{13}$R$^{14}$, —NR$^{13}$—(C$_2$-C$_6$)alkylene-O—C(=O)—NR$^{14}$R$^{15}$, —C(=O)—(C$_1$-C$_6$)alkylene-NR$^{13}$R$^{14}$, —C(=O)—(C$_1$-C$_6$)alkylene-OR$^{13}$;
wherein R$^{13}$, R$^{14}$ and R$^{15}$ are each independently selected from hydrogen, an optionally substituted —(C$_1$-C$_6$)haloalkyl, —(C$_1$-C$_6$)alkyl, —(C$_1$-C$_6$)cyanoalkyl, —(C$_3$-C$_7$)cycloalkyl, —(C$_1$-C$_6$)alkylene-(C$_3$-C$_7$)cycloalkyl, heteroaryl, aryl, heterocycle, —(C$_1$-C$_6$)alkylene-heteroaryl, —(C$_1$-C$_6$)alkylene-heterocycle and —(C$_1$-C$_6$)alkylene-aryl;
wherein optionally any two radicals selected from R$^{13}$, R$^{14}$ or R$^{15}$ on substituent B may be taken together to form a 3 to 10-membered carbocycle, heterocycle, aryl or heteroaryl ring; wherein each ring is optionally further substituted with 1 to 5 radicals independently selected from halogen, —CN, —NO$_2$, —OH, —NH$_2$, —(C$_1$-C$_6$)alkyl, —O—(C$_1$-C$_6$)alkyl and —N—((C$_1$-C$_6$)alkyl)$_2$;
wherein any two radicals B may be combined with the intervening atoms to form a 3 to 10-membered carbocycle, heterocycle, aryl or heteroaryl ring; wherein each ring is optionally further substituted with 1 to 5 radicals independently selected from halogen, —CN, —OH, —NH$_2$, —(C$_1$-C$_6$)alkyl, —O—(C$_1$-C$_6$)alkyl and —N—((C$_1$-C$_6$)alkyl)$_2$.
Preferably, in the compounds of Formula (II):
A, identical or different, are each independently selected from the group consisting of hydrogen, halogen, —CN, —CF$_3$, —OH, an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)alkylene-(C$_3$-C$_7$)cycloalkyl, —(C$_1$-C$_6$)alkylene-heterocycle, heterocycle, —OR$^{13}$, —(C$_1$-C$_6$)alkylene-OR$^{13}$, —O—(C$_2$-C$_6$)alkylene-OR$^{13}$, —NR$^{13}$(C$_2$-C$_6$)alkylene-OR$^{14}$, —O(C$_2$-C$_6$)alkylene-NR$^{13}$R$^{14}$, —NR$^{13}$—(C$_2$-C$_6$)alkylene-NR$^{14}$R$^{15}$, —NR$^{13}$R$^{14}$, —(C$_1$-C$_6$)alkylene-NR$^{13}$R$^{14}$, —NR$^{13}$C(=O)—R$^{14}$, —C(=O)—NR$^{13}$R$^{14}$, S(=O)$_2$NR$^{13}$R$^{14}$ or —NR$^{13}$—S(=O)$_2$R$^{14}$,
wherein R$^{13}$, R$^{14}$ and R$^{15}$ are each independently selected from hydrogen, an optionally substituted —(C$_1$-C$_3$)alkyl, —(C$_3$-C$_7$)cycloalkyl, —(C$_1$-C$_6$)alkylene-(C$_3$-C$_7$)cycloalkyl, heterocycle and —(C$_1$-C$_6$)alkylene-heterocycle;
wherein optionally radicals R$^{13}$, R$^{14}$ and R$^{15}$ on substituent A may be taken together to form a 3 to 6-membered carbocycle, heterocycle, aryl or heteroaryl ring; wherein each ring is optionally further substituted with 1 to 5 radicals independently selected from halogen, —CN, —OH, —NH$_2$, —(C$_1$-C$_6$)alkyl, —O—(C$_1$-C$_6$)alkyl and —N—((C$_1$-C$_6$)alkyl)$_2$;
wherein any two radicals A may be combined with the intervening atoms to form a 3 to 10-membered carbocycle, heterocycle, aryl or heteroaryl ring; wherein each ring is optionally further substituted with 1 to 5 radicals independently selected from halogen, —CN, —(C$_1$-C$_6$)alkyl, —O—(C$_1$-C$_6$)alkyl and —N—((C$_1$-C$_6$)alkyl)$_2$; and/or
B identical or different, are each independently selected from the group consisting of hydrogen, halogen, —CF$_3$, —CN, an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)alkylene-(C$_3$-C$_7$)cycloalkyl, —(C$_1$-C$_6$)alkylene-aryl, heterocycle, —OR$^{13}$, —(C$_1$-C$_6$)alkylene-OR$^{13}$, —O—(C$_2$-C$_6$)alkylene-OR$^{13}$, —NR$^{13}$(C$_2$-C$_6$)alkylene-OR$^{14}$, —NR$^{13}$R$^{14}$, —SR$^{13}$, —(C$_1$-C$_6$)alkylene-SR$^{13}$, —S(=O)—R$^{13}$, —S(=O)$_2$—R$^{13}$, —NR$^{13}$C(=O)—R$^{14}$, —C(=O)—NR$^{13}$R$^{14}$, —C(=O)—OR$^{13}$, —OC(=O)—R$^{13}$, —C(=O)—(C$_1$-C$_6$)alkylene-OR$^{13}$ or —C(=O)—R$^{13}$;
wherein R$^{13}$ and R$^{14}$ are each independently selected from hydrogen, an optionally substituted —(C$_1$-C$_6$)alkyl, —(C$_3$-C$_7$)cycloalkyl, —(C$_1$-C$_6$)alkylene-(C$_3$-C$_7$)cycloalkyl, heteroaryl, aryl, heterocycle, —(C$_1$-C$_6$)alkylene-heteroaryl, —(C$_1$-C$_6$)alkylene-heterocycle and —(C$_1$-C$_6$)alkylene-aryl;

wherein optionally any two radicals selected from R$^{13}$ and R$^{14}$ on substituent B may be taken together to form a 3 to 10-membered carbocycle, heterocycle, aryl or heteroaryl ring; wherein each ring is optionally further substituted with 1 to 5 radicals independently selected from halogen, CN, —OH, —NH$_2$, —(C$_1$-C$_6$)alkyl, —O—(C$_1$-C$_6$)alkyl and —N—((C$_1$-C$_6$)alkyl)$_2$;

wherein any two radicals B may be combined with the intervening atoms to form a 3 to 10-membered carbocycle, heterocycle, aryl or heteroaryl ring; wherein each ring is optionally further substituted with 1 to 5 radicals independently selected from halogen, —CN, —OH, —NH$_2$, —(C$_1$-C$_6$)alkyl, —O—(C$_1$-C$_6$)alkyl and —N—((C$_1$-C$_6$)alkyl)$_2$; and/or only one of G or E is N.

In a second preferred aspect of Formula (I), the invention provides a compound according to Formula (III):

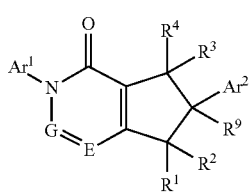

Formula (III)

wherein G, E, Ar$^1$, Ar$^2$, R$^1$, R$^2$, R$^3$, R$^4$ and R$^9$ are as defined above for compounds of Formula (I),
and the N-oxide forms thereof, the pharmaceutically acceptable salts and solvates thereof, or their optical isomers, racemates, diastereoisomers, enantiomers or tautomers thereof.

Preferably, in the compounds of Formula (III),

A, identical or different, are each independently selected from the group consisting of hydrogen, halogen, —CN, —CF$_3$, —OH, an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)alkylene-(C$_3$-C$_7$)cycloalkyl, —(C$_1$-C$_6$)alkylene-heterocycle, heterocycle, —OR$^{13}$, —(C$_1$-C$_6$)alkylene-OR$^{13}$, —O—(C$_2$-C$_6$)alkylene-OR$^{13}$, —NR$^{13}$(C$_2$-C$_6$)alkylene-OR$^{14}$, —O(C$_2$-C$_6$)alkylene-NR$^{13}$R$^{14}$, —NR$^{13}$—(C$_2$-C$_6$)alkylene-NR$^{14}$R$^{15}$, —NR$^{13}$R$^{14}$, —(C$_1$-C$_6$)alkylene-NR$^{13}$R$^{14}$, —NR$^{13}$C(=O)—R$^{14}$, —C(=O)—NR$^{13}$R$^{14}$, S(=O)$_2$NR$^{13}$R$^{14}$ or —NR$^{13}$—S(=O)$_2$R$^{14}$, wherein R$^{13}$ and R$^{14}$ are each independently selected from hydrogen, an optionally substituted —(C$_1$-C$_3$)alkyl, —(C$_3$-C$_7$)cycloalkyl, —(C$_1$-C$_6$)alkylene-(C$_3$-C$_7$)cycloalkyl, heterocycle and —(C$_1$-C$_6$)alkylene-heterocycle;

wherein optionally radicals R$^{13}$ and R$^{14}$ on substituent A may be taken together to form a 3 to 6-membered carbocycle, heterocycle, aryl or heteroaryl ring; wherein each ring is optionally further substituted with 1 to 5 radicals independently selected from halogen, —CN, —OH, —NH$_2$, —(C$_1$-C$_6$)alkyl, —O—(C$_1$-C$_6$)alkyl and —N—((C$_1$-C$_6$)alkyl)$_2$;

wherein any two radicals A may be combined with the intervening atoms to form a 3 to 10-membered carbocycle, heterocycle, aryl or heteroaryl ring; wherein each ring is optionally further substituted with 1 to 5 radicals independently selected from halogen, —CN, —(C$_1$-C$_6$)alkyl, —O—(C$_1$-C$_6$)alkyl and —N—((C$_1$-C$_6$)alkyl)$_2$; and/or B identical or different, are each independently selected from the group consisting of hydrogen, halogen, —CF$_3$, —CN, an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)alkylene-(C$_3$-C$_7$)cycloalkyl, —(C$_1$-C$_6$)alkylene-aryl, heterocycle, —OR$^{13}$, —(C$_1$-C$_6$)alkylene-OR$^{13}$, —O—(C$_2$-C$_6$)alkylene-OR$^{13}$, —NR$^{13}$(C$_2$-C$_6$)alkylene-OR$^{14}$, —NR$^{13}$R$^{14}$, —SR$^{13}$, —(C$_1$-C$_6$)alkylene-SR$^{13}$, —S(=O)—R$^{13}$, —S(=O)$_2$—R$^{13}$, —NR$^{13}$C(=O)—R$^{14}$, —C(=O)—NR$^{13}$R$^{14}$, —C(=O)—OR$^{13}$, —OC(=O)—R$^{13}$, —C(=O)—(C$_1$-C$_6$)alkylene-OR$^{13}$ or —C(=O)—R$^{13}$;

wherein R$^{13}$ and R$^{14}$ are each independently selected from hydrogen, an optionally substituted —(C$_1$-C$_6$)alkyl, —(C$_3$-C$_7$)cycloalkyl, —(C$_1$-C$_6$)alkylene-(C$_3$-C$_7$)cycloalkyl, heteroaryl, aryl, heterocycle, —(C$_1$-C$_6$)alkylene-heteroaryl, —(C$_1$-C$_6$)alkylene-heterocycle and —(C$_1$-C$_6$)alkylene-aryl;

wherein optionally any two radicals selected from R$^{13}$ and R$^{14}$ on substituent B may be taken together to form a 3 to 10-membered carbocycle, heterocycle, aryl or heteroaryl ring; wherein each ring is optionally further substituted with 1 to 5 radicals independently selected from halogen, CN, —OH, —NH$_2$, —(C$_1$-C$_6$)alkyl, —O—(C$_1$-C$_6$)alkyl and —N—((C$_1$-C$_6$)alkyl)$_2$;

wherein any two radicals B may be combined with the intervening atoms to form a 3 to 10-membered carbocycle, heterocycle, aryl or heteroaryl ring; wherein each ring is optionally further substituted with 1 to 5 radicals independently selected from halogen, —CN, —OH, —NH$_2$, —(C$_1$-C$_6$)alkyl, —O—(C$_1$-C$_6$)alkyl and —N—((C$_1$-C$_6$)alkyl)$_2$; and/or only one of G or E is N.

Preferably, in the compounds of Formula (III), G is a nitrogen and E is CR$^8$, wherein R$^8$ is defined as above.

Preferably, in the compounds of Formula (III), G is a nitrogen and E is CH.

The present invention also relates to a compound according to the invention as described herein, in the form of a racemic mixture or in the form of one or both of the individual optical isomers.

Particularly preferred compounds according to the invention include compounds in the following list (List of Preferred Compounds), as well as the N-oxide forms thereof, the pharmaceutically acceptable salts and solvates thereof, or their optical isomers, racemates, diastereoisomers, enantiomers or tautomers thereof:

6-(2,4-Dimethyl-phenyl)-2-pyridin-2-yl-5,6,7,8-tetrahydro-2H-phthalazin-1-one, 6-(3-methoxyphenyl)-2-(pyridin-2-yl)-5,6,7,8-tetrahydrophthalazin-1(2H)-one, 6-(4-methoxyphenyl)-2-(pyridin-2-yl)-5,6,7,8-tetrahydrophthalazin-1(2H)-one, (+)-6-(2,4-Dimethyl-phenyl)-2-pyridin-2-yl-5,6,7,8-tetrahydro-2H-phthalazin-1-one, (−)-6-(2,4-Dimethyl-phenyl)-2-pyridin-2-yl-5,6,7,8-tetrahydro-2H-phthalazin-1-one, 6-(2,4-dimethylphenyl)-2-(5-chloropyridin-2-yl)-5,6,7,8-tetrahydro-phthalazin-1(2H)-one, 2-(4-chloropyridin-2-yl)-6-(2,4-dimethylphenyl)-5,6,7,8-tetrahydrophthalazin-1(2H)-one, 2-(3-chloropyridin-2-yl)-6-(2,4-dimethylphenyl)-5,6,7,8-tetrahydrophthalazin-1(2H)-one, 2-(6-fluoropyridin-2-yl)-6-(2,4-dimethylphenyl)-5,6,7,8-tetrahydrophthalazin-1(2H)-one,
6-(2,4-dimethylphenyl)-2-(5-fluoropyridin-2-yl)-5,6,7,8-tetrahydrophthalazin-1(2H)-one,
6-(2,4-dimethylphenyl)-2-(4-fluoropyridin-2-yl)-5,6,7,8-tetrahydrophthalazin-1(2H)-one,
6-(2,4-dimethylphenyl)-2-(3-fluoropyridin-2-yl)-5,6,7,8-tetrahydrophthalazin-1(2H)-one,
6-(2,4-dimethylphenyl)-2-(6-methoxypyridin-2-yl)-5,6,7,8-tetrahydrophthalazin-1(2H)-one,
6-(2,4-dimethylphenyl)-2-(5-methoxypyridin-2-yl)-5,6,7,8-tetrahydrophthalazin-1(2H)-one,
6-(2,4-dimethylphenyl)-2-(4-methoxypyridin-2-yl)-5,6,7,8-tetrahydrophthalazin-1(2H)-one,
6-(2,4-dimethylphenyl)-2-(3-methoxypyridin-2-yl)-5,6,7,8-tetrahydrophthalazin-1(2H)-one,
6-(2,4-dimethylphenyl)-2-(6-methylpyridin-2-yl)-5,6,7,8-tetrahydrophthalazin-1(2H)-one,
6-(2,4-dimethylphenyl)-2-(5-methylpyridin-2-yl)-5,6,7,8-tetrahydrophthalazin-1(2H)-one,
6-(2,4-dimethylphenyl)-2-(4-methylpyridin-2-yl)-5,6,7,8-tetrahydrophthalazin-1(2H)-one,
6-(2,4-dimethylphenyl)-2-(3-methylpyridin-2-yl)-5,6,7,8-tetrahydrophthalazin-1(2H)-one,
6-(6-(2,4-dimethylphenyl)-1-oxo-5,6,7,8-tetrahydrophthalazin-2(1H)-yl)picolinonitrile,
6-(6-(2,4-dimethylphenyl)-1-oxo-5,6,7,8-tetrahydrophthalazin-2(1H)-yl)nicotinonitrile,
2-(6-(2,4-dimethylphenyl)-1-oxo-5,6,7,8-tetrahydrophthalazin-2(1H)-yl)isonicotinonitrile,
2-(6-(2,4-dimethylphenyl)-1-oxo-5,6,7,8-tetrahydrophthalazin-2(1H)-yl)nicotinonitrile,
6-(2,4-dimethylphenyl)-2-(5-hydroxypyridin-2-yl)-5,6,7,8-tetrahydrophthalazin-1(2H)-one,
6-(2,4-dimethylphenyl)-2-(4-hydroxypyridin-2-yl)-5,6,7,8-tetrahydrophthalazin-1(2H)-one,
6-(2,4-dimethylphenyl)-2-(5-(methoxymethyl)pyridin-2-yl)-5,6,7,8-tetrahydrophthalazin-1(2H)-one,
6-(2,4-dimethylphenyl)-2-(pyridin-3-yl)-5,6,7,8-tetrahydrophthalazin-1(2H)-one,
6-(2,4-dimethylphenyl)-2-(pyrimidin-2-yl)-5,6,7,8-tetrahydrophthalazin-1(2H)-one,
6-(2,4-dimethylphenyl)-2-(pyrazin-2-yl)-5,6,7,8-tetrahydrophthalazin-1(2H)-one,
6-(2,4-dimethylphenyl)-2-(pyrimidin-5-yl)-5,6,7,8-tetrahydrophthalazin-1(2H)-one,
6-(2,4-dimethylphenyl)-2-(thiazol-2-yl)-5,6,7,8-tetrahydrophthalazin-1(2H)-one,
6-(2,4-dimethylphenyl)-2-(thiazol-4-yl)-5,6,7,8-tetrahydrophthalazin-1(2H)-one,
6-(2,4-dimethylphenyl)-2-(1-methyl-1H-imidazol-4-yl)-5,6,7,8-tetrahydrophthalazin-1(2H)-one,
6-(2,4-dimethylphenyl)-2-(4-methoxypyrimidin-2-yl)-5,6,7,8-tetrahydrophthalazin-1(2H)-one,
6-(2,4-dimethylphenyl)-2-(4,6-dimethylpyrimidin-2-yl)-5,6,7,8-tetrahydrophthalazin-1(2H)-one,
2-(4-cyclopropylpyrimidin-2-yl)-6-(2,4-dimethylphenyl)-5,6,7,8-tetrahydrophthalazin-1(2H)-one,
2-(5-hydroxypyridin-2-yl)-6-(3-methoxy-2-methylphenyl)-5,6,7,8-tetrahydrophthalazin-1(2H)-one,
2-(5-(hydroxymethyl)pyridin-2-yl)-6-(3-methoxy-2-methylphenyl)-5,6,7,8-tetrahydrophthalazin-1(2H)-one,
6-(3-methoxy-2-methylphenyl)-2-(pyrimidin-2-yl)-5,6,7,8-tetrahydrophthalazin-1(2H)-one,
6-(3-methoxy-2-methylphenyl)-2-(5-methylpyrimidin-2-yl)-5,6,7,8-tetrahydrophthalazin-1(2H)-one,
6-(3-methoxy-2-methylphenyl)-2-(4-methoxypyrimidin-2-yl)-5,6,7,8-tetrahydrophthalazin-1(2H)-one,
2-(5-chloropyrimidin-2-yl)-6-(3-methoxy-2-methylphenyl)-5,6,7,8-tetrahydrophthalazin-1(2H)-one,
6-(3-methoxy-2-methylphenyl)-2-(5-methoxypyrazin-2-yl)-5,6,7,8-tetrahydrophthalazin-1(2H)-one,
2-(5-hydroxypyrimidin-2-yl)-6-(3-methoxy-2-methylphenyl)-5,6,7,8-tetrahydrophthalazin-1(2H)-one,
6-(3-methoxy-2-methylphenyl)-2-(4-morpholinopyrimidin-2-yl)-5,6,7,8-tetrahydrophthalazin-1(2H)-one,
6-(5-methoxy-2-methylphenyl)-2-(5-methylpyrimidin-2-yl)-5,6,7,8-tetrahydrophthalazin-1(2H)-one,
6-(5-methoxy-2-methylphenyl)-2-(5-methoxypyrimidin-2-yl)-5,6,7,8-tetrahydrophthalazin-1(2H)-one,
2-(5-chloropyrimidin-2-yl)-6-(5-methoxy-2-methylphenyl)-5,6,7,8-tetrahydrophthalazin-1(2H)-one,
6-(2,4-dimethylphenyl)-2-(pyridin-4-yl)-5,6,7,8-tetrahydrophthalazin-1(2H)-one,
2-(5-chloropyrimidin-2-yl)-6-(2,4-dimethylphenyl)-5,6,7,8-tetrahydro-phthalazin-1(2H)-one,
6-(2,4-dimethylphenyl)-2-(5-methylpyrimidin-2-yl)-5,6,7,8-tetrahydrophthalazin-1(2H)-one,
6-(2,4-dimethylphenyl)-2-(5-methoxypyrimidin-2-yl)-5,6,7,8-tetrahydrophthalazin-1(2H)-one,
6-(2,4-dimethylphenyl)-2-(5-fluoropyrimidin-2-yl)-5,6,7,8-tetrahydrophthalazin-1(2H)-one,
6-(2,4-dimethylphenyl)-2-(5-(trifluoromethyl)pyrimidin-2-yl)-5,6,7,8-tetrahydrophthalazin-1(2H)-one,
6-(2,4-dimethylphenyl)-2-(4-methoxy-5-methylpyrimidin-2-yl)-5,6,7,8-tetrahydrophthalazin-1(2H)-one,
6-(2,4-dimethylphenyl)-2-(5-(morpholinomethyl)pyrimidin-2-yl)-5,6,7,8-tetrahydrophthalazin-1(2H)-one,
6-(2-methoxyphenyl)-2-(pyridin-2-yl)-5,6,7,8-tetrahydrophthalazin-1(2H)-one,
6-(3-(dimethylamino)phenyl)-2-(pyridin-2-yl)-5,6,7,8-tetrahydrophthalazin-1(2H)-one,
6-(3-methoxy-2-methylphenyl)-2-(pyridin-2-yl)-5,6,7,8-tetrahydrophthalazin-1(2H)-one,
6-(5-methoxy-2-methylphenyl)-2-(pyridin-2-yl)-5,6,7,8-tetrahydrophthalazin-1(2H)-one,
2-(pyridin-2-yl)-6-(o-tolyl)-5,6,7,8-tetrahydrophthalazin-1(2H)-one,
6-(3-cyclopropylphenyl)-2-(pyridin-2-yl)-5,6,7,8-tetrahydrophthalazin-1(2H)-one,
6-(3-methoxy-4-methylphenyl)-2-(pyridin-2-yl)-5,6,7,8-tetrahydrophthalazin-1(2H)-one,
6-(3-(1-hydroxyethyl)phenyl)-2-(pyridin-2-yl)-5,6,7,8-tetrahydrophthalazin-1(2H)-one,
6-(3-cyclopropoxyphenyl)-2-(pyridin-2-yl)-5,6,7,8-tetrahydrophthalazin-1(2H)-one,
6-(2-methoxy-4-methylphenyl)-2-(pyridin-2-yl)-5,6,7,8-tetrahydrophthalazin-1(2H)-one,
6-(2-methoxy-3-methylphenyl)-2-(pyridin-2-yl)-5,6,7,8-tetrahydrophthalazin-1(2H)-one,
6-(1-methylindolin-4-yl)-2-(pyridin-2-yl)-5,6,7,8-tetrahydrophthalazin-1(2H)-one,
6-(2-methoxy-4-methylphenyl)-2-(pyrimidin-2-yl)-5,6,7,8-tetrahydrophthalazin-1(2H)-one,
6-(2-methoxy-3-methylphenyl)-2-(pyrimidin-2-yl)-5,6,7,8-tetrahydrophthalazin-1(2H)-one,
6-(2-chloro-3-methoxyphenyl)-2-(pyrimidin-2-yl)-5,6,7,8-tetrahydrophthalazin-1(2H)-one,
6-(5-methoxy-2-(trifluoromethyl)phenyl)-2-(pyrimidin-2-yl)-5,6,7,8-tetrahydrophthalazin-1(2H)-one,
6-(2-fluoro-5-methoxyphenyl)-2-(pyrimidin-2-yl)-5,6,7,8-tetrahydrophthalazin-1(2H)-one, 6-(2-chloro-5-methoxyphenyl)-2-(pyrimidin-2-yl)-5,6,7,8-tetrahydrophthalazin-1(2H)-one,
6-(2-methoxy-5-methylphenyl)-2-(pyrimidin-2-yl)-5,6,7,8-tetrahydrophthalazin-1(2H)-one,
6-(2-methyl-5-(pyrrolidin-1-yl)phenyl)-2-(pyrimidin-2-yl)-5,6,7,8-tetrahydrophthalazin-1(2H)-one,
6-(1-methylindolin-4-yl)-2-(pyrimidin-2-yl)-5,6,7,8-tetrahydrophthalazin-1(2H)-one,
6-(2-fluoro-3-methoxyphenyl)-2-(pyrimidin-2-yl)-5,6,7,8-tetrahydrophthalazin-1(2H)-one,
6-(5-methoxy-2-methylphenyl)-2-(pyrimidin-2-yl)-5,6,7,8-tetrahydrophthalazin-1(2H)-one,
6-(2,5-dimethylphenyl)-2-(pyrimidin-2-yl)-5,6,7,8-tetrahydrophthalazin-1(2H)-one,
6-(2,3-dimethylphenyl)-2-(pyrimidin-2-yl)-5,6,7,8-tetrahydrophthalazin-1(2H)-one,
6-(3-(methoxymethyl)phenyl)-2-(pyrimidin-2-yl)-5,6,7,8-tetrahydrophthalazin-1(2H)-one,
6-(5-cyclopropoxy-2-methylphenyl)-2-(pyrimidin-2-yl)-5,6,7,8-tetrahydrophthalazin-1(2H)-one,
6-(3-cyclopropoxyphenyl)-2-(pyrimidin-2-yl)-5,6,7,8-tetrahydrophthalazin-1(2H)-one,
6-(3-(cyclopentyloxy)phenyl)-2-(pyrimidin-2-yl)-5,6,7,8-tetrahydrophthalazin-1(2H)-one,
6-(4-methoxy-2-methylphenyl)-2-(pyrimidin-2-yl)-5,6,7,8-tetrahydrophthalazin-1(2H)-one,
6-(1,5-dimethyl-1H-indazol-4-yl)-2-(pyrimidin-2-yl)-5,6,7,8-tetrahydrophthalazin-1(2H)-one,
6-mesityl-2-(pyrimidin-2-yl)-5,6,7,8-tetrahydrophthalazin-1(2H)-one,
6-(2,6-difluoro-3-methoxyphenyl)-2-(pyrimidin-2-yl)-5,6,7,8-tetrahydrophthalazin-1(2H)-one,
6-(2-chloro-3-cyclopropoxyphenyl)-2-(pyrimidin-2-yl)-5,6,7,8-tetrahydrophthalazin-1(2H)-one,
6-(1-cyclopropylindolin-4-yl)-2-(pyrimidin-2-yl)-5,6,7,8-tetrahydrophthalazin-1(2H)-one,
6-(3-cyclopropoxy-2-methylphenyl)-2-(5-methylpyrimidin-2-yl)-5,6,7,8-tetrahydrophthalazin-1(2H)-one,
6-(2-chloro-3-methoxyphenyl)-2-(5-methylpyrimidin-2-yl)-5,6,7,8-tetrahydrophthalazin-1(2H)-one
6-(2-methoxyphenyl)-2-(pyridin-2-yl)-5,6,7,8-tetrahydrophthalazin-1(2H)-one,
6-(3-(dimethylamino)-2-methylphenyl)-2-(pyrimidin-2-yl)-5,6,7,8-tetrahydrophthalazin-1(2H)-one,
6-(5-methoxy-2,4-dimethylphenyl)-2-(pyrimidin-2-yl)-5,6,7,8-tetrahydrophthalazin-1(2H)-one,
6-(4-chloro-2-methylphenyl)-2-(pyrimidin-2-yl)-5,6,7,8-tetrahydrophthalazin-1(2H)-one,
6-(4-acetyl-2-methylphenyl)-2-(pyrimidin-2-yl)-5,6,7,8-tetrahydrophthalazin-1(2H)-one,
6-(3-(3-methoxypropoxy)-2-methylphenyl)-2-(pyrimidin-2-yl)-5,6,7,8-tetrahydrophthalazin-1(2H)-one,
6-(3-ethoxy-2-methylphenyl)-2-(pyrimidin-2-yl)-5,6,7,8-tetrahydrophthalazin-1(2H)-one,
6-(3-(cyclopropylmethoxy)-2-methylphenyl)-2-(pyrimidin-2-yl)-5,6,7,8-tetrahydrophthalazin-1(2H)-one,
6-(3-isopropoxy-2-methylphenyl)-2-(pyrimidin-2-yl)-5,6,7,8-tetrahydrophthalazin-1(2H)-one,
6-(3-cyclopropoxy-2-methylphenyl)-2-(pyrimidin-2-yl)-5,6,7,8-tetrahydrophthalazin-1(2H)-one,
6-(3-(2-methoxyethoxy)-2-methylphenyl)-2-(pyrimidin-2-yl)-5,6,7,8-tetrahydrophthalazin-1(2H)-one,
6-(3-(benzyloxy)-2-methylphenyl)-2-(pyrimidin-2-yl)-5,6,7,8-tetrahydrophthalazin-1(2H)-one,
2-(5-cyclopropylpyrimidin-2-yl)-6-(5-methoxy-2-methylphenyl)-5,6,7,8-tetrahydrophthalazin-1(2H)-one,
2-(5-cyclopropylpyrimidin-2-yl)-6-(2,4-dimethylphenyl)-5,6,7,8-tetrahydrophthalazin-1(2H)-one,
2-(5-cyclopropylpyridin-2-yl)-6-(2,4-dimethylphenyl)-5,6,7,8-tetrahydrophthalazin-1(2H)-one,
2-(5-cyclopropylpyridin-2-yl)-6-(3-methoxy-2-methylphenyl)-5,6,7,8-tetrahydrophthalazin-1(2H)-one,
6-(3-methoxy-2-methylphenyl)-2-(5-(pyrrolidin-1-yl)pyrimidin-2-yl)-5,6,7,8-tetrahydrophthalazin-1(2H)-one,
6-(3-methoxy-2-methylphenyl)-2-(5-morpholinopyrimidin-2-yl)-5,6,7,8-tetrahydrophthalazin-1(2H)-one,
6-(2,4-dimethylphenyl)-2-(5-morpholinopyridin-2-yl)-5,6,7,8-tetrahydrophthalazin-1(2H)-one,
6-(2,4-dimethylphenyl)-2-(5-morpholinopyridin-2-yl)-5,6,7,8-tetrahydrophthalazin-1(2H)-one,
6-(2,4-dimethylphenyl)-2-(5-morpholinopyrimidin-2-yl)-5,6,7,8-tetrahydrophthalazin-1(2H)-one,
2-(5-(azetidin-1-yl)pyrimidin-2-yl)-6-(2,4-dimethylphenyl)-5,6,7,8-tetrahydrophthalazin-1(2H)-one,
N-(2-(6-(2,4-dimethylphenyl)-1-oxo-5,6,7,8-tetrahydrophthalazin-2(1H)-yl)pyrimidin-5-yl)acetamide,
6-(3-methoxy-2-methylphenyl)-2-(5-(2-methoxyethoxy)pyrimidin-2-yl)-5,6,7,8-tetrahydrophthalazin-1(2H)-one,
(2-(5-(2-hydroxyethoxy)-pyrimidin-2-yl)-6-(3-methoxy-2-methylphenyl)-5,6,7,8-tetrahydrophthalazin-1(2H)-one,
6-(3-acetyl-2-methylphenyl)-2-(pyrimidin-2-yl)-5,6,7,8-tetrahydrophthalazin-1(2H)-one,
6-(2,4-dimethylphenyl)-2-(pyridin-2-yl)-2,5,6,7-tetrahydro-1H-cyclopenta[d]-pyridazin-1-one,
7-(2,4-dimethylphenyl)-3-(pyridin-2-yl)-5,6,7,8-tetrahydroquinazolin-4(3H)-one,
6-(1-cyclopropyl-1H-indol-4-yl)-2-(pyrimidin-2-yl)-5,6,7,8-tetrahydrophthalazin-1(2H)-one,
2-(5-cyclopropylpyrimidin-2-yl)-6-(3-methoxy-2-methylphenyl)-5,6,7,8-tetrahydrophthalazin-1(2H)-one
2-(5-bromopyrimidin-2-yl)-6-(3-cyclopropoxy-2-methylphenyl)-5,6,7,8-tetrahydrophthalazin-1(2H)-one,
N-(2-(6-(3-cyclopropoxy-2-methylphenyl)-1-oxo-5,6,7,8-tetrahydrophthalazin-2(1H)-yl)pyrimidin-5-yl)acetamide,
(+6-(3-cyclopropoxy-2-methylphenyl)-2-(pyrimidin-2-yl)-5,6,7,8-tetrahydrophthalazin-1(2H)-one,
(+)-6-(3-cyclopropoxy-2-methylphenyl)-2-(pyrimidin-2-yl)-5,6,7,8-tetrahydrophthalazin-1(2H)-one,
(−)-6-(2-chloro-3-cyclopropoxyphenyl)-2-(pyrimidin-2-yl)-5,6,7,8-tetrahydrophthalazin-1(2H)-one,
(+)-6-(2-chloro-3-cyclopropoxyphenyl)-2-(pyrimidin-2-yl)-5,6,7,8-tetrahydrophthalazin-1(2H)-one,
(−)-6-(3-cyclopropoxy-2-methylphenyl)-2-(5-methylpyrimidin-2-yl)-5,6,7,8-tetrahydrophthalazin-1(2H)-one,
(+)-6-(3-cyclopropoxy-2-methylphenyl)-2-(5-methylpyrimidin-2-yl)-5,6,7,8-tetrahydrophthalazin-1(2H)-one,
(−)-6-(2-chloro-3-methoxyphenyl)-2-(5-methylpyrimidin-2-yl)-5,6,7,8-tetrahydrophthalazin-1(2H)-one,
(+)-6-(2-chloro-3-methoxyphenyl)-2-(5-methylpyrimidin-2-yl)-5,6,7,8-tetrahydrophthalazin-1(2H)-one,
(−)—N-(2-(6-(2,4-dimethylphenyl)-1-oxo-5,6,7,8-tetrahydrophthalazin-2(1H)-yl)pyrimidin-5-yl)acetamide,
(+)—N-(2-(6-(2,4-dimethylphenyl)-1-oxo-5,6,7,8-tetrahydrophthalazin-2(1H)-yl)pyrimidin-5-yl)acetamide,
(+)-6-(1-cyclopropyl-1H-indol-4-yl)-2-(pyrimidin-2-yl)-5,6,7,8-tetrahydrophthalazin-1(2H)-one,
(−)-6-(1-cyclopropyl-1H-indol-4-yl)-2-(pyrimidin-2-yl)-5,6,7,8-tetrahydrophthalazin-1(2H)-one.
2-(5-bromopyrimidin-2-yl)-6-(5-methoxy-2-methylphenyl)-5,6,7,8-tetrahydrophthalazin-1(2H)-one,
2-(5-bromopyridin-2-yl)-6-(2,4-dimethylphenyl)-5,6,7,8-tetrahydrophthalazin-1(2H)-one, 2-(5-bromopyrimidin-2-yl)-6-(2,4-dimethylphenyl)-5,6,7,8-tetrahydrophthalazin-1(2H)-one,
2-(5-bromopyridin-2-yl)-6-(3-methoxy-2-methylphenyl)-5,6,7,8-tetrahydrophthalazin-1(2H)-one,
2-(5-bromopyrimidin-2-yl)-6-(3-methoxy-2-methylphenyl)-5,6,7,8-tetrahydrophthalazin-1(2H)-one, and
2-(5-bromo-4-methoxypyrimidin-2-yl)-6-(2,4-dimethylphenyl)-5,6,7,8-tetrahydrophthalazin-1(2H)-one.

The present invention also relates to the following compounds of formula (IV), (V), (VI), (VII), (VIII) and (IX) as intermediates for compounds of formula (I), (II) and (III)

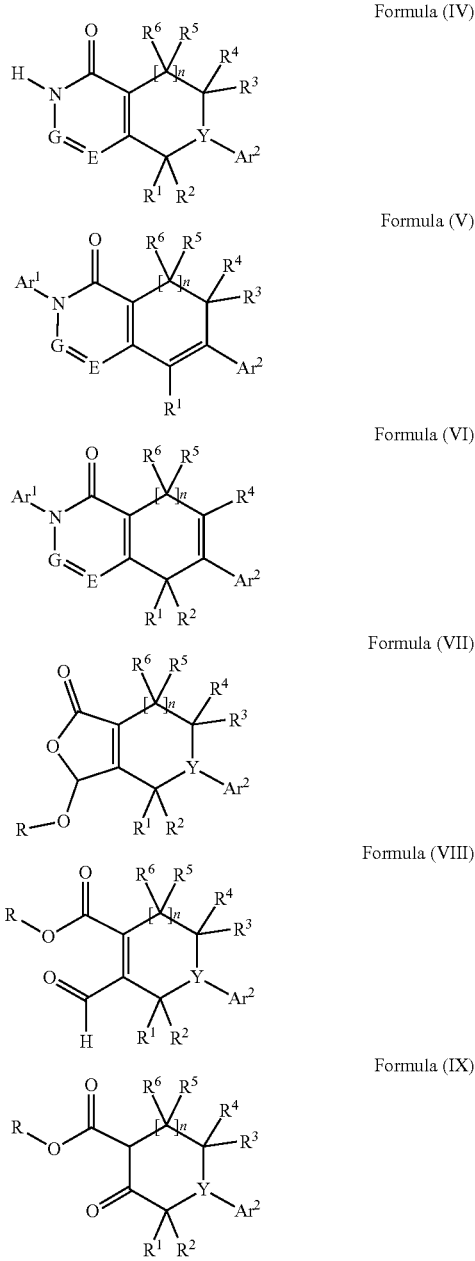

wherein G, E, Ar$^1$, Ar$^2$, R$^1$, R$^2$, R$^3$, R$^4$, R$^5$, R$^6$ and Y are as defined above for compounds of Formula (I), (II) and (III).

The disclosed compounds also include all pharmaceutically acceptable isotopic variations, in which at least one atom is replaced by an atom having the same atomic number, but an atomic mass different from the atomic mass usually found in nature. Examples of isotopes suitable for inclusion in the disclosed compounds include, without limitation, isotopes of hydrogen, such as $^2$H and $^3$H; isotopes of carbon, such as $^{11}$C, $^{13}$C and $^{14}$C; isotopes of nitrogen, such as $^{15}$N; isotopes of oxygen, such as $^{17}$O and $^{18}$O; isotopes of phosphorus, such as $^{32}$P and $^{33}$P; isotopes of sulfur, such as $^{35}$S; isotopes of fluorine, such as $^{18}$F; and isotopes of chlorine, such as $^{36}$Cl.

Use of isotopic variations (e.g., deuterium, $^2$H) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^3$H, or $^{14}$C), which may be useful in drug and/or substrate tissue distribution studies. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labelled compounds of Formula (I) to (III) can generally be used as radiolabelled tracers for imaging studies, prepared by conventional techniques known to those skilled in the art or by processes analogous to those described in the accompanying Examples using appropriate isotopically-labeled reagents in place of the non-labeled reagent previously employed.

In case of tautomeric forms, the name of the depicted tautomeric form of the structure was generated. However, it should be clear that the other non-depicted tautomeric form is also included within the scope of the present invention.

Definition of Terms

Listed below are definitions of various terms used in the specification and claims to describe the present invention.

In the context of the present invention, it has to be understood that definitions given for each substituent of the compounds of Formula (I) apply to the corresponding substituents in compounds of Formula (II) to (III).

In addition, it has to be understood that each definition of a substituent can be combined directly and without ambiguity with the definition of another substituent.

For the avoidance of doubt it is to be understood that in this specification "(C$_1$-C$_6$)" means a carbon radical having 1, 2, 3, 4, 5 or 6 carbon atoms. "(C$_0$-C$_6$)" means a carbon radical having 0, 1, 2, 3, 4, 5 or 6 carbon atoms.

In this specification "C" means a carbon atom, "N" means a nitrogen atom, "O" means an oxygen atom and "S" means a sulphur atom.

In the case where a subscript is the integer 0 (zero) the radical to which the subscript refers, indicates that the radical is absent, i.e. there is a direct bond between the radicals.

In the case where a subscript is the integer 0 (zero) and the radical to which the subscript refers is alkyl, this indicates the radical is a hydrogen atom.

In this specification, unless stated otherwise, the term "bond" refers to a saturated covalent bond. When two or more bonds are adjacent to one another, they are assumed to be equal to one bond. For example, in a radical —V—W—, wherein both V and W may be a bond, the radical is depicting a single bond.

In this specification, unless stated otherwise, the term "alkyl" includes both straight and branched chain alkyl radicals and may be methyl, ethyl, n-propyl, i-propyl, n-butyl, i-butyl, s-butyl, t-butyl, n-pentyl, i-pentyl, t-pentyl, neo-pentyl, n-hexyl, i-hexyl or t-hexyl. The term "($C_0$-$C_3$) alkyl" refers to an alkyl radical having 0, 1, 2 or 3 carbon atoms and may be methyl, ethyl, n-propyl and i-propyl.

In this specification, unless stated otherwise, the term "alkylene" includes both straight and branched difunctional saturated hydrocarbon radicals and may be methylene, ethylene, n-propylene, i-propylene, n-butylene, i-butylene, s-butylene, t-butylene, n-pentylene, i-pentylene, t-pentylene, neo-pentylene, n-hexylene, i-hexylene or t-hexylene.

In this specification, unless stated otherwise, the term "cycloalkyl" refers to an optionally substituted carbocycle containing no heteroatoms, including mono-, bi-, and tricyclic unsaturated carbocycles. Cycloalkyl includes fused ring systems and spirofused ring systems. Examples of cycloalkyl include cyclopropyl, cyclobutyl, cyclopentyl, cyclohexyl, decahydronaphthalene, adamantane, indanyl, fluorenyl and 1,2,3,4-tetrahydronaphthalene and the like. The term "($C_3$-$C_7$)cycloalkyl" may be cyclopropyl, cyclobutyl, cyclopentyl, cyclohexyl, cycloheptyl and the like.

In this specification, unless stated otherwise, the term "cycloalkenyl" refers to an optionally substituted carbocycle containing no heteroatoms, including mono-, bi-, and tricyclic unsaturated carbocycles. The term "($C_2$-$C_6$)cycloalkenyl" refers to a cycloalkyl radical having 2 to 6 carbon atoms and one or two double bonds, and may be, but is not limited to, cyclopentenyl and cyclohexenyl.

In this specification, unless stated otherwise, the term "alkenyl" includes both straight and branched chain alkenyl radicals. The term "($C_2$-$C_6$)alkenyl" refers to an alkenyl radical having 2 to 6 carbon atoms and one or two double bonds, and may be, but is not limited to vinyl, allyl, propenyl, i-propenyl, butenyl, i-butenyl, crotyl, pentenyl, i-pentenyl and hexenyl.

In this specification, unless stated otherwise, the term "alkenylene" includes both straight and branched chain disubstituted alkenyl radicals. The term "($C_2$-$C_6$)alkenylene" refers to an alkenylene radical having 2 to 6 carbon atoms and one or two double bonds, and may be, but is not limited to vinylene, allylene, propenylene, i-propenylene, butenylene, i-butenylene, crotylene, pentenylene, i-pentenylene and hexenylene.

In this specification, unless stated otherwise, the term "alkynyl" includes both straight and branched chain alkynyl radicals. The term ($C_2$-$C_6$)alkynyl having 2 to 6 carbon atoms and one or two triple bonds, and may be, but is not limited to ethynyl, propargyl, butynyl, pentynyl, and hexynyl.

In this specification, unless stated otherwise, the term "alkynylene" includes both straight and branched chain disubstituted alkynylene radicals. The term ($C_2$-$C_6$)alkynylene having 2 to 6 carbon atoms and one or two triple bonds, and may be, but is not limited to ethynylene, propargylene, butynylene, pentynylene, i-pentynylene and hexynylene.

The term "aryl" refers to an optionally substituted monocyclic or bicyclic hydrocarbon ring system containing at least one unsaturated 6 to 10-membered aromatic ring. Examples and suitable values of the term "aryl" are, but not limited to phenyl, naphthyl, 1,2,3,4-tetrahydronaphthyl, indyl, indenyl and the like.

In this specification, unless stated otherwise, the term "heteroaryl" refers to an optionally substituted 5 to 10-membered monocyclic or bicyclic unsaturated, aromatic ring system containing at least one heteroatom selected independently from N, O or S. Preferably the heteroaryl comprises from 1 to 3 heteroatom, preferably chosen among N, O or S. Examples of "heteroaryl" may be, but are not limited to thienyl, pyridinyl, thiazolyl, isothiazolyl, furyl, pyrrolyl, triazolyl, imidazolyl, triazinyl, oxadiazolyl, oxazolyl, isoxazolyl, pyrazolyl, imidazolonyl, oxazolonyl, thiazolonyl, tetrazolyl, thiadiazolyl, benzoimidazolyl, benzoxazolyl, benzothiazolyl, tetrahydrotriazolopyridinyl, tetrahydrotriazolopyrimidinyl, benzofuryl, benzothiophenyl, thionaphthyl, indolyl, isoindolyl, pyridonyl, pyridazinyl, pyrazinyl, pyrimidinyl, quinolyl, phtalazinyl, naphthyridinyl, quinoxalinyl, quinazolyl, imidazopyridinyl, oxazolopyridinyl, thiazolopyridinyl, imidazopyridazinyl, oxazolopyridazinyl, thiazolopyridazinyl, cynnolyl, pteridinyl, furazanyl, benzotriazolyl, pyrazolopyridinyl and purinyl.

In this specification, unless stated otherwise, the term "alkylene-aryl", "alkylene-heteroaryl" and "alkylene-cycloalkyl" refers respectively to a substituent that is attached via the alkyl radical to an aryl, heteroaryl or cycloalkyl radical, respectively. The term "($C_1$-$C_6$)alkylene-aryl" includes aryl-($C_1$-$C_6$)-alkyl radicals such as benzyl, 1-phenylethyl, 2-phenylethyl, 1-phenylpropyl, 2-phenylpropyl, 3-phenylpropyl, 1-naphthylmethyl and 2-naphthylmethyl. The term "($C_1$-$C_6$)alkylene-heteroaryl" includes heteroaryl-($C_1$-$C_6$)-alkyl radicals, wherein examples of heteroaryl are the same as those illustrated in the above definition, such as 2-furylmethyl, 3-furylmethyl, 2-thienylmethyl, 3-thienylmethyl, 1-imidazolylmethyl, 2-imidazolylmethyl, 3-imidazolylmethyl, 2-oxazolylmethyl, 3-oxazolylmethyl, 2-thiazolylmethyl, 3-thiazolylmethyl, 2-pyridinylmethyl, 3-pyridinylmethyl, 4-pyridinylmethyl, 1-quinolylmethyl and the like. The term "—($C_1$-$C_6$)alkylene-($C_3$-$C_7$)cycloalkyl" includes —($C_3$-$C_7$)-cycloalkyl-($C_1$-$C_6$)-alkyl radicals, wherein examples of cycloalkyl are the same as those illustrated in the above definition, such as cyclopropylmethyl, cyclobutylmethyl, cyclopentylmethyl, cyclopropyethyl and the like.

In this specification, unless stated otherwise, the term "carbocyle" refers to an optionally substituted, 5 to 10-membered monocyclic, bicyclic or tricyclic saturated or partially saturated ring system as well as fused ring systems, containing no heteroatom. Such fused ring systems can include one ring that is partially or fully unsaturated such as a benzene ring to form fused ring systems such as benzo-fused carbocycles.

In this specification, unless stated otherwise, the term "heterocycle" refers to an optionally substituted, 5 to 10-membered monocyclic or bicyclic saturated or partially saturated ring system containing at least one heteroatom selected independently from N, O and S. Preferably the heterocycle comprises from 1 to 3 heteroatom, preferably chosen among N, O or S.

In this specification, unless stated otherwise, a 5- or 6-membered ring containing one or more atoms independently selected from C, N, O and S, includes aromatic and heteroaromatic rings as well as carbocyclic and heterocyclic rings which may be saturated or unsaturated. Examples of such rings may be, but are not limited to, furyl, isoxazolyl, isothiazolyl, oxazolyl, pyrazinyl, pyrazolyl, pyridazinyl, pyridinyl, pyrimidinyl, pyrrolyl, thiazolyl, thienyl, imidazolyl, imidazolidinyl, imidazolinyl, triazolyl, morpholinyl, piperazinyl, piperidyl, piperidonyl, pyrazolidinyl, pyrazolinyl, pyrrolidinyl, pyrrolinyl, tetrahydropyranyl, tetrahydrothiopyranyl, oxazolidinonyl, thiomorpholinyl, oxadiazolyl, thiadiazolyl, tetrazolyl, phenyl, cyclohexyl, cyclopentyl, cyclohexenyl and cyclopentenyl.

In this specification, unless stated otherwise, a 3- to 10-membered ring containing one or more atoms independently selected from C, N, O and S, includes aromatic and heteroaromatic rings as well as carbocyclic and heterocyclic rings which may be saturated or unsaturated. Examples of such rings may be, but are not limited to imidazolidinyl, imidazolinyl, morpholinyl, piperazinyl, piperidyl, piperidonyl, pyrazolidinyl, pyrazolinyl, pyrrolidinyl, pyrrolinyl, tetrahydropyranyl, thiomorpholinyl, tetrahydrothiopyranyl, furyl, pyrrolyl, dihydropyrrolyl isoxazolyl, isothiazolyl, isoindolinonyl, dihydropyrrolo[1,2-b]pyrazolyl, oxazolyl, oxazolidinonyl, pyrazinyl, pyrazolyl, pyridazinyl, pyridinyl, tetrahydropyridinyl, pyrimidinyl, pyrrolyl, thiazolyl, thienyl, imidazolyl, triazolyl, phenyl, cyclopropyl, aziridinyl, cyclobutyl, azetidinyl, oxadiazolyl, thiadiazolyl, tetrazolyl, cyclopentyl, cyclopentenyl, cyclohexyl, cyclohexenyl, cycloheptyl, cycloheptenyl, cyclooctyl and cyclooctenyl.

In this specification, unless stated otherwise, the term "halo" or "halogen" may be fluoro, chloro, bromo or iodo.

In this specification, unless stated otherwise, the term "haloalkyl" means an alkyl radical as defined above, substituted with one or more halo radicals. The term "($C_1$-$C_6$) haloalkyl" may include, but is not limited to, fluoromethyl, difluoromethyl, trifluoromethyl, fluoroethyl, difluoroethyl and the like.

In this specification, unless stated otherwise, the term "cyanoalkyl" means an alkyl radical as defined above, substituted with one or more cyano (CN) radicals.

In this specification, unless stated otherwise, the term "optionally substituted" refers to radicals further bearing one or more substituents which may be ($C_1$-$C_6$)alkyl, hydroxy (—OH), ($C_1$-$C_6$)alkylene-OR wherein R is a H or ($C_1$-$C_6$) alkyl, mercapto (—SH), aryl, heteroaryl, heterocycle, ($C_1$-$C_6$)alkylene-aryl, ($C_1$-$C_6$)alkylene-heterocycle, ($C_1$-$C_6$)alkylene-($C_3$-$C_7$)cycloalkyl, ($C_1$-$C_6$)alkylene-heteroaryl, halogen, trifluoroalkyl (preferably trifluoromethyl), trifluoroalkoxy (preferably trifluoromethoxy), cyano (CN), cyanoakyl (preferably cyanomethyl), nitro ($NO_2$), amino ($NH_2$), carboxyl ($CO_2H$), carboxamide ($CONH_2$), carbamate (NH—C(═O)OR wherein R is a ($C_1$-$C_6$)alkyl, sulfonamide (S(═O)$_2$—$NH_2$), ester of formula C(O)OR wherein R is a ($C_1$-$C_6$)alkyl, and sulfonyl (S(═O)—R) wherein R is a ($C_1$-$C_6$)alkyl.

As used herein, the expression "pharmaceutically acceptable" refers to those compounds, materials, excipients, compositions or dosage forms which are, within the scope of sound medical judgment, suitable for contact with the tissues of human beings and animals without excessive toxicity, irritation, allergic response or other problem complications commensurate with a reasonable benefit/risk ratio.

As used herein, "pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like, including mono, di or tri-salts thereof; and the salts prepared from organic acids such as acetic, propionic, succinic, tartaric, citric, methanesulfonic, benzenesulfonic, glucoronic, glutamic, benzoic, salicylic, toluenesulfonic, oxalic, fumaric, maleic, lactic and the like. Further addition salts include ammonium salts such as tromethamine, meglumine, epolamine, etc., metal salts such as sodium, potassium, calcium, zinc or magnesium.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences,* 20$^{th}$ ed., Mack Publishing Company, Easton, PA, 2000, the disclosure of which is hereby incorporated by reference.

As used herein, "pharmaceutically acceptable solvate" refer to derivatives of the disclosed compounds wherein the parent compound is modified by making a solvate thereof. In this specification, unless stated otherwise, the term "solvate" refers to a complex of variable stoichiometry formed by a solute (e.g. a compound of Formula (I)) and a solvent. The invention embraces solid forms of the compounds of Formula (I) in any solvated form, including e.g. solvates with water, for example hydrates, or with organic solvents such as, e.g., methanol, ethanol or acetonitrile, referred as a methanolate, ethanolate or acetonitrilate, respectively; or in the form of any polymorph. Such solvent may not interfere with the biological activity of the solute.

Pharmaceutically acceptable prodrugs of compounds that can be used in the present invention, in particular the compounds of Formula (I), are derivatives which have chemically or metabolically cleavable groups and become, by solvolysis or under physiological conditions, the compounds used in the present invention which are pharmaceutically active in vivo. Prodrugs of compounds that can be used in the present invention may be formed in a conventional manner with a functional group of the compounds such as with an amino, hydroxy or carboxy group. The prodrug derivative form often offers advantages of solubility, tissue compatibility or delayed release in a mammal, including human (see, Bundgaard, H., Design of Prodrugs, pp. 7-9, 21-24, Elsevier, Amsterdam 1985). Prodrugs include acid derivatives well known to the person skilled in the art, such as esters prepared by reaction of the parent acidic compound with a suitable alcohol, or amides prepared by reaction of the parent acid compound with a suitable amine. When a compound employed in the present invention, in particular a compound of Formula (I), has a carboxyl group, an ester derivative prepared by reacting the carboxyl group with a suitable alcohol or an amide derivative prepared by reacting the carboxyl group with a suitable amine is exemplified as a prodrug. An especially preferred ester derivative as a prodrug is methylester, ethylester, n-propylester, i-propylester, n-butylester, or i-butylester. When a compound employed in the present invention has a hydroxy group, an acyloxy derivative prepared by reacting the hydroxy group with a suitable acylhalide or a suitable acid anhydride is exemplified as a prodrug. When a compound employed in the present invention has an amino group, an amide derivative prepared by reacting the amino group with a suitable acid halide or a suitable mixed anhydride is exemplified as a prodrug.

The compounds of Formula (I) or pharmaceutically acceptable salts, solvates or prodrugs thereof, may be administered as compounds per se or may be formulated as medicaments. Within the scope of the present invention are pharmaceutical compositions comprising as an active ingredient one or more compounds of Formula (I), or pharmaceutically acceptable salts, solvates or prodrugs thereof. The pharmaceutical compositions may optionally comprise one or more pharmaceutically acceptable excipients, such as carriers, diluents, fillers, disintegrants, lubricating agents, binders, colorants, pigments, stabilizers, preservatives, or antioxidants.

The pharmaceutical compositions may also comprise one or more solubility enhancers, such as, e.g., poly(ethylene glycol), including poly(ethylene glycol) having a molecular weight in the range of about 200 to about 5,000 Da, ethylene glycol, propylene glycol, non-ionic surfactants, tyloxapol, polysorbate 80, macrogol-15-hydroxystearate, phospholipids, lecithin, dimyristoyl phosphatidylcholine, dipalmitoyl phosphatidylcholine, distearoyl phosphatidylcholine, cyclodextrins, hydroxyethyl-3-cyclodextrin, hydroxypropyl-3-cyclodextrin, hydroxyethyl-γ-cyclodextrin, hydroxypropyl-Y-cyclodextrin, dihydroxypropyl-3-cyclodextrin, glucosyl-a-cyclodextrin, glucosyl-3-cyclodextrin, diglucosyl-3-cyclodextrin, maltosyl-a-cyclodextrin, maltosyl-3-cyclodextrin, maltosyl-Y-cyclodextrin, maltotriosyl-3-cyclodextrin, maltotriosyl-γ-cyclodextrin, dimaltosyl-3-cyclodextrin, methyl-3-cyclodextrin, carboxyalkyl thioethers, hydroxypropyl methylcellulose, hydroxypropylcellulose, polyvinylpyrrolidone, vinyl acetate copolymers, vinyl pyrrolidone, sodium lauryl sulfate, dioctyl sodium sulfosuccinate, or any combination thereof.

In this specification, unless stated otherwise, certain compounds may exist in one or more particular geometric, optical, enantiomeric, diastereoisomeric, epimeric, stereoisomeric, tautomeric, conformational, or anomeric forms, including, but not limited to, cis- and trans-forms; E- and Z-forms; endo- and exo-forms, R—, S—, and meso-forms; D- and L-forms; d- and l-forms; (+) and (−) forms; keto-, enol-, and enolate-forms; α- and β-forms; axial and equatorial forms; and combinations thereof, collectively referred to as "isomers" or "isomeric forms". Note that specifically included in the term "isomer" are compounds with one or more isotopic substitutions. For example, H may be in any isotopic form, including, but not limited to, $^1H$, $^2H$ (D), and $^3H$ (T); C may be in any isotopic form, including, but not limited to, $^{11}C$, $^{12}C$, $^{13}C$, $^{14}C$; O may be in any isotopic form, including, but not limited to, $^{16}O$ and $^{18}O$; and the like. F may be in any isotopic form, including, but not limited to, $^{19}F$ and $^{18}F$; and the like.

The present invention also related to composition, preferably pharmaceutical composition, comprising at least one compound according to the invention. Preferably, the compound according to the invention is contained in the composition in a therapeutically effective amount. "Therapeutically effective amount" means an amount of a compound/medicament according to the present invention effective in preventing or treating a pathological condition.

A therapeutically effective amount can be readily determined by the attending diagnostician, as one skilled in the art, using conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The composition may further comprise a pharmaceutically acceptable excipient. The carrier or diluent must be "acceptable" in the sense of being compatible with the other ingredients of the composition and not deleterious to the recipients thereof.

"Pharmaceutically" or "pharmaceutically acceptable" refer to molecular entities and compositions that do not produce an adverse, allergic or other untoward reaction when administered to an animal, or a human, as appropriate.

As used herein, "pharmaceutically acceptable excipient" includes any carriers, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well-known in the art. Except insofar as any conventional media or agent is incompatible with the active ingredient, its use in the therapeutic compositions is contemplated. Supplementary active ingredients can also be incorporated into the compositions as suitable therapeutic combinations.

The composition may be in various pharmaceutical forms for administration purposes. As appropriate compositions there may be cited all compositions usually employed for systemically or locally administering drugs.

The pharmaceutical compositions of this invention may be prepared by any methods well known in the art of pharmacy, for example, using methods such as those described in Gennaro et al. Remington's Pharmaceutical Sciences (18th ed., Mack Publishing Company, 1990, see especially Part 8: Pharmaceutical preparations and their Manufacture). To prepare the pharmaceutical compositions of this invention, a therapeutically effective amount of the particular compound, optionally in salt form, as the active ingredient is combined in intimate admixture with a pharmaceutically acceptable carrier or diluent, which carrier or diluent may take a wide variety of forms depending on the form of preparation desired for administration. These pharmaceutical compositions are desirable in unitary dosage form suitable, in particular, for oral, topical, rectal or percutaneous administration, by parenteral injection, by middle or inner ear administration, or by inhalation.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, teaspoonfuls, tablespoonfuls, and segregated multiples thereof.

Since the compounds according to the invention are orally administrable compounds, pharmaceutical compositions comprising said compounds for oral administration are especially advantageous.

In order to enhance the solubility and/or the stability of the compounds according to the invention in pharmaceutical compositions, it can be advantageous to employ α-, β- or γ-cyclodextrins or their derivatives, in particular hydroxyalkyl substituted cyclodextrins, e.g. 2-hydroxypropyl-cyclodextrin or sulfobutyl-cyclodextrin. Also, co-solvents such as alcohols may improve the solubility and/or the stability of the compounds according to the invention in pharmaceutical compositions.

The present invention also relates to a process for preparing the pharmaceutical composition according to the invention, characterized in that a pharmaceutically acceptable carrier is intimately mixed with a therapeutically effective amount of a compound according to the invention.

The present invention relates to the compounds described above for its use as a medicament.

The present invention also relates to the use of the compounds according to the invention or a composition according to the invention for the preparation of a medicinal product or a medicament.

The inventors have surprisingly found that the compounds described above are modulators of mGlu receptors, preferably modulators of mGluR7, preferably antagonists of mGluR7.

Accordingly, the present invention relates to the compounds according to the invention, or the composition according to the invention, for its use to modulate, preferably to reduce or inhibit or negatively modulate, the activity of mGlu receptors, in particular mGluR7.

The invention also relates to the use of the compounds according to the invention or of the composition according to the invention, for the preparation of a medicine to modulate, preferably to reduce or inhibit or negatively modulate, the activity of mGlu receptors, in particular mGluR7.

The present invention also relates to a method to modulate, preferably to reduce or inhibit or negatively modulate, the activity of mGlu receptors, in particular mGluR7, comprising the administration, to a patient in need thereof, of a therapeutically effective amount of the compounds according to the invention or of the composition according to the invention.

According to the invention, the terms "patient" or "patient in need thereof", are intended for an animal or a human being affected or likely to be affected with a pathological condition involving an active cysteine protease in its pathogenesis. Preferably, the patient is human.

The identification of those subjects who are in need of treatment of herein-described diseases and conditions is well within the ability and knowledge of one skilled in the art. A veterinarian or a physician skilled in the art can readily identify, by the use of clinical tests, physical examination, medical/family history or biological and diagnostic tests, those subjects who are in need of such treatment.

The present invention also relates to the compounds according to the invention, or the composition according to the invention, for its use for treating diseases associated with glutamate dysfunction.

The present invention also relates to the use of the compounds according to the invention, or the composition according to the invention, for the preparation of a medicine for the treatment of diseases associated with glutamate dysfunction.

In particular, the present invention thus also relates to a compound according to the invention or a composition according to the invention for its use for the prevention or treatment of disorders associated with glutamate dysfunction in a mammal, including a human.

The present invention also relates to a method for the treatment of diseases associated with glutamate dysfunction comprising the administration, to a patient in need thereof, of a therapeutically effective amount of the compounds according to the invention or of the composition according to the invention.

As used herein, the term "treatment" is intended to refer to all processes, wherein there may be a slowing, interrupting, arresting or stopping of the progression of a disease or an alleviation of symptoms, but does not necessarily indicate a total elimination of all symptoms.

The present invention also relates to the compounds of the invention, or the composition of the invention, for the use for the prevention or treatment of anxiety disorders such as agoraphobia, generalized anxiety disorder (GAD), obsessive-compulsive disorder (OCD), panic disorder, post-traumatic stress disorder (PTSD), social phobia, other phobias; mood disorders including bipolar disorders (I & II), cyclothymic disorder, depression, dysthymic disorder, major depressive disorder, substance-induced mood disorder, mood disorder due to a general medical condition, mania, manic depression, seasonal affective disorders; muscular spasms and disorders associated with muscular spasticity including tremors, epilepsy, convulsions, migraine; disorders selected from the group consisting of neurodegenratives disorders such as mild-cognitive impairment, Alzheimer's disease, Parkinson's disease, multiple sclerosis and amyotrophic lateral sclerosis; disorders selected from the group consisting of psychotic disorders such as schizophrenia, delusional disorder, schizoaffective disorder, schizophreniform disorder, substance-induced psychotic disorder; personality disorders including obsessive-compulsive personality disorder, schizoid, schizotypal disorder, borderline personality disorder, anxious-avoidant personality disorder; childhood disorders including attention-deficit/hyperactivity disorder, mental retardation, Down's syndrome, tics disorders, autistic spectrum disorders (such as Rett syndrome or Fragile X syndrome) and autism; otic disorders including inner ear diseases, disorders, impairments or conditions, such as sensorineural hearing loss, age-related hearing impairment (presbycusis), Meniere's disease, sudden hearing loss, noise-induced hearing loss, drug-induced hearing loss, hidden hearing loss, cisplatin-induced hearing loss, aminoglycosides-induced hearing loss, otitis media, ototoxicity, autoimmune inner ear disease, acute tinnitus, chronic tinnitus, central auditory processing disorders and vestibular disorders; disorders of the gastrointestinal tract including diarrhoea, constipation, gastro-esophageal reflux disease (GERD), lower esophageal sphincter diseases or disorders, diseases of gastrointestinal motility, colitis, Crohn's disease or irritable bowel syndrome (IBS); pain disorders including acute pain, chronic pain, severe pain, intractable pain, inflammatory pain, post-operative pain, headache pain, cancer pain, neuropathic pain, post-traumatic pain, and visceral pain; cognitive deficit and mood disorders associated with the aforementioned disorders; ocular disorders including ocular hypertension, glaucoma, normal tension glaucoma, neurodegenerative disease conditions of the retina and the optic nerve, retinal dystrophies, age-related Macular degeneration, and conditions of the eye such as conjunctivitis, keratoconjunctivitis sicca, and vernal conjunctivitis, inflammation and/or neurodegeneration; disorders resulting from traumatic brain injury, stroke, hemorrhagic stroke, ischemia, spinal cord injury, cerebral hypoxia, cerebral hemorrhage or intracranial hematoma.

In particular the present invention relates to the compounds of the invention, or the composition of the invention, for the use for the prevention or treatment of certain neurological and psychiatric disorders such as anxiety disorders, including but not limited to phobias, generalized anxiety disorders (GAD), panic disorder, obsessive compulsive disorders (OCD), acute and chronic stress-related disorders (such as post-traumatic stress disorders (PTSD); mood disorders, including but not limited to major depressive disorder, depression and treatment resistant depression, mania, bipolar disorders; amnestic and other cognitive disorders; disorders usually first diagnosed in infancy, childhood or adolescence, including but not limited to attention-deficit disorder such as Attention-Deficit/Hyperactivity Disorder, mental retardation, learning disorders, autistic spectrum disorder (such as Rett syndrome or Fragile X syndrome); substance-related disorders, including but not limited to alcohol dependence, alcohol abuse, drug dependence and drug abuse; schizophrenia and other psychotic disorders; somatoform disorders; sleep disorders; muscular spasms and disorders associated with muscular spasticity including tremors, epilepsy, convulsions, migraine; and traumatic brain injury.

In particular the present invention relates to the compounds of the invention, or the composition of the invention, for the use for the prevention or treatment of certain neurodegenerative conditions or diseases such as mild-cognitive impairment, dementia, Alzheimer's disease and Parkinson's disease.

In particular the present invention relates to the compounds of the invention, or the composition of the invention, for the use for the prevention or treatment of certain pain conditions or diseases such as acute pain, chronic pain, neuropathic pain, post-traumatic pain, and visceral pain.

In particular the present invention relates to the compounds of the invention, or the composition of the invention, for the use for the prevention or treatment of otic disorders, including age-related hearing loss (or presbycusis), noise-induced hearing loss, cisplatin-induced hearing loss, aminoglycosides-induced hearing loss, acute and chronic tinnitus, central auditory processing disorders and vestibular disorders.

The present invention also relates to a compound according to the invention or a composition according to the invention, for its use for the prevention or treatment of anxiety disorders, post-traumatic stress disorders, obsessive compulsive disorders, panic disorders, depression, bipolar disorders, schizophrenia, autistic spectrum disorder, otic disorders and pain.

All the diseases mentioned above are considered to be diseases associated with glutamate dysfunction according to the invention.

As already mentioned hereinabove, the term "treatment" does not necessarily indicate a total elimination or prevention of all symptoms but may also refer to symptomatic treatment or prophylactic intervention in any of the disorders mentioned above. In particular, symptoms that may be treated or prevented include but are not limited to, cognitive deficit, fear behavior, hypervigilance, aggressive behaviour, hearing deficit, pain, in particular in anxiety disorders, acute stress disorder, chronic stress disorder, post-traumatic stress disorder, schizophrenia, otic disorders and pain disorder.

The person skilled in the art will recognize that alternative nomenclatures, nosologies, and classification systems for disorders described herein exist, and that these evolve with medical and scientific progresses.

The invention also relates to the use of a compound according to the invention as a radiolabeled tracer for imaging metabotropic glutamate receptors, preferably mGluR7 in mammal, including human.

The invention also relates to a compound according to the general Formula (I), (II), (Ill), or a stereoisomeric form thereof, or an N-oxide thereof, or a pharmaceutically acceptable salt or a solvate thereof, in particular, a compound of Formula (I), (II), (Ill), or a stereoisomeric form thereof, or a pharmaceutically acceptable salt or a solvate thereof, or a pharmaceutical composition according to the invention, for use for the treatment or prevention of, in particular treatment of, a condition in a mammal, including a human, the treatment or prevention of which is affected or facilitated by the neuromodulatory effect of the compounds according to the invention on mGluR, especially mGluR7.

The present invention also relates to a compound according to the Formula (I) for use in the treatment, prevention, amelioration, control or reduction of the risk of various neurological and psychiatric disorders associated with glutamate dysfunction in a human, the treatment or prevention of which is affected or facilitated by the neuromodulatory effect of the compounds according to the invention on mGlu receptors, especially mGluR7.

The invention also relates to a method for the treatment or prevention of, in particular treatment of, a condition in a mammal, including a human, the treatment or prevention of which is affected or facilitated by the neuromodulatory effect of the compounds according to the invention on mGluR, especially mGluR7, comprising administering to a person in need thereof of a therapeutically effective amount of compound according to the general Formula (I), (II), (Ill), or a stereoisomeric form thereof, or an N-oxide thereof, or a pharmaceutically acceptable salt or a solvate thereof, in particular, a compound of Formula (I), (II), (Ill), or a stereoisomeric form thereof, or a pharmaceutically acceptable salt or a solvate thereof, or a pharmaceutical composition according to the invention.

The present invention also relates to a method for the treatment, prevention, amelioration, control or reduction of the risk of various neurological and psychiatric disorders associated with glutamate dysfunction in a human, the treatment or prevention of which is affected or facilitated by the neuromodulatory effect of the compounds according to the invention on mGlu receptors, especially mGluR7 compound according to the Formula (I).

The present invention also relates to a compound according to the Formula (I), (II), (Ill), or a stereoisomeric form thereof, or an N-oxide thereof, or a pharmaceutically acceptable salt or a solvate thereof, in particular, a compound of Formula (I), (II), (Ill), or a stereoisomeric form thereof, or a pharmaceutically acceptable salt or a solvate thereof, for the treatment or prevention, in particular treatment, of any one of the diseases mentioned hereinbefore.

The present invention also relates to the use of a compound according to the Formula (I), (II), (III), or a stereoisomeric form thereof, or an N-oxide thereof, or a pharmaceutically acceptable salt or a solvate thereof, in particular, a compound of (I), (II), (Ill), or a stereoisomeric form thereof, or a pharmaceutically acceptable salt or a solvate thereof, for the preparation of a medicine or medicinal product, for treatment or prevention, in particular treatment, of any one of the diseases mentioned hereinbefore.

The compounds of the present invention can be administered to mammals, preferably humans, for the treatment or prevention of any one of the diseases mentioned hereinbefore.

Therefore, the invention also relates to a method for the prevention and/or treatment of any one of the diseases mentioned hereinbefore comprising administering, to a patient in need thereof, a therapeutically effective amount of a compound according to the invention to a subject in need thereof.

One skilled in the art will recognize that a therapeutically effective amount of the compounds of the present invention is the amount sufficient to modulate, inhibit or reduce the activity of the mGluR, especially mGluR7, and that this amount varies, depending on the type of disease, the concentration of the compound in the therapeutic formulation, and the condition of the patient. In general, an amount of compound to be administered as a therapeutic agent for treating diseases in which modulation, inhibition or reduction of mGluR activity, preferably of the mGluR7, is beneficial, such as the disorders described herein, will be determined on a case by case by an attending physician.

In general, a suitable dose is one that results in a concentration of the compounds in the range of 0.5 nM to 200 µM, and more usually 5 nM to 50 µM. To obtain these treatment concentrations, a patient in need of treatment likely will be administered an effective therapeutic daily amount of about 0.01 mg/kg to about 50 mg/kg body weight, preferably from about 0.01 mg/kg to about 25 mg/kg body weight, more preferably from about 0.01 mg/kg to about 10 mg/kg body weight, more preferably from about 0.01 mg/kg to about 2.5 mg/kg body weight, even more preferably from about 0.05 mg/kg to about 1 mg/kg body weight, more preferably from about 0.1 to about 0.5 mg/kg body weight. The amount of a compound according to the present invention, also referred to here as the active ingredient, which is required to achieve a therapeutically effect will, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment, the compounds according to the invention are preferably formulated prior to admission. As described herein below, suitable pharmaceutical formulations are prepared by known procedures using well known and readily available ingredients.

Combination Therapy

The compounds of the present invention may be utilized in combination with one or more other drugs in the treatment, prevention, control, amelioration, or reduction of risk of diseases or conditions aforementioned for which compounds of the invention or the other drugs may have utility, where the combination of the drugs together are safer or more effective than either drug alone. In another aspect, the present invention relates to a combination therapy in which an active compound according to the present invention is administered together with another active compound. Such combinations may be fixed dose combinations (the active ingredients that are to be combined are subject of the same pharmaceutical formulation) or free dose combinations (active ingredients are in separate pharmaceutical formulations). Consequently, a further aspect of the present invention refers to a combination of each of the active compounds of the present invention, preferably at least one active compound according to the present invention, with another active compound, that modulate receptors or enzymes in a manner such that the efficacy and/or safety of the active compounds according to the invention is increased and/or unwanted side effects are reduced. The different drugs of such a combination or product may be combined in a single preparation together with pharmaceutically acceptable carriers or diluents, or they may each be present in a separate preparation together with pharmaceutically acceptable carriers or diluents.

Because modulators of mGluR, preferably of mGluR7, including compounds of the invention, modulate the response of mGluR, preferably mGluR7, to endogenous glutamate and/or mGluR7 agonists and/or Group III agonists, it is understood that the present invention extends to the treatment of disorders associated with glutamate dysfunction by administering an effective amount of a modulator of mGluR7, including compounds of the invention, in combination with an mGluR7 agonist and/or a Group III mGluR agonist.

The compounds of the present invention may also be utilized in combination with psychotherapies in the treatment, prevention, control, amelioration, or reduction of risk of diseases or conditions, for which compounds of the invention may have utility.

The present invention also relates to pharmaceutical composition according to the invention further comprising another compound which modulates the activity of mGluR, preferably which inhibits or reduces the activity of mGluR, preferably mGluR being mGluR7.

The present invention also relates to a kit comprising:
At least one compound according to the invention or a pharmaceutical composition comprising at least a compound according to the invention; and
At least another compound which modulates the activity of mGluR, preferably which inhibits or reduces the activity of mGluR, preferably mGluR being mGluR7 or a pharmaceutical composition comprising at least a compound which modulates the activity of mGluR, preferably which inhibits or reduces the activity of mGluR, preferably mGluR being mGluR7.

Dosage

The exact dosage (or as herein mentioned therapeutically effective amount) and frequency of administration depends on the particular compound of the invention used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The amount of a compound according to the invention that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg.

Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules or gel formulations that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

Preparation of Compounds

A. METHODS OF SYNTHESIS

The compounds according to the invention, in particular the compounds according to the Formula (I), (II) and (III) may be prepared by methods known to the person skilled in the art of organic synthesis or by using the following synthesis schemes. In all of the schemes described below it is understood that protecting groups for sensitive or reactive groups are employed where necessary in accordance with the general principles of organic chemistry. Protecting groups are manipulated according to standard methods (T. W. Green and P. G. M. Wuts, 1991, Protecting Groups in Organic Synthesis, John Wiley & Sons, Inc.). These groups are then removed at a convenient stage of the synthesis using methods that are readily apparent to those skilled in the art.

The compounds according to the invention may be represented as a mixture of enantiomers which may be resolved into their individual R- or S-enantiomers. If for instance, a particular enantiomer is required it may be obtained by separation from the racemic mixture by using chiral chromatography techniques, or prepared by asymmetric synthesis or by derivation with a chiral auxiliary and the resulting diastereomeric mixture separated. The auxiliary group can then be cleaved to provide the desired pure enantiomers. Alternatively, where the molecule contains a basic functional group such as an amino functional group or an acidic functional group such as a carboxyl functional group, resolution may be performed by fractional crystallization from various solvents as the salt of an optical active acid or by other methods known in the literature.

Resolution of the final product, an intermediate or a starting material may be performed by any suitable method known in the art (E. L. Eliel, S. H. Wilen and L. N. Mander, 1984, *Stereochemistry of Organic Compounds*, Wiley-Interscience).

Many of the heterocyclic compounds of Formula (I) to (III) where $Ar^1$ or $Ar^2$ is a heteroaromatic or heterocyclic group may be prepared using synthetic routes well known in the art (A. R. Katrizky and C. W. Rees, 1984, Comprehensive Heterocyclic Chemistry, Pergamon Press).

The synthesis of mGluR modulators disclosed in the present invention have been prepared using the following synthetic schemes. Specific conditions for carrying out these reactions are provided in the examples. The synthetic schemes described below show exemplified approaches to compounds of the present invention, but these routes should not be taken as the only possible synthetic routes to compounds of the present invention.

Compounds of Formula (I) to (III) may be converted in their pure enantiomeric forms (+) and (−) using for example chiral separation.

Compounds of Formula (I), (II) and (III) wherein $R^9$ is hydrogen, may be obtained according to Scheme 1 below:

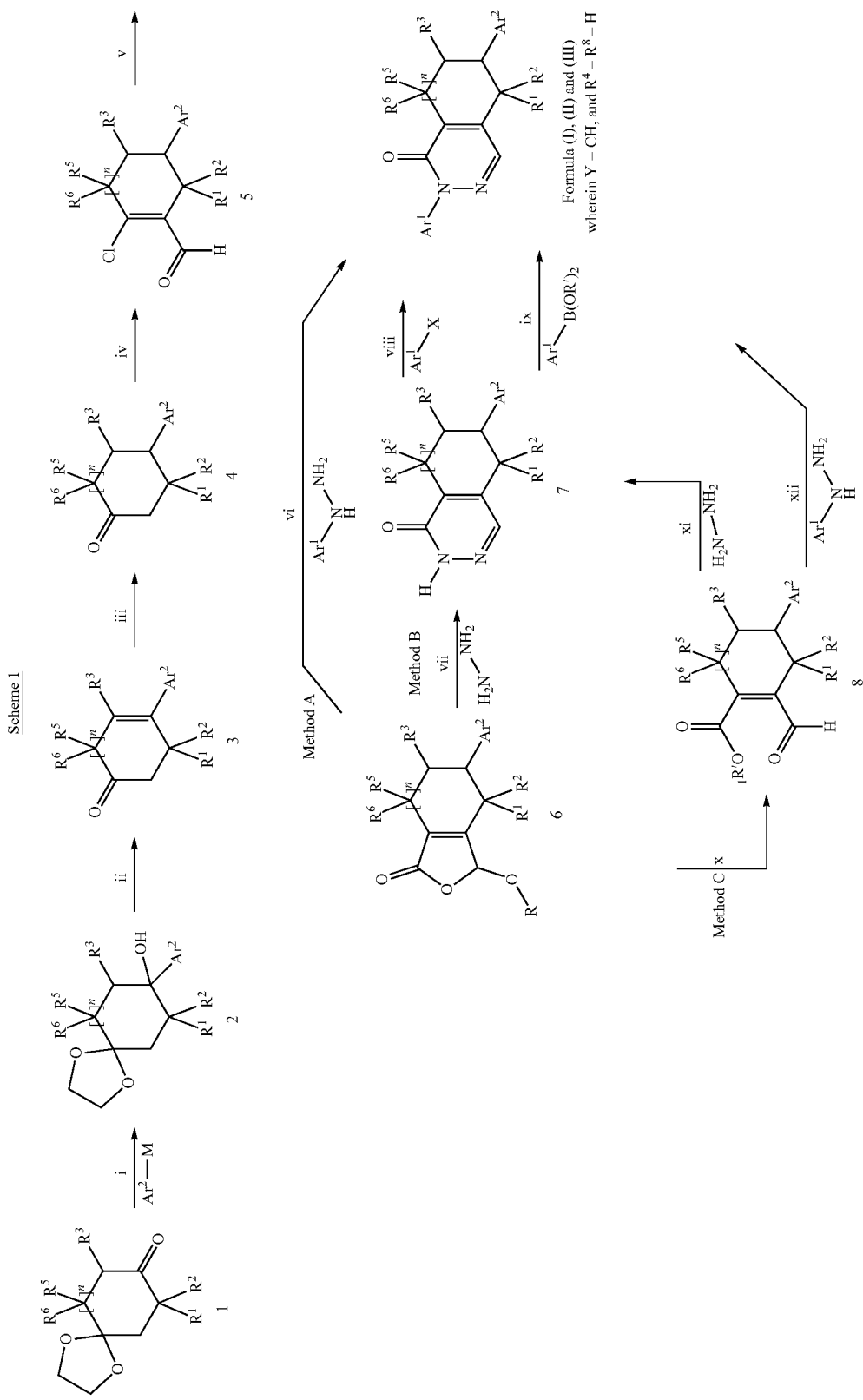

Cyclic ketone intermediates 1 are commercially available or may be synthesized by a person skilled in the art of organic chemistry using multiple ways described in the literature.

Secondary alcohol intermediates 2 may be obtained by nucleophilic addition of an organometallic $Ar^2$-M reagent (M=Li or MgX), which may be prepared for example from the corresponding suitably substituted aromatic ring by metal-halide exchange, using for example nBuLi or iPrMgCl, under inert atmosphere like for example nitrogen atmosphere, at controlled temperature like for example −78° C., in a non protic solvent like for example dry THF (step i). Intermediates 2 may be further dehydrated to form intermediates 3, under acidic condition like for example TFA neat or in the presence of DCM, at room temperature or under reflux (step ii).

The cycloalkenyl ketone intermediates 3 may be converted to the corresponding cycloalkyl ketone intermediates 4 by a hydrogenolysis using catalytic palladium like for example Pd/C, under hydrogen atmosphere, under pressure like for example 50 psi, at a temperature like for example 30° C. (step iii).

Ketone intermediates 4 may further react with $POCl_3$ in the presence of DMF to provide the chloro-carbonyl intermediates 5 (step iv), which is engaged in a carbonylative coupling reaction using a CO-releaser reagent like for example carbon monoxide, in the presence of a base such as $Et_3N$ or AcONa, and a transition metal catalyst such as $Pd(dppf)Cl_2$, or using the combination of a catalyst such as $Pd(OAc)_2$ and a ligand such as dppf, in a solvent like for example MeOH, at the appropriate temperature to provide lactone intermediates 6 (step v).

According to Method A in scheme 1, intermediates 6 may react with an aryl or heteroaryl hydrazines $Ar^1$—$NH_2$—$NH_2$, which may be commercially available or prepared by a person skilled in the art of organic chemistry, in the presence of a catalyst such as PTSA, and a solvent like for example toluene or EtOH, at an appropriate temperature (step ix), to provide final compounds of Formula (I), (II) and (III) wherein Y is CH and $R^4$, $R^8$ and $R^9$ are hydrogen.

Alternatively, according to Method B in scheme 1, intermediates 6 may react with hydrazine $NH_2NH_2$ in acidic condition, using either AcOH in the presence of a solvent like EtOH, or PTSA in the presence of a solvent like toluene, at the appropriate temperature (step vii), to provide intermediates 7. A cross-coupling reaction between intermediates 7 and (hetero)aromatic halides $Ar^1$—X (preferably $Ar^1$—Br) in the presence of a catalyst/ligand system like for example $Pd_2(dba)_3$/Xantphos, a base like t-BuOK, in a solvent like toluene, or alternatively a copper-mediated coupling reaction using CuI, a ligand such as DMEDA or in a cyclic diamine ligand, in the presence of a base like $K_3PO_4$, and a solvent like DMF or a mixture of solvents like DMF/dioxane, at the appropriate temperature (step viii), to provide final compounds of Formula (I), (II) and (III) wherein Y is CH and $R^4$, $R^8$ and $R^9$ are hydrogen.

Alternatively, intermediates 7 can be engaged in a Chan-Lam coupling reaction using a boronic acid or ester $Ar^1$—$B(OR')_2$, in the presence of a catalyst like for example $Cu(OAc)_2$, a base like for example pyridine, in a solvent like for example $CH_2Cl_2$, at an appropriate temperature (step ix), to provide final compounds of Formula (I), (II) and (III) wherein Y is CH and $R^4$, $R^8$ and $R^9$ are hydrogen.

Alternatively, according to Method C in scheme 1, lactone intermediates 6 can be converted in ester intermediates 8 using aqueous NaOH, followed by alkylation using an halo-alkyl reagent for example ethyl iodide, in the presence of DMF at the appropriate temperature (step x). Intermediates 8 may then be engaged in a 1- or 2-step sequence, according to step xi followed by steps viii or ix, or according to step xii, as per described in Method A and B, to provide final compounds of Formula (I), (II) and (III) wherein Y is CH and $R^4$ and $R^8$ are hydrogen.

Compounds of Formula (I), (II) and (III) wherein $R^9$ is hydrogen, may also be obtained according to Scheme 2 below:

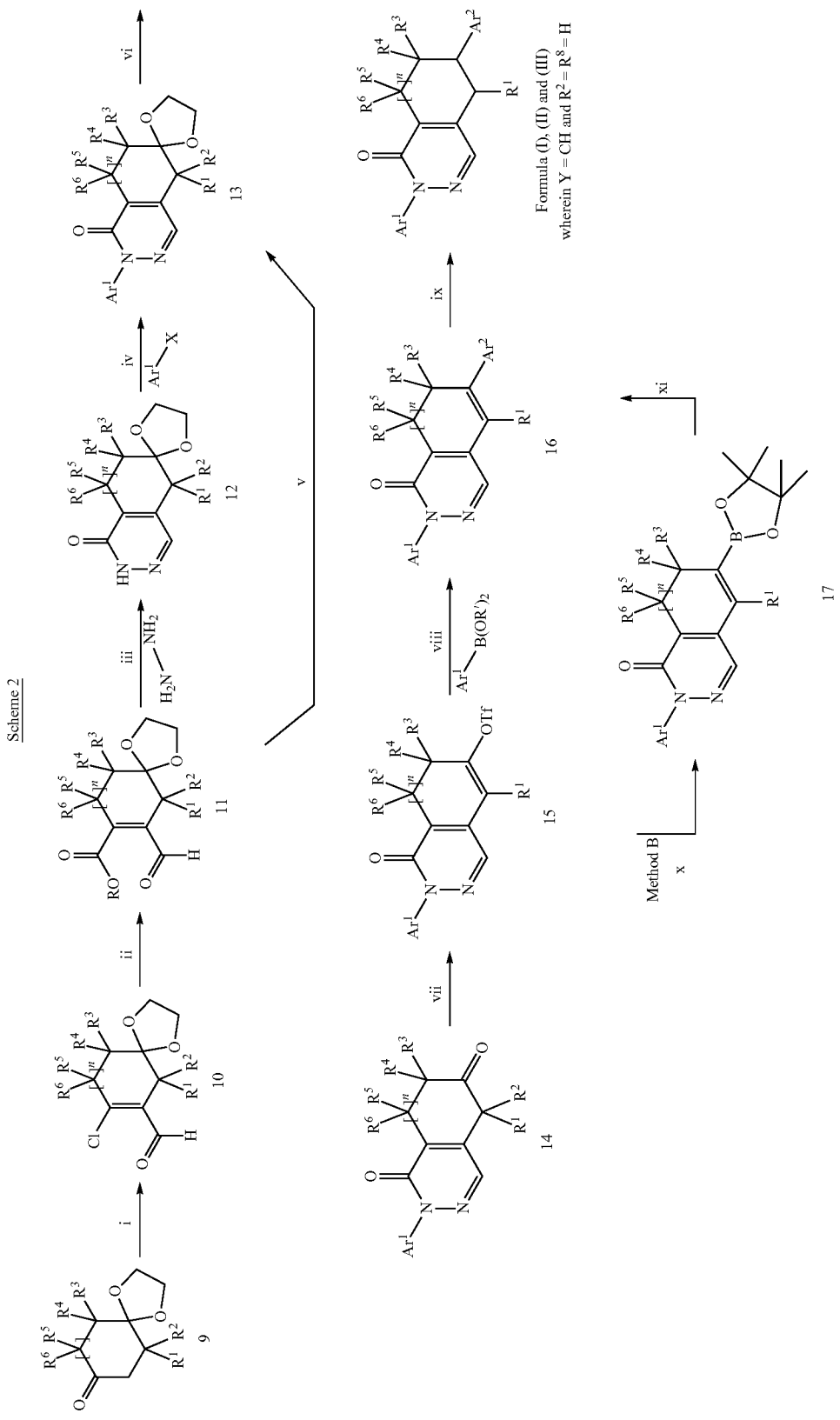

Cyclic keto-acetal intermediates 9 may react with POCl$_3$ in the presence of DMF to provide chloro-carbonyl intermediates 10 (step i). Intermediates 10 is engaged in a carbonylative coupling reaction using a CO-releaser reagent like for example carbon monoxide, in the presence of a base such as Et$_3$N or AcONa, and a transition metal catalyst such as Pd(dppf)Cl$_2$, or using the combination of a catalyst such as Pd(OAc)$_2$ and a ligand such as dppf, in a solvent like for example MeOH, at the appropriate temperature to provide ester-aldehyde intermediates 11 (step ii). Intermediates 12 may be obtained from the reaction of intermediates 11 with hydrazine NH$_2$NH$_2$ in acidic condition, using either AcOH in the presence of a solvent like EtOH, or PTSA in the presence of a solvent like toluene, at the appropriate temperature (step iii), followed by a cross-coupling reaction using an aromatic halide Ar$^1$—X (preferably Ar$^1$—Br) in the presence of a catalyst/ligand system like for example Pd$_2$(dba)$_3$/Xantphos, a base like t-BuOK, in a solvent like toluene, or alternatively a copper-mediated coupling reaction using CuI, a ligand such as DMEDA or in a cyclic diamine ligand, in the presence of a base like K$_3$PO$_4$, and a solvent like DMF or a mixture of solvents like DMF/dioxane, at the appropriate temperature (step iv).

Alternatively, intermediates 11 may react with an aryl hydrazine Ar$^1$—NH$_2$—NH$_2$, which may be commercially available or prepared by a person skilled in the art of organic chemistry, in the presence of a catalyst such as PTSA, and a solvent like for example toluene or EtOH, at an appropriate temperature to directly provide intermediates 13 (step v).

Intermediates 13 may be treated under acidic condition using aqueous TFA or HCl, in the presence of a solvent like acetonitrile or DCM, at the appropriate temperature to provide intermediates 14 (step vi). Ketone intermediates 14 may react with Tf$_2$O in the presence of a base such as Et$_3$N and a solvent like DCM at the appropriate temperature to provide key triflate intermediates 15 (step vii).

According to Method A in scheme 2, intermediates 15 may be engaged in a Suzuki coupling reaction using a boronic ester Ar$^1$—B(OR')$_2$ or boronic acid Ar$^1$—B(OH)$_2$ in the presence of a catalyst/ligand system like for example Pd(PPh$_3$)$_4$, a base like Na$_2$CO$_3$, or K$_2$CO$_3$, in a solvent like THF or a mixture dioxane/H$_2$O, at the appropriate temperature to provide intermediates 16 (step viii).

Alternatively, according to Method B in scheme 2, intermediates 15 may react with bispinacol-diborane ester in the presence of a base such as Na$_2$CO$_3$, or K$_2$CO$_3$ and a catalytic system such as Pd(dppf)Cl$_2$, in a solvent like dioxane, at the appropriate temperature to provide intermediates 17 (step x). Intermediates 17 may be engaged in a cross-coupling reaction using an aromatic halide Ar$^2$—X (preferably Ar$^e$—Br) in the presence of a catalyst/ligand system like for example Pd(dppf)Cl$_2$, a base like Na$_2$CO$_3$, in a solvent like dioxane-H$_2$O, at the appropriate temperature to provide intermediates 16 (step xi).

Finally, reduction of the cyclic double-bond in intermediates 16 may be performed by hydrogenolysis using for example palladium hydroxide, in the presence of ammonium formate, in a solvent like EtOH and at the appropriate a temperature, to provide final compounds of Formula (I), (II) and (III) wherein Y is CH and R$^2$ and R$^8$ are hydrogen (step ix).

Compounds of Formula (I), (II) and (III) may also be obtained according to Scheme 3 below:

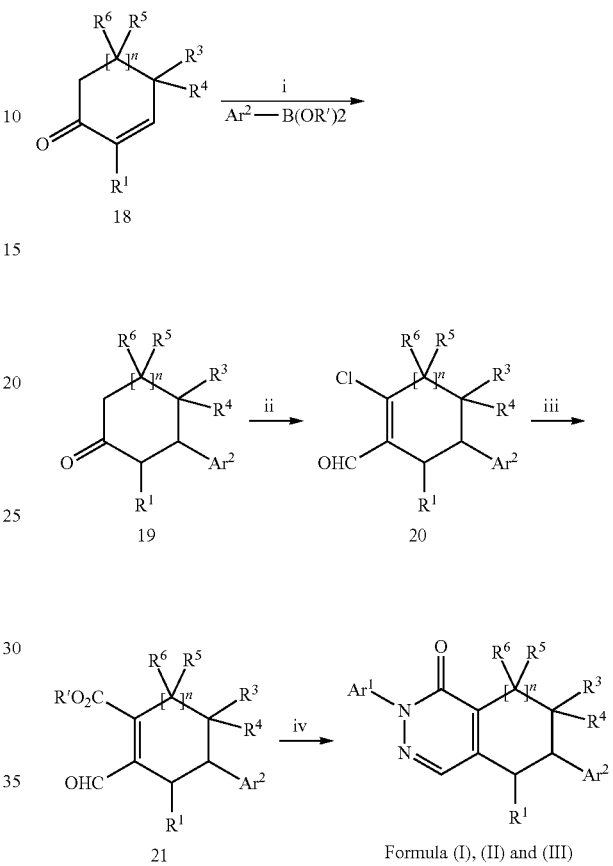

Formula (I), (II) and (III)
wherein Y = CH and R$^2$ = R$^8$ = H

Cyclic enone intermediates 18 are commercially available or may be synthesized by a person skilled in the art of organic chemistry using multiple ways described in the literature. The may be engaged in a cross-coupling reaction using a boronic ester Ar$^1$—B(OR')$_2$ or boronic acid Ar$^1$—B(OH)$_2$ in the presence of a catalyst/ligand system like for example Rh(COD)Cl$_2$, a base like KOH, in a solvent like dioxane/H$_2$O, at the appropriate temperature under inert atmosphere to provide intermediates 19 (step i). Ketone intermediates 19 may react with POCl$_3$ in the presence of DMF to provide intermediates 20 (step ii), which in turn be engaged in a carbonylative coupling reaction using a CO-releaser agent like for example carbon monoxide, in the presence of a base such as ET$_3$N or AcONa, and a transition metal catalyst such as Pd(dppf)Cl$_2$, in a solvent like for example EtOH, at the appropriate temperature to provide ester-aldehyde intermediates 21 (step iii). Intermediates 21 may react with an (hetero)aryl hydrazine Ar$^1$—NH$_2$—NH$_2$, which may be commercially available or prepared by a person skilled in the art of organic chemistry, in the presence of a catalyst such as PTSA, and a solvent like for example toluene or EtOH, at an appropriate temperature (step iv), to provide final compounds of Formula (I), (II) and (III) wherein Y is CH and R$^2$, R$^8$ and R$^9$ are hydrogen.

Compounds of Formula (I), (II) and (III) wherein R$^9$ is hydrogen, may also be obtained according to Scheme 4 below:

Scheme 4

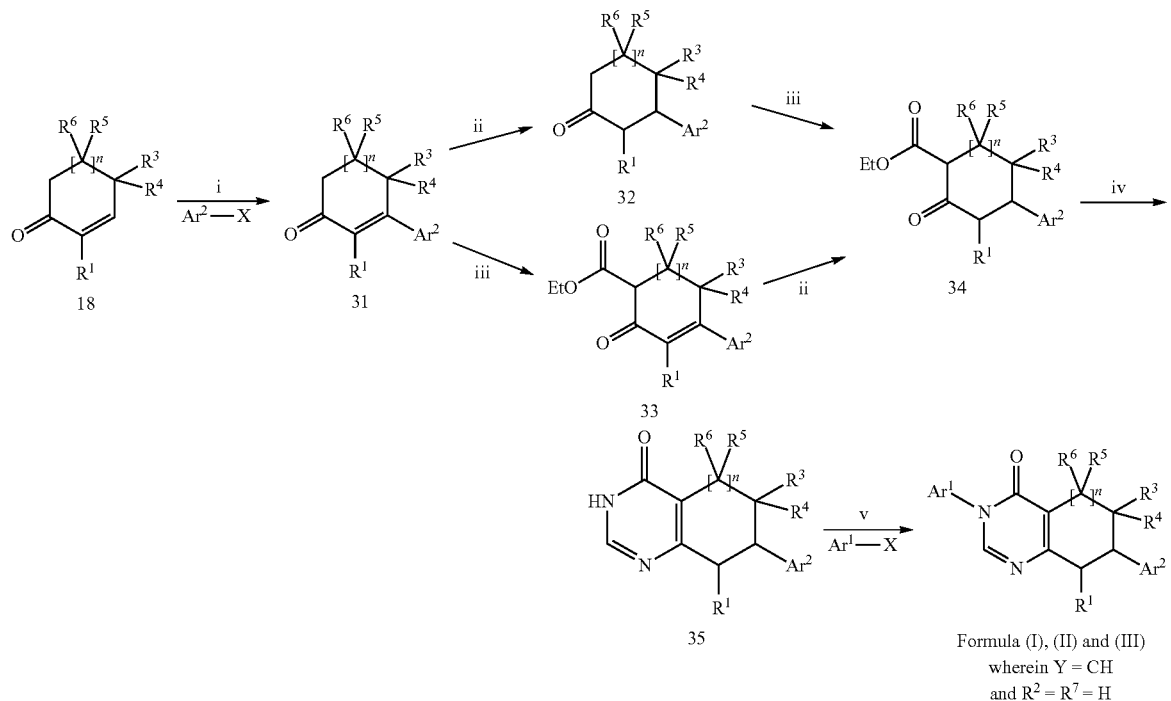

Cycloalkylene ketone intermediates 18 are commercially available or may be synthesized by a person skilled in the art of organic chemistry using multiple ways described in the literature. Intermediates 31 may be prepared by reacting intermediates 18 with a suitably substituted aromatic halide $Ar^2$—X (preferably $Ar^2$—Br or $Ar^2$—I) in a cross-coupling reaction in the presence of a transition metal catalyst like for example Pd(dppf)$Cl_2$, in a solvent like $Et_3N$ or $Na_2CO_3$, in the presence of a solvent such as DMSO, at an appropriate temperature (step i).

Cycloalkenyl ketone intermediates 31 may be converted to the corresponding keto-ester intermediates 34 by a two-step reaction sequence: (step ii) alpha-carboxylation using for example cyanoethylcarbonate or diethylcarbonate, in the presence of a base like for example LDA or NaH, in an aprotic solvent like for example THF, at a controlled temperature like for example −78° C.; followed by (step iii) the double-bond hydrogenolysis using catalytic palladium like for example Pd/C, under hydrogen atmosphere, under pressure like for example 50 psi, at the appropriate temperature.

This 2-step sequence may be reverted starting first by the hydrogenolysis step (iii), followed by the alpha-carboxylation step (ii) using the aforementioned conditions, to provide keto-ester intermediates 34.

Keto-ester intermediates 34 may react with formamidine in the presence of a base such as $K_2CO_3$ and a solvent like EtOH at the appropriate a temperature to provide intermediates 35 (step iv).

Intermediates 35 may be engaged in a cross-coupling reaction as described in Scheme 1, for example reacting with an aromatic halide $Ar^1$—X (preferably $Ar^1$—Br) in the presence of a catalyst/ligand system like for example $Pd_2(dba)_3$/Xantphos, a base like t-BuOK, in a solvent like toluene, or alternatively a copper-mediated coupling reaction using CuI, a ligand such as DMEDA or in a cyclic diamine ligand, in the presence of a base like $K_3PO_4$, and a solvent like DMF or a mixture of solvents like DMF/dioxane, at the appropriate temperature (step v), to provide final compounds of Formula (I), (II) and (III) wherein $R^2$, $R^7$ and $R^9$ are hydrogen.

Any compounds of Formula (I), (II) or (III) wherein $Ar^2$ is substituted by an OR group, may be obtained according to Scheme 5 below:

Scheme 5

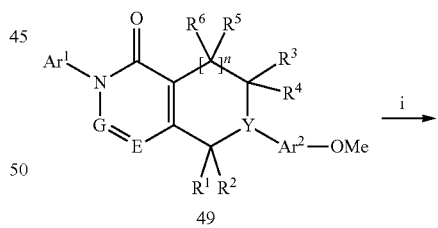

49

Formula (I), (II) and (III)
wherein $Ar^2$ is substituted by OMe

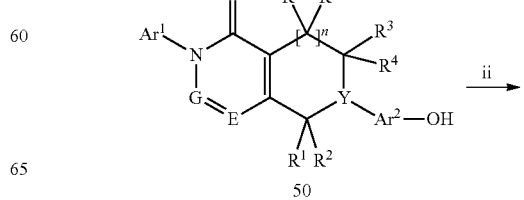

50

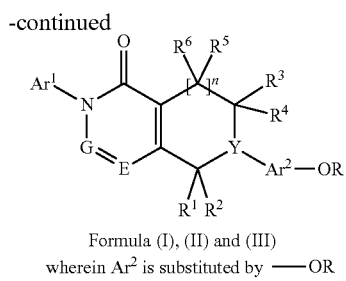

Formula (I), (II) and (III)
wherein Ar² is substituted by ——OR

Compounds of Formula (I), (II) and (III), represented by intermediates 49 wherein substituent B on Ar² is a methoxy group, may react with a dealkylating agent such as boron tribromide in a solvent like DCM at the appropriate temperature (step i) to provide hydroxy intermediates 50. The hydroxy function may then react with an alkylating agent such as alkyl halide (e.g. R²—I, R²—Br or R²—Cl) in the presence of a base like Cs₂CO₃ in a solvent like DMF at the appropriate temperature (step ii) to provide compounds of Formula (I), (II) and (III), wherein Ar² is substituted by an oxo group.

Any compounds of Formula (I) (II) and (III), wherein Ar¹ is substituted by an alkyl, aryl, heteroaryl, amino or alkoxy radical, may be obtained according to Scheme 6 below:

solvent like dioxane or dioxane-H₂O, at the appropriate temperature (step ii) to provide compounds of Formula (I), (II) and (III), wherein Ar¹ is bearing an alkyl, aryl or heteroaryl radical.

According to Method B, similar halide intermediates 52 (wherein A is a halide radical) may react with an amine R¹R²NH in the presence or not of a catalyst/ligand system like for example Pd(dppf)Cl₂, or RuPhos, a base like Na₂CO₃ or Cs₂CO₃, in a solvent like dioxane, at the appropriate temperature (step iii) to provide compounds of Formula (I), (II) and (III), wherein Ar¹ is bearing an amino radical.

Furthermore, according to Method C, intermediates 52, wherein A is a —OH radical, may react with an alkyl halide (like R—I, R—Br or R—Cl) in the presence of a base like Cs₂CO₃ in a solvent like DMF at the appropriate temperature (step iv) to provide compounds of Formula (I), (II) and (III), wherein Ar¹ is bearing an alkoxy radical.

Alternatively, compounds of Formula (I), (II) and (III) wherein Ar² is bearing a carbonyl group may be obtained according to Scheme 7 below:

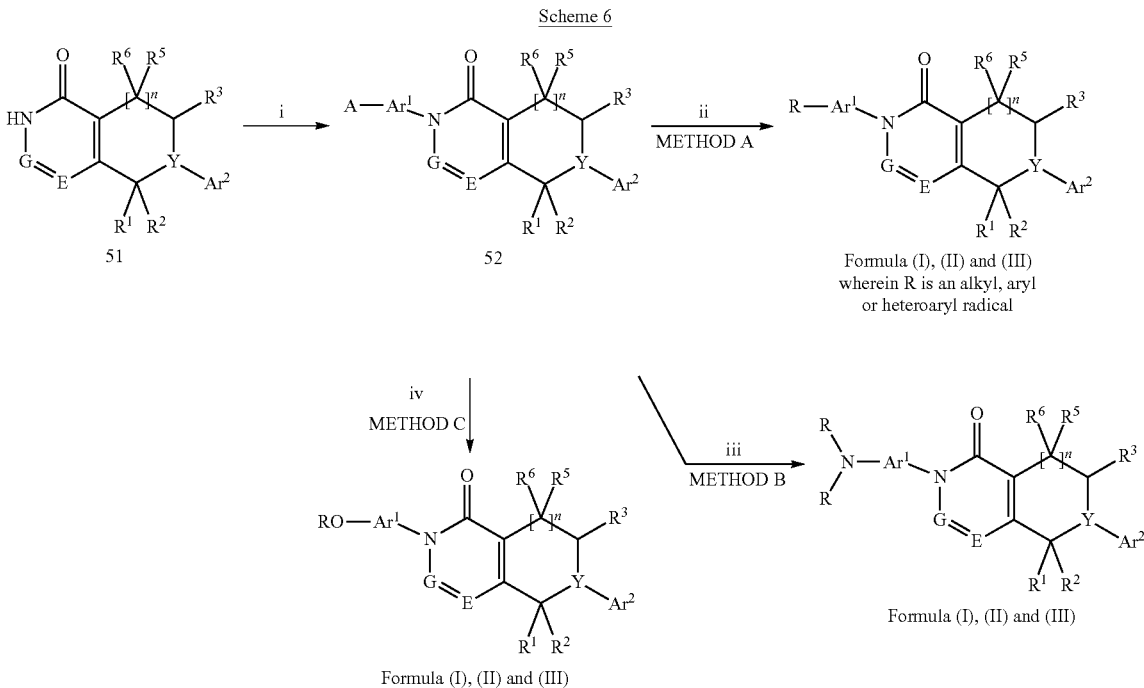

Intermediates 51, representing by but not limited to intermediates 7 in scheme 1 or 35 in scheme 4, may be engaged in a cross-coupling reaction using a halo (hetero)aryl of formula A-Ar¹—X, in the presence of a catalyst/ligand system (e.g. Pd₂(dba)₃/Xantphos), a base (e.g. t-BuOK), in a solvent (e.g. toluene), at an appropriate temperature to provide intermediates 51 (step i). According to Method A, intermediates 52 wherein A is a halide radical Cl, Br or I, may further react with boronic acid or boronic esters in the presence of a catalyst/ligand system like for example Pd(dppf)Cl₂, or RuPhos, a base like KOAc or Cs₂CO₃, in a

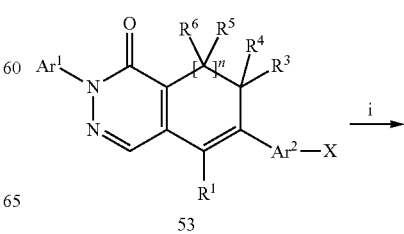

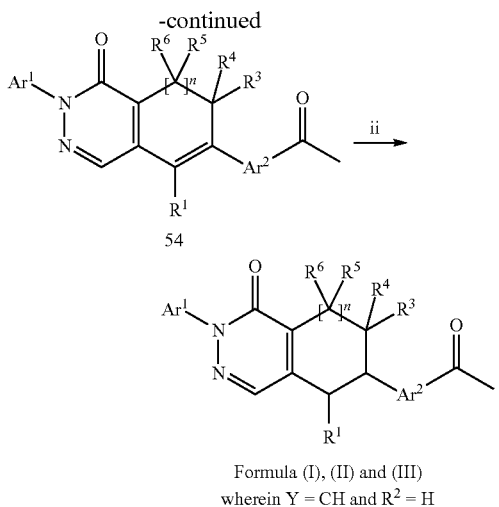

Formula (I), (II) and (III)
wherein Y = CH and R² = H

Intermediates 53 wherein X is Br may be engaged in a cross-coupling reaction using a tributyl tin ethoxyvinyl, in the presence of a catalyst/ligand system (e.g. Pd(PPh$_3$)$_4$, a base (e.g. t-BuOK), in a solvent (e.g. dioxane), at an appropriate temperature, followed by hydrolysis in acidic media, such as aqueous HCl, in a solvent like EtOH, to provide intermediates 54. Reduction of the cyclic double-bond in intermediates 54 may be performed by hydrogenolysis using for example palladium on charcoal, in the presence of ammonium formate, in a solvent like EtOH and at the appropriate a temperature (step ii) to provide final compounds of Formula (I), (II) and (III) wherein Y is CH, and Ar² is bearing an acetyl group.

B. EXPERIMENTAL

Several methods for preparing the compounds of this invention are illustrated in the following Examples. Unless otherwise noted, all starting materials were obtained from commercial suppliers and used without further purification. Specifically, the following abbreviations may be used in the examples and throughout the specification.

| | |
|---|---|
| ACN (acetonotrinile) | K$_3$PO$_4$ (potassium phosphate) |
| AcOH (acetic acid) | KOt-Bu (potassium tert-butoxide) |
| Bn (benzyl) | LCMS (Liquid Chromatography Mass Spectrum) |
| Boc$_2$O (di-tert-butyl dicarbonate) | LDA |
| CDCl$_3$ (deuterated chloroform) | M (molar) |
| CH$_2$Cl$_2$ (dichloromethane) | MeOH (methanol) |
| CO (carbon monoxide) | mg (milligrams) |
| Cu(OAc)$_2$ (Copper(II) acetate) | MHz (megahertz) |
| DIPEA | min (minutes) |
| DMEDA (N,N-Dimethylethylenediamine) | μL(microliters) |
| DMF (dimethylformamide) | μmol (micromoles) |
| DMA (dimethylacetamide) | mL (milliliters) |
| DMAP (dimethylaminopyridine) | mmol (millimoles) |
| DMFDMA (N,N-Dimethylformamide dimethyl acetal) | M.p. (melting point) |
| Dppf (1,1'-bis(diphenylphosphanyl)ferrocene) | MTBE |
| Et$_3$N (triethylamine) | n-BuLi (n-butyl lithium) |
| EtOAc (or EA: ethyl acetate) | N$_2$H$_4$ (hydrazine) |
| EtOH (ethanol) | NaBH$_3$CN (sodium cyanoborohydride) |
| g (grams) | NaBH(OAc)$_3$ |
| $^1$H (proton) | NaH (sodium hydride) |
| H$_2$ (hydrogen) | NaHCO$_3$ (sodium hydrogenocarbonate) |
| HATU (1-[Bis(dimethylamino)methylene]-1H-1,2,3-triazolo[4,5-b]pyridinium 3-oxid hexafluorophosphate) | NaIO$_4$ (sodium periodate) |
| HCl (hydrochloric acid) | NaOMe |
| HPLC (High Pressure Liquid Chromatography) | Na$_2$SO$_4$ (sodium sulphate) |
| Hz (Hertz) | NH$_4$Cl |
| Pd/C (palladium on charcoal) | NMR (Nuclear Magnetic Resonance) |
| Pd$_2$(dba)$_3$ (palladium (II)dibenzylideneacetone) | TFA (trifluoroacetic acid) |
| PdCl$_2$(dppf)$_2$ (Bis(1,1'-bis(diphenylphosphanyl)ferrocene palladium (II) dichloride | THF (tetrahydrofuran) |
| PdCl$_2$(PPh$_3$)$_2$ (Bis(triphenylphosphine) palladium (II) dichloride | TLC (thin layer chromatography) |
| PE (Petroleum ether) | TMG (trimethylguanidine) |
| POCl$_3$ (Phosphorus trichloride) | TsOH (Tosyl acid) |
| PtO$_2$ (Platinum Oxide) | Xantphos (4,5-Bis(diphenylphosphino)-9,9-dimethylxanthene) |
| RT (Retention Time) | XPhos (2-Dicyclohexylphosphino-2',4',6'-triisopropylbiphenyl) |
| RUPHOS (2-Dicyclohexylphosphino-2',6'-diisopropoxybiphenyl) | MnO$_2$ (Manganese dioxide) |

Unless otherwise indicated, all temperatures are expressed in ° C. (degrees Celsius). All reactions are conducted not under an inert atmosphere at room temperature unless otherwise noted.

Example 1: 6-(2,4-dimethyl-phenyl)-2-pyridin-2-yl-5,6,7,8-tetrahydro-2H-phthalazin-1-one, was Prepared According to Scheme 1, Method A

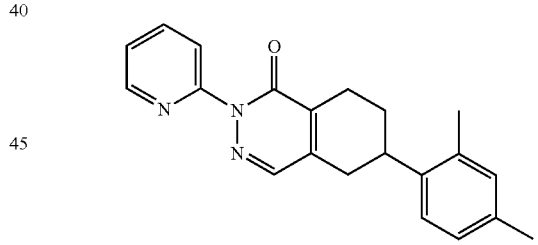

Intermediate 2a: 8-(2,4-dimethyl-phenyl)-1,4-dioxa-spiro[4.5]decan-8-ol

According to Scheme 1 Step i: To a solution of 1-bromo-2,4-dimethyl-benzene (20.00 g, 108.07 mmol, 1.00 eq) in THF (100 mL) under N$_2$ atmosphere and cooled to −70° C., was added n-BuLi (2.5 M, 45.39 mL, 1.05 eq) dropwise. The reaction mixture was stirred at −70° C. for 2 hr. Then a solution of 1,4-dioxa-spiro[4.5]decan-8-one (17.72 g, 113.47 mmol, 1.05 eq) in THF (100 mL) was added dropwise at −70° C., the reaction mixture was stirred at −70° C. for 2 hr. The reaction mixture was quenched by water (300 mL) and extracted with EtOAc (200 mL×2). The organic layer was dried over Na$_2$SO$_4$ and concentrated in vacuo. The crude product was purified by flash column chromatography on silicagel (PE:EtOAc 10/1 to 5/1). Intermediate 2a (24.00 g, 86.00 mmol, 79.57% yield) was obtained as a light-yellow solid.

¹H NMR (DMSO-d₆; 400 MHz) δ 7.31-7.29 (m, 1H), 6.90-6.89 (m, 2H), 4.66 (s, 1H), 3.87 (s, 4H), 2.49 (s, 3H), 2.21 (s, 3H), 2.00-1.94 (m, 4H), 1.79-1.76 (m, 2H), 1.53-1.51 (m, 2H).

Intermediate 3a:
4-(2,4-Dimethyl-phenyl)-cyclohex-3-enone

According to Scheme 1 Step ii: A solution of intermediate 2a (10.00 g, 38.12 mmol, 1.00 eq) in TFA (500.00 mL) was stirred at 15° C. for 1 hr, then the mixture was stirred and heated to 80° C. for 18 hr. The mixture was concentrated in vacuo. The residue was quenched by saturated NaHCO₃ solution and pH was adjusted to pH 7-8, extracted with EtOAc (200 mL×2). The organic layer was dried over Na₂SO₄ and concentrated in vacuo. The crude product was purified by column chromatography on silica gel (PE:EtOAc 10/1 to 5/1). The intermediate 3a (11.00 g, 54.92 mmol, 72.04% yield) was obtained as a light-yellow oil. ¹H NMR (CDCl₃; 400 MHz) δ 7.06-6.97 (m, 4H), 6.23-6.18 (m, 1H), 3.95-3.91 (m, 1H), 2.57-2.53 (m, 2H), 2.51 (s, 3H), 2.50-2.33 (m, 4H), 1.99-1.95 (m, 1H).

Intermediate 4a:
4-(2,4-dimethylphenyl)cyclohexan-1-one

According to Scheme 1 Step iii: To a solution intermediate 3a (10.00 g, 49.93 mmol, 1.00 eq) in EtOAc (100.00 mL) was added Pd/C (2.00 g, 49.93 mmol, 1.00 eq) under N₂ atmosphere. The suspension was degassed under vacuo and purged with H₂ several times. The mixture was stirred under H₂ (50 psi) at 30° C. for 4 hours. The mixture was filtered and filtrate was concentrated in vacuo. The crude product intermediate 4a (10.00 g, 49.43 mmol, 99.01% yield) was obtained and used directly in the next step as a brown solid. ¹H NMR (CDCl₃; 400 MHz) δ 7.12-7.02 (m, 3H), 3.25-3.22 (m, 1H), 2.57-2.53 (m, 4H), 2.41 (s, 3H), 2.33 (s, 3H), 2.16-2.15 (m, 2H), 1.96-1.94 (m, 2H).

Intermediate 5a: 2-Chloro-5-(2,4-dimethyl-phenyl)-cyclohex-1-enecarbaldehyde

According to Scheme 1 Step iv: To a solution of intermediate 4a (13.01 g, 177.96 mmol, 12.00 eq) in CH₂Cl₂ (10 mL) at 0° C. under N₂ atmosphere was added POCl₃ (6.82 g, 44.49 mmol, 3.00 eq) dropwise. After stirring at 10° C. for 1 hr, a solution of intermediate 1c (3.00 g, 14.83 mmol, 1.00 eq) in CH₂Cl₂ (40 mL) was added dropwise. The mixture was stirred at 50° C. for 4 hr. The mixture was quenched by saturated NaHCO₃ solution and pH adjusted to pH 7-8, extracted with CH₂Cl₂ (150 mL×2). The organic layer was dried over Na₂SO₄ and concentrated in vacuo. The residue was purified by flash chromatography over silicagel (PE/EtOAc=10/1), the intermediate 5a (1.70 g, 6.83 mmol, 46.06% yield) was obtained as a yellow oil. ¹H NMR (400 MHz, CDCl₃) δ 10.25 (s, 1H), 7.09-6.95 (m, 3H), 3.03-2.73 (m, 4H), 2.32 (d, J=2.6 Hz, 6H), 2.23-2.06 (m, 1H), 2.05-1.90 (m, 2H).

Intermediate 6a: 5-(2,4-dimethylphenyl)-3-methoxy-4,5,6,7-tetrahydroisobenzofuran-1(3H)-one According to Scheme 1 Step v: To a mixture of intermediate 5a (500.00 mg, 2.01 mmol, 1.00 eq), Pd(dppf)Cl₂ (147.08 mg, 201.01 µmol, 0.10 eq), Et₃N (610.19 mg, 6.03 mmol, 3.00 eq) in MeOH (10.00 mL) under N₂ atmosphere. The suspension was degassed under vacuum and purged with CO several times. The mixture was stirred under CO atmosphere (1 MPa) at 90° C. for 12 hours. The mixture was filtered and filtrate was concentrated in vacuo. The intermediate 6a (650.00 mg, crude) was obtained as brown solid. ¹H NMR: (400 MHz, CDCl₃) δ 7.09-6.98 (m, 3H), 5.67 (s, 1H), 3.60 (s, 3H), 3.19-3.05 (m, 1H), 2.70-2.59 (m, 1H), 2.57-2.44 (m, 2H), 2.33 (s, 3H), 2.31 (s, 3H), 2.06-1.95 (m, 1H), 1.88-1.76 (m, 1H).

Example 1: 6-(2,4-Dimethyl-phenyl)-2-pyridin-2-yl-5,6,7,8-tetrahydro-2H-phthalazin-1-one According to Scheme 1, Method A, step vi: A mixture of intermediate 6a (200.00 mg, 734.38 µmol, 1.00 eq) and pyridin-2-yl-hydrazine hydrochloride (160.28 mg, 1.47 mmol, 2.00 eq) in toluene (10.00 mL) was stirred and heated to 110° C. for 8 hours. The mixture was concentrated in vacuo. The residue was dissolved in EtOAc (100 mL) and water (100 mL), extracted with EtOAc (100 mL×2). The organic layer was dried over Na₂SO₄ and concentrated in vacuo. The crude product was purified by prep-HPLC and Example 1 (30.00 mg, 90.52 µmol, 6.16% yield) was obtained as a brown solid. ¹H-NMR (400 MHz, CDCl₃) δ 8.67 (d, J=4.0 Hz, 1H), 7.82-7.91 (m, 1H), 7.69-7.77 (m, 2H), 7.33-7.39 (m, 1H), 6.99-7.15 (m, 3H), 3.09-321 (m, 1H), 2.99 (d, J=17.6 Hz, 1H), 2.76-2.86 (m, 1H), 2.59-2.75 (m, 2H), 2.36 (s, 3H), 2.33 (s, 3H), 2.08-2.19 (m, 1H), 1.80-1.95 (m, 1H).

Example 2: 6-(3-methoxyphenyl)-2-(pyridin-2-yl)-5,6,7,8-tetrahydrophthalazin-1(2H)-one, was Prepared According to Scheme 1, Method A

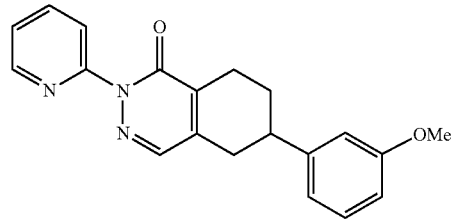 [SMILES: COc1cccc(C2CCc3c(cnn(-c4ccccn4)c3=O)C2)c1]

Intermediate 6b: 3-methoxy-5-(3-methoxyphenyl)-4,5,6,7-tetrahydroisobenzofuran-1(3H)-one According to Scheme 1 Step i to v: Intermediate 6b was prepared similarly to intermediate 6a in Example 1, starting from 1-bromo-3-methoxybenzene, and was obtained with an overall yield of 19% as a brown liquid. m/z (M+H)⁺=275.1.

Example 2: 6-(3-methoxyphenyl)-2-(pyridin-2-yl)-5,6,7,8-tetrahydrophthalazin-1(2H)-one According to Scheme 1, Method A, step vi: Example 2 was prepared as per Example 1 starting from intermediate 6b (800.00 mg, 832.35 µmol) and pyridin-2-yl-hydrazine hydrochloride (181.77 mg, 1.25 mmol) to provide Example 2 (8.20 mg, 24.60 µmol) as a yellow solid. (¹H-NMR (400 MHz, MeOD) δ 8.62-8.61 (m, 1H), 8.08-8.05 (m, 1H), 7.90 (s, 1H), 7.69-7.67 (m, 1H), 7.62-7.56 (m, 1H), 7.29-7.27 (m, 1H), 6.94-6.90 (m, 2H), 6.83-6.84 (1H), 3.07-2.86 (m, 4H), 2.68-2.57 (m, 1H), 1.99-1.96 (m, 1H), 1.96-1.93 (m, 1H).

Example 3: 6-(4-methoxyphenyl)-2-(pyridin-2-yl)-5,6,7,8-tetrahydrophthalazin-1(2H)-one, was Prepared According to Scheme 1, Method A

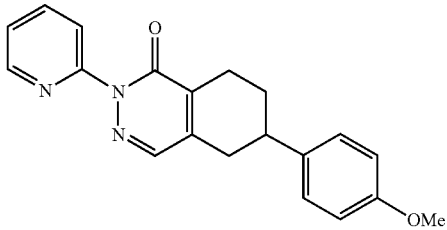 [SMILES: COc1ccc(C2CCc3c(cnn(-c4ccccn4)c3=O)C2)cc1]

Intermediate 6c: 3-methoxy-5-(4-methoxyphenyl)-4,5,6,7-tetrahydroisobenzofuran-1(3H)-one According to Scheme 1 Step I to v: Intermediate 6c was prepared similarly to intermediate 6a in Example 1, starting from 1-bromo-4-methoxybenzene, and was obtained with an overall yield of 14% as a brown liquid. $^1$H NMR (MeOD; 400 MHz) δ 7.22-7.20 (m, 2H), 6.91-6.87 (m, 2H), 5.88 (s, 1H), 3.93-3.91 (m, 1H), 3.83-3.81 (m, 1H), 3.77-3.80 (m, 3H), 2.95-2.85 (m, 1H), 2.64-2.59 (m, 1H), 2.31-2.42 (m, 3H), 2.05-2.03 (m, 1H), 1.85-1.80 (m, 1H), 1.30-1.25 (m, 3H).

Example 3: 6-(4-methoxyphenyl)-2-(pyridin-2-yl)-5,6,7,8-tetrahydrophthalazin-1(2H)-one According to Scheme 1, Method A, step vi: Example 3 was prepared as per Example 1 starting from intermediate 6c (200.00 mg, 693.63 μmol) and pyridin-2-yl-hydrazine hydrochloride (201.97 mg, 1.39 mmol) to provide Example 3 (26.00 mg, 77.99 μmol) as a green solid. ($^1$H-NMR (400 MHz, DMSO-d$_6$) δ 8.61-8.60 (m, 1H), 8.04-8.00 (m, 1H), 7.59-7.56 (m, 2H), 7.30-7.23 (m, 2H), 6.93-6.90 (m, 2H), 3.70 (s, 3H), 2.92-2.73 (m, 5H), 2.05-2.02 (m, 1H), 1.85-1.82 (m, 1H), 1.81-1.78 (m, 1H).

Example 4: (+6-(2,4-dimethyl-phenyl)-2-pyridin-2-yl-5,6,7,8-tetrahydro-2H-phthalazin-1-one and Example 5: (+)-6-(2,4-dimethyl-phenyl)-2-pyridin-2-yl-5,6,7,8-tetrahydro-2H-phthalazin-1-one

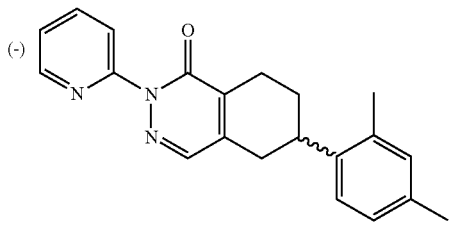

Example 4

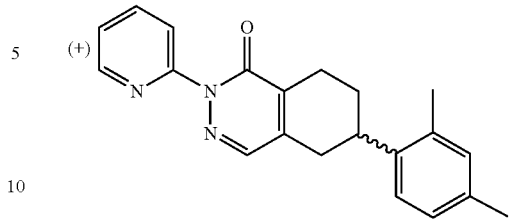

Example 5

The enantiomers constituting racemic Example 1 (400 mg) were separated by preparative SFC to give (−) 6-(2,4-Dimethyl-phenyl)-2-pyridin-2-yl-5,6,7,8-tetrahydro-2H-phthalazin-1-one Example 4 (72 mg, 18%) with an enantiomeric excess of 100%, and (+) 6-(2,4-Dimethyl-phenyl)-2-pyridin-2-yl-5,6,7,8-tetrahydro-2H-phthalazin-1-one Example 5 (59 mg, 15%) with an enantiomeric excess of 99%, both as yellow solid.

Example 4: $^1$H-NMR (400 MHz, CDCl$_3$) δ 8.67 (br.s., 1H), 7.82-7.91 (m, 1H), 7.69-7.77 (m, 2H), 7.33-7.39 (m, 1H), 6.99-7.15 (m, 3H), 3.09-321 (m, 1H), 2.99 (d, J=17.6 Hz, 1H), 2.76-2.86 (m, 1H), 2.59-2.75 (m, 2H), 2.36 (s, 3H), 2.33 (s, 3H), 2.08-2.19 (m, 1H), 1.80-1.95 (m, 1H).

Example 5: $^1$H-NMR (400 MHz, CDCl$_3$) δ 8.67 (br.s., 1H), 7.82-7.91 (m, 1H), 7.69-7.77 (m, 2H), 7.33-7.39 (m, 1H), 6.99-7.15 (m, 3H), 3.09-321 (m, 1H), 2.99 (d, J=17.6 Hz, 1H), 2.76-2.86 (m, 1H), 2.59-2.75 (m, 2H), 2.36 (s, 3H), 2.33 (s, 3H), 2.08-2.19 (m, 1H), 1.80-1.95 (m, 1H).

Example 6: 6-(2,4-dimethylphenyl)-2-(5-chloropyridin-2-yl)-5,6,7,8-tetrahydro-phthalazin-1(2H)-one, was Prepared According to Scheme 1, Method B

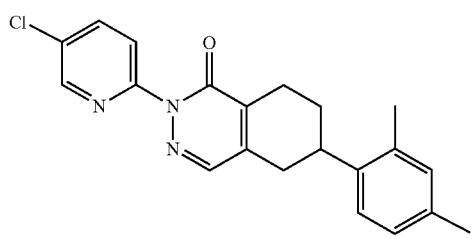 [SMILES: Cc1ccc(C2CCc3c(cnn(-c4ccc(Cl)cn4)c3=O)C2)c(C)c1]

Intermediate 7a: 6-(2,4-dimethylphenyl)-5,6,7,8-tetrahydrophthalazin-1(2H)-one According to Scheme 1 Step vii: To a solution of intermediate 6a (1.2 g, 4.19 mmol, 1 eq) in EtOH (10 mL) and AcOH (1 mL) was added N$_2$H$_4$·H$_2$O (427.66 mg, 8.37 mmol, 415.20 gt, 2.0 eq). The mixture was stirred at 80° C. for 3 hr, then cooled to 0° C. The white solid formed was collected after filtering. Intermediate 7a (830 mg, 3.26 mmol, 77.96% yield) was obtained as a white solid. $^1$H NMR (400 MHz, DMSO-d$_6$) δ 12.74 (s, 1H), 7.64 (s, 1H), 7.15-7.08 (m, 1H), 7.03-6.93 (m, 2H), 3.09-2.93 (m, 1H), 2.74-2.57 (m, 3H), 2.47-2.37 (m, 1H), 2.28 (s, 3H), 2.24 (s, 3H), 1.96-1.85 (m, 1H), 1.83-1.68 (m, 1H).

Example 6: 6-(2,4-dimethylphenyl)-2-(6-chloropyridin-2-yl)-5,6,7,8-tetrahydrophthalazin-1(2H)-one According to Scheme 1 Step viii: To a solution of intermediate 7a (100.00 mg, 353.87 μmol, 1.00 eq) in DMF (5.00 mL) was added 5-chloro-2-bromopyridine (204.30 mg, 1.06 mmol, 3.00 eq), DMEDA (18.72 mg, 212.32 μmol, 22.82 μL, 0.60 eq), CuI (33.70 mg, 176.94 μmol, 0.50 eq), K₃PO₄ (187.79 mg, 884.68 μmol, 2.50 eq) at 20° C. under N₂ atmosphere. Then the mixture was heated to 110° C. and stirred for 12 hours. The reaction was filtered and the filtrate was acidified to pH=5 with aqueous 12 M HCl and filtered. The filtrate was purified by prep-HPLC to provide Example 6 (71.93 mg, 196.61 μmol, 55.56% yield as an off-yellow solid. ¹H-NMR (400 MHz, CDCl₃) δ 8.62 (d, J=2.3 Hz, 1H), 7.87-7.82 (m, 1H), 7.78-7.73 (m, 2H), 7.14-7.09 (m, 1H), 7.08-7.04 (m, 2H), 3.20-3.11 (m, 1H), 3.04-2.95 (m, 1H), 2.87-2.78 (m, 1H), 2.77-2.60 (m, 2H), 2.34 (s, 3H), 2.33 (s, 3H), 2.20-2.11 (m, 1H), 1.95-1.83 (m, 1H).

Example 7: 2-(4-chloropyridin-2-yl)-6-(2,4-dimethylphenyl)-5,6,7,8-tetrahydrophthalazin-1(2H)-one, was Prepared According to Scheme 1, Method B

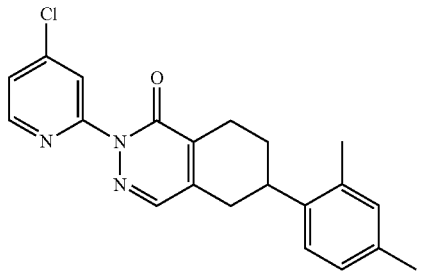 [SMILES: Cc1ccc(C2CCc3c(cnn(-c4cc(Cl)ccn4)c3=O)C2)c(C)c1]

According to Scheme 1 Step viii: Example 7 was prepared as per Example 6, starting from intermediate 7a (150.00 mg, 530.81 μmol) and 2-bromo-4-chloropyridine (306.45 mg, 1.59 mmol), to provide Example 7 (178.10 mg, 484.85 μmol, 91.34% yield) as brown solid. ¹H-NMR (400 MHz, CDCl₃) δ 8.49 (d, J=5.4 Hz, 1H), 7.75 (d, J=1.6 Hz, 1H), 7.66 (s, 1H), 7.29 (dd, J=1.8, 5.3 Hz, 1H), 7.05-7.00 (m, 1H), 6.99-6.94 (m, 2H), 3.12-3.02 (m, 1H), 2.96-2.86 (m, 1H), 2.80-2.69 (m, 1H), 2.67-2.53 (m, 2H), 2.28 (s, 3H), 2.25 (s, 3H), 2.10-2.02 (m, 1H), 1.86-1.74 (m, 1H).

Example 8: 2-(3-chloropyridin-2-yl)-6-(2,4-dimethylphenyl)-5,6,7,8-tetrahydrophthalazin-1(2H)-one, was Prepared According to Scheme 1, Method B

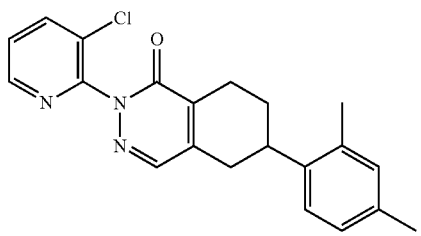

According to Scheme 1 Step viii: Example 8 was prepared as per Example 6, starting from intermediate 7a (200.00 mg, 707.74 μmol) and 2-bromo-3-chloropyridine (408.59 mg, 2.12 mmol), to provide Example 8 (24.40 mg, 66.69 μmol, 9.42% yield) as an off-yellow solid. ¹H-NMR (400 MHz, CDCl₃) δ 8.58 (dd, J=1.6, 4.7 Hz, 1H), 7.95 (dd, J=1.5, 8.0 Hz, 1H), 7.72 (s, 1H), 7.44 (dd, J=4.6, 8.0 Hz, 1H), 7.16-7.11 (m, 1H), 7.10-7.04 (m, 2H), 3.17 (br s, 1H), 3.02 (br d, J=19.6 Hz, 1H), 2.89-2.78 (m, 1H), 2.78-2.61 (m, 2H), 2.38 (s, 3H), 2.34 (s, 3H), 2.20-2.10 (m, 1H), 1.91 (br s, 1H).

Example 9: 6-(2,4-dimethylphenyl)-2-(6-fluoropyridin-2-yl)-5,6,7,8-tetrahydrophthalazin-1(2H)-one, was Prepared According to Scheme 1, Method B

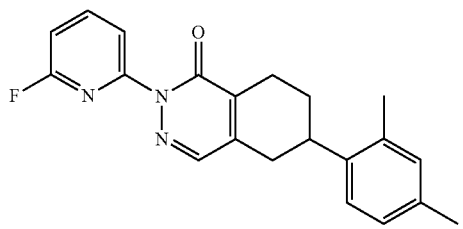 [SMILES: Cc1ccc(C2CCc3c(cnn(-c4cccc(F)n4)c3=O)C2)c(C)c1]

According to Scheme 1 Step viii: Example 9 was prepared as per Example 6, starting from intermediate 7a (70.00 mg, 275.23 μmol) and 2-bromo-6-fluoropyridine (145.31 mg, 825.69 μmol), to provide Example 9 (32.00 mg, 91.59 μmol, 33% yield) as a yellow solid. (¹H-NMR (400 MHz, DMSO-d₆) δ 8.23-8.21 (m, 1H), 7.88 (s, 1H), 7.61-7.59 (m, 1H), 7.36-7.34 (m, 1H), 7.16-7.13 (m, 1H), 7.02-7.00 (m, 2H).

Example 10: 6-(2,4-dimethylphenyl)-2-(5-fluoropyridin-2-yl)-5,6,7,8-tetrahydrophthalazin-1(2H)-one, was Prepared According to Scheme 1, Method B

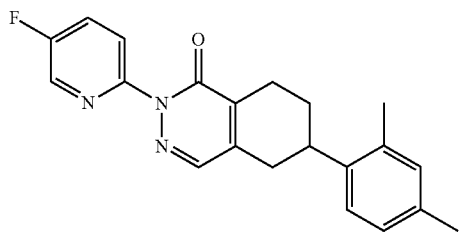 [SMILES: Cc1ccc(C2CCc3c(cnn(-c4ccc(F)cn4)c3=O)C2)c(C)c1]

According to Scheme 1 Step viii: Example 10 was prepared as per Example 6, starting from intermediate 7a (70.00 mg, 275.23 μmol) and 2-bromo-5-fluoropyridine (145.31 mg, 825.69 μmol), to provide Example 10 (32.00 mg, 91.59 μmol, 23% yield) as a yellow solid. (¹H-NMR (400 MHz, DMSO-d₆) δ 8.62-8.61 (m, 1H), 7.97-7.95 (m, 1H), 7.86 (s, 1H), 7.71-7.67 (m, 1H), 7.16-7.14 (m, 1H), 7.02-7.00 (m, 2H), 3.10-3.07 (m, 1H), 2.84-2.70 (m, 4H), 2.30 (s, 3H), 2.25 (s, 3H), 1.94-1.84 (m, 1H), 1.83-1.81 (m, 1H).

Example 11: 6-(2,4-dimethylphenyl)-2-(4-fluoro-pyridin-2-yl)-5,6,7,8-tetrahydrophthalazin-1(2H)-one, was Prepared According to Scheme 1, Method B

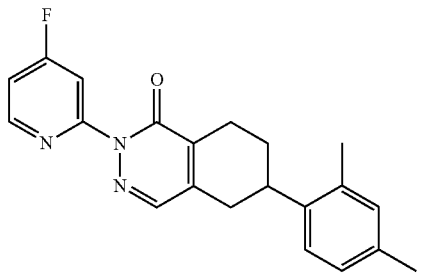 [SMILES: Cc1ccc(C2CCc3c(cnn(-c4cc(F)ccn4)c3=O)C2)c(C)c1]

According to Scheme 1 Step viii: Example 11 was prepared as per Example 6, starting from intermediate 7a (60.00 mg, 235.91 μmol) and 2-bromo-4-fluoropyridine (103.79 mg, 589.78 μmol), to provide Example 11 (24.00 mg, 68.69 μmol, 29% yield) as a yellow solid. $^1$H-NMR (400 MHz, DMSO-$d_6$) δ 8.66 (s, 1H), 7.88 (s, 1H), 7.66-7.61 (m, 1H), 7.53-7.51 (m, 1H), 7.16-7.14 (m, 1H), 7.03-7.00 (m, 2H), 3.08-3.01 (m, 1H), 2.84-2.58 (m, 4H), 2.30 (s, 3H), 2.25 (s, 3H), 1.94-1.84 (m, 1H), 1.83-1.81 (m, 1H).

Example 12: 6-(2,4-dimethylphenyl)-2-(3-fluoro-pyridin-2-yl)-5,6,7,8-tetrahydrophthalazin-1(2H)-one, was Prepared According to Scheme 1, Method B

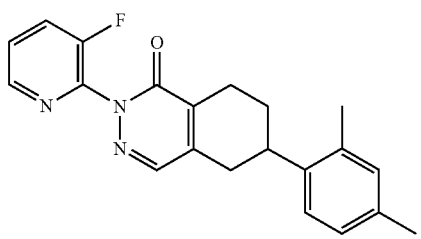

According to Scheme 1 Step viii: Example 12 was prepared as per Example 6, starting from intermediate 7a (90.00 mg, 353.87 μmol) and 2-bromo-3-fluoropyridine (186.83 mg, 1.06 mmol), to provide Example 12 (15.00 mg, 42.93 μmol, 12% yield) as a yellow solid. $^1$H-NMR (400 MHz, DMSO-$d_6$) δ 8.50-8.48 (m, 1H), 8.06-8.01 (m, 1H), 7.92 (s, 1H), 7.72-7.70 (s, 1H), 7.17-7.14 (m, 1H), 7.02-7.00 (m, 2H), 3.11-3.05 (m, 1H), 2.86-2.68 (m, 4H), 2.34 (s, 3H), 2.27 (s, 3H), 1.94-1.83 (m, 2H).

Example 13: 6-(2,4-dimethylphenyl)-2-(6-methoxy-pyridin-2-yl)-5,6,7,8-tetrahydrophthalazin-1(2H)-one, was Prepared According to Scheme 1, Method B

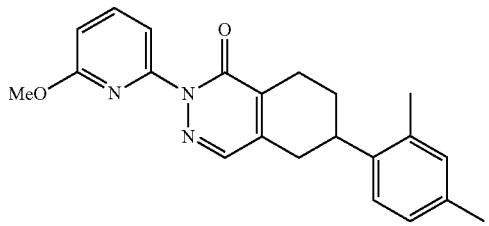 [SMILES: COc1cccc(-n2ncc3c(c2=O)CCC(c2ccc(C)cc2C)C3)n1]

According to Scheme 1 Step viii: Example 13 was prepared as per Example 6, starting from intermediate 7a (70.00 mg, 275.23 μmol) and 2-bromo-4-methoxypyrimidine (129.37 mg, 688.08 μmol, 84.56 μL), to provide Example 13 (45.00 mg, 124.50 μmol, 45% yield) as a yellow solid. $^1$H-NMR (400 MHz, DMSO-$d_6$) δ 7.93-7.84 (m, 1H), 7.84 (s, 1H), 7.16-7.12 (m, 2H), 7.02-7.00 (m, 2H), 6.96-6.94 (m, 1H), 3.83 (s, 3H), 3.10-3.07 (m, 1H), 2.81-2.66 (m, 4H), 2.31 (s, 3H), 2.25 (s, 3H), 1.95-1.93 (m, 1H), 1.83-1.80 (m, 1H).

Example 14: 6-(2,4-dimethylphenyl)-2-(5-methoxy-pyridin-2-yl)-5,6,7,8-tetrahydrophthalazin-1(2H)-one, was Prepared According to Scheme 1, Method B

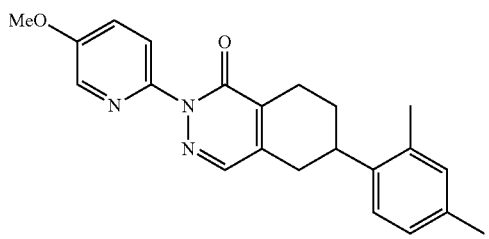 [SMILES: COc1ccc(-n2ncc3c(c2=O)CCC(c2ccc(C)cc2C)C3)nc1]

According to Scheme 1 Step viii: Example 14 was prepared as per Example 6, starting from intermediate 7a (70.00 mg, 275.23 μmol) and 2-bromo-5-methoxypyrimidine (129.37 mg, 688.08 μmol), to provide Example 14 (30.00 mg, 83.00 μmol, 30.16% yield) as a yellow solid. $^1$H-NMR (400 MHz, DMSO-$d_6$) δ 8.28-8.27 (m, 1H), 7.82 (s, 1H), 7.60-7.59 (m, 1H), 7.58-7.57 (m, 1H), 7.16-7.13 (m, 1H), 7.02-7.00 (m, 2H), 3.91 (s, 3H), 3.10-3.07 (m, 1H), 2.93-2.55 (m, 4H), 2.31 (s, 3H), 2.25 (s, 3H), 1.93-1.90 (m, 1H), 1.84-1.80 (m, 1H).

Example 15: 6-(2,4-dimethylphenyl)-2-(4-methoxy-pyridin-2-yl)-5,6,7,8-tetrahydrophthalazin-1(2H)-one, was Prepared According to Scheme 1, Method B

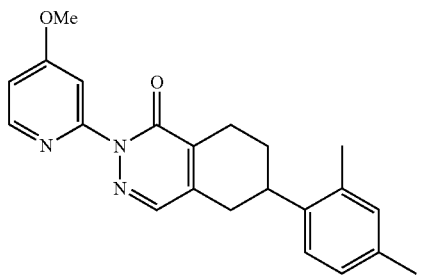

According to Scheme 1 Step viii: Example 15 was prepared as per Example 6, starting from intermediate 7a (70.00 mg, 275.23 μmol) and 2-bromo-4-methoxypyrimidine (129.37 mg, 688.08 μmol), to provide Example 15 (53.00 mg, 146.64 μmol, 53% yield) as a yellow solid. $^1$H-NMR (400 MHz, DMSO-$d_6$) δ 8.41-8.39 (m, 1H), 7.83 (s, 1H), 7.16-7.10 (m, 3H), 7.02-7.00 (m, 1H), 3.89 (s, 3H), 3.07-3.02 (m, 1H), 2.78-2.66 (m, 4H), 2.30 (s, 3H), 2.25 (s, 3H), 1.93-1.83 (m, 1H), 1.82-1.80 (m, 1H).

Example 16: 6-(2,4-dimethylphenyl)-2-(3-methoxy-pyridin-2-yl)-5,6,7,8-tetrahydrophthalazin-1(2H)-one, was Prepared According to Scheme 1, Method B

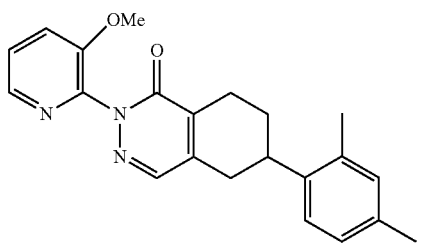 [SMILES: COc1cccnc1-n1ncc2c(c1=O)CCC(c1ccc(C)cc1C)C2]

According to Scheme 1 Step viii: Example 16 was prepared as per Example 6, starting from intermediate 7a (90.00 mg, 353.87 μmol) and 2-bromo-3-methoxypyrimidine (166.34 mg, 884.68 μmol), to provide Example 16 (17.00 mg, 47.03 μmol, 13% yield) as a yellow solid. $^1$H-NMR (400 MHz, DMSO-$d_6$) δ 8.15-8.13 (m, 1H), 7.81 (s, 1H), 7.72-7.70 (m, 1H), 7.57-7.55 (m, 1H), 7.16-7.14 (m, 1H), 7.02-7.00 (m, 2H), 3.80 (s, 3H), 3.10-3.07 (m, 1H), 2.82-2.67 (m, 4H), 2.31 (s, 3H), 2.25 (s, 3H), 1.92-1.81 (m, 2H).

Example 17: 6-(2,4-dimethylphenyl)-2-(6-methylpyridin-2-yl)-5,6,7,8-tetrahydrophthalazin-1(2H)-one, was Prepared According to Scheme 1, Method B

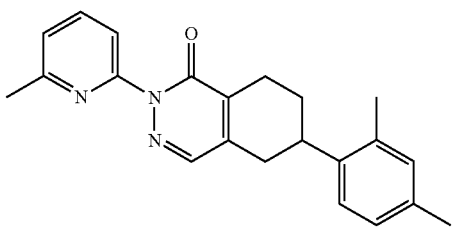

According to Scheme 1 Step viii: Example 17 was prepared as per Example 6, starting from intermediate 7a (80.00 mg, 283.10 μmol) and 2-bromo-6-methylpyridine (146.10 mg, 849.30 μmol, 96.75 μL), to provide Example 17 (59.06 mg, 170.97 μmol, 60.39% yield) as an off-yellow solid. $^1$H-NMR (400 MHz, CDCl$_3$) δ 7.81-7.69 (m, 2H), 7.45 (d, J=7.9 Hz, 1H), 7.24 (d, J=7.7 Hz, 1H), 7.12-7.08 (m, 1H), 7.07-7.02 (m, 2H), 3.19-3.08 (m, 1H), 3.03-2.92 (m, 1H), 2.86-2.76 (m, 1H), 2.73-2.59 (m, 5H), 2.35 (s, 3H), 2.32 (s, 3H), 2.12 (td, J=2.9, 10.4 Hz, 1H), 1.94-1.80 (m, 1H).

Example 18: 6-(2,4-dimethylphenyl)-2-(5-methylpyridin-2-yl)-5,6,7,8-tetrahydrophthalazin-1(2H)-one, was Prepared According to Scheme 1, Method B According to Scheme 1 Step viii: Example 18 was prepared as per Example 6, starting from intermediate 7a (80.00 mg, 283.10 μmol) and 2-bromo-5-methylpyridine (146.10 mg, 849.30 μmol), to provide Example 18 (52.33 mg, 151.49 μmol, 53.51% yield) as an off-yellow solid. $^1$H-NMR (400 MHz, CDCl$_3$) δ 8.49 (d, J=1.5 Hz, 1H), 7.73 (s, 1H), 7.71-7.66 (m, 1H), 7.64-7.60 (m, 1H), 7.14-7.10 (m, 1H), 7.08-7.04 (m, 2H), 3.21-3.09 (m, 1H), 3.06-2.94 (m, 1H), 2.87-2.77 (m, 1H), 2.76-2.60 (m, 2H), 2.43 (s, 3H), 2.37 (s, 3H), 2.34 (s, 3H), 2.19-2.09 (m, 1H), 1.96-1.81 (m, 1H).

Example 19: 6-(2,4-dimethylphenyl)-2-(4-methylpyridin-2-yl)-5,6,7,8-tetrahydrophthalazin-1(2H)-one, was prepared according to Scheme 1, Method B

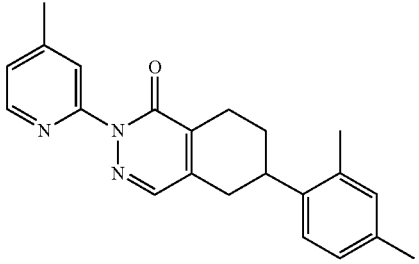 [SMILES: Cc1ccnc(-n2ncc3c(c2=O)CCC(c2ccc(C)cc2C)C3)c1]

According to Scheme 1 Step viii: Example 19 was prepared as per Example 6, starting from intermediate 7a (80.00 mg, 283.10 μmol) and 2-bromo-4-methylpyridine (146.10 mg, 849.30 μmol, 94.26 μL), to provide Example 19 (69.51 mg, 201.22 μmol, 71.08% yield) as a white solid. $^1$H-NMR (400 MHz, CDCl$_3$) δ 8.53 (d, J=5.1 Hz, 1H), 7.74 (s, 1H), 7.56 (s, 1H), 7.14-7.10 (m, 1H), 7.08-7.04 (m, 1H), 7.08-7.04 (m, 2H), 3.22-3.07 (m, 1H), 3.06-2.95 (m, 1H), 2.87-2.78 (m, 1H), 2.76-2.61 (m, 2H), 2.47 (s, 3H), 2.37 (s, 3H), 2.34 (s, 3H), 2.20-2.09 (m, 1H), 1.97-1.80 (m, 1H).

Example 20: 6-(2,4-dimethylphenyl)-2-(3-methylpyridin-2-yl)-5,6,7,8-tetrahydrophthalazin-1(2H)-one, was Prepared According to Scheme 1, Method B

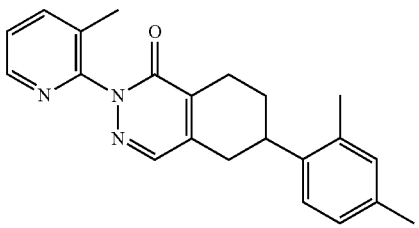 [SMILES: Cc1ccc(C2CCc3c(cnn(-c4ncccc4C)c3=O)C2)c(C)c1]

According to Scheme 1 Step viii: Example 20 was prepared as per Example 6, starting from intermediate 7a (80.00 mg, 283.10 μmol) and 2-bromo-3-methylpyridine (146.09 mg, 849.30 μmol), to provide Example 20 (8.60 mg, 24.75 μmol, 8.74% yield) as off-yellow solid. $^1$H-NMR (400 MHz, CDCl$_3$) δ 8.55-8.44 (m, 1H), 7.74 (d, J=6.7 Hz, 1H), 7.71 (s, 1H), 7.36 (dd, J=4.8, 7.7 Hz, 1H), 7.16-7.11 (m, 1H), 7.10-7.04 (m, 2H), 3.16 (br s, 1H), 3.07-2.94 (m, 1H), 2.88-2.78 (m, 1H), 2.77-2.61 (m, 2H), 2.38 (s, 3H), 2.36-2.33 (m, 1H), 2.34 (s, 3H), 2.27 (s, 3H), 2.20-2.09 (m, 1H), 1.98-1.83 (m, 1H).

Example 21: 6-(6-(2,4-dimethylphenyl)-1-oxo-5,6,7,8-tetrahydrophthalazin-2(1H)-yl)picolinonitrile, was Prepared According to Scheme 1, Method B

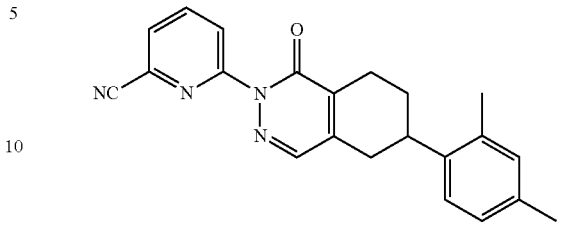

According to Scheme 1 Step viii: Example 21 was prepared as per Example 6, starting from intermediate 7a (80.00 mg, 283.10 μmol) and 6-bromopicolinonitrile (155.43 mg, 849.30 μmol), to provide Example 21 (53.43 mg, 146.31 μmol, 51.68% yield) as a white solid. $^1$H-NMR (400 MHz, CDCl$_3$) δ 8.05-7.99 (m, 2H), 7.81-7.75 (m, 2H), 7.13-7.10 (m, 1H), 7.08-7.05 (m, 2H), 3.21-3.11 (m, 1H), 2.99 (br dd, J=5.3, 19.1 Hz, 1H), 2.89-2.80 (m, 1H), 2.78-2.59 (m, 2H), 2.37 (s, 3H), 2.34 (s, 3H), 2.20-2.11 (m, 1H), 1.96-1.82 (m, 1H).

Example 22: 6-(6-(2,4-dimethylphenyl)-1-oxo-5,6,7,8-tetrahydrophthalazin-2(1H)-yl)nicotinonitrile, was Prepared According to Scheme 1, Method B

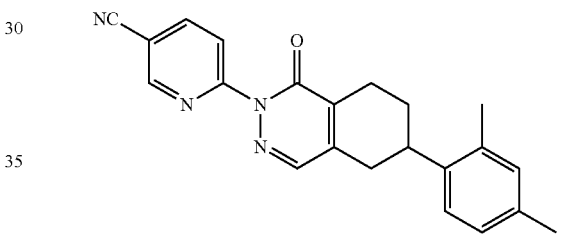

According to Scheme 1 Step viii: Example 22 was prepared as per Example 6, starting from intermediate 7a (80.00 mg, 283.10 μmol) and 6-bromonicotinonitrile (155.43 mg, 849.30 μmol), to provide Example 22 (21.19 mg, 59.45 μmol, 21.00% yield) as a white solid. $^1$H-NMR (400 MHz, CDCl$_3$) δ 8.86 (s, 1H), 8.03 (d, J=2.3 Hz, 1H), 7.98-7.91 (m, 1H), 7.73-7.67 (m, 1H), 6.98 (d, J=17.4 Hz, 3H), 3.13-3.01 (m, 1H), 2.97-2.85 (m, 1H), 2.79-2.70 (m, 1H), 2.68-2.52 (m, 2H), 2.27 (s, 3H), 2.25 (s, 3H), 2.11-2.02 (m, 1H), 1.87-1.74 (m, 1H).

Example 23: 2-(6-(2,4-dimethylphenyl)-1-oxo-5,6,7,8-tetrahydrophthalazin-2(1H)-yl)isonicotinonitrile, was Prepared According to Scheme 1, Method B

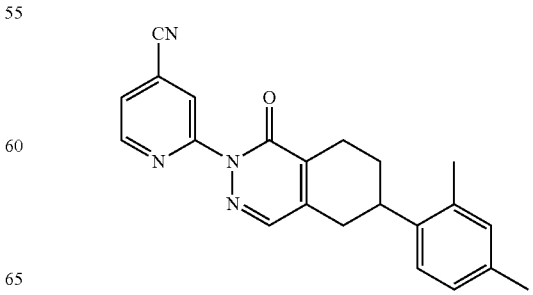

According to Scheme 1 Step viii: Example 23 was prepared as per Example 6, starting from intermediate 7a (80.00 mg, 283.10 μmol) and 2-bromoisonicotinonitrile (17.27 mg, 94.37 μmol), to provide Example 23 (28.72 mg, 80.58 μmol, 28.46% yield) as a white solid. $^1$H-NMR (400 MHz, CDCl$_3$) δ 8.85 (d, J=4.4 Hz, 1H), 8.13 (s, 1H), 7.78 (s, 1H), 7.59 (dd, J=1.3, 5.0 Hz, 1H), 7.16-7.03 (m, 3H), 3.22-3.12 (m, 1H), 3.06-2.96 (m, 1H), 2.89-2.80 (m, 1H), 2.79-2.62 (m, 2H), 2.37 (s, 3H), 2.34 (s, 3H), 2.21-2.12 (m, 1H), 1.98-1.83 (m, 1H).

Example 24: 2-(6-(2,4-dimethylphenyl)-1-oxo-5,6,7,8-tetrahydrophthalazin-2(1H)-yl)nicotinonitrile, was Prepared According to Scheme 1, Method B

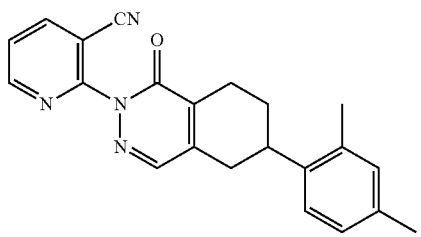 [SMILES: Cc1ccc(C2CCc3c(cnn(-c4ncccc4C#N)c3=O)C2)c(C)c1]

According to Scheme 1 Step viii: Example 24 was prepared as per Example 6, starting from intermediate 7a (80.00 mg, 283.10 μmol) and 2-bromonicotinonitrile (155.43 mg, 849.30 μmol), to provide Example 24 (8.80 mg, 24.69 μmol, 8.72% yield) as a white solid. $^1$H-NMR (400 MHz, CDCl$_3$) δ 8.88 (d, J=5.0 Hz, 1H), 8.20 (d, J=7.9 Hz, 1H), 7.75 (s, 1H), 7.61-7.52 (m, 1H), 7.15-7.04 (m, 3H), 3.22-3.13 (m, 1H), 3.08-3.00 (m, 1H), 2.88-2.79 (m, 1H), 2.78-2.64 (m, 2H), 2.38 (s, 3H), 2.34 (s, 3H), 2.15 (br s, 1H), 1.99-1.83 (m, 1H).

Example 25: 6-(2,4-dimethylphenyl)-2-(5-hydroxypyridin-2-yl)-5,6,7,8-tetrahydrophthalazin-1(2H)-one, was Prepared According to Scheme 1, Method B

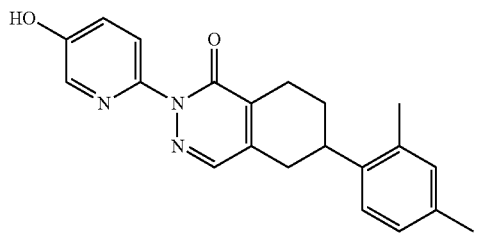 [SMILES: Cc1ccc(C2CCc3c(cnn(-c4ccc(O)cn4)c3=O)C2)c(C)c1]

According to Scheme 1 Step viii: Example 25 was prepared as per Example 6, starting from intermediate 7a (100.00 mg, 353.87 μmol) and 6-bromo-3-hydroxypyridine (184.72 mg, 1.06 mmol), to provide Example 25 (42.10 mg, 115.12 μmol, 32.53% yield) as an off-white solid. $^1$H-NMR (400 MHz, CDCl$_3$) δ 8.74 (s, 1H), 8.24 (dd, J=1.8, 4.8 Hz, 1H), 7.87 (dd, J=1.6, 7.8 Hz, 1H), 7.19 (dd, J=4.8, 7.8 Hz, 1H), 7.15-7.11 (m, 1H), 7.09-7.04 (m, 2H), 3.26-3.16 (m, 1H), 3.15-3.06 (m, 1H), 3.04-2.96 (m, 1H), 2.92-2.80 (m, 2H), 2.37 (s, 3H), 2.34 (s, 3H), 2.24-2.14 (m, 1H), 2.04-1.95 (m, 1H).

Example 26: 6-(2,4-dimethylphenyl)-2-(4-hydroxypyridin-2-yl)-5,6,7,8-tetrahydrophthalazin-1(2H)-one

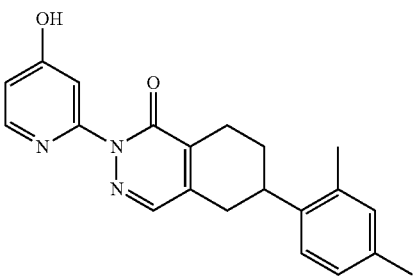 [SMILES: Cc1ccc(C2CCc3c(cnn(-c4cc(O)ccn4)c3=O)C2)c(C)c1]

To a solution of compound Example 15 (200.00 mg, 553.34 μmol, 1.00 eq) in CH$_2$Cl$_2$ (5.00 mL) was added BBr$_3$ (693.11 mg, 2.77 mmol, 266.58 μL, 5.00 eq). The mixture was stirred at 40° C. for 12 hours and desired product was detected. The mixture was added to water (30 mL), exerted with ethyl acetate (30 mL×3). The organic layer was dried over Na$_2$SO$_4$, filtered and concentrated under reduced pressure and the residue was purified by prep-TLC (PE:EtOAc=0:1). Example 26 (130.00 mg, 370.46 μmol, 66.95% yield) was obtained as a white solid. $^1$H-NMR (400 MHz, DMSO-d$_6$) δ 8.26 (br d, J=4.5 Hz, 1H), 7.81 (s, 1H), 7.15 (br d, J=7.9 Hz, 1H), 7.05-6.96 (m, 2H), 6.86 (br s, 2H), 3.07 (br s, 1H), 2.85-2.59 (m, 3H), 2.58-2.53 (m, 1H), 2.31 (s, 3H), 2.25 (s, 3H), 1.93 (br s, 1H), 1.88-1.75 (m, 1H).

Example 27: 6-(2,4-dimethylphenyl)-2-(5-(methoxymethyl)pyridin-2-yl)-5,6,7,8-tetrahydrophthalazin-1(2H)-one, was Prepared According to Scheme 1, Method B

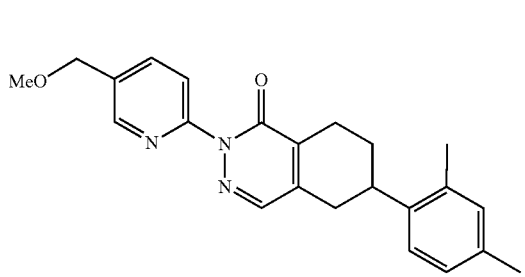 [SMILES: COCc1ccc(-n2ncc3c(c2=O)CCC(c2ccc(C)cc2C)C3)nc1]

According to Scheme 1 Step viii: Example 27 was prepared as per Example 6, starting from intermediate 7a (100.00 mg, 353.87 μmol) and 2-bromo-5-(methoxymethyl)pyridine (214.50 mg, 1.06 mmol), to provide Example 27 (56.21 mg, 149.71 μmol, 42.31% yield) as a white solid. $^1$H-NMR (400 MHz, CDCl$_3$) δ 8.74 (s, 1H), 8.24 (dd, J=1.8, 4.8 Hz, 1H), 7.87 (dd, J=1.6, 7.8 Hz, 1H), 7.19 (dd, J=4.8, 7.8 Hz, 1H), 7.15-7.11 (m, 1H), 7.09-7.04 (m, 2H), 3.26-3.16 (m, 1H), 3.15-3.06 (m, 1H), 3.04-2.96 (m, 1H), 2.92-2.80 (m, 2H), 2.37 (s, 3H), 2.34 (s, 3H), 2.24-2.14 (m, 1H), 2.04-1.95 (m, 1H).

Example 28: 6-(2,4-dimethylphenyl)-2-(pyridin-3-yl)-5,6,7,8-tetrahydrophthalazin-1(2H)-one, was Prepared According to Scheme 1, Method B

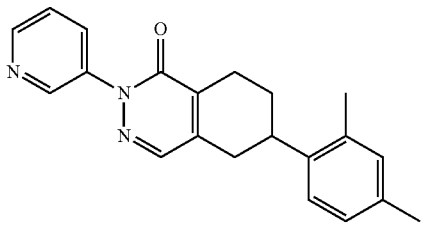 [SMILES: Cc1ccc(C2CCc3c(cnn(-c4cccnc4)c3=O)C2)c(C)c1]

According to Scheme 1 Step viii: Example 28 was prepared as per Example 6, starting from intermediate 7a (80.00 mg, 283.10 μmol) and 3-bromopyridine (134.19 mg, 849.30 μmol, 81.82 μL), to provide Example 28 (32.83 mg, 99.06 μmol, 34.99% yield) as a white solid. $^1$H-NMR (400 MHz, CDCl$_3$) δ 9.04-8.91 (m, 1H), 8.63 (br s, 1H), 8.09 (br d, J=8.3 Hz, 1H), 7.73 (d, J=1.9 Hz, 1H), 7.44 (br s, 1H), 7.18-7.01 (m, 3H), 3.16 (br s, 1H), 3.02 (br d, J=19.2 Hz, 1H), 2.88-2.79 (m, 1H), 2.77-2.61 (m, 2H), 2.37 (s, 3H), 2.34 (s, 3H), 2.17 (br d, J=13.1 Hz, 1H), 1.91 (br d, J=11.8 Hz, 1H).

Example 29: 6-(2,4-dimethylphenyl)-2-(pyrimidin-2-yl)-5,6,7,8-tetrahydrophthalazin-1(2H)-one, was Prepared According to Scheme 1, Method B

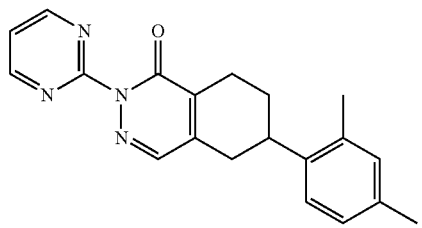 [SMILES: Cc1ccc(C2CCc3c(cnn(-c4ncccn4)c3=O)C2)c(C)c1]

According to Scheme 1 Step viii: Example 29 was prepared as per Example 6, starting from intermediate 7a (780 mg, 3.07 mmol) and 2-bromopyrimidine (585.11 mg, 3.68 mmol), to provide Example 29 (383.35 mg, 1.12 mmol, 36.48% yield) as white solid. $^1$H-NMR (400 MHz, CDCl$_3$) δ 8.95 (d, J=4.9 Hz, 2H), 7.71 (s, 1H), 7.44 (t, J=4.8 Hz, 1H), 7.14-7.10 (m, 1H), 7.08-7.04 (m, 2H), 3.21-3.11 (m, 1H), 3.08-2.98 (m, 1H), 2.87-2.78 (m, 1H), 2.76-2.63 (m, 2H), 2.37 (s, 3H), 2.34 (s, 3H), 2.14 (br dd, J=5.8, 13.5 Hz, 1H), 1.95-1.83 (m, 1H).

Example 30: 6-(2,4-dimethylphenyl)-2-(pyrazin-2-yl)-5,6,7,8-tetrahydrophthalazin-1(2H)-one, was Prepared According to Scheme 1, Method B

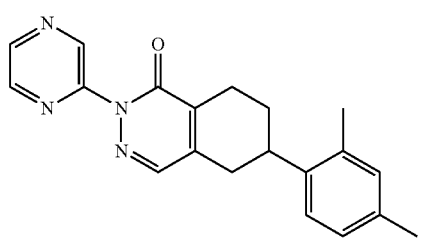 [SMILES: Cc1ccc(C2CCc3c(cnn(-c4cnccn4)c3=O)C2)c(C)c1]

According to Scheme 1 Step viii: Example 30 was prepared as per Example 6, starting from intermediate 7a (80.00 mg, 283.10 μmol) and 2-bromopyrazine (135.02 mg, 849.30 μmol), to provide Example 30 (48.17 mg, 144.92 μmol, 51.19% yield) as an off-yellow solid. $^1$H-NMR (400 MHz, CDCl$_3$) δ 9.05 (d, J=1.1 Hz, 1H), 8.60-8.50 (m, 1H), 7.69 (s, 1H), 7.05-7.01 (m, 1H), 7.00-6.94 (m, 2H), 3.13-3.02 (m, 1H), 3.13-3.02 (m, 1H), 2.98-2.87 (m, 1H), 2.80-2.71 (m, 1H), 2.69-2.54 (m, 2H), 2.28 (s, 3H), 2.25 (s, 3H), 2.12-2.02 (m, 1H), 1.88-1.74 (m, 1H).

Example 31: 6-(2,4-dimethylphenyl)-2-(pyrimidin-5-yl)-5,6,7,8-tetrahydrophthalazin-1(2H)-one, was Prepared According to Scheme 1, Method B

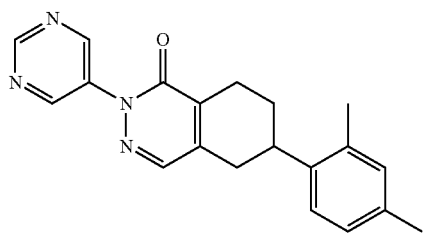 [SMILES: Cc1ccc(C2CCc3c(cnn(-c4cncnc4)c3=O)C2)c(C)c1]

According to Scheme 1 Step viii: Example 31 was prepared as per Example 6, starting from intermediate 7a (80.00 mg, 283.10 μmol) and 5-bromopyrimidine (135.02 mg, 849.30 μmol), to provide Example 31 (24.80 mg, 74.61 μmol, 26.35% yield) as a brown solid. $^1$H-NMR (400 MHz, CDCl$_3$) δ 9.23 (s, 2H), 9.19 (s, 1H), 7.74 (s, 1H), 7.12-7.08 (m, 1H), 7.08-7.03 (m, 2H), 3.20-3.10 (m, 1H), 3.06-2.95 (m, 1H), 2.87-2.77 (m, 1H), 2.76-2.60 (m, 2H), 2.36 (s, 3H), 2.33 (s, 3H), 2.21-2.11 (m, 1H), 1.95-1.82 (m, 1H).

Example 32: 6-(2,4-dimethylphenyl)-2-(thiazol-2-yl)-5,6,7,8-tetrahydrophthalazin-1(2H)-one, was prepared according to Scheme 1, Method B

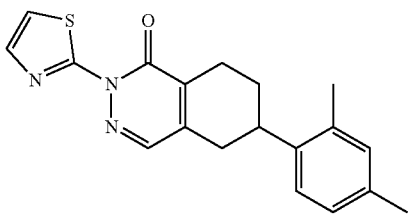 [SMILES: Cc1ccc(C2CCc3c(cnn(-c4nccs4)c3=O)C2)c(C)c1]

According to Scheme 1 Step viii: Example 32 was prepared as per Example 6, starting from intermediate 7a (120.00 mg, 471.83 μmol) and 2-bromothiazole (116.08 mg, 707.75 μmol, 63.78 μL), to provide Example 32 (12.00 mg, 34.51 μmol, 8.76% yield) as a yellow solid. $^1$H-NMR (400 MHz, CDCl$_3$) δ 1.84-1.96 (m, 1H) 2.12-2.21 (m, 1H) 2.33 (s, 3H) 2.36 (s, 3H) 2.66-2.81 (m, 2H) 2.82-2.92 (m, 1H) 3.07 (br dd, J=19.89, 5.08 Hz, 1H) 3.12-3.20 (m, 1H) 7.05 (br d, J=5.77 Hz, 2H) 7.07-7.12 (m, 1H) 7.30 (d, J=3.39 Hz, 1H) 7.81 (d, J=3.39 Hz, 1H) 7.90 (s, 1H).

Example 33: 6-(2,4-dimethylphenyl)-2-(thiazol-4-yl)-5,6,7,8-tetrahydrophthalazin-1(2H)-one, was Prepared According to Scheme 1, Method B

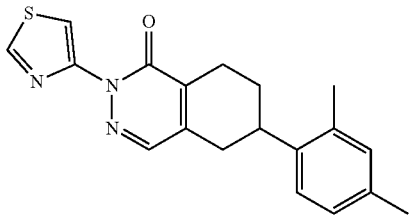 [SMILES: Cc1ccc(C2CCc3c(cnn(-c4cscn4)c3=O)C2)c(C)c1]

According to Scheme 1 Step viii: Example 33 was prepared as per Example 6, starting from intermediate 7a (80.00 mg, 314.55 umol) and 4-bromothiazole (77.39 mg, 471.83 µmol, 42.52 µL), to provide Example 33 (8.00 mg, 23.44 µmol, 7.45% yield) as an off-white solid. $^1$H-NMR (400 MHz, CDCl$_3$) δ 7.89 (s, 1H), 7.65 (s, 2H), 7.14 (d, J=8.4 Hz, 1H), 7.06-6.96 (m, 2H), 3.82 (s, 3H), 3.23-3.11 (m, 1H), 2.97-2.82 (m, 2H), 2.81-2.71 (m, 1H), 2.70-2.57 (m, 1H), 2.36 (s, 3H), 2.29 (s, 3H), 2.14-2.04 (m, 1H), 1.98-1.83 (m, 1H).

Example 34: 6-(2,4-dimethylphenyl)-2-(1-methyl-1H-imidazol-4-yl)-5,6,7,8-tetrahydrophthalazin-1(2H)-one, was Prepared According to Scheme 1, Method B

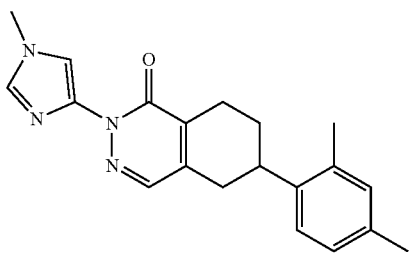 [SMILES: Cc1ccc(C2CCc3c(cnn(-c4cn(C)cn4)c3=O)C2)c(C)c1]

According to Scheme 1 Step viii: Example 34 was prepared as per Example 6, starting from intermediate 7a (100.00 mg, 353.87 µmol) and 4-bromo-1-methyl-1H-imidazole (113.95 mg, 707.74 µmol), to provide Example 34 (10.61 mg, 31.72 µmol, 8.97% yield) as a white solid. $^1$H-NMR (400 MHz, MeOD) δ 7.89 (s, 1H), 7.65 (s, 2H), 7.14 (d, J=8.4 Hz, 1H), 7.06-6.96 (m, 2H), 3.82 (s, 3H), 3.23-3.11 (m, 1H), 2.97-2.82 (m, 2H), 2.81-2.71 (m, 1H), 2.70-2.57 (m, 1H), 2.36 (s, 3H), 2.29 (s, 3H), 2.14-2.04 (m, 1H), 1.98-1.83 (m, 1H)

Example 35: 6-(2,4-dimethylphenyl)-2-(4-methoxypyrimidin-2-yl)-5,6,7,8-tetrahydrophthalazin-1(2H)-one, was Prepared According to Scheme 1, Method B

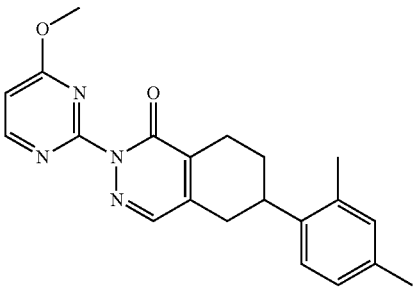 [SMILES: COc1ccnc(-n2ncc3c(c2=O)CCC(c2ccc(C)cc2C)C3)n1]

According to Scheme 1 Step viii: Example 35 was prepared as per Example 6, starting from intermediate 7a (0.2 g, 786.39 µmol) and 2-chloro-4-methoxypyrimidine (136.42 mg, 943.67 µmol), to provide Example 35 (0.118 g, 323.05 µmol, 41.08% yield) as white solid. $^1$H-NMR (400 MHz, CDCl$_3$) δ 8.60 (s, 1H), 7.74 (s, 1H), 7.15-7.00 (m, 3H), 6.87 (d, J=5.6 Hz, 1H), 4.06 (s, 3H), 3.21-3.10 (m, 1H), 3.09-3.01 (m, 1H), 2.88-2.79 (m, 1H), 2.77-2.61 (m, 2H), 2.36 (s, 3H), 2.33 (s, 3H), 2.18-2.10 (m, 1H), 1.95-1.81 (m, 1H).

Example 36: 6-(2,4-dimethylphenyl)-2-(4,6-dimethylpyrimidin-2-yl)-5,6,7,8-tetrahydrophthalazin-1(2H)-one, was Prepared According to Scheme 1, Method B

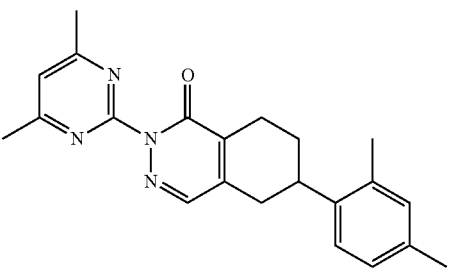

According to Scheme 1 Step viii: Example 36 was prepared as per Example 6, starting from intermediate 7a (0.2 g, 786.39 µmol) and 2-chloro-4,6-dimethylpyrimidine (168.19 mg, 1.18 mmol), to provide Example 36 (0.034 g, 89.61 µmol, 11.40% yield) as white solid. $^1$H-NMR (400 MHz, CDCl$_3$) δ 7.69 (s, 1H), 7.15 (s, 1H), 7.12-7.07 (m, 1H), 7.06-7.02 (m, 2H), 3.18-3.07 (m, 1H), 2.98-2.90 (m, 1H), 2.85-2.76 (m, 1H), 2.74-2.65 (m, 2H), 2.35 (s, 3H), 2.32 (s, 3H), 2.16-2.05 (m, 1H), 1.92-1.78 (m, 1H).

Example 37: 2-(4-cyclopropylpyrimidin-2-yl)-6-(2,4-dimethylphenyl)-5,6,7,8-tetrahydrophthalazin-1(2H)-one, was Prepared According to Scheme 1, Method B

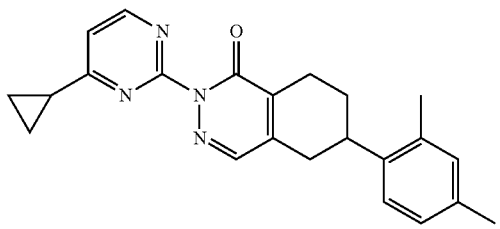 [SMILES: Cc1ccc(C2CCc3c(cnn(-c4nccc(C5CC5)n4)c3=O)C2)c(C)c1]

According to Scheme 1 Step viii: Example 37 was prepared as per Example 6, starting from intermediate 7a (0.2 g, 786.39 µmol) and 2-chloro-4-cyclopropylpyrimidine (145.89 mg, 943.67 µmol), to provide Example 37 (0.029 g, 77.86 µmol, 9.90% yield) was obtained as a white solid. $^1$H-NMR (400 MHz, CDCl$_3$) δ 8.64 (d, J=4.4 Hz, 1H), 7.65 (s, 1H), 7.18 (d, J=4.8 Hz, 1H), 7.13-7.07 (m, 1H), 7.06-6.97 (m, 2H), 3.14-3.11 (m, 1H), 3.04-2.92 (m, 1H), 2.84-2.74 (m, 1H), 2.69-2.63 (m, 2H), 2.35 (s, 3H), 2.32 (s, 3H), 2.15-2.08 (m, 2H), 1.92-1.85 (m, 1H), 1.28-1.12 (m, 4H).

Example 38: 2-(5-hydroxypyridin-2-yl)-6-(3-methoxy-2-methylphenyl)-5,6,7,8-tetrahydrophthalazin-1(2H)-one, was Prepared According to Scheme 1, Method B

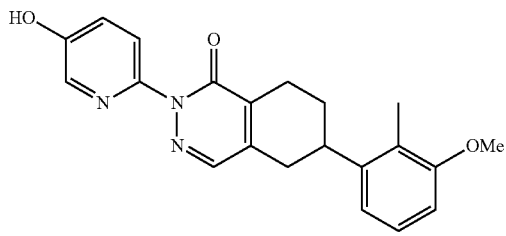 [SMILES: COc1cccc(C2CCc3c(cnn(-c4ccc(O)cn4)c3=O)C2)c1C]

Intermediate 6d: 3-methoxy-5-(3-methoxy-2-methylphenyl)-4,5,6,7-tetrahydroiso-benzofuran-1(3H)-one According to Scheme 1 Step i to v: Intermediate 6d was prepared similarly to intermediate 6a in Example 1, starting from 1-bromo-3-methoxy-2-methylbenzene, and was obtained with an overall yield 15% as a brown liquid. m/z (M+H)$^+$=289.1.

Intermediate 7b: 6-(3-methoxy-2-methylphenyl)-5,6,7,8-tetrahydrophthalazin-1(2H)-one According to Scheme 1 Step vii: Intermediate 7b was prepared similarly to intermediate 7a in Example 6, starting from Intermediate 6d (21.30 g, 73.87 mmol), to provide Intermediate 7b 15.30 g, 56.60 mmol, 76.62% yield) as white solid. $^1$H NMR (400 MHz, DMSO-d6) δ 12.76 (br s, 1H), 7.65 (s, 1H), 7.10-7.18 (m, 1H), 6.84 (t, J=8.72 Hz, 2H), 3.77 (s, 3H), 3.10 (br s, 1H), 2.55-2.75 (m, 3H), 2.35-2.47 (m, 1H), 2.15 (s, 3H), 1.90 (br s, 1H), 1.76 (dq, J=4.89, 11.84 Hz, 1H).

Example 38: 2-(5-hydroxypyridin-2-yl)-6-(3-methoxy-2-methylphenyl)-5,6,7,8-tetrahydrophthalazin-1(2H)-one According to Scheme 1 Step viii: Example 38 was prepared as per Example 6, starting from intermediate 7b (150.00 mg, 554.88 µmol) and 6-bromo-3-hydroxypyridine (115.86 mg, 665.85 µmol), to provide Example 38 (72.80 mg, 200.12 µmol, 36.07% yield) as white solid. $^1$H-NMR (400 MHz, DMSO-d$_6$) δ 10.40 (br s, 1H), 8.04-8.10 (m, 1H), 7.80 (s, 1H), 7.29-7.36 (m, 2H), 7.14-7.21 (m, 1H), 6.89 (d, J=7.65 Hz, 1H), 6.85 (d, J=8.16 Hz, 1H), 3.78 (s, 3H), 3.09-3.21 (m, 1H), 2.62-2.82 (m, 3H), 2.52-2.59 (m, 1H), 2.17 (s, 3H), 1.89-2.01 (m, 1H), 1.74-1.87 (m, 1H).

Example 39: 2-(5-(hydroxymethyl)pyridin-2-yl)-6-(3-methoxy-2-methylphenyl)-5,6,7,8-tetrahydrophthalazin-1(2H)-one, was Prepared According to Scheme 1, Method B

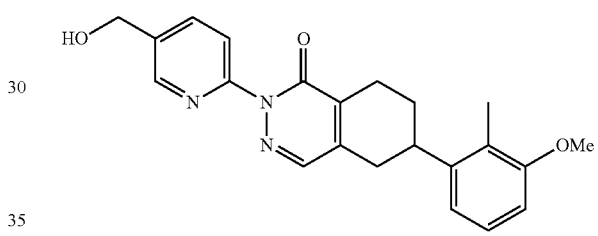

According to Scheme 1 Step viii: Example 39 was prepared as per Example 6, starting from intermediate 7b (150.00 mg, 554.88 µmol) and (6-bromopyridin-3-yl)methanol (125.19 mg, 665.86 µmol), to provide Example 39 (81.97 mg, 216.96 µmol, 39.10% yield) as white solid. $^1$H-NMR (400 MHz, DMSO-d$_6$) δ 8.52 (d, J=1.63 Hz, 1H), 7.92 (dd, J=2.20, 8.09 Hz, 1H), 7.84 (s, 1H), 7.52 (d, J=8.16 Hz, 1H), 7.18 (t, J=7.97 Hz, 1H), 6.89 (d, J=7.78 Hz, 1H), 6.85 (d, J=8.16 Hz, 1H), 5.45 (t, J=5.71 Hz, 1H), 4.62 (d, J=5.52 Hz, 2H), 3.78 (s, 3H), 3.12-3.22 (m, 1H), 2.64-2.86 (m, 3H), 2.55 (br d, J=9.66 Hz, 1H), 2.18 (s, 3H), 1.94 (br s, 1H), 1.78-1.89 (m, 1H).

Example 40: 6-(3-methoxy-2-methylphenyl)-2-(pyrimidin-2-yl)-5,6,7,8-tetrahydrophthalazin-1(2H)-one, was Prepared According to Scheme 1, Method B

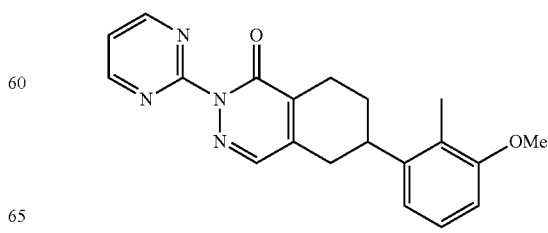

According to Scheme 1 Step viii: Example 40 was prepared as per Example 6, starting from intermediate 7b (150.00 mg, 554.88 μmol) and 5-bromopyrimidine (105.86 mg, 665.86 μmol), to provide Example 40 (45.56 mg, 128.81 μmol, 23.21% yield) as a brown solid. $^1$H-NMR (400 MHz, DMSO-$d_6$) δ 9.02 (d, J=4.89 Hz, 2H), 7.85 (s, 1H), 7.71 (t, J=4.89 Hz, 1H), 7.14-7.21 (m, 1H), 6.87 (dd, J=7.97, 17.63 Hz, 2H), 3.78 (s, 3H), 3.14-3.24 (m, 1H), 2.78-2.87 (m, 1H), 2.66-2.77 (m, 2H), 2.56 (br d, J=10.04 Hz, 1H), 2.18 (s, 3H), 1.94 (br s, 1H), 1.78-1.91 (m, 1H).

Example 41: 6-(3-methoxy-2-methylphenyl)-2-(5-methylpyrimidin-2-yl)-5,6,7,8-tetrahydrophthalazin-1(2H)-one, was Prepared According to Scheme 1, Method B

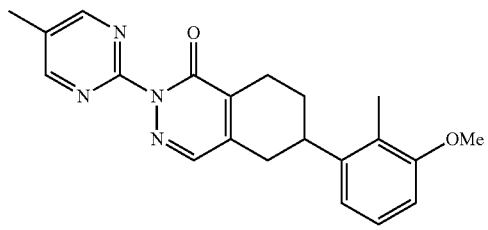 [SMILES: COc1cccc(C2CCc3c(cnn(-c4ncc(C)cn4)c3=O)C2)c1C]

According to Scheme 1 Step viii: Example 41 was prepared as per Example 6, starting from intermediate 7b (150.00 mg, 554.88 μmol) and 2-bromo-5-methylpyrimidine (116.51 mg, 665.86 μmol), to provide Example 41 (75.16 mg, 206.05 μmol, 37.13% yield) as a white solid. $^1$H-NMR (400 MHz, DMSO-$d_6$) δ 8.84 (s, 2H), 7.83 (s, 1H), 7.14-7.23 (m, 1H), 6.87 (dd, J=7.91, 16.69 Hz, 2H), 3.78 (s, 3H), 3.13-3.23 (m, 1H), 2.64-2.87 (m, 3H), 2.52-2.60 (m, 1H), 2.38 (s, 3H), 2.18 (s, 3H), 1.94 (br s, 1H), 1.75-1.90 (m, 1H).

Example 42: 6-(3-methoxy-2-methylphenyl)-2-(4-methoxypyrimidin-2-yl)-5,6,7,8-tetrahydrophthalazin-1(2H)-one, was Prepared According to Scheme 1, Method B

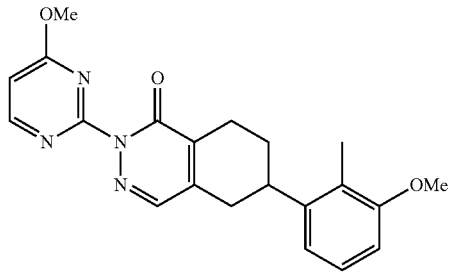 [SMILES: COc1ccnc(-n2ncc3c(c2=O)CCC(c2cccc(OC)c2C)C3)n1]

According to Scheme 1 Step viii: Example 42 was prepared as per Example 6, starting from intermediate 7b (150.00 mg, 554.88 μmol) and 2-bromo-4-methoxypyrimidine (125.85 mg, 665.85 μmol), to provide Example 42 (97.29 mg, 256.84 μmol, 46.29% yield) as red solid. $^1$H-NMR (400 MHz, DMSO-$d_6$) δ 8.69 (d, J=5.77 Hz, 1H), 7.83 (s, 1H), 7.18 (t, J=7.97 Hz, 1H), 7.13 (d, J=5.90 Hz, 1H), 6.89 (d, J=7.65 Hz, 1H), 6.85 (d, J=8.16 Hz, 1H), 3.93 (s, 3H), 3.78 (s, 3H), 3.13-3.24 (m, 1H), 2.64-2.86 (m, 3H), 2.56 (br d, J=9.41 Hz, 1H), 2.18 (s, 3H), 1.94 (br s, 1H), 1.78-1.90 (m, 1H).

Example 43: 2-(5-chloropyrimidin-2-yl)-6-(3-methoxy-2-methylphenyl)-5,6,7,8-tetrahydrophthalazin-1(2H)-one, was Prepared According to Scheme 1, Method B

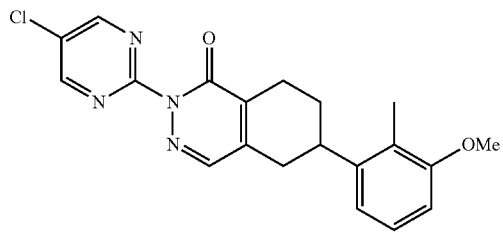 [SMILES: COc1cccc(C2CCc3c(cnn(-c4ncc(Cl)cn4)c3=O)C2)c1C]

According to Scheme 1 Step viii: Example 43 was prepared as per Example 6, starting from intermediate 7b (150.00 mg, 554.88 μmol) and 2-bromo-5-chloropyrimidine (128.80 mg, 665.86 μmol), to provide Example 43 (98.84 mg, 257.92 μmol, 46.48% yield) as a white solid. $^1$H-NMR (400 MHz, DMSO-$d_6$)) δ 9.16 (s, 2H), 7.87 (s, 1H), 7.15-7.20 (m, 1H), 6.89 (d, J=7.65 Hz, 1H), 6.85 (d, J=8.03 Hz, 1H), 3.78 (s, 3H), 3.12-3.24 (m, 1H), 2.78-2.86 (m, 1H), 2.65-2.76 (m, 2H), 2.53-2.61 (m, 1H), 2.18 (s, 3H), 1.91-2.00 (m, 1H), 1.76-1.90 (m, 1H).

Example 44: 6-(3-methoxy-2-methylphenyl)-2-(5-methoxypyrazin-2-yl)-5,6,7,8-tetrahydrophthalazin-1(2H)-one, was Prepared According to Scheme 1, Method B

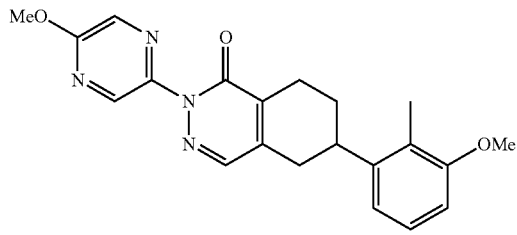 [SMILES: COc1cnc(-n2ncc3c(c2=O)CCC(c2cccc(OC)c2C)C3)cn1]

According to Scheme 1 Step viii: Example 44 was prepared as per Example 6, starting from intermediate 7b (150.00 mg, 554.88 μmol) and 2-bromo-5-methoxypyrazine (125.85 mg, 665.86 μmol), to provide Example 44 (111.11 mg, 290.09 μmol, 52.28% yield) as a white solid. $^1$H-NMR (400 MHz, DMSO-$d_6$) δ 8.47 (d, J=1.25 Hz, 1H), 8.35 (d, J=1.25 Hz, 1H), 7.89 (s, 1H), 7.14-7.22 (m, 1H), 6.89 (d, J=7.65 Hz, 1H), 6.85 (d, J=8.16 Hz, 1H), 3.99 (s, 3H), 3.78 (s, 3H), 3.10-3.22 (m, 1H), 2.64-2.86 (m, 3H), 2.56 (br d, J=9.41 Hz, 1H), 2.18 (s, 3H), 1.94 (br s, 1H), 1.78-1.89 (m, 1H).

Example 45: 2-(5-hydroxypyrimidin-2-yl)-6-(3-methoxy-2-methylphenyl)-5,6,7,8-tetrahydrophthalazin-1(2H)-one, was Prepared According to Scheme 1, Method B

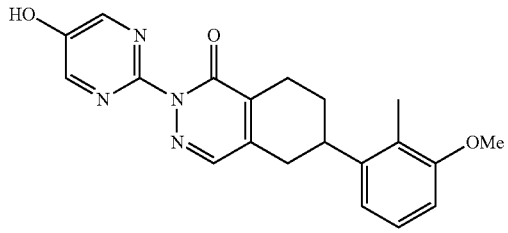 [SMILES: COc1cccc(C2CCc3c(cnn(-c4ncc(O)cn4)c3=O)C2)c1C]

According to Scheme 1 Step viii: Example 45 was prepared as per Example 6, starting from intermediate 7b (450 mg, 1.66 mmol) and 2-bromo-5-hydroxypyrimidine (349.55 mg, 2.00 mmol), to provide Example 45 (520 mg, 1.43 mmol, 85.72% yield) as a brown solid. $^1$H-NMR (400 MHz, DMSO-$d_6$) δ 8.43 (s, 2H), 7.79 (s, 1H), 7.14-7.21 (m, 1H), 6.89 (d, J=7.78 Hz, 1H), 6.85 (d, J=8.28 Hz, 1H), 3.76-3.81 (m, 3H), 3.11-3.25 (m, 1H), 2.67-2.84 (m, 3H), 2.55-2.60 (m, 1H), 2.18 (s, 3H), 1.93 (br s, 1H), 1.76-1.89 (m, 1H).

Example 46: 6-(3-methoxy-2-methylphenyl)-2-(4-morpholinopyrimidin-2-yl)-5,6,7,8-tetrahydrophthalazin-1(2H)-one, was Prepared According to Scheme 1, Method B

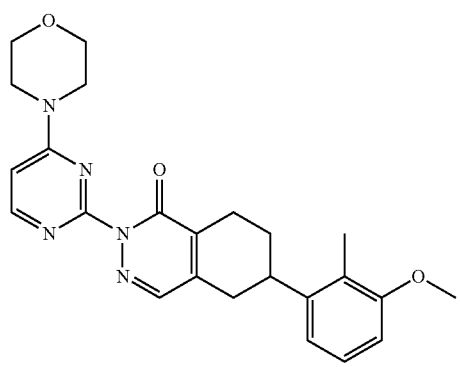 [SMILES: COc1cccc(C2CCc3c(cnn(-c4nccc(N5CCOCC5)n4)c3=O)C2)c1C]

According to Scheme 1 Step viii: Example 46 was prepared as per Example 6, starting from intermediate 7b (70 mg, 258.95 μmol) and 4-(2-bromopyrimidin-4-yl)morpholine (75.85 mg, 310.74 μmol), to provide Example 46 (32.49 mg, 74.12 μmol, 28.62% yield) as off-white solid. $^1$H-NMR (400 MHz, DMSO-$d_6$) δ 8.35 (d, J=6.15 Hz, 1H), 7.77 (s, 1H), 7.15-7.21 (m, 1H), 6.96 (d, J=6.27 Hz, 1H), 6.89 (d, J=7.78 Hz, 1H), 6.85 (d, J=8.16 Hz, 1H), 3.79 (s, 3H), 3.67 (br d, J=5.02 Hz, 4H), 3.62 (br d, J=4.77 Hz, 4H), 3.17 (br t, J=8.97 Hz, 1H), 2.62-2.83 (m, 3H), 2.52-2.59 (m, 1H), 2.18 (s, 3H), 1.93 (br s, 1H), 1.83 (dq, J=4.83, 11.90 Hz, 1H).

Example 47: 6-(5-methoxy-2-methylphenyl)-2-(5-methylpyrimidin-2-yl)-5,6,7,8-tetrahydrophthalazin-1(2H)-one, was Prepared According to Scheme 1, Method B

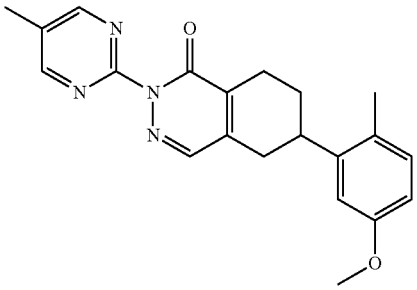 [SMILES: COc1ccc(C)c(C2CCc3c(cnn(-c4ncc(C)cn4)c3=O)C2)c1]

Intermediate 6e: 3-methoxy-5-(5-methoxy-2-methylphenyl)-4,5,6,7-tetrahydroisobenzofuran-1(3H)-one According to Scheme 1 Steps i to v: Intermediate 6e was prepared similarly to intermediate 6a in example 1, starting from 2-bromo-4-methoxy-1-methylbenzene, and was obtained with an overall yield of 9.3% as a yellow solid. $^1$H NMR: (CDCl$_3$, 400 MHz) δ 7.02 (d, J=8.4 Hz, 1H), 6.70-6.61 (m, 2H), 5.58 (s, 1H), 3.71 (s, 3H), 3.51 (s, 3H), 3.05-2.90 (m, 1H), 2.47-2.36 (m, 2H), 2.31-2.14 (m, 5H), 1.94-1.86 (m, 1H), 1.75-1.62 (m, 1H).

Intermediate 7c: 6-(5-methoxy-2-methylphenyl)-5,6,7,8-tetrahydrophthalazin-1(2H)-one According to Scheme 1 Step vii: Intermediate 7c was prepared similarly to intermediate 7a in Example 6, starting from intermediate 6e (1.30 g, 4.51 mmol) to provide intermediate 7c (0.4 g, 1.48 mmol, 32.82% yield) as white solid. $^1$H NMR: (CDCl$_3$, 400 MHz) δ 7.55 (s, 1H), 7.09 (d, J=8.0 Hz, 1H), 6.73-6.68 (m, 2H), 3.78 (s, 3H), 3.12-3.08 (m, 1H), 2.93-2.91 (m, 1H), 2.74-2.71 (m, 1H), 2.65-2.58 (m, 2H), 2.28 (s, 3H), 2.13-2.09 (m, 1H), 1.90-1.69 (m, 1H).

Example 47: 6-(5-methoxy-2-methylphenyl)-2-(5-methylpyrimidin-2-yl)-5,6,7,8-tetrahydro-phthalazin-1(2H)-one According to Scheme 1 Step viii: Example 47 was prepared as per Example 6, starting from intermediate 7c (0.1 g, 369.92 μmol) and 2-chloro-5-methylpyrimidine (142.67 mg, 1.11 mmol), to provide Example 47 (0.005 g, 13.80 μmol, 3.73% yield) as yellow solid. $^1$H-NMR (400 MHz, CDCl$_3$) δ 8.75 (s, 2H), 7.70 (s, 1H), 7.12 (br d, J=8.4 Hz, 1H), 6.77 (s, 1H), 6.72 (m, d, J=8.4 Hz, 1H), 3.80 (s, 3H), 3.17-2.96 (m, 2H), 2.87-2.76 (m, 1H), 2.71-2.65 (m, 2H), 2.43 (s, 3H), 2.31 (s, 3H), 2.15-2.11 (m, 1H), 1.90-1.85 (m, 1H).

Example 48: 6-(5-methoxy-2-methylphenyl)-2-(5-methoxypyrimidin-2-yl)-5,6,7,8-tetrahydrophthalazin-1(2H)-one, was Prepared According to Scheme 1, Method B

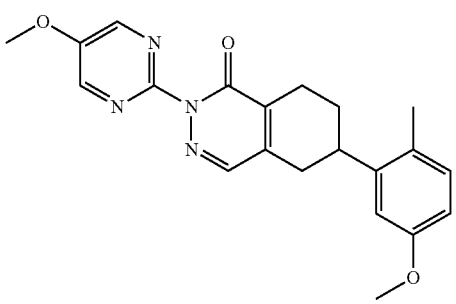 [SMILES: COc1cnc(-n2ncc3c(c2=O)CCC(c2cc(OC)ccc2C)C3)nc1]

According to Scheme 1 Step viii: Example 48 was prepared as per Example 6, starting from intermediate 7c (0.1 g, 369.92 μmol) and 2-chloro-5-methoxypyrimidine (160.43 mg, 1.11 mmol), to provide Example 48 (0.003 g, 7.93 μmol, 2.14% yield) as white solid. $^1$H-NMR (400 MHz, CDCl$_3$) δ 8.46 (s, 2H), 7.59 (s, 1H), 7.04 (d, J=8.4 Hz, 1H), 6.73-6.64 (m, 2H), 3.93 (s, 3H), 3.73 (s, 3H), 3.04-2.97 (m, 2H), 2.71-2.46 (m, 3H), 2.23 (s, 3H), 2.08 (m, 1H), 1.80 (m, 1H).

Example 49: 2-(5-chloropyrimidin-2-yl)-6-(5-methoxy-2-methylphenyl)-5,6,7,8-tetrahydrophthalazin-1(2H)-one, was Prepared According to Scheme 1, Method B

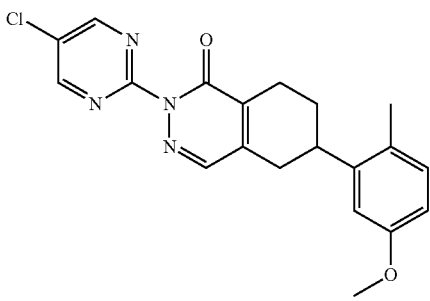 [SMILES: COc1ccc(C)c(C2CCc3c(cnn(-c4ncc(Cl)cn4)c3=O)C2)c1]

According to Scheme 1 Step viii: Example 49 was prepared as per Example 6, starting from intermediate 7c (0.1 g, 369.92 μmol) and 2-bromo-5-chloropyrimidine (214.66 mg, 1.11 mmol), to provide Example 49 (0.011 g, 28.73 μmol, 7.77% yield) as white solid. $^1$H-NMR (400 MHz, CDCl$_3$) δ 8.85 (s, 2H), 7.69 (s, 1H), 7.12 (d, J=8.4 Hz, 1H), 6.76 (s, 1H), 6.72 (dd, J=8.0, 2.4 Hz, 1H), 3.80 (s, 3H), 3.18-3.08 (m, 1H), 3.07-2.97 (m, 1H), 2.86-2.76 (m, 1H), 2.71-2.65 (m, 2H), 2.31 (s, 3H), 2.15 (m, 1H), 1.88-1.81 (m, 1H).

Example 50: 6-(2,4-dimethylphenyl)-2-(pyridin-4-yl)-5,6,7,8-tetrahydrophthalazin-1(2H)-one, was Prepared According to Scheme 1, Method B

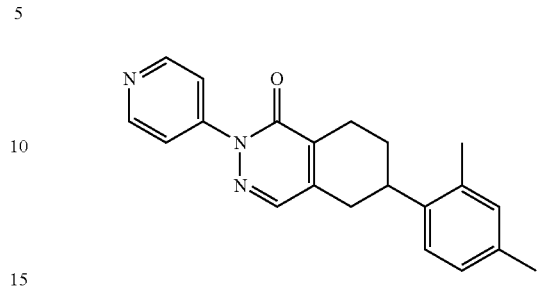

According to Scheme 1 Step ix: To a mixture of intermediate 7a (150.00 mg, 530.81 μmol, 1.00 eq), 4-pyridiyl boronic acid (130.49 mg, 1.06 mmol, 2.00 eq) in dioxane (5.00 mL) was added DMAP (194.55 mg, 1.59 mmol, 3.00 eq), pyridine (41.99 mg, 530.81 μmol, 42.84 μL, 1.00 eq) and Cu(OAc)$_2$ (96.41 mg, 530.81 μmol, 1.00 eq). The mixture was heated to 90° C. and stirred for 12 hour. The reactant mixture was filtered, the filtrate was acidified to pH=5 with 12 M HCl and filtered. The obtained solution was purified by pre-HPLC to give Example 50 (8.98 mg, 26.01 μmol, 4.90% yield) as a yellow solid. $^1$H-NMR (400 MHz, DMSO-d$_6$) δ 8.76 (br s, 2H), 7.97 (s, 1H), 7.78 (br s, 2H), 7.15 (d, J=8.5 Hz, 1H), 7.04-6.98 (m, 2H), 3.13-3.01 (m, 1H), 2.86-2.73 (m, 2H), 2.71-2.64 (m, 1H), 2.63-2.55 (m, 1H), 2.30 (s, 3H), 2.25 (s, 3H), 2.00-1.91 (m, 1H), 1.88-1.75 (m, 1H).

Example 51: 2-(5-chloropyrimidin-2-yl)-6-(2,4-dimethylphenyl)-5,6,7,8-tetrahydrophthalazin-1(2H)-one, was Prepared According to Scheme 1, Method C

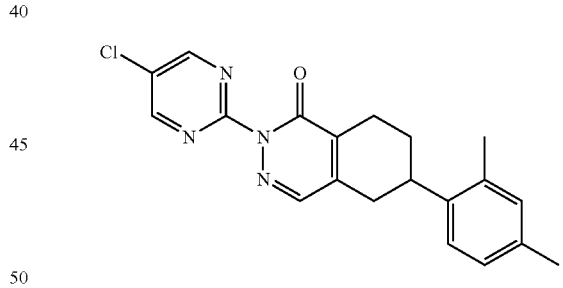

Intermediate 6a': 5-formyl-2',4'-dimethyl-1,2,3,6-tetrahydro-[1,1'-biphenyl]-4-carboxylic acid A solution of intermediate 6a (6 g, 22.03 mmol, 1 eq) in MeOH (100 mL) was added NaOH (2.64 g, 66.09 mmol, 3 eq) in H$_2$O (40 mL), then stirred at 20° C. for 24 hours. The organic solvent was removed under reduced pressure. The residue was acidified to pH=3 by addition 2N HCl at 20° C., and then extracted with EtOAc (30 mL×3). The combined organic layers were washed with brine to pH=7, dried over Na$_2$SO$_4$, filtered and concentrated under reduced pressure. The residue was purified by silica gel chromatography (PE/EtOAc=50/1, 1/1) to afford intermediate 6a' (2 g, 7.74 mmol, 35.14% yield) as a light-yellow oil. $^1$H NMR (400 MHz, CDCl$_3$) δ 7.16-6.93 (m, 3H), 6.03 (s, 1H), 3.20-3.01

(m, 1H), 2.79-2.64 (m, 1H), 2.56-2.42 (m, 2H), 2.36-2.31 (m, 7H), 2.04-1.96 (m, 1H), 1.90-1.73 (m, 1H).

Intermediate 8a: Ethyl 5-formyl-2',4'-dimethyl-1,2,3,6-tetrahydro-[1,1'-biphenyl]-4-carboxylate According the scheme 1, step x: To a solution of intermediate 6a' (2 g, 7.74 mmol, 1 eq) in DMF (20 mL) was added TMG (1.34 g, 11.61 mmol, 1.46 mL, 1.5 eq) at 20° C. After addition, the mixture was stirred at this temperature for half an hour. Ethyl iodide (3.02 g, 19.36 mmol, 1.55 mL, 2.5 eq) was added at 20° C. and the resulting mixture was immediately heated at 45° C. for 14 hours. The solvent was removed under reduced pressure. The residue was dissolved in water (20 mL), and then adjusted pH=4 with 4N HCl and extracted with EtOAc (15 mL×3). The combined organic layers were washed with water (10 mL×2), dried over $Na_2SO_4$, filtered and concentrated under reduced pressure. The residue was purified by silica gel chromatography (PE/EtOAc=20/1, 1/1) to afford intermediate 8a (1.8 g, 6.29 mmol, 81.18% yield) as a yellow oil.
$^1$H NMR (400 MHz, $CDCl_3$) δ 10.08 (s, 1H), 7.13-6.94 (m, 3H), 4.34 (q, J=7.2 Hz, 2H), 3.00-2.88 (m, 1H), 2.83-2.71 (m, 2H), 2.70-2.57 (m, 1H), 2.31 (s, 6H), 2.25-2.13 (m, 1H), 1.99 (m, 1H), 1.87-1.72 (m, 1H), 1.38 (t, J=7.2 Hz, 3H).

Example 51: (2-(5-chloropyrimidin-2-yl)-6-(2,4-dimethylphenyl)-5,6,7,8-tetrahydro-phthalazin-1(2H)-one According the scheme 1, step xii: To a mixture of intermediate 8a (53.08 mg, 367.19 µmol, 1 eq) in EtOH (10 mL) and AcOH (5 mL) was added 2-hydrazineyl-5-chloropyrimidine (105.15 mg, 367.19 µmol, 1 eq) in one portion at 20° C. The mixture was stirred at 100° C. for 12 hours. The mixture was filtered and concentrated in vacuo. The residue was purified by prep-HPLC to afford Example 51 (0.009 g, 24.53 µmol, 6.68% yield) as a white solid. $^1$H-NMR (400 MHz, $CDCl_3$) δ 8.86 (s, 2H), 7.69 (s, 1H), 7.16-6.99 (m, 3H), 3.14 (m, 1H), 3.01 (m, 1H), 2.86-2.77 (m, 1H), 2.75-2.60 (m, 2H), 2.35 (s, 3H), 2.33 (s, 3H), 2.12 (m, 1H), 1.93-1.82 (m, 1H).

Example 52: 6-(2,4-dimethylphenyl)-2-(5-methylpyrimidin-2-yl)-5,6,7,8-tetrahydrophthalazin-1(2H)-one, was Prepared According to Scheme 1, Method C

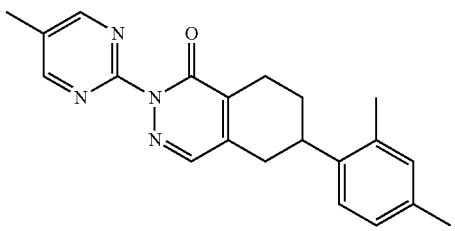

According the scheme 1, step xii: Example 52 was prepared as per Example 51, starting from intermediate 8a (105.15 mg, 367.19 µmol) and 2-hydrazineyl-5-methylpyrimidine (45.58 mg, 367.19 µmol), to provide Example 52 (0.023 g, 66.39 µmol, 18.08% yield) as white solid. $^1$H-NMR (400 MHz, $CDCl_3$) δ 8.74 (s, 2H), 7.68 (s, 1H), 7.16-6.99 (m, 3H), 3.14 (m, 1H), 3.06-2.96 (m, 1H), 2.86-2.76 (m, 1H), 2.69 (m, 2H), 2.43 (s, 3H), 2.36 (s, 3H), 2.32 (s, 3H), 2.16-2.08 (m, 1H), 1.93-1.81 (m, 1H).

Example 53: 6-(2,4-dimethylphenyl)-2-(5-methoxypyrimidin-2-yl)-5,6,7,8-tetrahydrophthalazin-1(2H)-one, was Prepared According to Scheme 1, Method C

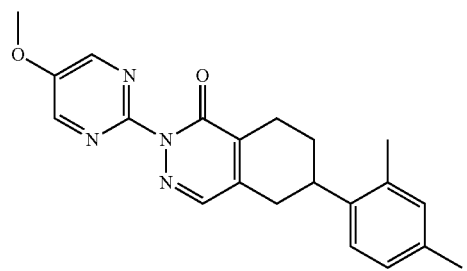 [SMILES: COc1cnc(-n2ncc3c(c2=O)CCC(c2ccc(C)cc2C)C3)nc1]

According the scheme 1, step xii: Example 53 was prepared as per Example 51, starting from intermediate 8a (105.15 mg, 367.19 µmol) and 2-hydrazineyl-5-methoxypyrimidine (51.46 mg, 367.19 µmol), to provide Example 53 (0.059 g, 161.16 µmol, 43.89% yield) as white solid. $^1$H-NMR (400 MHz, $CDCl_3$) δ 8.53 (s, 2H), 7.67 (s, 1H), 7.15-6.97 (m, 3H), 4.00 (s, 3H), 3.14 (br s, 1H), 2.99 (m, 1H), 2.85-2.76 (m, 1H), 2.74-2.59 (m, 2H), 2.35 (s, 3H), 2.32 (s, 3H), 2.12 (m, 1H), 1.87 (m, 1H).

Example 54: 6-(2,4-dimethylphenyl)-2-(5-fluoropyrimidin-2-yl)-5,6,7,8-tetrahydrophthalazin-1(2H)-one, was Prepared According to Scheme 1, Method C

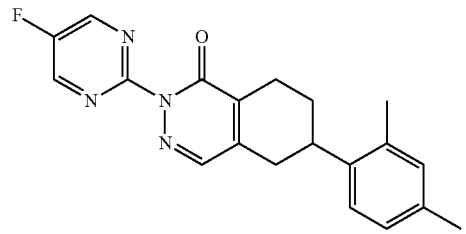

According the scheme 1, step xii: Example 54 was prepared as per Example 51, starting from intermediate 8a (105.15 mg, 367.19 µmol) and 5-fluoro-2-hydrazineylpyrimidine (47.04 mg, 367.19 µmol), to provide Example 54 (0.077 g, 217.32 µmol, 59.18% yield) as white solid. $^1$H-NMR (400 MHz, $CDCl_3$) δ 8.77 (s, 2H), 7.68 (s, 1H), 7.13-6.99 (m, 3H), 3.15 (m, 1H), 3.00 (m, 1H), 2.87-2.77 (m, 1H), 2.70 (m, 2H), 2.36 (s, 3H), 2.32 (s, 3H), 2.15-2.08 (m, 1H), 1.95-1.82 (m, 1H).

Example 55: 6-(2,4-dimethylphenyl)-2-(5-(trifluoromethyl)pyrimidin-2-yl)-5,6,7,8-tetrahydrophthalazin-1(2H)-one, was Prepared According to Scheme 1, Method C

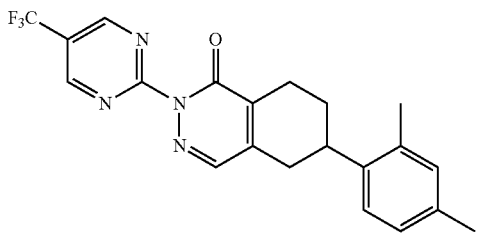 [SMILES: Cc1ccc(C2CCc3c(cnn(-c4ncc(C(F)(F)F)cn4)c3=O)C2)c(C)c1]

According the scheme 1, step xii: Example 55 was prepared as per Example 51, starting from intermediate 8a (105.15 mg, 367.19 μmol) and 2-hydrazineyl-5-(trifluoromethyl)pyrimidine (65.40 mg, 367.19 μmol), to provide Example 55 (0.023 g, 55.36 μmol, 15.08% yield) as white solid. $^1$H-NMR (400 MHz, CDCl$_3$) δ 9.08 (s, 2H), 7.65 (s, 1H), 7.08-6.96 (m, 3H), 3.21-3.10 (m, 1H), 3.07-2.97 (m, 1H), 2.87-2.78 (m, 1H), 2.36 (s, 3H), 2.33 (s, 3H), 2.14 (m, 1H), 1.95-1.83 (m, 1H).

Example 56: 6-(2,4-dimethylphenyl)-2-(4-methoxy-5-methylpyrimidin-2-yl)-5,6,7,8-tetrahydrophthalazin-1(2H)-one, was Prepared According to Scheme 1, Method C

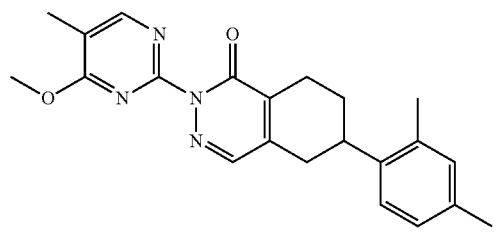

Intermediate 56': 2-(5-bromo-4-methoxypyrimidin-2-yl)-6-(2,4-dimethylphenyl)-5,6,7,8-tetrahydrophthalazin-1(2H)-one According the scheme 1, step xii: Intermediate 56' was prepared as per Example 51, starting from intermediate 8a (392.32 mg, 1.37 mmol) and 5-bromo-2-hydrazineyl-4-methoxypyrimidine (0.3 g, 1.37 mmol), to provide intermediate 56' (0.17 g, 385.21 μmol, 28.12% yield) as white solid. $^1$H NMR (400 MHz, CDCl$_3$) δ 8.71 (s, 1H), 7.66 (s, 1H), 7.14-6.99 (m, 3H), 4.13 (s, 3H), 3.20-3.08 (m, 1H), 3.04-2.94 (m, 1H), 2.85-2.75 (m, 1H), 2.75-2.65 (m, 2H), 2.35 (s, 3H), 2.32 (s, 3H), 2.19-2.09 (m, 1H), 1.92-1.85 (m, 1H).

Example 56: 6-(2,4-dimethylphenyl)-2-(4-methoxy-5-methylpyrimidin-2-yl)-5,6,7,8-tetrahydrophthalazin-1(2H)-one To a mixture of methylboronic acid (27.13 mg, 453.19 μmol) and intermediate 56' (0.1 g, 226.59 μmol) in dioxane (10 mL) was added Pd(dppf)Cl$_2$ (16.58 mg, 22.66 μmol, 0.1 eq) and K$_2$CO$_3$ (93.95 mg, 679.78 μmol, 3 eq) in one portion at 20° C. under N$_2$. The mixture was stirred at 100° C. for 12 hours. The mixture was filtered and concentrated under reduced pressure. The residue was purified by prep-HPLC to afford Example 56 (0.044 g, 116.27 μmol, 51.31% yield) as white solid. $^1$H-NMR (400 MHz, CDCl$_3$) δ 8.71 (s, 1H), 7.66 (s, 1H), 7.14-6.99 (m, 3H), 4.13 (s, 3H), 3.20-3.08 (m, 1H), 3.04-2.94 (m, 1H), 2.85-2.75 (m, 1H), 2.75-2.65 (m, 2H), 2.35 (s, 3H), 2.32 (s, 3H), 2.19-2.09 (m, 1H), 1.92-1.85 (m, 1H).

Example 57: 6-(2,4-dimethylphenyl)-2-(5-(morpholinomethyl)pyrimidin-2-yl)-5,6,7,8-tetrahydrophthalazin-1(2H)-one, was Prepared According to Scheme 1, Method C

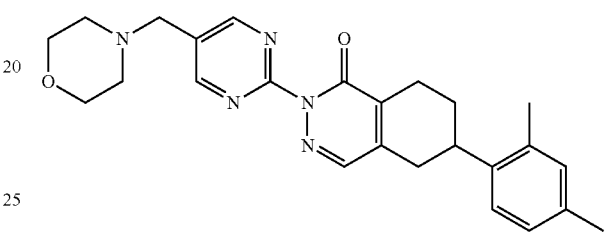

According the scheme 1, step xii: Example 57 was prepared as per Example 51, starting from intermediate 8a (105.15 mg, 367.19 μmol) and 4-((2-hydrazineylpyrimidin-5-yl)methyl)morpholine (76.83 mg, 367.19 μmol), to provide Example 57 (0.023 g, 53.30 μmol, 14.52% yield) as white solid. $^1$H-NMR (400 MHz, CDCl$_3$) δ 8.87 (s, 2H), 7.69 (s, 1H), 7.17-6.98 (m, 3H), 3.78-3.70 (m, 4H), 3.60 (s, 2H), 3.15 (m, 1H), 3.01 (m, 1H), 2.87-2.76 (m, 1H), 2.70 (m, 1H), 2.75-2.61 (m, 1H), 2.51 (m, 4H), 2.36 (s, 3H), 2.32 (s, 3H), 2.11 (m, 1H), 1.95-1.81 (m, 1H).

Example 58: 6-(2-methoxyphenyl)-2-(pyridin-2-yl)-5,6,7,8-tetrahydrophthalazin-1(2H)-one, was Prepared According to Scheme 2, Method A

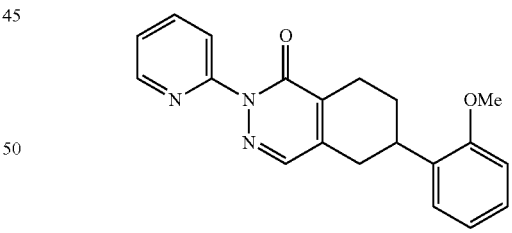

Intermediate 10: 8-chloro-1,4-dioxaspiro[4.5]dec-7-ene-7-carbaldehyde

According to scheme 2, step i: To a solution of DMF (187.11 g, 2.56 mol, 196.96 mL, 2.00 eq) in CH$_2$Cl$_2$ (2.00 L) was added POCl$_3$ (490.66 g, 3.20 mol, 297.37 mL, 2.50 eq) dropwise at 0° C. The mixture was stirred at 0° C. for 2 h. Then 1,4-dioxaspiro[4.5]decan-8-one (200.00 g, 1.28 mol, 1.00 eq) in CH$_2$Cl$_2$ (500.00 mL) was added dropwise at 0° C. The reaction mixture was stirred at 0° C. for 2 h. The reaction mixture poured into saturated NaHCO$_3$ aqueous (2 L) and keep at pH>7 by added solid NaHCO$_3$, extracted by CH$_2$Cl$_2$ (5 L×2), CH$_2$Cl$_2$ phase was concentrated. The obtained residue was purified by column chromatography (PE/EtOAc=20/1). Intermediate 56a (120.00 g, 506.34 mmol, 39.56% yield) was obtained as a yellow oil. $^1$H NMR (400 MHz, CDCl$_3$) δ 10.19-10.10 (m, 1H), 4.05-3.94 (m, 4H), 2.91-2.75 (m, 2H), 2.57-2.42 (m, 2H), 1.99-1.83 (m, 2H).

Intermediate 11: methyl 7-formyl-1,4-dioxaspiro
[4.5]dec-7-ene-8-carboxylate

According to scheme 2, step ii: To a solution of intermediate 10 (122.00 g, 514.78 mmol, 1.00 eq) in MeOH (800.00 mL) and DMA (400.00 mL) was added Pd(OAc)$_2$ (17.34 g, 77.22 mmol, 0.15 eq), DPPF (42.81 g, 77.22 mmol, 0.15 eq) and AcONa (84.45 g, 1.03 mol, 2.00 eq). The reaction was stirred at 80° C. under CO (50 Psi) for 12 h. The reaction mixture was filtered and the filtrate was concentrated and the residue was poured into water (2000 mL×2), extracted by ethyl acetate (2000 mL×3). The combined organic layers were washed by saturated salt water (1000 ml×3) and then concentrated under reduced pressure. The residue was purified by column chromatography (PE:EtOAc=20:1 to 3:1). Intermediate 11 (78.50 g, 329.64 mmol, 64.04% yield) was obtained as a yellow oil. $^1$H NMR (400 MHz, CDCl$_3$) δ 5.61 (d, J=1.1 Hz, 1H), 4.03-3.99 (m, 4H), 3.53 (s, 3H), 2.62-2.53 (m, 1H), 2.49-2.40 (m, 3H), 1.85 (t, J=6.3 Hz, 2H).

Intermediate 12: 7,8-dihydro-2H-spiro[phthalazine-6,2'-[1,3]dioxolan]-1(5H)-one

According to scheme 2, step iii: To a solution of intermediate 11 (78.50 g, 329.64 mmol, 1.00 eq) in EtOH (750.00 mL) and AcOH (75.00 mL) was added N$_2$H$_4$·H$_2$O (33.68 g, 659.28 mmol, 32.70 mL, 2.00 eq). The mixture was stirred at 80° C. for 12 hours. The reactant mixture was concentrated and adjusted to pH=7 with saturated NaHCO$_3$ aqueous solution. Then it was extracted with CH$_2$Cl$_2$ (30.00 mL×3). The combined organic layer was dried over Na$_2$SO$_4$, filtered and concentrated. Intermediate 12 (66.00 g, 316.99 mmol, 96.16% yield) was obtained as a yellow solid.

$^1$H NMR (400 MHz, DMSO-d$_6$) δ 7.58 (s, 1H), 3.93 (s, 4H), 2.72 (s, 2H), 2.54 (br t, J=6.7 Hz, 2H), 1.80 (t, J=6.7 Hz, 2H).

Intermediate 13a: 2-(pyridin-2-yl)-7,8-dihydro-2H-spirolphthalazine-6,2'-[1,3]dioxolan]-1(5H)-one According to scheme 2, step v: To a solution of intermediate 12 (40.00 g, 192.11 mmol, 1.00 eq) and 2-bromo pyridine (36.42 g, 230.53 mmol, 21.94 mL, 1.20 eq) in dioxane (500.00 mL) was added CuI (7.32 g, 38.42 mmol, 0.20 eq), (1S,2S)—N$^1$,N$^2$-dimethylcyclohexane-1,2-diamine (5.47 g, 38.42 mmol, 0.20 eq) and K$_3$PO$_4$ (101.95 g, 480.28 mmol, 2.50 eq). The mixture was stirred at 100° C. for 12 hours. The reaction was filtered and concentrated. The filter cake was washed by CH$_2$Cl$_2$ (200 mL×3). The residue was added water (2.0 L) and extracted with CH$_2$Cl$_2$ (1.0 L×3). The combined organic layer was dried over Na$_2$SO$_4$, filtered and concentrated. The residue was re-crystallized from MTBE (100 mL) at 20° C. Intermediate 13a (56.00 g, crude) was obtained as a gray solid. $^1$H NMR (400 MHz, CDCl$_3$) δ 8.67 (br s, 1H), 7.92-7.79 (m, 1H), 7.68 (br s, 2H), 7.35 (br s, 1H), 4.04 (s, 4H), 2.87 (br t, J=6.0 Hz, 2H), 2.81 (s, 2H), 1.94 (br t, J=6.5 Hz, 2H).

Intermediate 14a: 2-(pyridin-2-yl)-7,8-dihydrophthalazine-1,6(2H,5H)-dione

According to scheme 2, step vi: To a solution of intermediate 13a (25.00 g, 87.63 mmol, 1.00 eq) in CH$_2$Cl$_2$ (250.00 mL) and TFA (75.00 mL) was added H$_2$O (3.16 g, 175.26 mmol, 3.16 mL, 2.00 eq). The mixture was stirred at 20° C. for 12 hours. The reaction was poured into saturated NaHCO$_3$ aqueous solution (500.0 mL) and extracted with CH$_2$Cl$_2$ (500.0 mL×3). The combined organic layer was dried over Na$_2$SO$_4$, filtered and concentrated. The residue was purified by column chromatography (SiO$_2$, CH$_2$Cl$_2$:EtOAc=1:2 to 0:1). Intermediate 14a (8.80 g, 33.20 mmol, 37.88% yield) was obtained as yellow solid. $^1$H NMR (400 MHz, CDCl$_3$) δ 8.67 (dd, J=1.1, 4.9 Hz, 1H), 7.89 (dt, J=1.9, 7.7 Hz, 1H), 7.75 (s, 1H), 7.70 (d, J=8.0 Hz, 1H), 7.39 (ddd, J=0.9, 4.9, 7.4 Hz, 1H), 3.46 (s, 2H), 3.16 (t, J=7.0 Hz, 2H), 2.67 (t, J=7.0 Hz, 2H).

Intermediate 15a: 1-oxo-2-(pyridin-2-yl)-1,2,7,8-tetrahydrophthalazin-6-yl trifluoromethane-sulfonate According to scheme 2, step vii: To a solution of intermediate 14a (5.00 g, 18.86 mmol, 1.00 eq) in CH$_2$Cl$_2$ (50.00 mL) was added Et$_3$N (2.29 g, 22.63 mmol, 3.14 mL, 1.20 eq) and Tf$_2$O (5.85 g, 20.75 mmol, 3.42 mL, 1.10 eq) at 0° C. The reaction was stirred for 12 hours at 20° C. The reactant mixture was concentrated to give a residue. The residue was purified by column chromatography (SiO$_2$, PE:EtOAc=5:1 to 1:1). Intermediate 15a (4.40 g, 11.43 mmol, 60.62% yield) was obtained as yellow solid. $^1$H NMR (400 MHz, CDCl$_3$) δ 8.68-8.63 (m, 1H), 7.88 (dt, J=1.9, 7.8 Hz, 1H), 7.78 (s, 1H), 7.69 (d, J=8.0 Hz, 1H), 7.38 (ddd, J=0.9, 4.9, 7.4 Hz, 1H), 6.36 (t, J=1.4 Hz, 1H), 3.18-3.10 (m, 2H), 2.84-2.75 (m, 2H).

Intermediate 16a: 6-(2-methoxyphenyl)-2-(pyridin-2-yl)-7,8-dihydrophthalazin-1(2H)-one According to scheme 2, step viii: A mixture of intermediate 15a (200.00 mg, 518.07 µmol, 1.00 eq), (2-methoxyphenyl)-boronic acid (157.45 mg, 1.04 mmol, 2.00 eq), Pd(PPh$_3$)$_4$ (119.73 mg, 103.61 µmol, 0.20 eq), Na$_2$CO$_3$ (2 M, 1.17 mL, 4.50 eq) in THF (4.00 mL) was degassed and purged with N$_2$ for 3 times, and then the mixture was stirred at 70° C. for 3 hours under N$_2$ atmosphere. The mixture was added water (20 mL), extracted with AcOEt (20 mL×3), the organic layer was dried over Na$_2$SO$_4$, filtered and concentrated under reduced pressure to give a residue. The residue was purified by prep-TLC (PE:EtOAc=0:1) to give intermediate 16a (190.00 mg, crude) as a yellow oil.

Example 58: 6-(2-methoxyphenyl)-2-(pyridin-2-yl)-5,6,7,8-tetrahydrophthalazin-1(2H)-one According to scheme 2, step ix: A mixture of intermediate 16a (200.00 mg, 283.67 µmol, 1.00 eq), Pd(OH)$_2$ (79.68 mg, 56.73 µmol, 10% purity, 0.20 eq) and ammonium formate (178.88 mg, 2.84 mmol, 10.00 eq) in EtOH (20.00 mL) was degassed and purged with N$_2$ for 3 times, and then the mixture was stirred at 60° C. for 2 hours under N$_2$ atmosphere. The mixture was filtered, concentrated under reduced pressure and purified by prep-HPLC to give Example 58 (27.59 mg, 82.68 µmol, 29.15% yield) as a white solid. $^1$H-NMR (400 MHz, CDCl$_3$) δ 8.68 (dd, J=1.1, 4.8 Hz, 1H), 7.88 (dt, J=1.9, 7.8 Hz, 1H), 7.78-7.72 (m, 2H), 7.37 (ddd, J=0.9, 4.9, 7.3 Hz, 1H), 7.28-7.25 (m, 1H), 7.21

(dd, J=1.5, 7.5 Hz, 1H), 7.02-6.97 (m, 1H), 6.94 (d, J=8.3 Hz, 1H), 3.88 (s, 3H), 3.45-3.31 (m, 1H), 3.05-2.88 (m, 2H), 2.75-2.60 (m, 2H), 2.22-2.13 (m, 1H), 2.05-1.89 (m, 1H).

Example 59: 6-(3-(dimethylamino)phenyl)-2-(pyridin-2-yl)-5,6,7,8-tetrahydrophthalazin-1(2H)-one, was Prepared According to Scheme 2, Method A

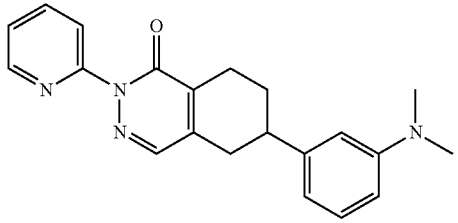 [SMILES: CN(C)c1cccc(C2CCc3c(cnn(-c4ccccn4)c3=O)C2)c1]

Intermediate 16b: 6-(3-(dimethylamino)phenyl)-2-(pyridin-2-yl)-7,8-dihydrophthalazin-1(2H)-one According to scheme 2, step viii: Intermediate 16b was prepared following the procedure described for intermediate 16a in Example 58, starting from intermediate 15a (200.00 mg, 486.46 μmol) and (3-(dimethylamino)phenyl)boronic acid (160.53 mg, 972.92 μmol) to give intermediate 16b (160.00 mg, 427.40 μmol, 87.86% yield) as a yellow oil.

Example 59: 6-(3-(dimethylamino)phenyl)-2-(pyridin-2-yl)-5,6,7,8-tetrahydrophthalazin-1(2H)-one According to scheme 2, step ix: Example 59 was prepared following the same procedure described for Example 58, starting from intermediate 16b (160.00 mg, 427.40 μmol) to yield Example 59 (15.47 mg, 43.85 μmol, 10.26% yield) as a white solid. $^1$H-NMR (400 MHz, CDCl$_3$) δ 8.69 (dd, J=1.1, 4.8 Hz, 1H), 7.89 (dt, J=1.9, 7.8 Hz, 1H), 7.78-7.73 (m, 2H), 7.38 (ddd, J=1.0, 4.9, 7.4 Hz, 1H), 7.26 (t, J=8.1 Hz, 1H), 6.70-6.63 (m, 3H), 3.05-2.98 (m, 1H), 3.05-2.98 (m, 7H), 2.96-2.86 (m, 2H), 2.84-2.75 (m, 1H), 2.72-2.59 (m, 1H), 2.30-2.21 (m, 1H), 1.98-1.85 (m, 1H).

Example 60: 6-(3-methoxy-2-methylphenyl)-2-(pyridin-2-yl)-5,6,7,8-tetrahydrophthalazin-1(2H)-one, was Prepared According to Scheme 2, Method A

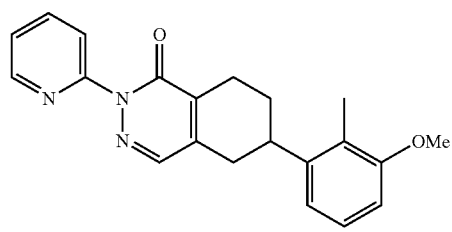

Intermediate 16c: 6-(3-methoxy-2-methylphenyl)-2-(pyridin-2-yl)-7,8-dihydrophthalazin-1(2H)-one According to scheme 2, step viii: Intermediate 16c was prepared following the procedure described for intermediate 16a in Example 58, starting from intermediate 15a (200.00 mg, 518.07 μmol) and (3-methoxy-2-methylphenyl)boronic acid (85.99 mg, 518.07 μmol) to give intermediate 16c (200.00 mg, 272.16 μmol, 52.53% yield) as a yellow oil.

Example 60: 6-(3-methoxy-2-methylphenyl)-2-(pyridin-2-yl)-7,8-dihydrophthalazin-1(2H)-one According to scheme 2, step ix: Example 60 was prepared following the same procedure described for Example 58, starting from intermediate 16c (170.00 mg, 492.20 μmol) to yield Example 60 (24.35 mg, 69.95 μmol, 14.21% yield) as white solid. $^1$H-NMR (400 MHz, CDCl$_3$) δ 8.69 (dd, J=1.1, 4.8 Hz, 1H), 7.89 (dt, J=1.9, 7.8 Hz, 1H), 7.79-7.71 (m, 2H), 7.38 (ddd, J=0.9, 4.9, 7.4 Hz, 1H), 7.26-7.18 (m, 1H), 6.91-6.78 (m, 2H), 3.87 (s, 3H), 3.31-3.18 (m, 1H), 3.06-2.94 (m, 1H), 2.89-2.79 (m, 1H), 2.78-2.63 (m, 2H), 2.27 (s, 3H), 2.20-2.12 (m, 1H), 1.98-1.85 (m, 1H).

Example 61: 6-(5-methoxy-2-methylphenyl)-2-(pyridin-2-yl)-5,6,7,8-tetrahydrophthalazin-1(2H)-one, was Prepared According to Scheme 2, Method A

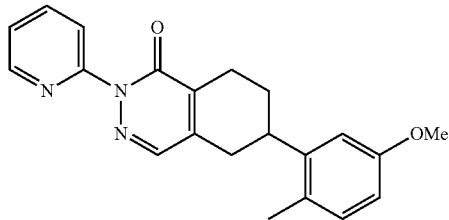 [SMILES: COc1ccc(C)c(C2CCc3c(cnn(-c4ccccn4)c3=O)C2)c1]

Intermediate 16d: 6-(5-methoxy-2-methylphenyl)-2-(pyridin-2-yl)-7,8-dihydrophthalazin-1(2H)-one According to scheme 2, step viii: Intermediate 16d was prepared following the procedure described for intermediate 16a in Example 58, starting from intermediate 15a (227.51 mg, 589.32 μmol) and (5-methoxy-2-methylphenyl)boronic acid (97.82 mg, 589.32 μmol) to give intermediate 16d (200.00 mg, crude) as a yellow oil.

Example 61: 6-(5-methoxy-2-methylphenyl)-2-(pyridin-2-yl)-5,6,7,8-tetrahydrophthalazin-1(2H)-one According to scheme 2, step ix: Example 61 was prepared following the same procedure described for Example 58, starting from intermediate 16d (200.00 mg, 579.06 μmol) to yield Example 61 (19.01 mg, 52.64 μmol, 9.09% yield) was obtained as a white solid. $^1$H-NMR (400 MHz, CDCl$_3$) δ 8.69 (dd, J=1.1, 4.8 Hz, 1H), 7.89 (dt, J=1.9, 7.8 Hz, 1H), 7.77-7.73 (m, 2H), 7.38 (ddd, J=1.0, 4.9, 7.4 Hz, 1H), 7.15 (d, J=8.3 Hz, 1H), 6.80 (d, J=2.6 Hz, 1H), 6.74 (dd, J=2.6, 8.3 Hz, 1H), 3.82 (s, 3H), 3.20-3.10 (m, 1H), 3.08-2.99 (m, 1H), 2.88-2.80 (m, 1H), 2.75-2.62 (m, 2H), 2.33 (s, 3H), 2.22-2.13 (m, 1H), 1.95-1.83 (m, 1H).

Example 62: 2-(pyridin-2-yl)-6-(o-tolyl)-5,6,7,8-tetrahydrophthalazin-1(2H)-one, was Prepared According to Scheme 2, Method A

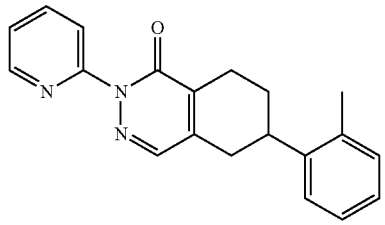 [SMILES: Cc1ccccc1C1CCc2c(cnn(-c3ccccn3)c2=O)C1]

Intermediate 16e: 2-(pyridin-2-yl)-6-(o-tolyl)-7,8-dihydrophthalazin-1(2H)-one According to scheme 2, step viii: Intermediate 16e was prepared following the procedure described for intermediate 16a in Example 58, starting from intermediate 15a (200.00 mg, 486.46 μmol) and o-tolylboronic acid (132.28 mg, 972.92 μmol) to give intermediate 16e (70.00 mg, 210.86 μmol, 43.35% yield) as brown solid.

Example 62: 2-(pyridin-2-yl)-6-(o-tolyl)-5,6,7,8-tetrahydrophthalazin-1(2H)-one According to scheme 2, step ix: Example 62 was prepared following the same procedure described for Example 58, starting from intermediate 16e (70.00 mg, 210.86 μmol) to yield Example 62 (12.55 mg, 39.07 μmol, 18.53% yield) as white solid. $^1$H-NMR (400 MHz, CDCl$_3$) δ 8.59 (dd, J=1.1, 4.8 Hz, 1H), 7.80 (dt, J=1.9, 7.7 Hz, 1H), 7.70-7.62 (m, 2H), 7.29 (ddd, J=0.9, 4.9, 7.5 Hz, 1H), 7.17-7.07 (m, 4H), 3.16-3.05 (m, 1H), 2.98-2.86 (m, 1H), 2.81-2.71 (m, 1H), 2.69-2.53 (m, 2H), 2.32 (s, 3H), 2.13-2.03 (m, 1H), 1.89-1.76 (m, 1H).

Example 63: 6-(3-cyclopropylphenyl)-2-(pyridin-2-yl)-5,6,7,8-tetrahydrophthalazin-1(2H)-one, was Prepared According to Scheme 2, Method A

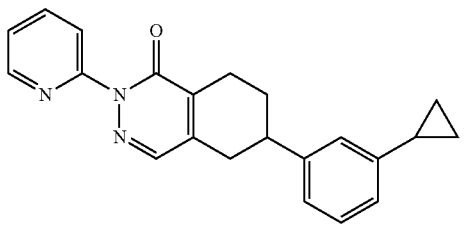 [SMILES: O=c1c2c(cnn1-c1ccccn1)CC(c1cccc(C3CC3)c1)CC2]

Intermediate 16f: 6-(3-cyclopropylphenyl)-2-(pyridin-2-yl)-7,8-dihydrophthalazin-1(2H)-one According to scheme 2, step viii: Intermediate 16f was prepared following the procedure described for intermediate 16a in Example 58, starting from intermediate 15a (100.00 mg, 243.23 μmol) and (3-cyclopropylphenyl)boronic acid pinacol ester (89.07 mg, 364.85 μmol) to give intermediate 16f (20.00 mg, 42.76 μmol, 17.58% yield) as a brown solid.

Example 63: 6-(3-cyclopropylphenyl)-2-(pyridin-2-yl)-5,6,7,8-tetrahydrophthalazin-1(2H)-one According to scheme 2, step ix: Example 63 was prepared following the same procedure described for Example 58, starting from intermediate 16f (10.00 mg, 21.38 μmol) to yield Example 63 (4.63 mg, 13.48 μmol, 63.06% yield) as a white solid. $^1$H-NMR (400 MHz, CDCl$_3$) δ 8.68 (br d, J=3.8 Hz, 1H), 7.94-7.84 (m, 1H), 7.79-7.71 (m, 2H), 7.42-7.34 (m, 1H), 7.31-7.23 (m, 2H), 7.09-7.01 (m, 2H), 6.97 (br d, J=7.4 Hz, 1H), 3.05-2.84 (m, 3H), 2.82-2.60 (m, 2H), 2.24 (br d, J=8.9 Hz, 1H), 1.98-1.83 (m, 2H), 1.06-0.95 (m, 2H), 0.74 (q, J=4.9 Hz, 2H).

Example 64: 6-(3-methoxy-4-methylphenyl)-2-(pyridin-2-yl)-5,6,7,8-tetrahydrophthalazin-1(2H)-one, was Prepared According to Scheme 2, Method A

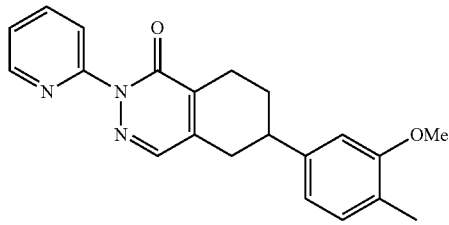 [SMILES: COc1cc(C2CCc3c(cnn(-c4ccccn4)c3=O)C2)ccc1C]

Intermediate 16g: 6-(3-methoxy-4-methylphenyl)-2-(pyridin-2-yl)-7,8-dihydrophthalazin-1(2H)-one According to scheme 2, step viii: Intermediate 16g was prepared following the procedure described for intermediate 16a in Example 58, starting from intermediate 15a (200.00 mg, 518.07 μmol) and (3-methoxy-4-methylphenyl)boronic acid (171.98 mg, 1.04 mmol) to give intermediate 16g (130.00 mg, 299.60 μmol, 57.83% yield) as a yellow solid. m/z (M+H)$^+$=346.1.

Example 64: 6-(3-methoxy-4-methylphenyl)-2-(pyridin-2-yl)-5,6,7,8-tetrahydrophthalazin-1(2H)-one According to scheme 2, step ix: Example 64 was prepared following the same procedure described for Example 58, starting from intermediate 16g (130.00 mg, 299.60 μmol) to yield Example 64 (31.00 mg, 89.23 μmol, 29.78% yield) as a white solid. $^1$H-NMR (400 MHz, CDCl$_3$) δ 8.62-8.56 (m, 1H), 7.83-7.76 (m, 1H), 7.68-7.62 (m, 2H), 7.32-7.25 (m, 1H), 7.04 (d, J=7.5 Hz, 1H), 6.69 (d, J=7.5 Hz, 1H), 6.66 (s, 1H), 3.79 (s, 3H), 2.96-2.76 (m, 3H), 2.74-2.49 (m, 2H), 2.21-2.10 (m, 4H), 1.88-1.73 (m, 1H).

Example 65: 6-(3-(1-hydroxyethyl)phenyl)-2-(pyridin-2-yl)-5,6,7,8-tetrahydrophthalazin-1(2H)-one, was Prepared According to Scheme 2, Method A

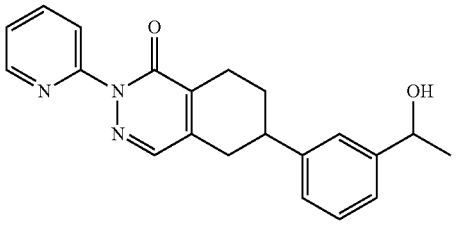 [SMILES: CC(O)c1cccc(C2CCc3c(cnn(-c4ccccn4)c3=O)C2)c1]

Intermediate 16h: 6-(3-acetylphenyl)-2-(pyridin-2-yl)-7,8-dihydrophthalazin-1(2H)-one According to scheme 2, step viii: Intermediate 16h was prepared following the procedure described for intermediate 16a in Example 58, starting from intermediate 15a (100.00 mg, 243.23 μmol) and (3-acetylphenyl)boronic acid (59.82 mg, 364.85 μmol) to give intermediate 16h (70.00 mg, 156.97 μmol, 64.54% yield) as off-white solid. m/z (M+H)$^+$=344.1.

Example 65: 6-(3-(1-hydroxyethyl)phenyl)-2-(pyridin-2-yl)-5,6,7,8-tetrahydrophthalazin-1(2H)-one According to scheme 2, step ix: Example 65 was prepared following the same procedure described for Example 58, starting from intermediate 16h (70.00 mg, 156.97 μmol) to yield Example 65 (4.05 mg, 11.54 μmol, 4.31% yield) as white solid. $^1$H-NMR (400 MHz, CDCl$_3$) δ 8.68 (br d, J=3.9 Hz, 1H), 7.93-7.85 (m, 1H), 7.79-7.70 (m, 2H), 7.41-7.35 (m, 2H), 7.32 (br d, J=7.9 Hz, 2H), 7.21 (br d, J=7.5 Hz, 1H), 4.95 (q, J=6.3 Hz, 1H), 3.06-2.96 (m, 2H), 2.95-2.86 (m, 1H), 2.84-2.74 (m, 1H), 2.73-2.61 (m, 1H), 2.26 (br d, J=9.0 Hz, 1H), 1.98-1.88 (m, 1H), 1.88-1.77 (m, 1H), 1.55 (d, J=6.5 Hz, 3H).

Example 66: 6-(3-cyclopropoxyphenyl)-2-(pyridin-2-yl)-5,6,7,8-tetrahydrophthalazin-1(2H)-one, was Prepared According to Scheme 2, Method A

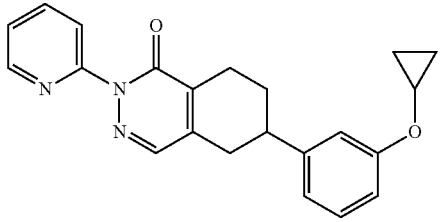 [SMILES: O=c1c2c(cnn1-c1ccccn1)CC(c1cccc(OC3CC3)c1)CC2]

Intermediate 16i: 6-(3-cyclopropoxyphenyl)-2-(pyridin-2-yl)-7,8-dihydrophthalazin-1(2H)-one According to scheme 2, step viii: Intermediate 16i was prepared following the procedure described for intermediate 16a in Example 58, starting from intermediate 15a (100.00 mg, 243.23 μmol) and (3-cyclopropoxyphenyl)boronic acid pinacol ester (96.85 mg, 364.84 μmol) to give intermediate 16i (80.00 mg, 118.63 μmol, 48.78% yield) as an off-white solid. m/z (M+H)$^+$=358.1.

Example 66: 6-(3-cyclopropoxyphenyl)-2-(pyridin-2-yl)-5,6,7,8-tetrahydrophthalazin-1(2H)-one According to scheme 2, step ix: Example 66 was prepared following the same procedure described for Example 58, starting from intermediate 16i (40.00 mg, 59.32 μmol) to yield Example 66 (8.54 mg, 23.74 μmol, 40.01% yield) as a white solid. $^1$H-NMR (400 MHz, CDCl$_3$) δ 8.68 (br d, J=4.3 Hz, 1H), 7.89 (dt, J=1.6, 7.7 Hz, 1H), 7.78-7.72 (m, 2H), 7.38 (dd, J=5.0, 7.2 Hz, 1H), 7.34-7.29 (m, 1H), 7.01 (dd, J=2.0, 8.2 Hz, 1H), 6.94 (s, 1H), 6.90 (d, J=7.7 Hz, 1H), 3.82-3.71 (m, 1H), 3.03-2.86 (m, 3H), 2.82-2.59 (m, 2H), 2.25 (br d, J=13.2 Hz, 1H), 1.97-1.83 (m, 1H), 0.84-0.79 (m, 4H).

Example 67: 6-(2-methoxy-4-methylphenyl)-2-(pyridin-2-yl)-5,6,7,8-tetrahydrophthalazin-1(2H)-one, was Prepared According to Scheme 2, Method A

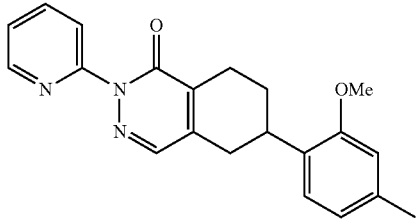 [SMILES: COc1cc(C)ccc1C1CCc2c(cnn(-c3ccccn3)c2=O)C1]

Intermediate 16j: 6-(2-methoxy-4-methylphenyl)-2-(pyridin-2-yl)-7,8-dihydrophthalazin-1(2H)-one According to scheme 2, step viii: Intermediate 16j was prepared following the procedure described for intermediate 16a in Example 58, starting from intermediate 15a (200.00 mg, 519.68 μmol) and (2-methoxy-4-methylphenyl)boronic acid (129.38 mg, 779.52 μmol) to give intermediate 16j (180.00 mg, crude) as brown oil. m/z (M+H)$^+$=346.1.

Example 67: 6-(2-methoxy-4-methylphenyl)-2-(pyridin-2-yl)-5,6,7,8-tetrahydrophthalazin-1(2H)-one According to scheme 2, step ix: Example 67 was prepared following the same procedure described for Example 58, starting from intermediate 16j (180.00 mg, 521.15 μmol) to yield Example 67 (24.94 mg, 71.64 μmol, 13.75% yield) as white solid. $^1$H-NMR (400 MHz, CDCl$_3$) δ 8.94 (d, J=4.8 Hz, 2H), 7.70 (s, 1H), 7.42 (t, J=4.9 Hz, 1H), 7.08 (dt, J=1.4, 8.0 Hz, 1H), 6.93-6.87 (m, 1H), 6.81 (t, J=6.5 Hz, 1H), 3.92 (s, 3H), 3.41-3.28 (m, 1H), 3.04-2.88 (m, 2H), 2.81-2.63 (m, 2H), 2.24-2.14 (m, 1H), 2.02-1.91 (m, 1H).

Example 68: 6-(2-methoxy-3-methylphenyl)-2-(pyridin-2-yl)-5,6,7,8-tetrahydrophthalazin-1(2H)-one, was Prepared According to Scheme 2, Method A

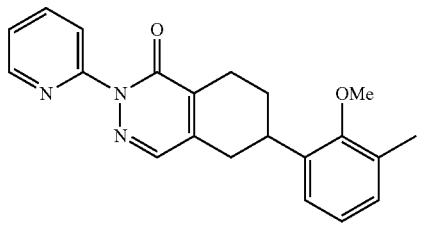 [SMILES: COc1c(C)cccc1C1CCc2c(cnn(-c3ccccn3)c2=O)C1]

Intermediate 16k: 6-(2-methoxy-3-methylphenyl)-2-(pyridin-2-yl)-7,8-dihydrophthalazin-1(2H)-one According to scheme 2, step viii: Intermediate 16k was prepared following the procedure described for intermediate 16a in Example 58, starting from intermediate 15a (200.00 mg, 519.68 μmol) and (2-methoxy-3-methylphenyl)boronic acid pinacol ester (214.90 mg, 779.51 μmol) to give intermediate 16k (190.00 mg, crude) as a brown oil. m/z (M+H)$^+$ =346.1.

Example 68: 6-(2-methoxy-3-methylphenyl)-2-(pyridin-2-yl)-5,6,7,8-tetrahydrophthalazin-1(2H)-one According to scheme 2, step ix: Example 68 was prepared following the same procedure described for Example 58, starting from intermediate 16k (190.00 mg, 550.10 μmol) to yield Example 68 (16.44 mg, 46.80 μmol, 8.51% yield) as white solid. $^1$H-NMR (400 MHz, DMSO-d$_6$) δ 8.43 (s, 2H), 7.79 (s, 1H), 7.14-7.21 (m, 1H), 6.89 (d, J=7.78 Hz, 1H), 6.85 (d, J=8.28 Hz, 1H), 3.76-3.81 (m, 3H), 3.11-3.25 (m, 1H), 2.67-2.84 (m, 3H), 2.55-2.60 (m, 3H), 2.18 (s, 3H), 1.93 (br s, 1H), 1.76-1.89 (m, 1H).

Example 69: 6-(1-methylindolin-4-yl)-2-(pyridin-2-yl)-5,6,7,8-tetrahydrophthalazin-1(2H)-one, was Prepared According to Scheme 2, Method A

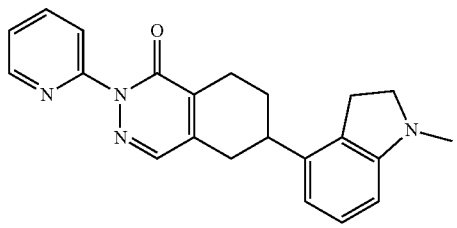 [SMILES: CN1CCc2c(C3CCc4c(cnn(-c5ccccn5)c4=O)C3)cccc21]

Intermediate 16l: 6-(1-methylindolin-4-yl)-2-(pyridin-2-yl)-7,8-dihydrophthalazin-1(2H)-one According to scheme 2, step viii: Intermediate 16l was prepared following the procedure described for intermediate 16a in Example 58, starting from intermediate 15a (0.2 g, 535.75 μmol) and (1-methylindolin-4-yl)boronic acid pinacol ester (138.84 mg, 535.75 μmol) to give intermediate 16l (0.15 g, crude) as yellow solid. m/z (M+H)$^+$=357.3; $^1$H NMR (MeOD, 400 MHz) δ 8.60 (br d, J=4.4 Hz, 1H), 7.94-8.08 (m, 2H), 7.67 (br d, J=7.6 Hz, 1H), 7.46-7.56 (m, 1H), 7.13 (br t, J=7.6 Hz, 1H), 6.77 (br d, J=8.0 Hz, 1H), 6.47-6.59 (m, 2H), 3.04-3.14 (m, 2H), 2.87-2.97 (m, 2H), 2.79-2.86 (m, 2H), 2.76 (s, 3H).

Example 69: 6-(1-methylindolin-4-yl)-2-(pyridin-2-yl)-5,6,7,8-tetrahydrophthalazin-1(2H)-one According to scheme 2, step ix: Example 69 was prepared following the same procedure described for Example 58, starting from intermediate 16l (0.15 g, 420.85 μmol), to provide Example 69 (55 mg, 151.30 μmol, 35.95% yield) as white solid. $^1$H-NMR (400 MHz, DMSO-d$_6$) δ 8.67 (br d, J=3.6 Hz, 1H), 7.87 (td, J=7.8, 2.0 Hz, 1H), 7.71-7.78 (m, 2H), 7.36 (dd, J=6.4, 5.0 Hz, 1H), 7.13 (t, J=7.8 Hz, 1H), 6.58 (d, J=7.8 Hz, 1H), 6.42 (d, J=7.8 Hz, 1H), 3.29-3.41 (m, 2H), 2.89-3.11 (m, 4H), 2.75-2.88 (m, 5H), 2.53-2.72 (m, 1H), 2.17 (m, 1H), 1.80-1.98 (m, 1H).

Example 70: 6-(2-methoxy-4-methylphenyl)-2-(pyrimidin-2-yl)-5,6,7,8-tetrahydrophthalazin-1(2H)-one, was Prepared According to Scheme 2, Method A

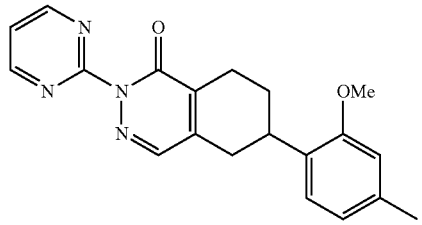 [SMILES: COc1cc(C)ccc1C1CCc2c(cnn(-c3ncccn3)c2=O)C1]

Intermediate 13b: 2-(pyrimidin-2-yl)-7,8-dihydro-2H-spiro[phthalazine-6,2'-[1,3]dioxolan]-1(5H)-one According to scheme 2, step iv: Intermediate 13b was prepared following the procedure described for intermediate 13a, starting from intermediate 12 (40.00 g, 192.11 mmol) and 2-bromopyrimidine (36.65 g, 230.53 mmol), to provide intermediate 13b (62.00 g, crude) as a gray solid. $^1$H NMR (400 MHz, CDCl$_3$) δ 8.92 (d, J=4.8 Hz, 2H), 7.63 (s, 1H), 7.40 (t, J=4.8 Hz, 1H), 4.05 (s, 4H), 2.91 (br t, J=6.7 Hz, 2H), 2.81 (s, 2H), 1.94 (t, J=6.7 Hz, 2H).

Intermediate 14b: 2-(pyrimidin-2-yl)-7,8-dihydrophthalazine-1,6(2H,5H)-dione

According to scheme 2, step vi: Intermediate 14b was prepared following a similar procedure described for intermediate 14a, starting from intermediate 13b (18.00 g, 62.87 mmol) to provide intermediate 14b (7.60 g, 18.83 mmol, 29.95% yield) as brown solid. $^1$H NMR (400 MHz, DMSO-d6) δ 9.04 (d, J=4.8 Hz, 2H), 7.88 (s, 1H), 7.79 (d, J=6.4 Hz, 1H), 3.55 (s, 2H), 2.95 (br t, J=6.9 Hz, 2H), 2.56 (t, J=7.0 Hz, 2H).

Intermediate 15b: 1-oxo-2-(pyrimidin-2-yl)-1,2,7,8-tetrahydrophthalazin-6-yl trifluoromethane-sulfonate According to scheme 2, step vii: Intermediate 15b was prepared following the procedure described for intermediate 15a, starting from intermediate 14b (3.50 g, 14.45 mmol), to provide Intermediate 15b (4.30 g, 8.62 mmol, 59.63% yield) as yellow solid. $^1$H NMR (400 MHz, MeOD) δ 9.03-8.94 (m, 2H), 8.03-7.92 (m, 1H), 7.70-7.59 (m, 1H), 6.66 (t, J=1.4 Hz, 1H), 3.15-3.05 (m, 2H), 2.92-2.83 (m, 2H).

Intermediate 16m: 6-(2-methoxy-4-methylphenyl)-2-(pyrimidin-2-yl)-7,8-dihydrophthalazin-1(2H)-one According to scheme 2, step viii: Intermediate 16m was prepared following the procedure described for intermediate 16a in Example 58, starting from intermediate 15b (200.00 mg, 480.91 μmol) and (2-methoxy-4-methylphenyl)boronic acid (119.73 mg, 721.37 μmol) to give intermediate 16m (177.00 mg, crude) as yellow oil. m/z (M+H)$^+$=347.1.

Example 70: 6-(2-methoxy-4-methylphenyl)-2-(pyrimidin-2-yl)-5,6,7,8-tetrahydrophthalazin-1(2H)-one According to scheme 2, step ix: Example 70 was prepared following the same procedure described for Example 58, starting from intermediate 16m (177.00 mg, 511.00 μmol) to provide Example 70 (23.80 mg, 62.85 μmol, 12.30% yield) as white solid. $^1$H-NMR (400 MHz, CDCl$_3$) δ 9.03 (s, 1H), 9.02 (s, 1H), 7.85 (s, 1H), 7.72 (t, J=4.89 Hz, 1H), 7.12-7.18 (m, 1H), 6.88 (d, J=3.39 Hz, 1H), 6.86 (d, J=3.89 Hz, 1H), 4.43-4.71 (m, 1H), 3.12-3.22 (m, 1H), 2.66-2.86 (m, 3H), 2.56 (br d, J=9.91 Hz, 1H), 2.18 (s, 3H), 1.91-2.00 (m, 1H), 1.79-1.90 (m, 1H), 1.28 (d, J=6.02 Hz, 6H).

Example 71: 6-(2-methoxy-3-methylphenyl)-2-(pyrimidin-2-yl)-5,6,7,8-tetrahydrophthalazin-1(2H)-one, was Prepared According to Scheme 2, Method A

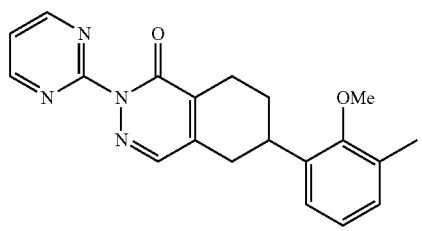 [SMILES: COc1c(C)cccc1C1CCc2c(cnn(-c3ncccn3)c2=O)C1]

Intermediate 16n: 6-(2-methoxy-3-methylphenyl)-2-(pyrimidin-2-yl)-7,8-dihydrophthalazin-1(2H)-one According to scheme 2, step viii: Intermediate 16n was prepared following the procedure described for Intermediate 16a, starting from intermediate 15b (200.00 mg, 480.90 μmol) and (2-methoxy-3-methylphenyl)boronic acid pinacol ester (198.88 mg, 721.35 μmol) to provide Intermediate 16n (180.00 mg, crude) as a brown oil. m/z (M+H)$^+$=347.1.

Example 71: 6-(2-methoxy-3-methylphenyl)-2-(pyrimidin-2-yl)-5,6,7,8-tetrahydrophthalazin-1(2H)-one According to scheme 2, step ix: Example 71 was prepared following the same procedure described for Example 58, starting from intermediate 16n (180.00 mg, 519.66 μmol) to yield Example 71 (13.00 mg, 37.31 μmol, 7.18% yield) as white solid. $^1$H-NMR (400 MHz, CDCl$_3$) δ 9.04 (s, 1H), 9.02 (s, 1H), 7.86 (s, 1H), 7.72 (t, J=4.89 Hz, 1H), 7.12-7.20 (m, 1H), 6.90 (d, J=7.65 Hz, 1H), 6.86 (d, J=8.03 Hz, 1H), 4.09 (dd, J=3.89, 5.40 Hz, 2H), 3.66-3.74 (m, 2H), 3.12-3.23 (m, 1H), 2.65-2.88 (m, 3H), 2.57 (br d, J=8.28 Hz, 1H), 2.20 (s, 3H), 1.95 (br s, 1H), 1.78-1.90 (m, 1H).

Example 72: 6-(2-chloro-3-methoxyphenyl)-2-(pyrimidin-2-yl)-5,6,7,8-tetrahydrophthalazin-1(2H)-one, was Prepared According to Scheme 2, Method A

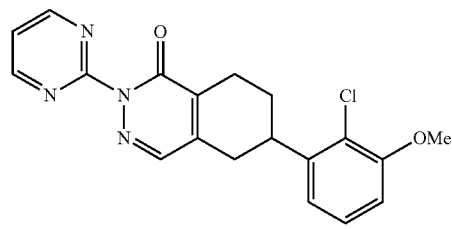 [SMILES: COc1cccc(C2CCc3c(cnn(-c4ncccn4)c3=O)C2)c1Cl]

Intermediate 16o: 6-(2-chloro-3-methoxyphenyl)-2-(pyrimidin-2-yl)-7,8-dihydrophthalazin-1(2H)-one According to scheme 2, step viii: Intermediate 16o was prepared following the procedure described for Intermediate 16a, starting from intermediate 15b (200.00 mg, 480.91 μmol) and (2-chloro-3-methoxyphenyl)boronic acid pinacolester (134.46 mg, 721.37 μmol) to provide intermediate 16o (190.00 mg, crude) as yellow oil. m/z (M+H)$^+$=367.0, 369.0.

Example 72: 6-(2-chloro-3-methoxyphenyl)-2-(pyrimidin-2-yl)-5,6,7,8-tetrahydrophthalazin-1(2H)-one According to scheme 2, step ix: Example 72 was prepared following the same procedure described for Example 58, starting from intermediate 16o (190.00 mg, 517.99 μmol), to provide Example 72 (29.90 mg, 80.42 μmol, 15.53% yield), as a white solid. $^1$H-NMR (400 MHz, DMSO-d$_6$) δ 9.03 (s, 1H), 9.01 (s, 1H), 7.85 (s, 1H), 7.71 (t, J=4.83 Hz, 1H), 7.45-7.51 (m, 2H), 7.41 (t, J=7.40 Hz, 2H), 7.30-7.35 (m, 1H), 7.13-7.19 (m, 1H), 6.94 (d, J=8.16 Hz, 1H), 6.91 (d, J=7.78 Hz, 1H), 5.11 (s, 2H), 3.13-3.25 (m, 1H), 2.65-2.88 (m, 3H), 2.56 (br d, J=9.41 Hz, 1H), 2.24 (s, 3H), 1.95 (br s, 1H), 1.77-1.90 (m, 1H).

Example 73: 6-(5-methoxy-2-(trifluoromethyl)phenyl)-2-(pyrimidin-2-yl)-5,6,7,8-tetrahydrophthalazin-1(2H)-one, was Prepared According to Scheme 2, Method A

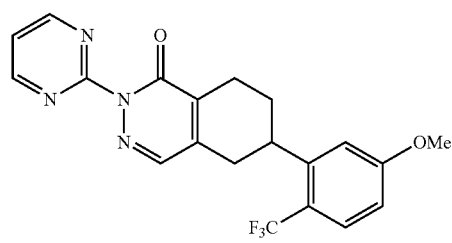 [SMILES: COc1ccc(C(F)(F)F)c(C2CCc3c(cnn(-c4ncccn4)c3=O)C2)c1]

Intermediate 16p: 6-(5-methoxy-2-(trifluoromethyl)phenyl)-2-(pyrimidin-2-yl)-7,8-dihydrophthalazin-1(2H)-one According to scheme 2, step viii: Intermediate 16p was prepared following the procedure described for Intermediate 16a, starting from intermediate 15b (200.00 mg, 480.91 μmol) and (5-methoxy-2-(trifluoromethyl)phenyl)boronic acid pinacol ester (242.14 mg, 721.37 μmol) to provide Intermediate 16p (72.00 mg, crude) as yellow solid. m/z (M+H)$^+$=401.1.

Example 73: 6-(5-methoxy-2-(trifluoromethyl)phenyl)-2-(pyrimidin-2-yl)-5,6,7,8-tetrahydrophthalazin-1(2H)-one According to scheme 2, step ix: Example 73 was prepared following the same procedure described for Example 58, starting from intermediate 16p (72.00 mg, 179.84 μmol), to provide Example 73 (8.30 mg, 19.84 μmol, 11.03% yield) as white solid. $^1$H-NMR (400 MHz, CDCl$_3$) δ 8.94 (d, J=4.8 Hz, 2H), 7.70 (s, 1H), 7.42 (t, J=4.8 Hz, 1H), 7.13 (d, J=8.3 Hz, 1H), 6.78 (d, J=2.5 Hz, 1H), 6.72 (dd, J=2.6, 8.3 Hz, 1H), 3.81 (s, 3H), 3.19-2.99 (m, 2H), 2.88-2.78 (m, 1H), 2.75-2.61 (m, 2H), 2.32 (s, 3H), 2.21-2.10 (m, 1H), 1.94-1.81 (m, 1H)

Example 74: 6-(2-fluoro-5-methoxyphenyl)-2-(pyrimidin-2-yl)-5,6,7,8-tetrahydrophthalazin-1(2H)-one, was Prepared According to Scheme 2, Method A

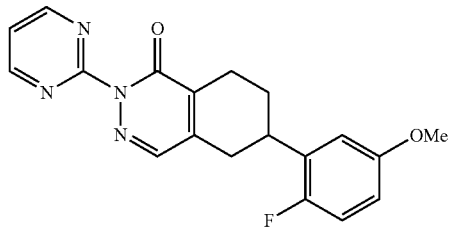 [SMILES: COc1ccc(F)c(C2CCc3c(cnn(-c4ncccn4)c3=O)C2)c1]

Intermediate 16q: 6-(2-fluoro-5-methoxyphenyl)-2-(pyrimidin-2-yl)-7,8-dihydrophthalazin-1(2H)-one According to scheme 2, step viii: Intermediate 16q was prepared following the procedure described for Intermediate 16a, starting from intermediate 15b (200.00 mg, 480.91 μmol) and (2-fluoro-5-methoxyphenyl)boronic acid pinacol ester (122.60 mg, 721.37 μmol) to provide Intermediate 16q (60.00 mg, crude) as brown solid. m/z (M+H)$^+$=351.0.

Example 74: 6-(2-fluoro-5-methoxyphenyl)-2-(pyrimidin-2-yl)-5,6,7,8-tetrahydrophthalazin-1(2H)-one According to scheme 2, step ix: Example 74 was prepared following the same procedure described for Example 58, starting from intermediate 16q (60.00 mg, 171.26 μmol), to provide Example 74 (7.70 mg, 21.66 μmol, 12.65% yield) as white solid. $^1$H-NMR (400 MHz, CDCl$_3$) δ 8.94 (d, J=4.9 Hz, 2H), 7.70 (s, 1H), 7.43 (t, J=4.8 Hz, 1H), 7.10 (d, J=7.7 Hz, 1H), 7.04-6.97 (m, 2H), 3.20-3.10 (m, 1H), 3.04 (br dd, J=5.1, 19.4 Hz, 1H), 2.86-2.61 (m, 3H), 2.34 (s, 6H), 2.18-2.09 (m, 1H), 1.95-1.83 (m, 1H).

Example 75: 6-(2-chloro-5-methoxyphenyl)-2-(pyrimidin-2-yl)-5,6,7,8-tetrahydrophthalazin-1(2H)-one, was Prepared According to Scheme 2, Method A

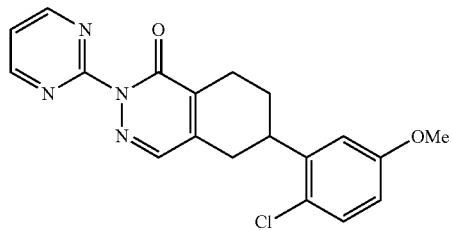 [SMILES: COc1ccc(Cl)c(C2CCc3c(cnn(-c4ncccn4)c3=O)C2)c1]

Intermediate 16r: 6-(2-chloro-5-methoxyphenyl)-2-(pyrimidin-2-yl)-7,8-dihydrophthalazin-1(2H)-one According to scheme 2, step viii: Intermediate 16r was prepared following the procedure described for Intermediate 16a, starting from intermediate 15b (200.00 mg, 480.91 μmol) and (2-chloro-5-methoxyphenyl)boronic acid pinacol ester (193.72 mg, 721.37 μmol), to provide Intermediate 16r (160.00 mg, crude) as brown solid. m/z (M+H)$^+$=367.0, 369.0.

Example 75: 6-(2-chloro-5-methoxyphenyl)-2-(pyrimidin-2-yl)-5,6,7,8-tetrahydrophthalazin-1(2H)-one According to scheme 2, step ix: Example 75 was prepared following the same procedure described for Example 58, starting from intermediate 16r (160.00 mg, 436.21 μmol), to provide Example 75 (5.80 mg, 15.65 μmol, 3.59% yield) as white solid. $^1$H-NMR (400 MHz, CDCl$_3$) δ 8.94 (d, J=4.9 Hz, 2H), 7.71 (s, 1H), 7.42 (t, J=4.8 Hz, 1H), 7.32 (d, J=8.8 Hz, 1H), 6.82 (d, J=2.9 Hz, 1H), 6.76 (dd, J=2.9, 8.7 Hz, 1H), 3.82 (s, 3H), 3.48-3.37 (m, 1H), 3.08-2.93 (m, 2H), 2.76-2.57 (m, 2H), 2.25-2.16 (m, 1H), 1.97-1.84 (m, 1H).

Example 76: 6-(2-methoxy-5-methylphenyl)-2-(pyrimidin-2-yl)-5,6,7,8-tetrahydrophthalazin-1(2H)-one, was Prepared According to Scheme 2, Method A

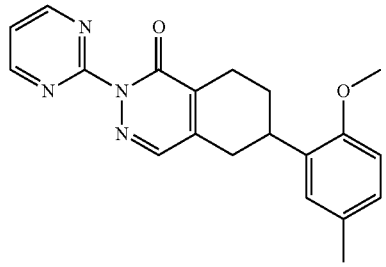 [SMILES: COc1ccc(C)cc1C1CCc2c(cnn(-c3ncccn3)c2=O)C1]

Intermediate 16s: 6-(2-methoxy-5-methylphenyl)-2-(pyrimidin-2-yl)-7,8-dihydrophthalazin-1(2H)-one According to scheme 2, step viii: Intermediate 16s was prepared following the procedure described for Intermediate 16a, starting from intermediate 15b (200.00 mg, 480.91 µmol) and (5-methoxy-2-methylphenyl)boronic acid (119.73 mg, 721.37 µmol), to provide Intermediate 16s (120.00 mg, crude) as yellow solid. m/z (M+H)$^+$=347.1.

Example 76: 6-(2-methoxy-5-methylphenyl)-2-(pyrimidin-2-yl)-5,6,7,8-tetrahydrophthalazin-1(2H)-one According to scheme 2, step ix: Example 76 was prepared following the same procedure described for Example 58, starting from intermediate 16s (120.00 mg, 346.44 µmol), to provide Example 76 (15.00 mg, 54.38 µmol, 15.70% yield) as white solid. $^1$H-NMR (400 MHz, CDCl$_3$) δ 8.94 (d, J=4.8 Hz, 2H), 7.69 (s, 1H), 7.41 (t, J=4.9 Hz, 1H), 7.07-6.98 (m, 2H), 6.81 (d, J=8.3 Hz, 1H), 3.83 (s, 3H), 3.39-3.26 (m, 1H), 3.06-2.85 (m, 2H), 2.73-2.59 (m, 2H), 2.31 (s, 3H), 2.14 (br dd, J=3.5, 13.3 Hz, 1H), 1.99-1.87 (m, 1H).

Example 77: 6-(2-methyl-5-(pyrrolidin-1-yl)phenyl)-2-(pyrimidin-2-yl)-5,6,7,8-tetrahydrophthalazin-1(2H)-one, was Prepared According to Scheme 2, Method A

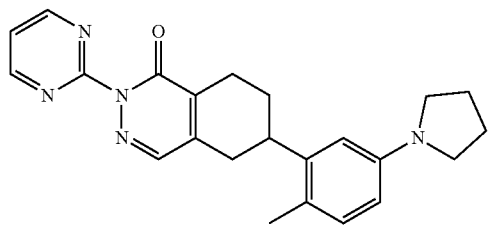 [SMILES: Cc1ccc(N2CCCC2)cc1C1CCc2c(cnn(-c3ncccn3)c2=O)C1]

Intermediate 16t: 6-(2-methyl-5-(pyrrolidin-1-yl)phenyl)-2-(pyrimidin-2-yl)-7,8-dihydrophthalazin-1(2H)-one According to scheme 2, step viii: Intermediate 16t was prepared following the procedure described for intermediate 16a in Example 58, starting from intermediate 15b (250.00 mg, 500.95 µmol) and (2-methyl-5-(pyrrolidin-1-yl)phenyl) boronic acid pinacol ester (334.07 mg, 751.43 µmol) to give intermediate 16t (110.00 mg, crude) as yellow solid. m/z (M+H)$^+$=386.2.

Example 77: 6-(2-methyl-5-(pyrrolidin-1-yl)phenyl)-2-(pyrimidin-2-yl)-5,6,7,8-tetrahydrophthalazin-1(2H)-one According to scheme 2, step ix: Example 77 was prepared following the same procedure described for Example 58, starting from intermediate 16t (110.00 mg, 285.37 µmol), to provide Example 77 (9.84 mg, 24.20 µmol, 8.48% yield) as a yellow solid. $^1$H-NMR (400 MHz, CDCl$_3$) δ 8.94 (d, J=4.8 Hz, 2H), 7.70 (s, 1H), 7.42 (t, J=4.8 Hz, 1H), 7.09-7.03 (m, 1H), 6.46-6.40 (m, 2H), 3.31-3.25 (m, 4H), 3.18-3.01 (m, 2H), 2.87-2.62 (m, 3H), 2.28 (s, 3H), 2.21-2.14 (m, 1H), 2.01 (td, J=3.3, 6.6 Hz, 4H), 1.95-1.84 (m, 1H).

Example 78: 6-(1-methylindolin-4-yl)-2-(pyrimidin-2-yl)-5,6,7,8-tetrahydrophthalazin-1(2H)-one, was Prepared According to Scheme 2, Method A

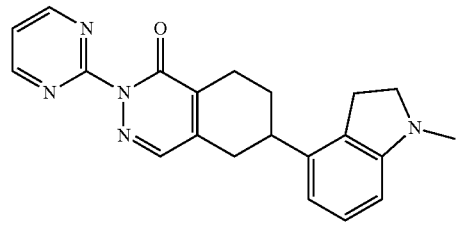 [SMILES: CN1CCc2c(C3CCc4c(cnn(-c5ncccn5)c4=O)C3)cccc21]

Intermediate 16u: 6-(1-methylindolin-4-yl)-2-(pyrimidin-2-yl)-7,8-dihydrophthalazin-1(2H)-one According to scheme 2, step viii: Intermediate 16u was prepared following the procedure described for intermediate 16a in Example 58, starting from intermediate 15b (250.00 mg, 500.94 µmol) and (1-methylindolin-4-yl)boronic acid pinacol ester (241.60 mg, 751.41 µmol) to give intermediate 16u (140.00 mg, crude) as a yellow solid. m/z (M+H)$^+$=358.2.

Example 78: 6-(2-methyl-5-(pyrrolidin-1-yl)phenyl)-2-(pyrimidin-2-yl)-5,6,7,8-tetrahydrophthalazin-1(2H)-one According to scheme 2, step ix: Example 78 was prepared following the same procedure described for Example 58, starting from intermediate 16u (140.00 mg, 391.71 µmol), to provide Example 78 (26.79 mg, 71.41 µmol, 18.23% yield) as yellow solid. $^1$H-NMR (400 MHz, CDCl$_3$) δ 8.94 (d, J=4.9 Hz, 2H), 7.70 (s, 1H), 7.42 (t, J=4.9 Hz, 1H), 7.13 (d, J=8.4 Hz, 1H), 6.92 (dd, J=2.5, 8.3 Hz, 1H), 6.86 (d, J=2.5 Hz, 1H), 3.79-3.66 (m, 1H), 3.19-3.09 (m, 1H), 3.08-2.98 (m, 1H), 2.87-2.78 (m, 1H), 2.74-2.61 (m, 2H), 2.32 (s, 3H), 2.19-2.10 (m, 1H), 1.93-1.79 (m, 1H), 0.79-0.76 (m, 4H).

Example 79: 6-(2-fluoro-3-methoxyphenyl)-2-(pyrimidin-2-yl)-5,6,7,8-tetrahydrophthalazin-1(2H)-one, was Prepared According to Scheme 2, Method A

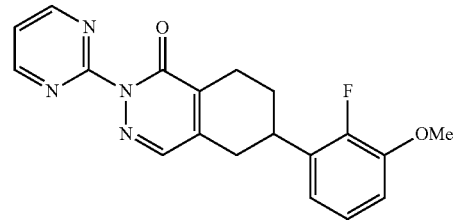 [SMILES: COc1cccc(C2CCc3c(cnn(-c4ncccn4)c3=O)C2)c1F]

Intermediate 16v: 6-(2-fluoro-3-methoxyphenyl)-2-(pyrimidin-2-yl)-7,8-dihydrophthalazin-1(2H)-one According to scheme 2, step viii: Intermediate 16v was prepared following the procedure described for intermediate 16a in Example 58, starting from intermediate 15b (250.00 mg, 500.95 µmol) and (2-fluoro-3-methoxyphenyl)boronic acid pinacol ester (189.43 mg, 751.42 µmol) to give intermediate 16v (140.00 mg, crude) as a yellow solid. m/z (M+H)$^+$=351.0.

Example 79: 6-(2-fluoro-3-methoxyphenyl)-2-(pyrimidin-2-yl)-5,6,7,8-tetrahydrophthalazin-1(2H)-one According to scheme 2, step ix: Example 79 was prepared following the same procedure described for Example 58, starting from intermediate 16v (140.00 mg, 399.60 µmol), to provide Example 79 (9.04 mg, 25.45 µmol, 6.37% yield) as white solid. $^1$H-NMR (400 MHz, CDCl$_3$) δ 8.94 (d, J=4.9 Hz, 2H), 7.70 (s, 1H), 7.42 (t, J=4.8 Hz, 1H), 7.31-7.27 (m, 1H), 7.00 (dd, J=1.7, 8.2 Hz, 1H), 6.93 (t, J=1.9 Hz, 1H), 6.88 (d, J=7.7 Hz, 1H), 3.79-3.70 (m, 1H), 3.05-2.85 (m, 3H), 2.80-2.60 (m, 2H), 2.29-2.17 (m, 1H), 1.95-1.81 (m, 1H), 0.83-0.77 (m, 4H).

Example 80: 6-(5-methoxy-2-methylphenyl)-2-(pyrimidin-2-yl)-5,6,7,8-tetrahydrophthalazin-1(2H)-one, was Prepared According to Scheme 2, Method A

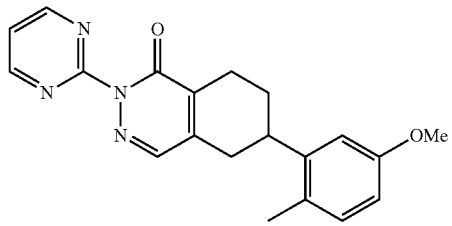

Intermediate 16w: 6-(5-methoxy-2-methylphenyl)-2-(pyrimidin-2-yl)-7,8-dihydrophthalazin-1(2H)-one According to scheme 2, step viii: Intermediate 16w was prepared following the procedure described for Intermediate 16a, starting from intermediate 15b (250.00 mg, 500.94 µmol) and (5-methoxy-2-methylphenyl)boronic acid (124.72 mg, 751.41 µmol), to give intermediate 16w (110.00 mg, crude) as brown solid. m/z (M+H)$^+$=347.1

Example 80: 6-(5-methoxy-2-methylphenyl)-2-(pyrimidin-2-yl)-5,6,7,8-tetrahydrophthalazin-1(2H)-one According to scheme 2, step ix: Example 80 was prepared following the same procedure described for Example 58, starting from intermediate 16w (110.00 mg, 317.57 µmol), to provide Example 80 (23.99 mg, 68.58 µmol, 21.60% yield) as a white solid. $^1$H-NMR (400 MHz, CDCl$_3$) δ 9.03 (s, 1H), 9.02 (s, 1H), 7.85 (s, 1H), 7.71 (t, J=4.89 Hz, 1H), 7.16 (t, J=7.91 Hz, 1H), 6.90 (d, J=7.53 Hz, 1H), 6.85 (d, J=8.16 Hz, 1H), 6.08 (tdd, J=4.99, 10.42, 17.25 Hz, 1H), 5.43 (dd, J=1.76, 17.32 Hz, 1H), 5.26 (dd, J=1.69, 10.60 Hz, 1H), 4.56 (d, J=4.89 Hz, 2H), 3.12-3.24 (m, 1H), 2.65-2.87 (m, 3H), 2.56 (br d, J=8.53 Hz, 1H), 2.22 (s, 3H), 1.95 (br s, 1H), 1.79-1.91 (m, 1H).

Example 81: 6-(2,5-dimethylphenyl)-2-(pyrimidin-2-yl)-5,6,7,8-tetrahydrophthalazin-1(2H)-one, was Prepared According to Scheme 2, Method A

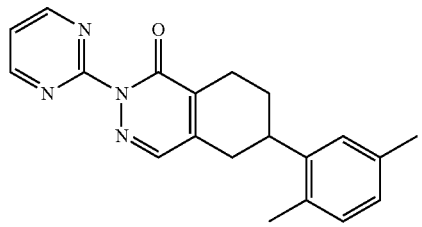 [SMILES: Cc1ccc(C)c(C2CCc3c(cnn(-c4ncccn4)c3=O)C2)c1]

Intermediate 16x: 6-(2,5-dimethylphenyl)-2-(pyrimidin-2-yl)-7,8-dihydrophthalazin-1(2H)-one According to scheme 2, step viii: Intermediate 16x was prepared following the procedure described for Intermediate 16a, starting from intermediate 15b (250.00 mg, 500.94 µmol) and (2,5-dimethylphenyl)boronic acid (112.70 mg, 751.41 µmol), to give intermediate 16x (75.00 mg, crude) as yellow solid. m/z (M+H)$^+$=331.2.

Example 81: 6-(2,5-dimethylphenyl)-2-(pyrimidin-2-yl)-5,6,7,8-tetrahydrophthalazin-1(2H)-one According to scheme 2, step ix: Example 81 was prepared following the same procedure described for Example 58, starting from intermediate 16x (75.00 mg, 227.01 µmol), to provide example 81 (16.9 mg, 50.69 µmol, 22.33% yield) as a white solid. $^1$H-NMR (400 MHz, CDCl$_3$) δ 8.18 (s, 2H), 7.78 (s, 1H), 7.14-7.21 (m, 1H), 6.89 (d, J=7.91 Hz, 1H), 6.85 (d, J=8.03 Hz, 1H), 3.78 (s, 3H), 3.27-3.34 (m, 4H), 3.13-3.22 (m, 1H), 2.65-2.83 (m, 3H), 2.52-2.58 (m, 1H), 2.18 (s, 3H), 1.91-2.05 (m, 5H), 1.77-1.89 (m, 1H).

Example 82: 6-(2,3-dimethylphenyl)-2-(pyrimidin-2-yl)-5,6,7,8-tetrahydrophthalazin-1(2H)-one, was Prepared According to Scheme 2, Method A

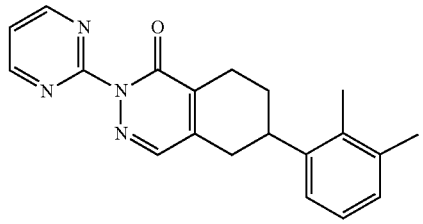 [SMILES: Cc1cccc(C2CCc3c(cnn(-c4ncccn4)c3=O)C2)c1C]

Intermediate 16y: 6-(2,3-dimethylphenyl)-2-(pyrimidin-2-yl)-7,8-dihydrophthalazin-1(2H)-one According to scheme 2, step viii: Intermediate 16y was prepared following the procedure described for Intermediate 16a, starting from intermediate 15b (250.00 mg, 500.94 µmol) and (2,3-dimethylphenyl)boronic acid (112.70 mg, 751.41 µmol), to provide intermediate 16y (100.00 mg, crude) as yellow solid. m/z (M+H)$^+$=331.2.

Example 82: 6-(2,3-dimethylphenyl)-2-(pyrimidin-2-yl)-5,6,7,8-tetrahydrophthalazin-1(2H)-one According to scheme 2, step ix: Example 82 was prepared following the same procedure described for Example 58, starting from intermediate 16y (100.00 mg, 302.68 μmol), to provide Example 82 (4.78 mg, 13.70 μmol, 4.53% yield) as a yellow solid. $^{1}$H-NMR (400 MHz, DMSO-$d_{6}$) δ 8.61 (s, 2H), 7.81 (s, 1H), 7.14-7.22 (m, 1H), 6.88 (dd, J=7.91, 16.81 Hz, 2H), 3.75-3.82 (m, 7H), 3.34 (br s, 4H), 3.12-3.22 (m, 1H), 2.76-2.86 (m, 1H), 2.63-2.75 (m, 2H), 2.56 (br s, 1H), 2.18 (s, 3H), 1.94 (br s, 1H), 1.77-1.90 (m, 1H).

Example 83: 6-(3-(methoxymethyl)phenyl)-2-(pyrimidin-2-yl)-5,6,7,8-tetrahydrophthalazin-1(2H)-one, was Prepared According to Scheme 2, Method A

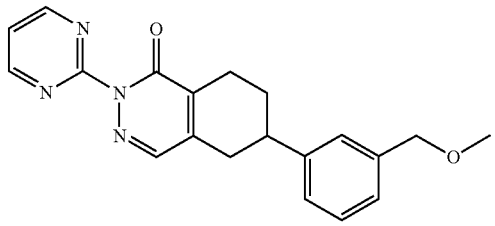 [SMILES: COCc1cccc(C2CCc3c(cnn(-c4ncccn4)c3=O)C2)c1]

Intermediate 16z: 6-(3-(methoxymethyl)phenyl)-2-(pyrimidin-2-yl)-7,8-dihydrophthalazin-1(2H)-one According to scheme 2, step viii: Intermediate 16z was prepared following the procedure described for Intermediate 16a, starting from intermediate 15b (590 mg, 1.18 mmol) and (3-(methoxymethyl)phenyl)boronic acid (196.23 mg, 1.18 mmol), to provide intermediate 16z (280 mg, crude) as a yellow solid. m/z (M+H)$^{+}$=347.1.

Example 83: 6-(3-(methoxymethyl)phenyl)-2-(pyrimidin-2-yl)-5,6,7,8-tetrahydrophthalazin-1(2H)-one According to scheme 2, step ix: Example 83 was prepared following the same procedure described for Example 58, starting from intermediate 16z (260 mg, 750.62 μmol), to provide Example 83 (24.91 mg, 70.28 μmol, 9.36% yield) as a white solid. $^{1}$H-NMR (400 MHz, DMSO-$d_{6}$) δ 8.72 (s, 2H), 7.82 (s, 1H), 7.14-7.21 (m, 1H), 6.89 (d, J=7.65 Hz, 1H), 6.85 (d, J=8.16 Hz, 1H), 5.03 (t, J=5.46 Hz, 1H), 4.24-4.31 (m, 2H), 3.75-3.80 (m, 5H), 3.13-3.22 (m, 1H), 2.67-2.86 (m, 3H), 2.55 (br d, J=9.79 Hz, 1H), 2.18 (s, 3H), 1.93 (br s, 1H), 1.78-1.89 (m, 1H).

Example 84: 6-(5-cyclopropoxy-2-methylphenyl)-2-(pyrimidin-2-yl)-5,6,7,8-tetrahydrophthalazin-1(2H)-one, was Prepared According to Scheme 2, Method A

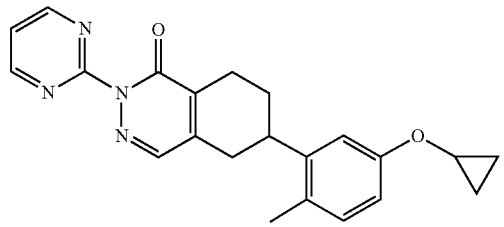 [SMILES: Cc1ccc(OC2CC2)cc1C1CCc2c(cnn(-c3ncccn3)c2=O)C1]

Intermediate 16aa: 6-(5-cyclopropoxy-2-methylphenyl)-2-(pyrimidin-2-yl)-7,8-dihydrophthalazin-1(2H)-one According to scheme 2, step viii: Intermediate 16aa was prepared following the procedure described for Intermediate 16a, starting from intermediate 15b (200 mg, 523.65 μmol) and (5-cyclopropoxy-2-methylphenyl)boronic acid pinacol ester (244.71 mg, 785.47 μmol), to provide intermediate 16aa (210 mg, crude) as a yellow solid. m/z (M+H)$^{+}$=373.2.

Example 84: 6-(5-cyclopropoxy-2-methylphenyl)-2-(pyrimidin-2-yl)-5,6,7,8-tetrahydrophthalazin-1(2H)-one According to scheme 2, step ix: Example 84 was prepared following the same procedure described for Example 58, starting from intermediate 16aa (210 mg, 563.88 μmol), to provide example 84 (13.78 mg, 36.77 μmol, 6.52% yield) as a white solid. $^{1}$H-NMR (400 MHz, DMSO-$d_{6}$) δ 8.35 (d, J=6.15 Hz, 1H), 7.77 (s, 1H), 7.15-7.21 (m, 1H), 6.96 (d, J=6.27 Hz, 1H), 6.89 (d, J=7.78 Hz, 1H), 6.85 (d, J=8.16 Hz, 1H), 3.79 (s, 3H), 3.67 (br d, J=5.02 Hz, 4H), 3.62 (br d, J=4.77 Hz, 4H), 3.17 (br t, J=8.97 Hz, 1H), 2.62-2.83 (m, 3H), 2.52-2.59 (m, 1H), 2.18 (s, 3H), 1.93 (br s, 1H), 1.83 (dq, J=4.83, 11.90 Hz, 1H).

Example 85: 6-(3-cyclopropoxyphenyl)-2-(pyrimidin-2-yl)-5,6,7,8-tetrahydrophthalazin-1(2H)-one, was Prepared According to Scheme 2, Method A

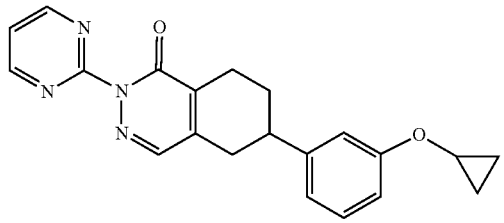 [SMILES: O=c1c2c(cnn1-c1ncccn1)CC(c1cccc(OC3CC3)c1)CC2]

Intermediate 16ab: 6-(3-cyclopropoxyphenyl)-2-(pyrimidin-2-yl)-7,8-dihydrophthalazin-1(2H)-one According to scheme 2, step viii: Intermediate 16ab was prepared following the procedure described for Intermediate 16a, starting from intermediate 15b (200 mg, 523.65 µmol) and (3-cyclopropoxyphenyl)boronic acid pinacol ester (241.24 mg, 785.48 µmol), to provide intermediate 16ab (170 mg, crude) as a yellow solid. m/z (M+H)⁺=359.2.

Example 85: 6-(3-cyclopropoxyphenyl)-2-(pyrimidin-2-yl)-5,6,7,8-tetrahydrophthalazin-1(2H)-one According to scheme 2, step ix: Example 85 was prepared following the same procedure described for Example 58, starting from intermediate 16ab (170 mg, 474.34 µmol), to provide example 85 (12.36 mg, 33.03 µmol, 6.96% yield) as a white solid. ¹H-NMR (400 MHz, CDCl₃) δ 8.93 (d, J=4.8 Hz, 2H), 7.70 (s, 1H), 7.42 (t, J=4.9 Hz, 1H), 7.27-7.22 (m, 1H), 6.82 (d, J=7.8 Hz, 1H), 6.80-6.76 (m, 2H), 4.78 (qd, J=2.9, 5.7 Hz, 1H), 3.03-2.84 (m, 3H), 2.80-2.71 (m, 1H), 2.71-2.60 (m, 1H), 2.26-2.16 (m, 1H), 1.96-1.78 (m, 7H), 1.68-1.59 (m, 2H).

Example 86: 6-(3-(cyclopentyloxy)phenyl)-2-(pyrimidin-2-yl)-5,6,7,8-tetrahydrophthalazin-1(2H)-one, was Prepared According to Scheme 2, Method A

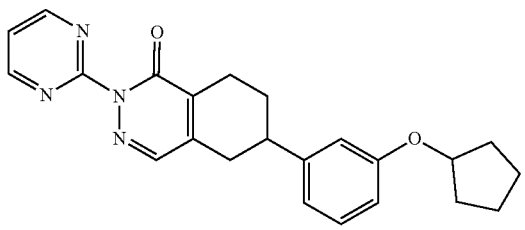 [SMILES: O=c1c2c(cnn1-c1ncccn1)CC(c1cccc(OC3CCCC3)c1)CC2]

Intermediate 16ac: 6-(3-(cyclopentyloxy)phenyl)-2-(pyrimidin-2-yl)-7,8-dihydrophthalazin-1(2H)-one According to scheme 2, step viii: Intermediate 16ac was prepared following the procedure described for Intermediate 16a, starting from intermediate 15b (300 mg, 785.48 µmol) and (3-(cyclopentyloxy)phenyl)boronic acid pinacol ester (425.50 mg, 1.18 mmol), to provide intermediate 16ac (240 mg, crude) as a yellow solid. m/z (M+H)⁺=387.1.

Example 86: 6-(3-(cyclopentyloxy)phenyl)-2-(pyrimidin-2-yl)-5,6,7,8-tetrahydrophthalazin-1(2H)-one According to scheme 2, step ix: Example 86 was prepared following the same procedure described for Example 58, starting from intermediate 16ac (240 mg, 621.04 µmol), to provide Example 86 (29.15 mg, 73.01 µmol, 11.76% yield) as a white solid. ¹H-NMR (400 MHz, CDCl₃) δ 8.93 (d, J=4.8 Hz, 2H), 7.70 (s, 1H), 7.42 (t, J=4.9 Hz, 1H), 7.27-7.22 (m, 1H), 6.82 (d, J=7.8 Hz, 1H), 6.80-6.76 (m, 2H), 4.78 (qd, J=2.9, 5.7 Hz, 1H), 3.03-2.84 (m, 3H), 2.80-2.71 (m, 1H), 2.71-2.60 (m, 1H), 2.26-2.16 (m, 1H), 1.96-1.78 (m, 7H), 1.68-1.59 (m, 2H).

Example 87: 6-(4-methoxy-2-methylphenyl)-2-(pyrimidin-2-yl)-5,6,7,8-tetrahydrophthalazin-1(2H)-one, was Prepared According to Scheme 2, Method A

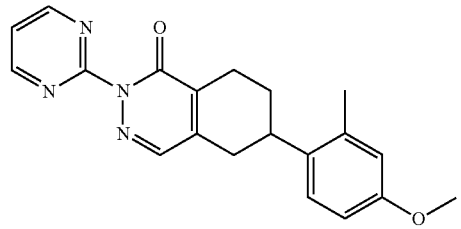 [SMILES: COc1ccc(C2CCc3c(cnn(-c4ncccn4)c3=O)C2)c(C)c1]

Intermediate 16ad: 6-(4-methoxy-2-methylphenyl)-2-(pyrimidin-2-yl)-7,8-dihydrophthalazin-1(2H)-one According to scheme 2, step viii: Intermediate 16ad was prepared following the procedure described for Intermediate 16a, starting from intermediate 15b (0.3 g, 801.51 µmol) and (4-methoxy-2-methylphenyl)boronic acid (133.04 mg, 801.51 µmol), to provide Intermediate 16ad (0.2 g, crude) as yellow solid. m/z (M+H)⁺=347.1; ¹H NMR (DMSO-d₆, 400 MHz) δ 9.02 (d, J=4.8 Hz, 2H), 8.00 (s, 1H), 7.71 (t, J=4.8 Hz, 1H), 7.21 (d, J=8.4 Hz, 1H), 6.86 (d, J=2.4 Hz, 1H), 6.81 (dd, J=8.4, 2.4 Hz, 1H), 6.40 (s, 1H), 3.75 (s, 3H), 2.75-2.85 (m, 2H), 2.60-2.70 (m, 2H), 2.36 (s, 3H).

Example 87: 6-(4-methoxy-2-methylphenyl)-2-(pyrimidin-2-yl)-5,6,7,8-tetrahydrophthalazin-1(2H)-one According to scheme 2, step ix: Example 87 was prepared following the same procedure described for Example 58, starting from intermediate 16ad (0.15 g, 433.05 µmol), to provide Example 87 (42 mg, 120.55 µmol, 27.84% yield) as white solid. ¹H-NMR (400 MHz, DMSO-d₆) δ 9.02 (d, J=4.8 Hz, 2H), 7.85 (s, 1H), 7.71 (t, J=4.8 Hz, 1H), 7.13-7.23 (m, 1H), 6.77 (br d, J=2.8 Hz, 2H), 3.72 (s, 3H), 3.07 (m, 1H), 2.57-2.85 (m, 4H), 2.32 (s, 3H), 1.78-1.99 (m, 2H).

Example 88: 6-(1,5-dimethyl-1H-indazol-4-yl)-2-(pyrimidin-2-yl)-5,6,7,8-tetrahydrophthalazin-1(2H)-one, was Prepared According to Scheme 2, Method A

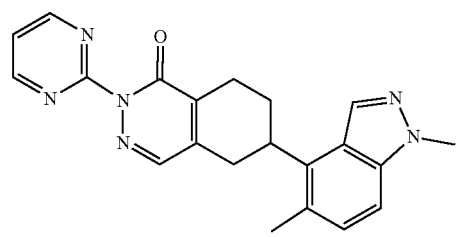 [SMILES: Cc1ccc2c(cnn2C)c1C1CCc2c(cnn(-c3ncccn3)c2=O)C1]

Intermediate 16ae: 6-(1,5-dimethyl-1H-indazol-4-yl)-2-(pyrimidin-2-yl)-7,8-dihydrophthalazin-1(2H)-one According to scheme 2, step viii: Intermediate 16ae was prepared following the procedure described for Intermediate 16a, using intermediate 15b (0.2 g, 534.34 μmol) and (1,5-dimethyl-1H-indazol-4-yl)boronic acid pinacol ester (145.42 mg, 534.34 μmol) to provide intermediate 16ae (50 mg, 134.99 μmol, 25.26% yield) as yellow solid. m/z (M+H)⁺=371.2.

Example 88: 6-(1,5-dimethyl-1H-indazol-4-yl)-2-(pyrimidin-2-yl)-5,6,7,8-tetrahydrophthalazin-1(2H)-one According to scheme 2, step ix: Example 88 was prepared following the same procedure described for Example 58, starting from intermediate 16ae (51.39 mg, 138.73 μmol), to provide example 88 (4 mg, 10.74 μmol, 7.74% yield) as light yellow solid. $^1$H-NMR (400 MHz, DMSO-$d_6$) δ 9.03 (d, J=4.8 Hz, 3H), 8.24 (s, 1H), 7.85 (s, 1H), 7.68-7.76 (m, 1H), 7.41 (d, J=8.4 Hz, 1H), 7.23 (d, J=8.4 Hz, 1H), 4.01 (s, 3H), 3.19 (m, 1H), 3.12-3.12 (m, 1H), 2.73-2.94 (m, 4H), 2.44 (s, 3H), 1.99 (m, 2H).

Example 89: 6-mesityl-2-(pyrimidin-2-yl)-5,6,7,8-tetrahydrophthalazin-1(2H)-one, was Prepared According to Scheme 2, Method A

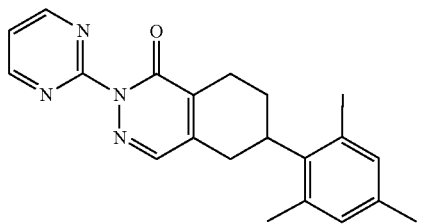 [SMILES: Cc1cc(C)c(C2CCc3c(cnn(-c4ncccn4)c3=O)C2)c(C)c1]

Intermediate 16af: 6-mesityl-2-(pyrimidin-2-yl)-7,8-dihydrophthalazin-1(2H)-one

According to scheme 2, step viii: Intermediate 16af was prepared following the procedure described for Intermediate 16a, starting from intermediate 15b (200.00 mg, 534.34 μmol) and mesitylboronic acid (87.64 mg, 534.34 μmol) to provide intermediate 16af (0.15 g, 435.53 μmol, 81.51% yield) as yellow solid. m/z (M+H)⁺=345.3; $^1$H NMR (DMSO-$d_6$, 400 MHz) δ 9.03 (d, J=4.8 Hz, 2H), 7.99 (s, 1H), 7.71 (t, J=4.8 Hz, 1H), 6.92 (s, 2H), 6.26 (s, 1H), 2.78-2.91 (m, 2H), 2.52-2.56 (m, 2H), 2.24 (s, 3H), 2.20 (s, 6H).

Example 89: 6-mesityl-2-(pyrimidin-2-yl)-5,6,7,8-tetrahydrophthalazin-1(2H)-one

According to scheme 2, step ix: Example 89 was prepared following the same procedure described for Example 58, starting from intermediate 16af (150.00 mg, 435.53 μmol), to provide Example 89 (8 mg, 22.61 μmol, 5.19% yield) as white solid. $^1$H-NMR (400 MHz, DMSO-$d_6$) δ 9.01 (d, J=4.8 Hz, 2H), 7.81 (s, 1H), 7.67-7.73 (m, 1H), 6.81 (s, 2H), 3.28-3.30 (m, 1H), 2.95-3.08 (m, 1H), 2.64-2.84 (m, 2H), 2.32 (s, 6H), 2.18 (s, 3H), 1.89 (m, 2H).

Example 90: 6-(2,6-difluoro-3-methoxyphenyl)-2-(pyrimidin-2-yl)-5,6,7,8-tetrahydrophthalazin-1(2H)-one, was Prepared According to Scheme 2, Method A

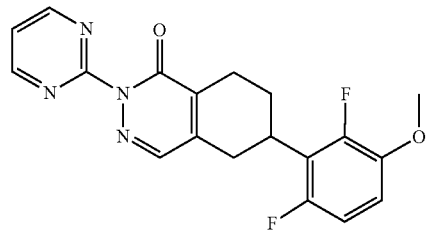 [SMILES: COc1ccc(F)c(C2CCc3c(cnn(-c4ncccn4)c3=O)C2)c1F]

Intermediate 16ag: 6-(2,6-difluoro-3-methoxyphenyl)-2-(pyrimidin-2-yl)-7,8-dihydrophthalazin-1(2H)-one According to scheme 2, step viii: Intermediate 16ag was prepared following the procedure described for Intermediate 16a, starting from intermediate 15b (0.2 g, 534.34 μmol) and (2,6-difluoro-3-methoxyphenyl)boronic acid (100.42 mg, 534.34 μmol) to provide intermediate 16ag (0.15 g, 407.24 μmol, 76.21% yield) as yellow solid. m/z (M+H)⁺=369.1; $^1$H NMR (DMSO-$d_6$, 400 MHz) δ 9.03 (d, J=4.8 Hz, 2H), 8.04 (s, 1H), 7.72 (t, J=4.8 Hz, 1H), 7.06-7.34 (m, 2H), 6.71 (s, 1H), 3.86 (s, 3H), 2.76-2.89 (m, 2H), 2.62-2.73 (m, 2H).

Example 90: 6-(2,6-difluoro-3-methoxyphenyl)-2-(pyrimidin-2-yl)-5,6,7,8-tetrahydrophthalazin-1(2H)-one According to scheme 2, step ix: Example 90 was prepared following the same procedure described for Example 58, starting from intermediate 16ag (0.15 g, 407.24 μmol), to provide Example 90 (60 mg, 162.01 μmol, 39.78% yield) as white solid. $^1$H-NMR (400 MHz, DMSO-$d_6$) δ 9.02 (d, J=4.8 Hz, 2H), 7.83 (s, 1H), 7.71 (t, J=4.8 Hz, 1H), 6.99-7.19 (m, 3H), 3.83 (s, 3H), 3.36-3.43 (m, 1H), 2.71-3.04 (m, 4H), 1.97-2.18 (m, 3H).

Example 91: 6-(2-chloro-3-cyclopropoxyphenyl)-2-(pyrimidin-2-yl)-5,6,7,8-tetrahydrophthalazin-1(2H)-one, was Prepared According to Scheme 2, Method A

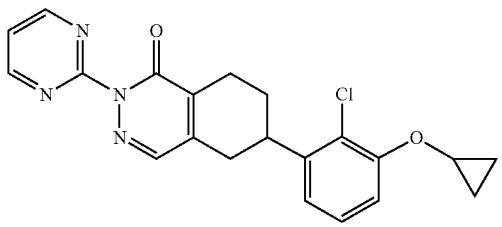 [SMILES: O=c1c2c(cnn1-c1ncccn1)CC(c1cccc(OC3CC3)c1Cl)CC2]

Intermediate 16ah: 6-(2-chloro-3-cyclopropoxyphenyl)-2-(pyrimidin-2-yl)-7,8-dihydrophthalazin-1(2H)-one According to scheme 2, step viii: Intermediate 16ah was prepared following the procedure described for Intermediate 16a, starting from intermediate 15b (2.50 g, 6.68 mmol) and (2-chloro-3-cyclopropoxyphenyl)boronic acid pinacol ester (1.83 g, 6.21 mmol) to provide intermediate 16ah (1.60 g, 3.84 mmol, 57.4% yield) as a yellow solid. $^1$H NMR (400 MHz, CDCl$_3$) δ 8.94 (d, J=4.8 Hz, 2H), 7.79 (s, 1H), 7.42 (t, J=4.8 Hz, 1H), 7.35-7.30 (m, 1H), 7.29-7.24 (m, 2H), 6.91 (dd, J=1.6, 7.6 Hz, 1H), 6.35 (t, J=1.6 Hz, 1H), 3.84 (tt, J=3.2, 5.9 Hz, 1H), 3.08-2.98 (m, 2H), 2.84-2.72 (m, 2H), 0.92-0.82 (m, 4H).

Example 91: 6-(2-chloro-3-cyclopropoxyphenyl)-2-(pyrimidin-2-yl)-5,6,7,8-tetrahydro-phthalazin-1(2H)-one According to scheme 2, step ix: Example 91 was prepared following the same procedure described for Example 58 starting from intermediate 16ah (1.20 g, 2.88 mmol), to provide Example 91 (517 mg, 1.26 mmol, 43.9% yield) as a white solid. $^1$H-NMR (400 MHz, CDCl$_3$) δ 8.93 (d, J=4.8 Hz, 2H), 7.70 (s, 1H), 7.42 (t, J=4.8 Hz, 1H), 7.26-7.22 (m, 2H), 6.95-6.86 (m, 1H), 3.83 (tt, J=3.0, 5.8 Hz, 1H), 3.58-3.47 (m, 1H), 3.04-2.92 (m, 2H), 2.82-2.57 (m, 2H), 2.24-2.14 (m, 1H), 1.99-1.86 (m, 1H), 0.93-0.80 (m, 4H).

Example 92: 6-(1-cyclopropylindolin-4-yl)-2-(pyrimidin-2-yl)-5,6,7,8-tetrahydrophthalazin-1(2H)-one, was Prepared According to Scheme 2, Method A

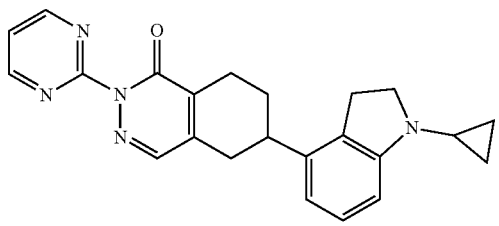 [SMILES: O=c1c2c(cnn1-c1ncccn1)CC(c1cccc3c1CCN3C1CC1)CC2]

Intermediate 16ai: 6-(1-cyclopropylindolin-4-yl)-2-(pyrimidin-2-yl)-7,8-dihydrophthalazin-1(2H)-one According to scheme 2, step viii: Intermediate 16ai was prepared following the procedure described for Intermediate 16a, starting from intermediate 15b (2.00 g, 5.34 mmol) and 1-cyclopropylindolin-4-yl)boronic acid pinacol ester (1.50 g, 5.26 mmol), to provide Intermediate 16ai (1.70 g, 4.43 mmol, 83.0% yield) a yellow solid. m/z (M+H)$^+$=384.0

Example 92: 6-(1-cyclopropylindolin-4-yl)-2-(pyrimidin-2-yl)-5,6,7,8-tetrahydrophthalazin-1(2H)-one According to scheme 2, step ix: Example 92 was prepared following a similar procedure than for Example 58, starting from intermediate 16ai (1.70 g, 4.43 mmol to provide Example 92 (230 mg, 549.19 μmol, 35.10% yield) as a light-yellow solid. $^1$H-NMR (400 MHz, CDCl$_3$) δ 8.94 (d, J=4.8 Hz, 1H), 8.97-8.90 (m, 1H), 7.69 (s, 1H), 7.42 (t, J=5.0 Hz, 1H), 7.13 (t, J=7.6 Hz, 1H), 6.77 (d, J=7.6 Hz, 1H), 6.61 (d, J=7.6 Hz, 1H), 3.46-3.39 (m, 2H), 3.06-2.89 (m, 4H), 2.85-2.59 (m, 3H), 2.19-2.11 (m, 2H), 1.95-1.83 (m, 1H), 0.73-0.63 (m, 4H).

Example 93: 6-(3-cyclopropoxy-2-methylphenyl)-2-(5-methylpyrimidin-2-yl)-5,6,7,8-tetrahydrophthalazin-1(2H)-one, was Prepared According to Scheme 2, Method A

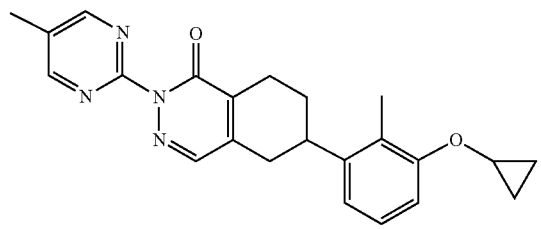 [SMILES: Cc1cnc(-n2ncc3c(c2=O)CCC(c2cccc(OC4CC4)c2C)C3)nc1]

Intermediate 16aj: 6-(3-cyclopropoxy-2-methylphenyl)-2-(5-methylpyrimidin-2-yl)-7,8-dihydrophthalazin-1(2H)-one According to scheme 2, step viii: Intermediate 16aj was prepared following the procedure described for Intermediate 16a, starting from intermediate 15c (3.00 g, 7.49 mmol) and (3-cyclopropoxy-2-methylphenyl)boronic acid pinacol ester (2.25 g, 7.49 mmol), to provide Intermediate 16aj (2.10 g, 5.28 mmol, 70.5% yield) as a yellow solid. $^1$H NMR (400 MHz, CDCl$_3$) δ 8.74 (s, 2H), 7.75 (s, 1H), 7.25-7.16 (m, 2H), 6.81 (dd, J=1.8, 7.0 Hz, 1H), 6.23 (s, 1H), 3.80-3.73 (m, 1H), 3.03-2.94 (m, 2H), 2.72-2.63 (m, 2H), 2.43 (s, 3H), 2.18 (s, 3H), 0.85-0.73 (m, 4H).

Example 93: 6-(3-cyclopropoxy-2-methylphenyl)-2-(5-methylpyrimidin-2-yl)-5,6,7,8-tetrahydrophthalazin-1(2H)-one According to scheme 2, step ix: Example 93 was prepared following the same procedure described for Example 58, starting from intermediate 16aj (1.20 g, 3.02 mmol), to provide Example 93 (500 mg, 1.27 mmol, 42.1% yield) as a white solid. $^1$H-NMR (400 MHz, CDCl$_3$) δ 8.74 (s, 2H), 7.68 (s, 1H), 7.24-7.13 (m, 2H), 6.86 (d, J=6.5 Hz, 1H), 3.78-3.71 (m, 1H), 3.26-3.17 (m, 1H), 3.04-2.95 (m, 1H), 2.86-2.76 (m, 1H), 2.75-2.60 (m, 2H), 2.43 (s, 3H), 2.19 (s, 3H), 2.17-2.09 (m, 1H), 1.95-1.82 (m, 1H), 0.82-0.76 (m, 4H).

Example 94: 6-(2-chloro-3-methoxyphenyl)-2-(5-methylpyrimidin-2-yl)-5,6,7,8-tetrahydrophthalazin-1(2H)-one, was Prepared According to Scheme 2, Method A

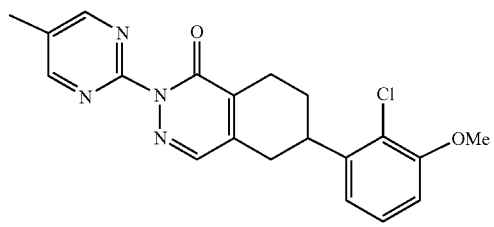 [SMILES: COc1cccc(C2CCc3c(cnn(-c4ncc(C)cn4)c3=O)C2)c1Cl]

Intermediate 16ak: 6-(2-chloro-3-methoxyphenyl)-2-(5-methylpyrimidin-2-yl)-7,8-dihydrophthalazin-1(2H)-one According to scheme 2, step viii: Intermediate 16ak was prepared following the procedure described for Intermediate 16a, starting from intermediate 15c (3.00 g, 7.49 mmol) and (2-chloro-3-methoxyphenyl)boronic acid pinacol ester (1.40 g, 7.49 mmol), to provide Intermediate 16ak (2.40 g, 6.15 mmol, 82.1% yield, 97.6% purity) as a yellow solid. $^1$H NMR (400 MHz, CDCl$_3$) δ 8.75 (s, 2H), 7.83-7.74 (m, 1H), 7.33-7.21 (m, 1H), 7.04-6.81 (m, 2H), 6.36 (s, 1H), 4.10-3.89 (m, 3H), 3.18-2.96 (m, 2H), 2.88-2.73 (m, 2H), 2.44 (s, 3H).

Example 94: 6-(2-chloro-3-methoxyphenyl)-2-(5-methylpyrimidin-2-yl)-5,6,7,8-tetrahydrophthalazin-1(2H)-one According to scheme 2, step ix: Example 94 was prepared following the same procedure described for Example 58, starting from intermediate 16ak (600 mg, 1.54 mmol), to provide Example 94 (230 mg, 588 μmol, 38.2% yield, 97.8% purity) was obtained as a white solid. $^1$H-NMR (400 MHz, CDCl$_3$) δ 8.73 (s, 2H), 7.69 (s, 1H), 7.26-7.23 (m, 1H), 6.88 (dd, J=4.4, 8.0 Hz, 2H), 3.93 (s, 3H), 3.61-3.49 (m, 1H), 3.02-2.92 (m, 2H), 2.82-2.58 (m, 2H), 2.43 (s, 3H), 2.19 (td, J=2.8, 10.0 Hz, 1H), 1.98-1.85 (m, 1H).

Example 95: 6-(2-chloro-4-methylphenyl)-2-(pyrimidin-2-yl)-5,6,7,8-tetrahydrophthalazin-1(2H)-one, was Prepared According to Scheme 2, Method B

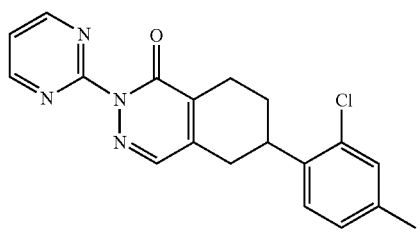 [SMILES: Cc1ccc(C2CCc3c(cnn(-c4ncccn4)c3=O)C2)c(Cl)c1]

Intermediate 17a: 2-(pyrimidin-2-yl)-6-(4,4,5,5-tetramethyl-1,3,2-dioxaborolan-2-yl)-7,8-dihydrophthalazin-1(2H)-one According to Scheme 2, step x: To a solution of intermediate 15b (1 g, 2.67 mmol, 1 eq), Pd(dppf)Cl$_2$ (97.74 mg, 133.58 μmol, 0.05 eq) and KOAc (524.41 mg, 5.34 mmol, 2 eq) in dioxane (20 mL) was added Pin$_2$B$_2$ (1.02 g, 4.01 mmol, 1.5 eq) in one portion at 25° C. under N$_2$. The mixture was stirred at 100° C. for 12 hours. The mixture was filtered, the filtrate was concentrated under reduced pressure to give a residue. The residue was purified by silica gel chromatography (PE:EtOAc=1:1) to afford intermediate 17a (0.85 g, 2.41 mmol, 90.33% yield) as a yellow solid.

m/z (M+H)$^+$=353.3; $^1$H NMR (CDCl$_3$, 400 MHz) δ 8.92 (d, J=4.8 Hz, 2H), 7.77 (s, 1H), 7.41 (t, J=4.8 Hz, 1H), 6.99 (s, 1H), 2.74-2.89 (t, J=8.8 Hz, 2H), 2.46-2.61 (t, J=8.8 Hz, 2H), 1.32 (s, 12H).

Intermediate 16al: 6-(2-chloro-4-methylphenyl)-2-(pyrimidin-2-yl)-7,8-dihydrophthalazin-1(2H)-one According to Scheme 2, step xi: To a mixture of intermediate 17a (247.04 mg, 1.20 mmol, 64.34 μL, 1.5 eq) and 1-bromo-2-chloro-4-methylbenzene (0.3 g, 801.51 μmol, 1 eq) in dioxane (10 mL) was added Na$_2$CO$_3$ (339.80 mg, 3.21 mmol, 4 eq) in H$_2$O (1 mL) and Pd(dppf)Cl$_2$·CH$_2$Cl$_2$ (65.45 mg, 80.15 μmol, 0.1 eq) in one portion at 20° C. under N$_2$. The mixture was stirred at 100° C. for 12 hours. The mixture was filtered and concentrated in vacuo. The residue was purified by silica gel chromatography (PE:EtOAc=0:1, 1:0) to afford intermediate 16al (0.15 g, 427.59 μmol, 53.35% yield) as a yellow solid. $^1$H NMR (400 MHz, CDCl$_3$) δ 9.07-9.03 (m, 3H), 8.04 (s, 1H), 7.76-7.68 (m, 2H), 7.40 (s, 1H), 7.34 (d, J=8.0 Hz, 1H), 7.24 (d, J=8.0 Hz, 1H), 6.57 (s, 1H), 2.87-2.79 (m, 2H), 2.77-2.67 (m, 2H), 2.35 (s, 3H).

Example 95: 6-(2-methoxyphenyl)-2-(pyridin-2-yl)-5,6,7,8-tetrahydrophthalazin-1(2H)-one According to scheme 2, step ix: Example 95 was prepared following the same procedure described for Example 58, starting from intermediate 16al (0.15 g, 427.59 μmol) to yield Example 95 (0.018 g, 51.02 μmol, 11.93% yield) as a white solid. $^1$H-NMR (400 MHz, CDCl$_3$) δ 8.94 (d, J=4.0 Hz, 2H), 7.71 (s, 1H), 7.42 (t, J=4.4 Hz, 1H), 7.25 (s, 1H), 7.17-7.12 (m, 1H), 7.12-7.06 (m, 1H), 3.52-3.39 (m, 1H), 3.04-2.92 (m, 2H), 2.76-2.58 (m, 2H), 2.34 (s, 3H), 2.22-2.05 (m, 2H), 1.97-1.85 (m, 1H).

Example 96: 6-(3-(dimethylamino)-2-methylphenyl)-2-(pyrimidin-2-yl)-5,6,7,8-tetrahydrophthalazin-1(2H)-one, was Prepared According to Scheme 2, Method B

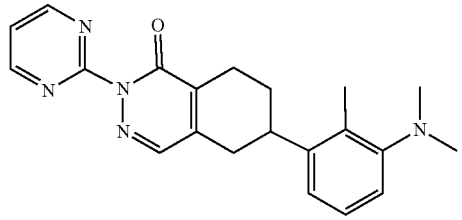 [SMILES: Cc1c(C2CCc3c(cnn(-c4ncccn4)c3=O)C2)cccc1N(C)C]

Intermediate 16 am: 6-(3-(dimethylamino)-2-methylphenyl)-2-(pyrimidin-2-yl)-7,8-dihydrophthalazin-1(2H)-one According to Scheme 2, step xi: intermediate 16 am was prepared following the same procedure described for intermediate 16al, starting from intermediate 17a (0.2 g, 567.87 μmol) and 3-bromo-N,N,2-trimethylaniline (121.58 mg, 567.87 μmol) to yield intermediate 16 am (0.15 g, 417.33 μmol, 73.49% yield) as yellow solid. m/z (M+H)$^+$=360.3; $^1$H NMR (CDCl$_3$, 400 MHz) δ 8.94 (d, J=4.9 Hz, 3H), 7.78 (s, 1H), 7.44-7.40 (m, 2H), 7.20 (t, J=8.0 Hz, 1H), 7.06 (d, J=8.0 Hz, 1H), 6.90 (d, J=7.6 Hz, 1H), 6.26 (s, 1H), 2.96-3.07 (m, 2H), 2.66-2.76 (m, 8H), 2.35 (s, 3H).

Example 96: 6-(3-(dimethylamino)-2-methylphenyl)-2-(pyrimidin-2-yl)-5,6,7,8-tetrahydrophthalazin-1(2H)-one According to scheme 2, step ix: Example 96 was prepared following the same procedure described for Example 58, starting from intermediate 16 am (0.15 g, 417.33 µmol) to yield Example 96 (14 mg, 34.93 µmol, 8.37% yield) as white solid. $^1$H-NMR (400 MHz, CDCl$_3$) δ 8.94 (d, J=4.8 Hz, 2H), 7.70 (s, 1H), 7.42 (t, J=4.8 Hz, 1H), 7.28 (m, 1H), 7.02 (d, J=8.0 Hz, 1H), 6.98 (d, J=8.0 Hz, 1H), 3.16 (m, 1H), 2.97-2.92 (m, 1H), 2.91-2.75 (m, 7H), 2.65-2.59 (m, 2H), 2.35 (s, 3H), 2.08-2.06 (m, 1H), 1.86-1.81 (m, 1H).

Example 97: 6-(5-methoxy-2,4-dimethylphenyl)-2-(pyrimidin-2-yl)-5,6,7,8-tetrahydrophthalazin-1(2H)-one, was Prepared According to Scheme 2, Method B

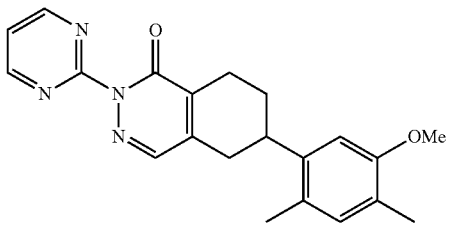 [SMILES: COc1cc(C2CCc3c(cnn(-c4ncccn4)c3=O)C2)c(C)cc1C]

Intermediate 16an: 6-(5-methoxy-2,4-dimethylphenyl)-2-(pyrimidin-2-yl)-7,8-dihydrophthalazin-1(2H)-one According to Scheme 2, step xi: intermediate 16an was prepared following the same procedure described for intermediate 16al, starting from intermediate 17a (0.3 g, 851.80 µmol) and 1-bromo-5-methoxy-2,4-dimethylbenzene (183.21 mg, 851.80 µmol) to yield intermediate 16an (0.2 g, 554.93 µmol, 65.15% yield) as yellow solid. m/z (M+H)$^+$ =361.3; $^1$H NMR (CDCl$_3$, 400 MHz) δ 9.03 (d, J=4.8 Hz, 2H), 8.01 (s, 1H), 7.71 (t, J=4.8 Hz, 1H), 7.04 (s, 1H), 6.80 (s, 1H), 6.44 (s, 1H), 3.79 (s, 3H), 2.76-2.89 (m, 2H), 2.61-2.73 (m, 2H), 2.26 (s, 3H), 2.14 (s, 3H).

Example 97: 6-(5-methoxy-2,4-dimethylphenyl)-2-(pyrimidin-2-yl)-5,6,7,8-tetrahydrophthalazin-1(2H)-one According to scheme 2, step ix: Example 97 was prepared following the same procedure described for Example 58, starting from intermediate 16nj (0.2 g, 554.93 µmol) to yield Example 97 (8 mg, 22.07 µmol, 3.98% yield) as white solid. $^1$H-NMR (400 MHz, DMSO-d$_6$) δ 9.02 (d, J=4.4 Hz, 2H), 7.86 (s, 1H), 7.71 (t, J=4.4 Hz, 1H), 6.93 (s, 1H), 6.83 (s, 1H), 3.77 (s, 3H), 3.07 (m, 1H), 2.72-2.88 (m, 4H), 2.23 (s, 3H), 2.09 (s, 3H), 1.78-2.01 (m, 2H).

Example 98 6-(4-chloro-2-methylphenyl)-2-(pyrimidin-2-yl)-5,6,7,8-tetrahydrophthalazin-1(2H)-one, was Prepared According to Scheme 2, Method B

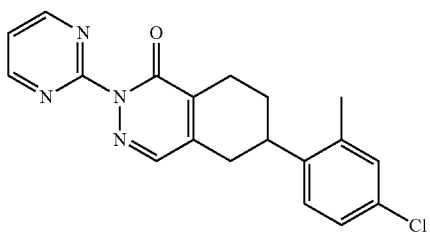 [SMILES: Cc1cc(Cl)ccc1C1CCc2c(cnn(-c3ncccn3)c2=O)C1]

Intermediate 16ao: 6-(4-chloro-2-methylphenyl)-2-(pyrimidin-2-yl)-7,8-dihydrophthalazin-1(2H)-one According to scheme 2, step viii: Intermediate 16ao was prepared following the procedure described for intermediate 16a in Example 58, starting from intermediate 15b (0.3 g, 801.51 µmol) and (4-chloro-2-methylphenyl)boronic acid (136.58 mg, 801.51 µmol) to give intermediate 16ao (0.15 g, 427.59 µmol, 53.35% yield) as yellow solid. m/z (M+H)$^+$ =351.1.

Example 98: 6-(4-chloro-2-methylphenyl)-2-(pyrimidin-2-yl)-5,6,7,8-tetrahydrophthalazin-1(2H)-one According to scheme 2, step ix: Example 98 was prepared following the same procedure described for Example 58, starting from intermediate 16ao (120 mg, 342.07 µmol) to yield Example 98 (13 mg, 36.85 µmol, 10.77% yield) as white solid. $^1$H-NMR (400 MHz, DMSO-d$_6$) δ 9.02 (d, J=4.8 Hz, 2H), 7.85 (s, 1H), 7.71 (t, J=4.8 Hz, 1H), 7.22-7.34 (m, 3H), 3.14 (m, 1H), 2.65-2.89 (m, 4H), 2.36 (s, 2H), 1.81-2.01 (m, 2H).

Example 99: 6-(4-acetyl-2-methylphenyl)-2-(pyrimidin-2-yl)-5,6,7,8-tetrahydrophthalazin-1(2H)-one, was Prepared According to Scheme 2, Method B

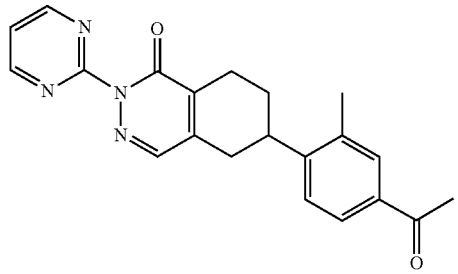 [SMILES: CC(=O)c1ccc(C2CCc3c(cnn(-c4ncccn4)c3=O)C2)c(C)c1]

Intermediate 16ap: 6-(4-acetyl-2-methylphenyl)-2-(pyrimidin-2-yl)-7,8-dihydrophthalazin-1(2H)-one According to Scheme 2, step xi: intermediate 16ap was prepared following the same procedure described for intermediate 16al, starting from intermediate 17a (0.3 g, 851.80 µmol) and 1-(4-bromo-3-methylphenyl)ethan-1-one (181.49 mg, 851.80 µmol) to provide intermediate 16ap (0.18 g, 502.24 µmol, 58.96% yield) as yellow solid. m/z (M+H)$^+$ =359.2; $^1$H NMR (DMSO-d$_6$, 400 MHz) δ 9.03 (d, J=4.8 Hz, 2H), 8.03 (s, 1H), 7.88 (s, 1H), 7.83 (br d, J=8.0 Hz, 1H), 7.72 (t, J=4.8 Hz, 1H), 7.41 (d, J=8.0 Hz, 1H), 6.52 (s, 1H), 2.80-2.89 (m, 2H), 2.66-2.75 (m, 2H), 2.59 (s, 3H), 2.44 (s, 3H).

Example 99: 6-(4-acetyl-2-methylphenyl)-2-(pyrimidin-2-yl)-5,6,7,8-tetrahydrophthalazin-1(2H)-one According to scheme 2, step ix: Example 99 was prepared following the same procedure described for Example 58, starting from intermediate 16ap (150.00 mg, 418.53 µmol) to yield Example 99 (22 mg, 61.04 µmol, 14.58% yield) as white solid. ¹H-NMR (400 MHz, DMSO-d₆) δ 9.02 (d, J=4.8 Hz, 2H), 7.85 (s, 1H), 7.76-7.83 (m, 2H), 7.71 (t, J=4.8 Hz, 1H), 7.43 (br d, J=8.0 Hz, 1H), 3.16-3.27 (m, 1H), 2.65-2.93 (m, 4H), 2.55 (s, 3H), 2.43 (s, 3H), 1.83-2.03 (m, 2H).

Example 100: 6-(3-(3-methoxypropoxy)-2-methylphenyl)-2-(pyrimidin-2-yl)-5,6,7,8-tetrahydrophthalazin-1(2H)-one, was Prepared According to Scheme 5

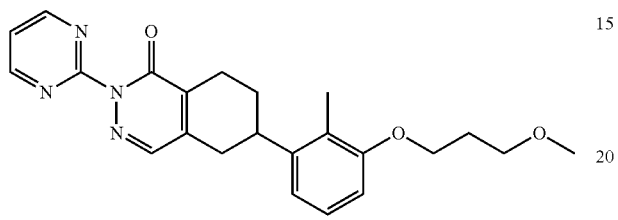

Intermediate 50: 6-(3-hydroxy-2-methylphenyl)-2-(pyrimidin-2-yl)-5,6,7,8-tetrahydro-phthalazin-1(2H)-one According to Scheme 5, step i: To a solution of compound Example 40 (2.50 g, 7.18 mmol, 1.00 eq) in CH₂Cl₂ (30.00 mL) was added BBr₃ (8.99 g, 35.90 mmol, 3.46 mL, 5.00 eq) dropwise at 0° C. under N₂. The mixture was stirred at 0° C. for 1.5 hours. The mixture was poured into H₂O (80 mL) at 0° C. The pH of aqueous phase was adjusted about 6-7 by addition of K₂CO₃ solid. Large quantities precipitate formed. The mixture was filtered and the combined aqueous phase was extracted with CH₂Cl₂ (60 mL×5), filtered and concentrated in vacuo. The filter cake was dissolved with CH₂Cl₂/MeOH (1/10, 100 mL) and stirred for 1 hour. The mixture was filtered. All organic phases were combined and dried in vacuo. Intermediate 50 was obtained (2.60 g, 5.99 mmol, 83.39% yield) as a brown solid. ¹H NMR (400 MHz, DMSO-d₆) δ 9.03 (s, 1H), 9.01 (s, 1H), 7.85 (s, 1H), 7.71 (t, J=4.89 Hz, 1H), 6.88-6.95 (m, 1H), 6.63-6.69 (m, 1H), 6.60 (d, J=7.65 Hz, 1H), 3.07-3.15 (m, 1H), 2.66-2.85 (m, 3H), 2.56 (br s, 1H), 2.13 (s, 3H), 1.91-1.99 (m, 1H), 1.74-1.86 (m, 1H).

Example 100: (6-(3-(3-methoxypropoxy)-2-methylphenyl)-2-(pyrimidin-2-yl)-5,6,7,8-tetrahydro-phthalazin-1(2H)-one According to Scheme 5, step ii A mixture of intermediate 50 (80 mg, 239.26 μmol, 1 eq) and 1-bromo-3-methoxypropane (73.22 mg, 478.52 μmol, 38.27 μL, 2 eq) in DMF (2 mL) was added Cs₂CO₃ (116.93 mg, 358.89 μmol, 1.5 eq) in one portion at 25° C. under N₂. The mixture was stirred at 100° C. for 12 hours. The mixture was filtered and the filtrate was concentrated under reduced pressure and purified by prep-HPLC to afford Example 100 (25 mg, 61.50 μmol, 25.71% yield) as a white solid. ¹H-NMR (400 MHz, DMSO-d₆) δ 9.02 (d, J=4.8 Hz, 2H), 7.85 (s, 1H), 7.71 (t, J=4.8 Hz, 1H), 7.15 (t, J=8.0 Hz, 1H), 6.80-6.93 (m, 2H), 4.00 (t, J=6.2 Hz, 2H), 3.51 (t, J=6.2 Hz, 2H), 3.26 (s, 3H), 3.16-3.19 (m, 1H), 2.58-2.87 (m, 4H), 2.19 (s, 3H), 1.76-2.02 (m, 4H).

Example 101: 6-(3-ethoxy-2-methylphenyl)-2-(pyrimidin-2-yl)-5,6,7,8-tetrahydrophthalazin-1(2H)-one, was Prepared According to Scheme 5

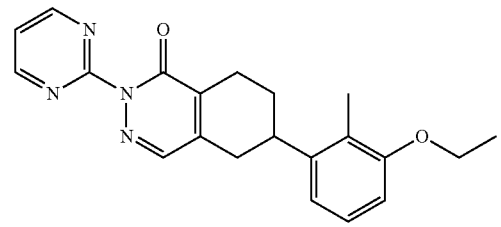 [SMILES: CCOc1cccc(C2CCc3c(cnn(-c4ncccn4)c3=O)C2)c1C]

According to Scheme 5, step ii: Example 101 was prepared following the same procedure described for Example 100, starting from intermediate 50 (80 mg, 239.26 μmol) and iodoethane (74.63 mg, 478.51 μmol) to yield intermediate Example 101 (25 mg, 68.98 μmol, 28.83% yield) as white solid. ¹H-NMR (400 MHz, DMSO-d₆) δ 9.02 (d, J=4.8 Hz, 2H), 7.84 (s, 1H), 7.71 (br t, J=4.8 Hz, 1H), 7.15 (br t, J=7.8 Hz, 1H), 7.07-7.26 (m, 1H), 6.85 (br dd, J=19.0, 7.8 Hz, 2H), 4.01 (q, J=6.8 Hz, 2H), 3.16-3.18 (m, 1H), 2.56-2.93 (m, 4H), 2.19 (s, 3H), 1.75-2.03 (m, 2H), 1.36 (br t, J=6.8 Hz, 3H).

Example 102: 6-(3-(cyclopropylmethoxy)-2-methylphenyl)-2-(pyrimidin-2-yl)-5,6,7,8-tetrahydrophthalazin-1(2H)-one, was Prepared According to Scheme 5

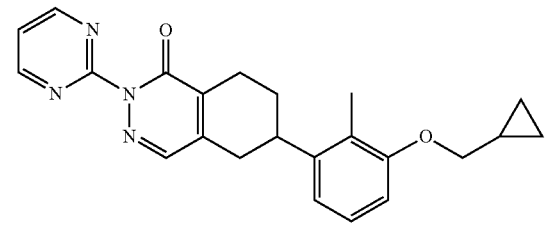 [SMILES: Cc1c(OCC2CC2)cccc1C1CCc2c(cnn(-c3ncccn3)c2=O)C1]

According to Scheme 5, step ii: Example 102 was prepared following the same procedure described for Example 100, starting from intermediate 50 (150.00 mg, 345.43 μmol) and (bromomethyl)cyclopropane (233.16 mg, 1.73 mmol) to yield intermediate Example 102 ((58.63 mg, 150.78 μmol, 43.65% yield) as a white solid. ¹H-NMR (400 MHz, DMSO-d₆) δ 9.03 (s, 1H), 9.02 (s, 1H), 7.85 (s, 1H), 7.71 (t, J=4.83 Hz, 1H), 7.10-7.17 (m, 1H), 6.88 (d, J=7.65 Hz, 1H), 6.81 (d, J=8.16 Hz, 1H), 3.82 (d, J=6.65 Hz, 2H), 3.12-3.23 (m, 1H), 2.65-2.87 (m, 3H), 2.52-2.62 (m, 1H), 2.21 (s, 3H), 1.94 (br s, 1H), 1.76-1.89 (m, 1H), 1.19-1.30 (m, 1H), 0.52-0.61 (m, 2H), 0.29-0.37 (m, 2H).

Example 103: 6-(3-isopropoxy-2-methylphenyl)-2-(pyrimidin-2-yl)-5,6,7,8-tetrahydrophthalazin-1(2H)-one, was Prepared According to Scheme 5

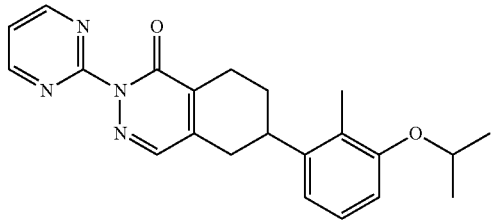 [SMILES: Cc1c(OC(C)C)cccc1C1CCc2c(cnn(-c3ncccn3)c2=O)C1]

According to Scheme 5, step ii: Example 103 was prepared following the same procedure described for Example 100, starting from intermediate 50 (180.00 mg, 414.51 μmol) and 2-bromopropane (352.31 mg, 2.07 mmol) to yield intermediate Example 103 (71.78 mg, 190.68 μmol, 46.00% yield) as a white solid. $^1$H-NMR (400 MHz, DMSO-d$_6$) δ 9.03 (s, 1H), 9.02 (s, 1H), 7.85 (s, 1H), 7.72 (t, J=4.89 Hz, 1H), 7.12-7.18 (m, 1H), 6.88 (d, J=3.39 Hz, 1H), 6.86 (d, J=3.89 Hz, 1H), 4.43-4.71 (m, 1H), 3.12-3.22 (m, 1H), 2.66-2.86 (m, 3H), 2.56 (br d, J=9.91 Hz, 1H), 2.18 (s, 3H), 1.91-2.00 (m, 1H), 1.79-1.90 (m, 1H), 1.28 (d, J=6.02 Hz, 6H).

Example 104: 6-(3-cyclopropoxy-2-methylphenyl)-2-(pyrimidin-2-yl)-5,6,7,8-tetrahydrophthalazin-1(2H)-one, was prepared according to Scheme 5

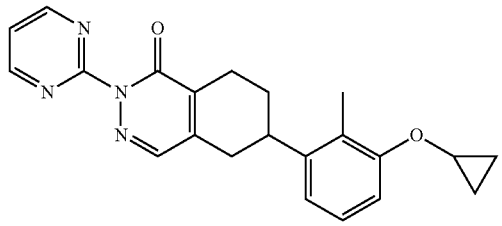 [SMILES: Cc1c(OC2CC2)cccc1C1CCc2c(cnn(-c3ncccn3)c2=O)C1]

According to Scheme 5, step ii: Example 104 was prepared following the same procedure described for Example 100, starting from intermediate 50 (150 mg, 345.42 μmol) and 2-bromocyclopropane (417.88 mg, 3.45 mmol) to yield intermediate Example 104 (19.84 mg, 51.56 μmol, 14.93% yield) as a white solid. $^1$H-NMR (400 MHz, DMSO-d$_6$) δ 9.03 (s, 1H), 9.02 (s, 1H), 7.85 (s, 1H), 7.71 (t, J=4.89 Hz, 1H), 7.16 (t, J=7.91 Hz, 1H), 6.90 (d, J=7.53 Hz, 1H), 6.85 (d, J=8.16 Hz, 1H), 6.08 (tdd, J=4.99, 10.42, 17.25 Hz, 1H), 5.43 (dd, J=1.76, 17.32 Hz, 1H), 5.26 (dd, J=1.69, 10.60 Hz, 1H), 4.56 (d, J=4.89 Hz, 2H), 3.12-3.24 (m, 1H), 2.65-2.87 (m, 3H), 2.56 (br d, J=8.53 Hz, 1H), 2.22 (s, 3H), 1.95 (br s, 1H), 1.79-1.91 (m, 1H).

Example 105: 6-(3-(2-methoxyethoxy)-2-methylphenyl)-2-(pyrimidin-2-yl)-5,6,7,8-tetrahydrophthalazin-1(2H)-one, was prepared according to Scheme 5

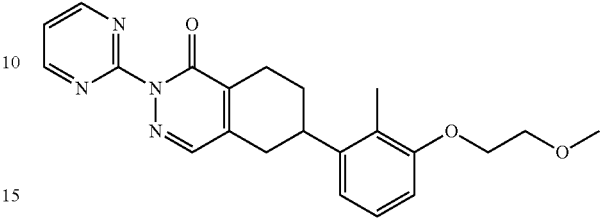

According to Scheme 5, step ii: Example 105 was prepared following the same procedure described for Example 100, starting from intermediate 50 (200.00 mg, 460.57 μmol) and 1-bromo-2-methoxyethane (320.07 mg, 2.30 mmol) to yield intermediate Example 105 (41.81 mg, 106.54 μmol, 23.13% yield) as a white solid. $^1$H-NMR (400 MHz, DMSO-d$_6$) δ 9.04 (s, 1H), 9.02 (s, 1H), 7.86 (s, 1H), 7.72 (t, J=4.89 Hz, 1H), 7.12-7.20 (m, 1H), 6.90 (d, J=7.65 Hz, 1H), 6.86 (d, J=8.03 Hz, 1H), 4.09 (dd, J=3.89, 5.40 Hz, 2H), 3.66-3.74 (m, 2H), 3.12-3.23 (m, 1H), 2.65-2.88 (m, 3H), 2.57 (br d, J=8.28 Hz, 1H), 2.20 (s, 3H), 1.95 (br s, 1H), 1.78-1.90 (m, 1H).

Example 106: 6-(3-(benzyloxy)-2-methylphenyl)-2-(pyrimidin-2-yl)-5,6,7,8-tetrahydrophthalazin-1(2H)-one, was Prepared According to Scheme 5

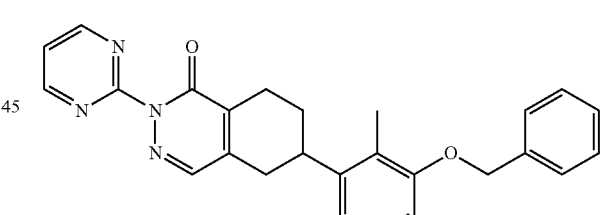

According to Scheme 5, step ii: Example 106 was prepared following the same procedure described for Example 100, starting from intermediate 50 (180.00 mg, 414.51 μmol) and (bromomethyl)benzene (212.68 mg, 1.24 mmol) to yield intermediate Example 106 (61.03 mg, 143.77 μmol, 34.68% yield) as a white solid. $^1$H-NMR (400 MHz, DMSO-d$_6$) δ 9.03 (s, 1H), 9.01 (s, 1H), 7.85 (s, 1H), 7.71 (t, J=4.83 Hz, 1H), 7.45-7.51 (m, 2H), 7.41 (t, J=7.40 Hz, 2H), 7.30-7.35 (m, 1H), 7.13-7.19 (m, 1H), 6.94 (d, J=8.16 Hz, 1H), 6.91 (d, J=7.78 Hz, 1H), 5.11 (s, 2H), 3.13-3.25 (m, 1H), 2.65-2.88 (m, 3H), 2.56 (br d, J=9.41 Hz, 1H), 2.24 (s, 3H), 1.95 (br s, 1H), 1.77-1.90 (m, 1H).

Example 107: 2-(5-cyclopropylpyrimidin-2-yl)-6-(5-methoxy-2-methylphenyl)-5,6,7,8-tetrahydrophthalazin-1(2H)-one, was Prepared According to Scheme 6, Method A

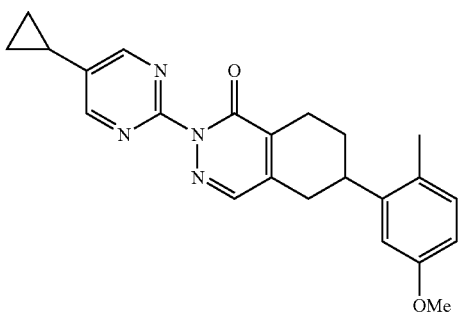 [SMILES: COc1ccc(C)c(C2CCc3c(cnn(-c4ncc(C5CC5)cn4)c3=O)C2)c1]

Intermediate 52a: 2-(5-bromopyrimidin-2-yl)-6-(5-methoxy-2-methylphenyl)-5,6,7,8-tetrahydrophthalazin-1(2H)-one According to Scheme 6, step i: To a mixture of Intermediate 7c (0.1 g, 369.92 μmol, 1 eq) and 2,5-dibromopyrimidine (263.99 mg, 1.11 mmol, 3 eq) in dioxane (20 mL) was added CuI (35.23 mg, 184.96 μmol, 0.5 eq), K$_3$PO$_4$ (196.31 mg, 924.81 μmol, 2.5 eq) and DMEDA (16.30 mg, 184.96 μmol, 0.5 eq) in one portion at 25° C. under N$_2$. The mixture was stirred at 25° C. for 5 min, then heated to 110° C. and stirred for 12 hours. The reaction mixture was filtered and the filter was concentrated. The residue was purified by silica gel chromatography (PE:EtOAc=15/1~1/1) to provide intermediate 52a (0.08 g, 187.22 μmol, 50.61% yield) as a yellow solid. $^1$H NMR: (CDCl$_3$, 400 MHz) H) δ 8.88 (s, 2H), 7.61 (s, 1H), 7.05 (d, J=8.4 Hz, 1H), 6.75-6.58 (m, 2H), 3.73 (s, 3H), 3.07-2.85 (m, 2H), 2.75-2.65 (m, 1H), 2.61-2.57 (m, 2H), 2.23 (s, 3H), 2.08-2.05 (m, 1H), 1.81-1.76 (m, 1H).

Example 107 2-(5-cyclopropylpyrimidin-2-yl)-6-(3-methoxy-2-methylphenyl)-5,6,7,8-tetrahydrophthalazin-1(2H)-one According to Scheme 6, step ii: To a mixture of intermediate 52a (0.2 g, 468.06 μmol, 1 eq) and cyclopropylboronic acid (78.25 mg, 0.94 mmol, 5 eq) in dioxane (20 mL) was added Pd(dppf)Cl$_2$ (17.12 mg, 23.40 μmol, 0.05 eq) and K$_2$CO$_3$ (77.61 mg, 0.56 mmol, 3.0 eq) in one portion at 25° C. under N$_2$. The mixture was stirred at 25° C. for 5 min, then heated to 110° C. and stirred for 12 hours. The reaction mixture was filtered and the filter was concentrated. The residue was pre-purified by column chromatography followed by preparative HPLC, to provide the Example 107 (0.053 g, 136.44 μmol, 29.15% yield) as a white solid. $^1$H-NMR (400 MHz, CDCl$_3$) δ 8.77 (s, 2H), 7.84 (s, 1H), 7.11 (d, J=8.4 Hz, 1H), 6.84 (d, J=2.4 Hz, 1H), 6.73 (dd, J=2.4, 8.4 Hz, 1H), 3.78 (s, 3H), 3.11 (m, 1H), 2.80-2.52 (m, 4H), 2.28 (s, 3H), 2.09-2.06 (m, 1H), 1.93-1.84 (m, 3H), 1.14-1.14 (m, 2H), 1.00-0.97 (m, 2H).

Example 108: 2-(5-cyclopropylpyridin-2-yl)-6-(2,4-dimethylphenyl)-5,6,7,8-tetrahydrophthalazin-1(2H)-one, was Prepared According to Scheme 6, Method A

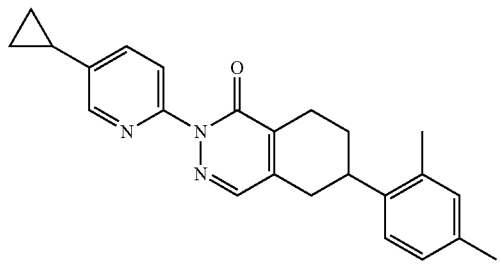 [SMILES: Cc1ccc(C2CCc3c(cnn(-c4ccc(C5CC5)cn4)c3=O)C2)c(C)c1]

Intermediate 52b: 2-(5-bromopyridin-2-yl)-6-(2,4-dimethylphenyl)-5,6,7,8-tetrahydrophthalazin-1(2H)-one According to Scheme 6, step i: Intermediate 52b was prepared following the same procedure described for intermediate 52a, starting from Intermediate 7a (0.5 g, 1.97 mmol) and 2,5-dibromopyridine (558.87 mg, 2.36 mmol), to provide intermediate 52b (0.7 g, 1.71 mmol, 86.78% yield) was obtained as a light-yellow solid. $^1$H NMR (400 MHz, CDCl$_3$) δ 8.72 (s, 1H), 7.98 (dd, J=8.4, 2.0 Hz, 1H), 7.80-7.66 (m, 2H), 7.18-6.95 (m, 3H), 3.14 (m, 1H), 3.06-2.93 (m, 1H), 2.86-2.76 (m, 1H), 2.76-2.61 (m, 2H), 2.35 (s, 3H), 2.32 (s, 3H), 2.14 (m, H), 1.96-1.78 (m, 1H).

Example 108 2-(5-cyclopropylpyridin-2-yl)-6-(2,4-dimethylphenyl)-5,6,7,8-tetrahydrophthalazin-1(2H)-one According to Scheme 6, step ii: Example 108 was prepared following the same procedure described for intermediate Example 107, starting from Intermediate 52b (0.2, 487.44 μmol) and cyclopropylboronic acid (209.35 mg, 2.44 mmol) to provide Example 108 (0.08 g, 213.20 μmol, 43.74% yield) as white solid. $^1$H-NMR (400 MHz, CDCl$_3$) δ 8.63 (s, 2H), 7.69 (s, 1H), 7.17-6.97 (m, 3H), 3.14 (m, 1H), 3.00 (m, 1H), 2.86-2.76 (m, 1H), 2.75-2.59 (m, 2H), 2.35 (s, 3H), 2.32 (s, 3H), 2.12 (m, 1H), 2.03-1.95 (m, 1H), 1.98 (m, 1H), 1.93-1.77 (m, 1H), 1.25-1.10 (m, 2H), 0.88 (m, 2H).

Example 109: 2-(5-cyclopropylpyrimidin-2-yl)-6-(2,4-dimethylphenyl)-5,6,7,8-tetrahydrophthalazin-1(2H)-one, was Prepared According to Scheme 6, Method A

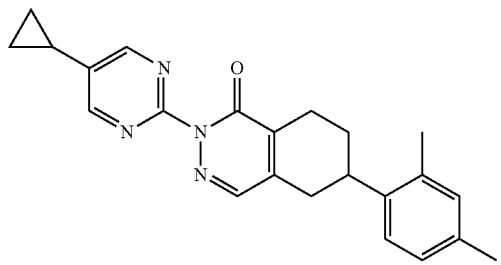 [SMILES: Cc1ccc(C2CCc3c(cnn(-c4ncc(C5CC5)cn4)c3=O)C2)c(C)c1]

Intermediate 52c: 2-(5-bromopyrimidin-2-yl)-6-(2, 4-dimethylphenyl)-5,6,7,8-tetrahydrophthalazin-1(2H)-one According to Scheme 6, step i: Intermediate 52c was prepared following the same procedure described for intermediate 52a, starting from Intermediate 7a (1 g, 3.93 mmol) and 2,5-dibromopyrimidine (1.12 g, 4.72 mmol), to provide intermediate 52c (1.2 g, 2.92 mmol, 74.20% yield) was obtained as a light-yellow solid. $^1$H NMR (400 MHz, CDCl$_3$) δ 8.95 (s, 2H), 7.69 (s, 1H), 7.14-6.99 (m, 3H), 3.26-3.09 (m, 1H), 3.00 (m, 1H), 2.86-2.75 (m, 1H), 2.75-2.59 (m, 2H), 2.35 (s, 3H), 2.32 (s, 3H), 2.12 (m, 1H), 1.93-1.79 (m, 1H).

Example 109 2-(5-cyclopropylpyrimidin-2-yl)-6-(2, 4-dimethylphenyl)-5,6,7,8-tetrahydrophthalazin-1(2H)-one According to Scheme 6, step ii: Example 109 was prepared following the same procedure described for intermediate Example 107, starting from Intermediate 52c (200.48 mg, 487.44 μmol) and cyclopropylboronic acid (209.35 mg, 2.44 mmol) to provide Example 109 (0.124 g, 329.59 μmol, 67.62% yield) as light-yellow solid. $^1$H-NMR (400 MHz, CDCl$_3$) δ 8.44 (s, 1H), 7.71 (s, 1H), 7.59 (d, J=8.4 Hz, 1H), 7.46 (dd, J=2.0, 8.4 Hz, 1H), 7.13-7.07 (m, 1H), 7.06-7.00 (m, 2H), 3.19-3.09 (m, 1H), 3.04-2.92 (m, 1H), 2.85-2.76 (m, 1H), 2.74-2.58 (m, 2H), 2.35 (s, 3H), 2.32 (s, 3H), 2.15-2.10 (m, 1H), 2.03-1.94 (m, 1H), 1.93-1.81 (m, 1H), 1.13-1.05 (m, 2H), 0.82-0.74 (m, 2H).

Example 110: 2-(5-cyclopropylpyridin-2-yl)-6-(3-methoxy-2-methylphenyl)-5,6,7,8-tetrahydrophthalazin-1(2H)-one, was Prepared According to Scheme 6, Method A

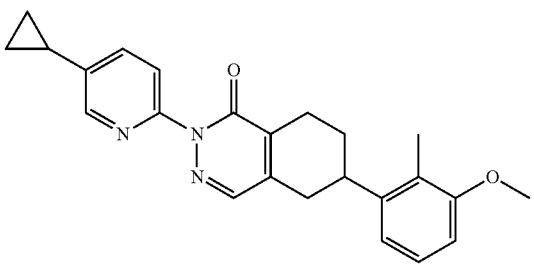 [SMILES: COc1cccc(C2CCc3c(cnn(-c4ccc(C5CC5)cn4)c3=O)C2)c1C]

Intermediate 52d: 2-(5-bromopyridin-2-yl)-6-(3-methoxy-2-methylphenyl)-5,6,7,8-tetrahydrophthalazin-1(2H)-one According to Scheme 6, step i: Intermediate 52d was prepared following the same procedure described for intermediate 52a, starting from Intermediate 7b (1 g, 3.70 mmol) and 2,5-dibromopyridine (2.63 g, 11.10 mmol), to provide intermediate 52d (1.2 g, 2.81 mmol, 76.09% yield) as yellow solid. $^1$H NMR (DMSO-d$_6$, 400 MHz) δ 8.76 (m, 1H), 8.28 (dd, J=2.0, 8.4 Hz, 1H), 7.95 (m, 1H), 7.63 (br s, 1H), 7.18 (t, J=8.0 Hz, 1H), 7.00-6.85 (m, 2H), 3.79 (s, 3H), 3.17 (m, 1H), 2.87-2.65 (m, 4H), 2.25 (m, 1H), 2.18 (s, 3H), 1.88-1.81 (m, 1H).

Example 110: 2-(5-cyclopropylpyridin-2-yl)-6-(3-methoxy-2-methylphenyl)-5,6,7,8-tetrahydrophthalazin-1(2H)-one According to Scheme 6, step ii: Example 110 was prepared following the same procedure described for intermediate Example 107, starting from Intermediate 52d (0.3 g, 703.72 μmol) and cyclopropylboronic acid (302.24 mg, 3.52 mmol) to provide Example 110 (0.09 g, 232.27 μmol, 33.01% yield) as yellow solid. $^1$H-NMR (400 MHz, DMSO-d$_6$) δ 8.41 (s, 1H), 7.83 (s, 1H), 7.61 (d, J=8.4 Hz, 1H), 7.42 (d, J=8.4 Hz, 1H), 7.19 (t, J=8.0 Hz, 1H), 6.90 (d, J=8.0 Hz, 1H), 6.85 (d, J=8.0 Hz, 1H), 3.79 (s, 3H), 3.15 (m, 1H), 2.87-2.65 (m, 4H), 2.34 (m, 1H), 2.18 (s, 3H), 2.05 (m, 1H), 1.85 (m, 1H), 1.08-1.05 (m, 2H), 0.83 (m, 2H).

Example 111: 6-(3-methoxy-2-methylphenyl)-2-(5-(pyrrolidin-1-yl)pyrimidin-2-yl)-5,6,7,8-tetrahydrophthalazin-1(2H)-one, was Prepared According to Scheme 6, Method B

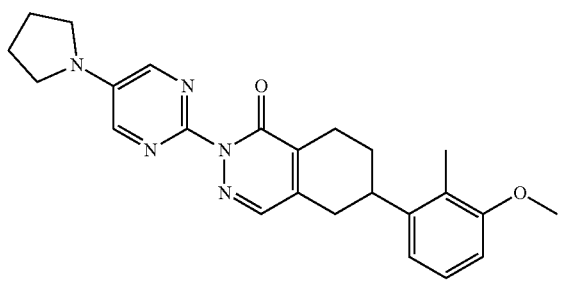 [SMILES: COc1cccc(C2CCc3c(cnn(-c4ncc(N5CCCC5)cn4)c3=O)C2)c1C]

According to scheme 6, step iii: To a mixture of Example 43 (180 mg, 470.17 μmol, 1 eq) and pyrrolidine (66.88 mg, 940.33 μmol, 78.49 μL, 2 eq) in dioxane (5 mL) were added RUPHOS precatalyst (36.52 mg, 47.02 μmol, 0.1 eq) and Cs$_2$CO$_3$ (382.97 mg, 1.18 mmol, 2.5 eq) at 20° C. under N$_2$. The mixture was stirred at 100° C. for 12 hours. The mixture was poured into H$_2$O (15 mL). The aqueous phase was filtered and extracted with CH$_2$Cl$_2$ (20 mL×2). The combined organic phase was concentrated in vacuo and combined with the filter cake to give the crude product which was purified by prep-HPLC. Example 111 (0.98 mg, 2.21 μmol, 0.5% yield) was obtained as a white solid. $^1$H-NMR (400 MHz, DMSO-d$_6$) δ 8.18 (s, 2H), 7.78 (s, 1H), 7.14-7.21 (m, 1H), 6.89 (d, J=7.91 Hz, 1H), 6.85 (d, J=8.03 Hz, 1H), 3.78 (s, 3H), 3.27-3.34 (m, 4H), 3.13-3.22 (m, 1H), 2.65-2.83 (m, 3H), 2.52-2.58 (m, 1H), 2.18 (s, 3H), 1.91-2.05 (m, 5H), 1.77-1.89 (m, 1H).

Example 112: (6-(3-methoxy-2-methylphenyl)-2-(5-morpholinopyrimidin-2-yl)-5,6,7,8-tetrahydrophthalazin-1(2H)-one, was Prepared According to Scheme 6, Method B

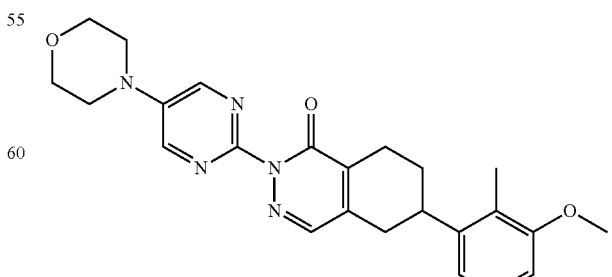

According to Scheme 6, step iii: Example 112 was prepared following the same procedure described for Example 111, starting from Example 43 (150 mg, 391.81 µmol) and morpholine (68.27 mg, 783.61 µmol, 68.96 µL) to provide Example 112 (37.27 mg, 83.31 µmol, 21.26% yield) as a white solid. $^1$H-NMR (400 MHz, DMSO-d$_6$) δ 8.61 (s, 2H), 7.81 (s, 1H), 7.14-7.22 (m, 1H), 6.88 (dd, J=7.91, 16.81 Hz, 2H), 3.75-3.82 (m, 7H), 3.34 (br s, 4H), 3.12-3.22 (m, 1H), 2.76-2.86 (m, 1H), 2.63-2.75 (m, 2H), 2.56 (br s, 1H), 2.18 (s, 3H), 1.94 (br s, 1H), 1.77-1.90 (m, 1H).

Example 113: 6-(3-methoxy-2-methylphenyl)-2-(5-morpholinopyridin-2-yl)-5,6,7,8-tetrahydrophthalazin-1(2H)-one, was Prepared According to Scheme 6, Method B

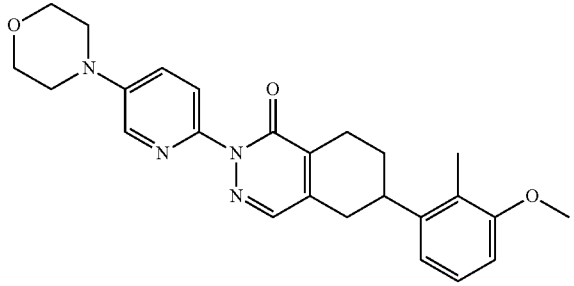 [SMILES: COc1cccc(C2CCc3c(cnn(-c4ccc(N5CCOCC5)cn4)c3=O)C2)c1C]

According to Scheme 6, step iii: Example 113 was prepared following the same procedure described for Example 111, starting from Intermediate 52d (0.2 g, 469.15 µmol) and morpholine (81.74 mg, 938.29 µmol, 82.57 µL) to provide Example 113 (0.092 g, 212.71 µmol, 45.34% yield) as yellow solid. $^1$H-NMR (400 MHz, CDCl$_3$) δ 8.45 (br s, 1H), 8.03 (br s, 1H), 7.81 (br s, 1H), 7.59 (br s, 1H), 7.23 (br t, J=7.8 Hz, 1H), 6.95-6.81 (m, 2H), 3.94 (m, 4H), 3.88 (s, 3H), 3.37 (br s, 4H), 3.25 (br s, 1H), 2.99 (m, 1H), 2.92-2.82 (m, 1H), 2.81-2.65 (m, 3H), 2.27 (s, 3H), 2.16 (br s, 1H), 1.93-1.90 (m, 1H).

Example 114: 6-(2,4-dimethylphenyl)-2-(5-morpholinopyridin-2-yl)-5,6,7,8-tetrahydrophthalazin-1(2H)-one, was Prepared According to Scheme 6, Method B

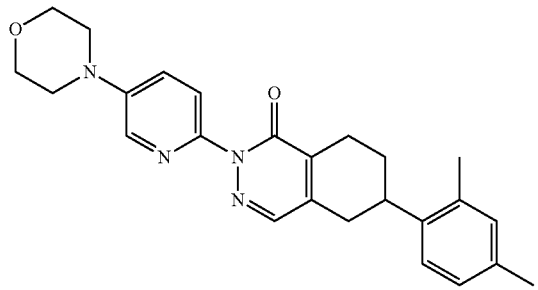 [SMILES: Cc1ccc(C2CCc3c(cnn(-c4ccc(N5CCOCC5)cn4)c3=O)C2)c(C)c1]

According to Scheme 6, step iii: Example 114 was prepared following the same procedure described for Example 111, starting from Intermediate 52b (0.15 g, 365.58 µmol) and morpholine (63.70 mg, 731.16 µmol, 64.34 µL) to provide Example 114 (0.029 g, 66.14 µmol, 18.09% yield) as light-yellow solid. $^1$H-NMR (400 MHz, CDCl$_3$) δ 8.42 (s, 1H), 8.02-7.90 (m, 1H), 7.78 (s, 1H), 7.54 (d, J=8.8 Hz, 1H), 7.13-7.01 (m, 3H), 3.97-3.87 (m, 4H), 3.40-3.29 (m, 4H), 3.20-3.08 (m, 1H), 2.98 (m, 1H), 2.89-2.78 (m, 1H), 2.71 (m, 2H), 2.35 (s, 3H), 2.33 (s, 3H), 2.15-2.10 (m, 1H), 1.95-1.82 (m, 1H).

Example 115: 6-(2,4-dimethylphenyl)-2-(5-morpholinopyrimidin-2-yl)-5,6,7,8-tetrahydrophthalazin-1(2H)-one, was Prepared According to Scheme 6, Method B

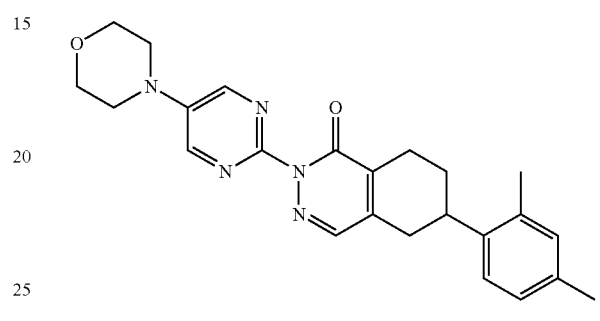

According to Scheme 6, step iii: Example 115 was prepared following the same procedure described for Example 111, starting from Intermediate 52c (0.15 g, 364.70 µmol) and morpholine (63.55 mg, 729.40 µmol, 64.19 µL) to provide Example 115 (0.053 g, 126.95 µmol, 34.81% yield) as light-yellow solid. $^1$H-NMR (400 MHz, CDCl$_3$) δ 8.48 (s, 2H), 7.69 (s, 1H), 7.13-6.99 (m, 3H), 3.97-3.88 (m, 4H), 3.38-3.28 (m, 4H), 3.20-3.08 (m, 1H), 2.99 (m, 1H), 2.88-2.75 (m, 1H), 2.70 (m, 2H), 2.35 (s, 3H), 2.32 (s, 3H), 2.17-2.05 (m, 1H), 1.95-1.80 (m, 1H).

Example 116: 2-(5-(azetidin-1-yl)pyrimidin-2-yl)-6-(2,4-dimethylphenyl)-5,6,7,8-tetrahydrophthalazin-1(2H)-one, was Prepared According to Scheme 6, Method B

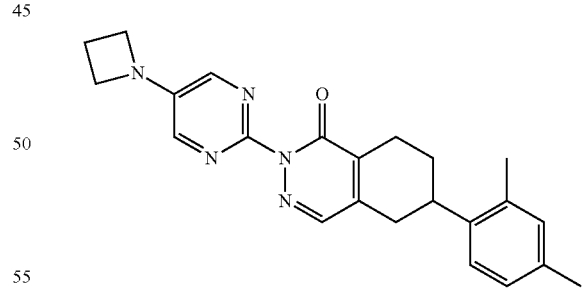

According to Scheme 6, step iii: Example 116 was prepared following the same procedure described for Example 111, starting from Intermediate 52c (0.15, 364.70 µmol) and azetidine (136.48 mg, 1.46 mmol, 161.32 µL) to provide Example 116 (0.004 g, 9.81 µmol, 2.69% yield) as light-yellow solid. $^1$H-NMR (400 MHz, CDCl$_3$) δ 8.01 (s, 2H), 7.65 (s, 1H), 7.17-6.99 (m, 3H), 4.08 (t, J=7.2 Hz, 4H), 3.12 (m, 1H), 3.02-2.95 (m, 1H), 2.83-2.75 (m, 1H), 2.70-2.62 (m, 2H), 2.62-2.52 (m, 2H), 2.35 (s, 3H), 2.32 (s, 3H), 2.12-2.06 (m, 1H), 1.92-1.80 (m, 1H).

Example 117: N-(2-(6-(2,4-dimethylphenyl)-1-oxo-5,6,7,8-tetrahydrophthalazin-2(1H)-yl)pyrimidin-5-yl)acetamide, was Prepared According to Scheme 6, Method B

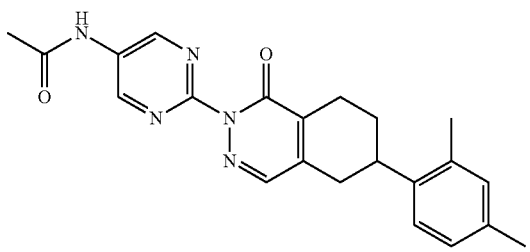 [SMILES: CC(=O)Nc1cnc(-n2ncc3c(c2=O)CCC(c2ccc(C)cc2C)C3)nc1]

According to Scheme 6, step iii: To a mixture of intermediate 52c (0.1 g, 243.13 μmol, 1 eq) and acetamide (28.72 mg, 486.27 μmol, 2 eq) in dioxane was added (1S,2S)—N,N-dimethylcyclohexane-1,2-diamine (6.92 mg, 48.63 μmol, 0.2 eq), CuI (9.24 mg, 48.63 μmol, 0.2 eq) and K₃PO₄ (129 mg, 607.82 μmol, 2.5 eq) in one portion at 25° C. under N₂. The mixture was stirred at 25° C. for 5 min, then heated to 100° C. and stirred for 12 hours. The reaction mixture was filtered and the filter was concentrated. The residue was further purification by pre-HPLC to provide Example 117 (0.021 g, 53.92 μmol, 22.18% yield) as a white solid. ¹H-NMR (400 MHz, CDCl₃) δ 8.93 (s, 2H), 8.58 (s, 1H), 7.66 (s, 1H), 7.03-6.97 (m, 3H), 3.12-3.06 (m, 1H), 2.98-2.88 (m, 1H), 2.82-2.72 (m, 1H), 2.72-2.61 (m, 2H), 2.29 (s, 3H), 2.25 (s, 3H), 2.15 (s, 3H), 2.12-2.05 (m, 1H), 1.88-1.82 (m, 1H).

Example 118: 6-(3-methoxy-2-methylphenyl)-2-(5-(2-methoxyethoxy)pyrimidin-2-yl)-5,6,7,8-tetrahydrophthalazin-1(2H)-one, was Prepared According to Scheme 6, Method C

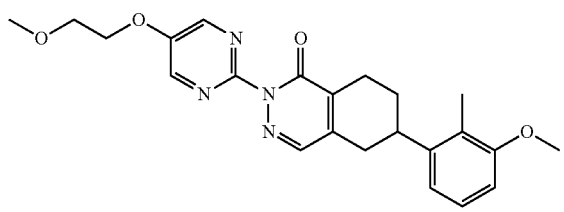

According to scheme 6, step iv: To a solution of compound Example 45 (150 mg, 411.64 μmol, 1 eq) in DMA (3 mL) was added Cs₂CO₃ (268.24 mg, 823.28 μmol, 2 eq) and 1-bromo-2-methoxyethane (572.14 mg, 4.12 mmol, 386.58 μL, 10 eq). The mixture was stirred at 20° C. for 12 hours. The pH of the mixture was adjusted to 7 by the addition of HCl (6 N). The mixture was filtered. The filtrate was concentrated to give the crude product. The crude product was purified by prep-HPLC and Example 118 (79.75 mg, 186.50 μmol, 45.31% yield) was obtained as a white solid. ¹H-NMR (400 MHz, CDCl₃) δ 8.75 (s, 2H), 7.70 (s, 1H), 7.12 (br d, J=8.4 Hz, 1H), 6.77 (s, 1H), 6.72 (m, d, J=8.4 Hz, 1H), 3.80 (s, 3H), 3.17-2.96 (m, 2H), 2.87-2.76 (m, 1H), 2.71-2.65 (m, 2H), 2.43 (s, 3H), 2.31 (s, 3H), 2.15-2.11 (m, 1H), 1.90-1.85 (m, 1H).

Example 119: 2-(5-(2-hydroxyethoxy)pyrimidin-2-yl)-6-(3-methoxy-2-methylphenyl)-5,6,7,8-tetrahydrophthalazin-1(2H)-one, was Prepared According to Scheme 6, Method C

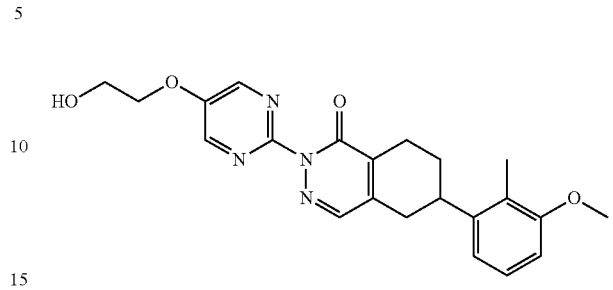

According to Scheme 6, step iv: Example 119 was prepared following the same procedure described for Example 118, starting from Example 45 (150 mg, 411.64 μmol) and 2-bromoethan-1-ol (514.40 mg, 4.12 mmol) to provide Example 119 (45.04 mg, 107.73 μmol, 26.17% yield) as a white solid. ¹H-NMR (400 MHz, CDCl₃) δ 8.46 (s, 2H), 7.59 (s, 1H), 7.04 (d, J=8.4 Hz, 1H), 6.73-6.64 (m, 2H), 3.93 (s, 3H), 3.73 (s, 3H), 3.04-2.97 (m, 2H), 2.71-2.46 (m, 3H), 2.23 (s, 3H), 2.08 (m, 1H), 1.80 (m, 1H).

Example 120: 6-(3-acetyl-2-methylphenyl)-2-(pyrimidin-2-yl)-5,6,7,8-tetrahydrophthalazin-1(2H)-one, was Prepared According to Scheme 7

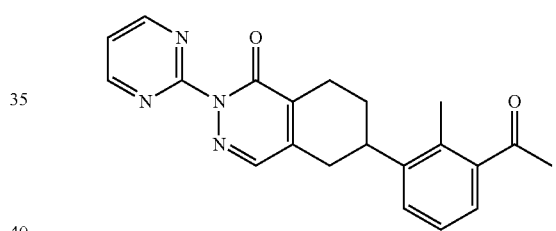

Intermediate 53: 6-(3-bromo-2-methylphenyl)-2-(pyrimidin-2-yl)-5,6,7,8-tetrahydrophthalazin-1(2H)-one According to scheme 2, step viii: To a mixture of intermediate 15b (2 g, 5.68 mmol, 1 eq) and 1,3-dibromo-2-methylbenzene (1.42 g, 5.68 mmol, 72.57 μL, 1 eq) in dioxane (30 mL) and H₂O (2 mL) were added Pd(dppf)Cl₂ (207.76 mg, 283.93 μmol, 0.05 eq) and Na₂CO₃ (1.81 g, 17.04 mmol, 3 eq) in one portion at 25° C. under N₂. The mixture was stirred at 90° C. for 12 hours. The residue was poured into ice-water (w/w=1/1) (50 mL). The aqueous phase was extracted with ethyl acetate (50 mL×3). The combined organic phase was washed with brine (50 mL), dried with anhydrous Na₂SO₄, filtered and concentrated in vacuo to afford Intermediate 53 (1.4 g, 3.54 mmol, 62.37% yield) as a yellow solid. ¹H NMR (CDCl₃, 400 MHz) δ 8.92 (d, J=4.8 Hz, 2H), 7.75 (s, 1H), 7.54 (d, J=7.6 Hz, 1H), 7.40 (t, J=4.8 Hz, 1H), 7.11-7.06 (m, 2H), 6.24 (s, 1H), 3.00 (t, J=9.6 Hz, 2H), 2.64 (t, J=9.6 Hz, 2H), 2.42 (s, 3H).

Intermediate 54: 6-(3-acetyl-2-methylphenyl)-2-(pyrimidin-2-yl)-7,8-dihydrophthalazin-1(2H)-one According to scheme 7, step i: A mixture of intermediate 53 (0.2 g, 506.01 μmol, 1 eq) and tributyl(1-ethoxyvinyl)

stannane (365.49 mg, 1.01 mmol, 341.58 μL, 2 eq) in dioxane (20 mL) was added Pd(PPh$_3$)$_2$C$_{12}$ (17.76 mg, 25.30 μmol, 0.05 eq) in one portion at 25° C. under N$_2$. The mixture was stirred at 100° C. for 3 hours. HCl (3M; 20 mL) was added to the reaction and stirred 30 min at 25° C., concentrated in vacuo. The residue was purified by silica gel chromatography (PE/EtOAc=0/1) to afford intermediate 54 (0.15 g, crude) as yellow solid. $^1$H NMR (DMSO-d$_6$, 400 MHz) δ 9.01 (d, J=4.8 Hz, 2H), 7.99 (s, 1H), 7.65-7.75 (m, 1H), 7.36 (s, 1H), 6.42 (s, 1H), 2.78-2.87 (m, 2H), 2.60-2.68 (m, 2H), 2.56 (s, 3H), 2.36 (s, 3H).

Example 120: 6-(3-acetyl-2-methylphenyl)-2-(pyrimidin-2-yl)-5,6,7,8-tetrahydrophthalazin-1(2H)-one According to scheme 7, step ii: A mixture of intermediate 54 (150.00 mg, 418.53 μmol, 1 eq) and ammonium formate (131.96 mg, 2.09 mmol, 5 eq) in EtOH (30 mL) was added Pd/C (0.3 g, 5% purity) under N$_2$. The mixture was stirred 16 hours at 25° C. The mixture was filtered, concentrated under reduced pressure and the residue obtained was purified by PREP-HPLC to afford Example 120 (4 mg, 10.86 μmol, 2.60% yield) as a white solid. (DMSO-d$_6$) δ 9.02 (d, J=4.8 Hz, 2H), 7.85 (s, 1H), 7.71 (br t, J=4.8 Hz, 1H), 7.48 (m, 2H), 7.29-7.36 (m, 1H), 3.27 (m, 1H), 2.65-2.95 (m, 4H), 2.54 (s, 3H), 2.35 (s, 3H), 1.88-2.03 (m, 2H).

Example 121: 6-(2,4-dimethylphenyl)-2-(pyridin-2-yl)-2,5,6,7-tetrahydro-1H-cyclopenta[d]-pyridazin-1-one, was Prepared According to Scheme 3

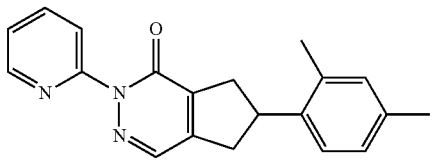 [SMILES: Cc1ccc(C2Cc3cnn(-c4ccccn4)c(=O)c3C2)c(C)c1]

Intermediate 19:
3-(2,4-dimethylphenyl)cyclopentan-1-one

According to scheme 3, step i: To a mixture of Rh(COD)Cl$_2$ (180.17 mg, 0.37 mmol) in dioxane (20 mL) and H$_2$O (4 mL) was added KOH (4.10 g, 73.08 mmol). The resulting mixture was stirred at 20° C. under N$_2$ for 0.5 hour. Then to the resulting mixture was added the solution of cyclopent-2-en-1-one (6.00 g, 73.08 mmol) and (2,4-dimethylphenyl)boronic acid (21.92 g, 146.16 mmol) in dioxane (20 mL) dropwise at 20° C. The resulting mixture was stirred at 20° C. for 1.5 hours. LCMS showed the desired product. The reaction mixture was diluted with 200 mL ethyl acetate and washed by water (60 mL×3). Then the organic phase was dried over anhydrous Na$_2$SO$_4$ and evaporated in vacuo. The residue was purified by column chromatography on silica gel (PE:EtOAc=20:1). The intermediate 19 (11.00 g, 80% yield) was obtained as a yellow liquid. $^1$H NMR (CDCl$_3$; 400 MHz) δ 7.17-7.10 (m, 1H), 7.07-7.02 (m, 2H), 3.67-3.54 (m, 1H), 2.70-2.60 (m, 1H), 2.55-2.45 (m, 1H), 2.43-2.39 (m, 1H), 2.381 (s, 3H), 2.37-2.35 (m, 1H), 2.34 (s, 3H), 2.31-2.26 (m, 1H), 2.10-1.96 (m, 1H).

Intermediate 20: 2-chloro-4-(2,4-dimethylphenyl)cyclopent-1-ene-1-carbaldehyde

According to scheme 3, step ii: To a mixture of DMF (7.76 g, 106.24 mmol, 8.2 mL) in CH$_2$Cl$_2$ (100 mL) was added at −20° C. POCl$_3$ (13.03 g, 84.99 mmol, 7.9 mL). Then the mixture was stirred at 0° C. for 1 hours. Then to the mixture was added a solution of intermediate 19 (10.00 g, 53.12 mmol) in CH$_2$Cl$_2$ (20 mL) at −20° C. The reaction was stirred at 0° C. for 2 hours. Then the reaction was stirred at 25° C. for 12 hours. LCMS showed the reaction was finished. The reaction was quenched with water (100 mL) at 0° C. Then the mixture was extracted with CH$_2$Cl$_2$ (100 mL×3). The combined organic layer was dried over anhydrous Na$_2$SO$_4$ and filtered. The filtrate was concentrated. The residue was purified by chromatography on silica gel (PE:EtOAc=10:1) The mixture of 2-chloro-4-(2,4-dimethylphenyl)cyclopent-1-ene-1-carbaldehyde 20 and its regioisomer 2-chloro-5-(2,4-dimethylphenyl)cyclopent-1-ene-1-carbaldehyde 20' (3.00 g, 24% yield) was obtained as a yellow oil which was engaged in the next step.

Intermediate 21: ethyl 4-(2,4-dimethylphenyl)-2-formylcyclopent-1-ene-1-carboxylate To a mixture of intermediates 20 and 20' (1.5 g, 6.39 mmol) and Et$_3$N (1.29 g, 12.78 mmol, 1.77 mL) in EtOH (40 mL) was added Pd(dppf)Cl$_2$ (467.61 mg, 0.64 mmol) at 25° C. under N$_2$ protection. The suspension was degassed under vacuo and purged with CO several times. The mixture was stirred under CO (3 Mpa) at 120° C. for 12 hours. Then the reaction mixture was concentrated. The crude mixture of intermediates 21 and its regioisomer 21' (1.5 g, crude) was obtained as black solid and engaged in the next step.

Example 121: 6-(2,4-dimethylphenyl)-2-(pyridin-2-yl)-2,5,6,7-tetrahydro-1H-cyclopenta[d]-pyridazin-1-one To a mixture of intermediates 21 and its regioisomer 21' (3.00 g, 11.02 mmol) and 2-pyridylhydrazine (2.41 g, 16.53 mmol HCl) in toluene (100 mL) was added TsOH (1.90 g, 11.02 mmol) at 25° C. under N$_2$. The mixture was stirred at 120° C. for 48 hours. The reaction mixture was concentrated. The residue was purified by chromatography on silica gel (PE/EtOAc=3:1) to give a crude product which was further purified by prep-HPLC. Example 121 (180 mg, 5% yield) was obtained as a yellow oil. $^1$H-NMR (400 MHz, CDCl$_3$) δ 8.75 (s, 1H), 8.10-7.96 (m, 2H), 7.90-7.80 (m, 1H), 7.55-7.45 (m, 1H), 7.13 (d, J=7.6 Hz, 1H), 7.07-6.99 (m, 2H), 4.10-3.99 (m, 1H), 3.50-3.37 (m, 2H), 3.06-3.01 (m, 2H), 2.38 (s, 3H), 2.33 (s, 3H).

Example 122: 7-(2,4-dimethylphenyl)-3-(pyridin-2-yl)-5,6,7,8-tetrahydroquinazolin-4(3H)-one, was Prepared According to Scheme 4

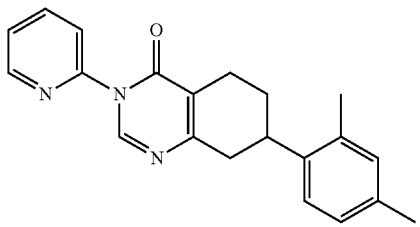 [SMILES: Cc1ccc(C2CCc3c(ncn(-c4ccccn4)c3=O)C2)c(C)c1]

Intermediate 31: 2',4'-dimethyl-5,6-dihydro-[1,1'-biphenyl]-3(4H)-one

According to scheme 4, step i: A solution of cyclohex-2-en-1-one (3.50 g, 36.41 mmol, 1.00 eq), 1-iodo-2,4-dimethylbenzene (10.81 g, 46.60 mmol, 1.28 eq), Na₂CO₃ (6.04 g, 72.82 mmol, 2.00 eq), Pd(PPh₃)₂Cl₂ (2.56 g, 3.64 mmol, 0.10 eq), XPhos (2.08 g, 4.37 mmol, 0.12 eq) in DMSO (100.00 mL) was stirred at 100° C. under N₂ atmosphere for 2 hours. LCMS showed the desired product and the reaction was finished. The reaction mixture was diluted with ethyl acetate (100 mL) and washed with H₂O (40 mL×3). The organic layers dried over Na₂SO₄, filtered and concentrated under reduced pressure. The crude product was purified by column chromatography (PE:EtOAc=5:1). Intermediate 31 (1.60 g, 7.99 mmol, 22% yield) was obtained as a brown liquid. ¹H NMR (CDCl₃; 400 MHz) δ 7.19-6.94 (m, 3H), 5.92-5.90 (m, 1H), 2.53-2.50 (m, 2H), 2.45-2.40 (m, 2H), 2.26 (s, 3H), 2.21 (s, 3H), 2.09-2.05 (m, 2H).

Intermediate 33: ethyl 2',4'-dimethyl-5-oxo-2,3,4,5-tetrahydro-[1,1'-biphenyl]-4-carboxylate According to scheme 4, step iii: To a solution of intermediate 31 (2.40 g, 11.98 mmol, 1.00 eq) in THF (60.00 mL) at −78° C. was added LDA (2 M, 8.99 mL, 1.50 eq) dropwise. The resulting mixture was stirred at −78° C. for 1 hours. To the reaction mixture was added cyano ethyl acetate (1.66 g, 16.77 mmol, 1.65 mL, 1.40 eq) at −78° C. dropwise and stirred for 4 hours. The reaction mixture was quenched with NH₄Cl aqueous (20 mL) and extracted with ethyl acetate 150 mL The combined organic layers were washed with H₂O 100 mL, dried over Na₂SO₄ filtered and concentrated under reduced pressure. The crude product was purified by silica gel chromatography (PE:EtOAc=5:1). Intermediate 33 (2.10 g, 7.71 mmol, 64.37% yield) was obtained as a yellow oil. ¹H NMR (CDCl₃; 400 MHz) δ 7.04-7.04 (m, 3H), 6.09-6.05 (m, 1H), 4.25-4.3 (m, 2H), 2.73-2.53 (m, 4H), 2.35 (s, 3H), 2.30 (s, 3H) 1.66-1.60 (m, 3H).

Intermediate 34: ethyl 4-(2,4-dimethylphenyl)-2-oxocyclohexane-1-carboxylate

According to scheme 4, step ii: A solution of Intermediate 33 (1.40 g, 5.14 mmol, 1.00 eq) in MeOH (20.00 mL) was added Pd/C (500 mg, 10% purity) under N₂ atmosphere. The suspension was degassed in vacuo and purged with H₂ several times. The mixture was stirred under H₂ (50 psi) at 20° C. for 16 hours. The reaction mixture was filtered and concentrated under reduced pressure. The crude product was purified by flash silica gel chromatography (PE:EtOAc=10: 1). Intermediate 34 (500.00 mg, 1.82 mmol, 35.40% yield) has been obtained as a yellow oil Intermediate 35: 7-(2,4-dimethylphenyl)-5,6,7,8-tetrahydroquinazolin-4(3H)-one According to scheme 4, step iv: The mixture of Intermediate 34 (200 mg, 729.00 μmol, 1.00 eq), K₂CO₃ (403.02 mg, 2.92 mmol, 4.00 eq) and formimidamide (113.84 mg, 1.09 mmol, 1.50 eq) in EtOH (8.00 mL) was stirred at 90° C. for 3 hours. The reaction mixture was concentrated and the residue was diluted with ethyl acetate (100 ml). The solution was washed with H₂O (40 mL×3). The organic phase was dried with anhydrous Na₂SO₄, filtered and concentrated in vacuo. The Intermediate 35 (120.00 mg, 471.83 μmol, 65% yield) was obtained as a light-yellow solid. ¹H NMR (DMSO-d₆; 400 MHz) δ 12.30 (s, 1H), 7.99 (s, 1H), 7.17-7.11 (m, 1H), 6.97-6.99 (m, 1H), 3.11-3.08 (m, 1H), 2.68-2.39 (m, 4H), 2.28 (s, 3H), 2.24 (s, 3H), 1.86-1.84 (m, 2H), 1.75-1.1.72 (m, 2H).

Example 122: 7-(2,4-dimethylphenyl)-3-(pyridin-2-yl)-5,6,7,8-tetrahydroquinazolin-4(3H)-one According to scheme 4, step v: The mixture of intermediate 35 (100.00 mg, 393.19 μmol, 1.00 eq), 2-bromopyridine (80.76 mg, 511.15 μmol, 1.30 eq), CuI (7.49 mg, 39.32 μmol, 0.10 eq), 1,10-phenanthroline (14.17 mg, 78.64 μmol, 0.20 eq) and KOH (44.12 mg, 786.38 μmol, 2.00 eq) in DMF (4.00 mL) was stirred at 100° C. for 12 hours under N₂ atmosphere. The reaction mixture was diluted with 100 mL ethyl acetate and washed by water (30 mL×3). The organic phase was dried over Na₂SO₄, evaporated in vacuo. The crude product was purified by prep-HPLC (formic acid as additive). Example 122 (45.00 mg, 135.78 μmol, 34.53% yield) was obtained as a yellow solid. ¹H-NMR (400 MHz, DMSO-d₆) δ 8.66-8.65 (m, 1H), 8.48 (s, 1H), 8.06-8.04 (m, 1H), 7.77-7.75 (m, 1H), 7.59-7.55 (m, 1H), 7.18-7.15 (m, 1H), 7.02-6.99 (m, 1H), 3.16-3.14 (m, 1H), 2.75-2.66 (m, 4H), 2.30 (s, 3H), 2.25 (s, 3H), 1.94-1.921 (m, 1H), 1.83-1.81 (m, 2H).

Example 124: 6-(1-cyclopropyl-1H-indol-4-yl)-2-(pyrimidin-2-yl)-5,6,7,8-tetrahydrophthalazin-1(2H)-one

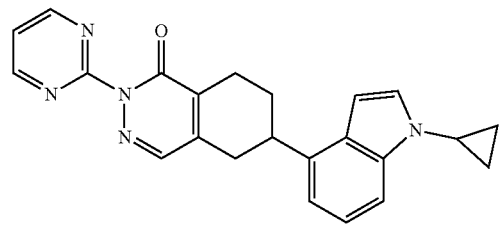 [SMILES: O=c1c2c(cnn1-c1ncccn1)CC(c1cccc3c1ccn3C1CC1)CC2]

To a mixture of Example 92 (50.0 mg, 130 μmol, 1.00 eq) in DCM (2.00 mL) was added MnO₂ (113 mg, 1.30 mmol, 10.0 eq) at 25° C. The mixture was stirred at 25° C. for 23 h. The reaction was filtered and concentrated. The residue was purified by column chromatography (SiO₂, PE/EtOAc=1/1 to 0:1, Rf=0.48) to give Example 124 (37.0 mg, 94.7 μmol) as a green solid. ¹H-NMR (400 MHz, CDCl₃) δ 8.94 (d, J=4.8 Hz, 2H), 7.71 (s, 1H), 7.51 (d, J=8.2 Hz, 1H), 7.42 (t, J=4.8 Hz, 1H), 7.24 (t, J=7.8 Hz, 1H), 7.18 (d, J=3.4 Hz, 1H), 6.99 (d, J=7.4 Hz, 1H), 6.50 (d, J=3.4 Hz, 1H), 3.48-3.33 (m, 2H), 3.07-2.87 (m, 3H), 2.80-2.66 (m, 1H), 2.37-2.28 (m, 1H), 2.14-2.06 (m, 1H), 1.11-1.02 (m, 4H).

Example 125: 2-(5-cyclopropylpyrimidin-2-yl)-6-(3-methoxy-2-methylphenyl)-5,6,7,8-tetrahydrophthalazin-1(2H)-one, was Prepared According to Scheme 6, Method A

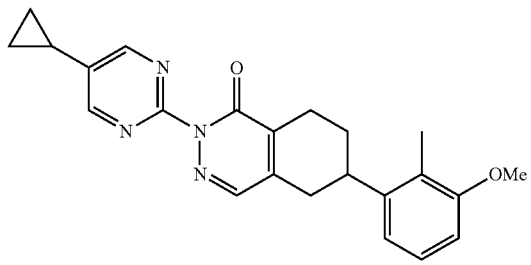 [SMILES: COc1cccc(C2CCc3c(cnn(-c4ncc(C5CC5)cn4)c3=O)C2)c1C]

Intermediate 52e: 2-(5-bromopyrimidin-2-yl)-6-(3-methoxy-2-methylphenyl)-5,6,7,8-tetrahydrophthalazin-1(2H)-one According to Scheme 6, step i: Intermediate 52e was prepared following the same procedure described for intermediate 52a, starting from Intermediate 7b (500 mg, 1.85 mmol) and 2,5-dibromopyridine (527.98 mg, 2.22 mmol), to provide intermediate 52e (0.5 g, 1.01 mmol, 54.41% yield) as red solid. m/z (M+H)$^+$=427.0, 429.0.

Example 125: 2-(5-cyclopropylpyrimidin-2-yl)-6-(3-methoxy-2-methylphenyl)-5,6,7,8-tetrahydrophthalazin-1(2H)-one According to Scheme 6, step ii: Example 125 was prepared following the same procedure described for Example 107, starting from Intermediate 52e (180 mg, 421.26 μmol) and cyclopropylboronic acid (72.37 mg, 842.51 μmol), to provide Example 125 (14.61 mg, 37.35 μmol, 8.87% yield) as a light pink solid. $^1$H-NMR (400 MHz, DMSO-d$_6$) δ 8.76 (s, 2H), 7.83 (s, 1H), 7.18 (t, J=7.97 Hz, 1H), 6.90 (d, J=7.65 Hz, 1H), 6.86 (d, J=8.16 Hz, 1H), 3.79 (s, 3H), 3.13-3.24 (m, 1H), 2.64-2.85 (m, 3H), 2.57 (br s, 1H), 2.18 (s, 3H), 2.04-2.12 (m, 1H), 1.94 (br s, 1H), 1.78-1.90 (m, 1H), 1.08-1.18 (m, 2H), 0.90-1.01 (m, 2H).

Example 126: 2-(5-bromopyrimidin-2-yl)-6-(3-cyclopropoxy-2-methylphenyl)-5,6,7,8-tetrahydrophthalazin-1(2H)-one, was prepared according to scheme 1, Method B

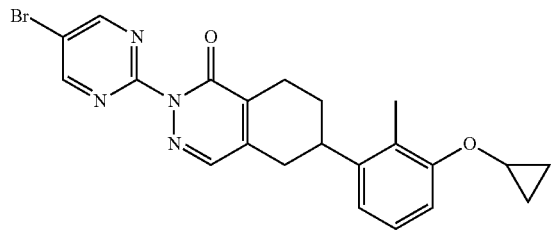 [SMILES: Cc1c(OC2CC2)cccc1C1CCc2c(cnn(-c3ncc(Br)cn3)c2=O)C1]

Intermediate 6f: 5-(3-cyclopropoxy-2-methylphenyl)-3-methoxy-4,5,6,7-tetrahydroisobenzofuran-1(3H)-one According to Scheme 1 Step i to v: Intermediate 6f was prepared similarly to intermediate 6a in Example 1, starting from 1-bromo-3-cyclopropoxy-2-methylbenzene, and was obtained with an overall yield of 6% as a colorless oil. m/z (M+H)$^+$=315.3.

Intermediate 7d: 6-(3-cyclopropoxy-2-methylphenyl)-5,6,7,8-tetrahydrophthalazin-1(2H)-one According to Scheme 1 Step vii: Intermediate 7b was prepared similarly to intermediate 7a in Example 6, starting from Intermediate 6f (1.77 g, 5.60 mmol), to provide Intermediate 7d (1.52 g, 4.56 mmol, 81.5% yield) as light yellow solid. $^1$H NMR (400 MHz, DMSO-d$_6$) δ 10.73 (br s, 1H), 7.56 (s, 1H), 7.22-7.11 (m, 1H), 6.84 (d, J=7.4 Hz, 1H), 3.77-3.70 (m, 1H), 3.22-3.11 (m, 1H), 2.99-2.88 (m, 1H), 2.81-2.71 (m, 1H), 2.71-2.54 (m, 2H), 2.18 (s, 3H), 2.15-2.08 (m, 1H), 1.92-1.80 (m, 1H), 0.82-0.77 (m, 4H).

Example 126: 2-(5-bromopyrimidin-2-yl)-6-(3-cyclopropoxy-2-methylphenyl)-5,6,7,8-tetrahydrophthalazin-1(2H)-one According to Scheme 1 Step viii: Example 126 was prepared as per Example 6, starting from intermediate 7d (1.00 g, 3.00 mmol) and 2,5-dibromopyrimidine (856 mg, 3.60 mmol), to provide Example 126 (0.74 g, 1.52 mmol, 50.7% yield) as red solid. $^1$H NMR (400 MHz, CDCl$_3$) δ 8.95 (s, 2H), 7.69 (s, 1H), 7.24-7.14 (m, 2H), 6.85 (d, J=7.6 Hz, 1H), 3.77-3.70 (m, 1H), 3.20 (br s, 1H), 3.00 (br d, J=16.3 Hz, 1H), 2.86-2.78 (m, 1H), 2.70 (br dd, J=9.2, 16.8 Hz, 2H), 2.20-2.18 (m, 3H), 2.13 (br s, 1H), 1.94-1.85 (m, 1H), 0.82-0.77 (m, 4H).

Example 127: N-(2-(6-(3-cyclopropoxy-2-methylphenyl)-1-oxo-5,6,7,8-tetrahydrophthalazin-2(1H)-yl)pyrimidin-5-yl)acetamide, was Prepared According to Scheme 6, Method B

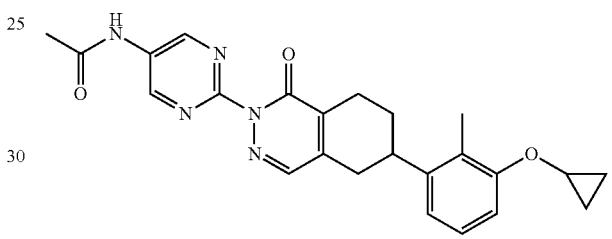

According to Scheme 6, step iii: Example 127 was prepared as per Example 117, starting from Example 126 (0.85 g, 1.88 mmol) and acetamide (222 mg, 3.75 mmol), to provide Example 127 (242 mg, 558.61 μmol, 29.79% yield) as a light yellow solid. $^1$H NMR (400 MHz, CDCl$_3$) δ 9.07-9.00 (m, 1H), 8.97 (s, 2H), 7.76 (s, 1H), 7.24-7.15 (m, 2H), 6.86 (br d, J=7.4 Hz, 1H), 3.75 (br s, 1H), 3.25 (br s, 1H), 3.00 (br d, J=19.4 Hz, 1H), 2.92-2.82 (m, 1H), 2.82-2.64 (m, 2H), 2.20 (s, 6H), 2.17-2.13 (m, 1H), 1.93 (br d, J=7.2 Hz, 1H), 0.80 (br s, 4H).

Example 128: (+6-(3-cyclopropoxy-2-methylphenyl)-2-(pyrimidin-2-yl)-5,6,7,8-tetrahydrophthalazin-1(2H)-one and EXAMPLE 129: (+)-6-(3-cyclopropoxy-2-methylphenyl)-2-(pyrimidin-2-yl)-5,6,7,8-tetrahydrophthalazin-1(2H)-one Example 128

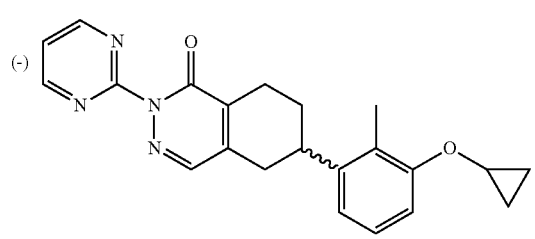

-continued

Example 129

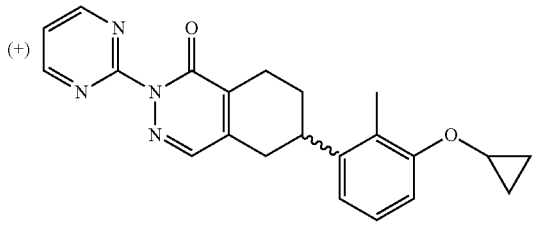

The enantiomers constituting racemic Example 104 (483 mg) were separated by preparative SFC to give (−)-6-(3-cyclopropoxy-2-methylphenyl)-2-(pyrimidin-2-yl)-5,6,7,8-tetrahydrophthalazin-1(2H)-one Example 128 (188 mg, 39%) with an enantiomeric excess of 100%, and (+)-6-(3-cyclopropoxy-2-methylphenyl)-2-(pyrimidin-2-yl)-5,6,7,8-tetrahydrophthalazin-1(2H)-one Example 129 (199 mg, 41%) with an enantiomeric excess of 99.9%, both as white solid.

Example 128: $^1$H-NMR (400 MHz, CDCl$_3$) δ 8.94 (d, J=4.4 Hz, 2H), 7.70 (s, 1H), 7.42 (t, J=4.8 Hz, 1H), 7.28-7.15 (m, 2H), 6.85 (d, J=7.6 Hz, 1H), 3.75 (tt, J=6.0, 3.2 Hz, 1H), 3.25-3.17 (m, 1H), 3.05-2.95 (m, 1H), 2.87-2.76 (m, 1H), 2.75-2.60 (m, 2H), 2.20-2.10 (m, 1H), 1.95-1.83 (m, 1H), 0.85-0.75 (m, 4H).

Example 129: $^1$H-NMR (400 MHz, CDCl$_3$) δ 8.94 (d, J=4.4 Hz, 2H), 7.70 (s, 1H), 7.42 (t, J=4.8 Hz, 1H), 7.25-7.15 (m, 2H), 6.86 (d, J=7.6 Hz, 1H), 3.75 (tt, J=6.0, 3.2 Hz, 1H), 3.25-3.17 (m, 1H), 3.05-2.95 (m, 1H), 2.83-2.76 (m, 1H), 2.75-2.60 (m, 2H), 2.20-2.07 (m, 1H), 1.95-1.82 (m, 1H), 0.85-0.75 (m, 4H).

Example 130: (+6-(2-chloro-3-cyclopropoxyphenyl)-2-(pyrimidin-2-yl)-5,6,7,8-tetrahydrophthalazin-1(2H)-one and EXAMPLE 131: (+)-6-(2-chloro-3-cyclopropoxyphenyl)-2-(pyrimidin-2-yl)-5,6,7,8-tetrahydrophthalazin-1(2H)-one Example 130

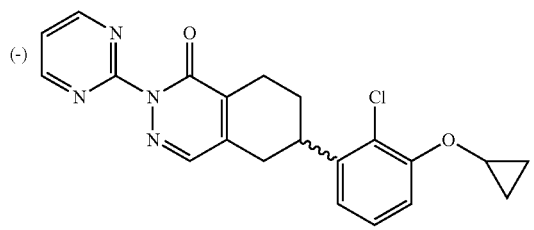

Example 131

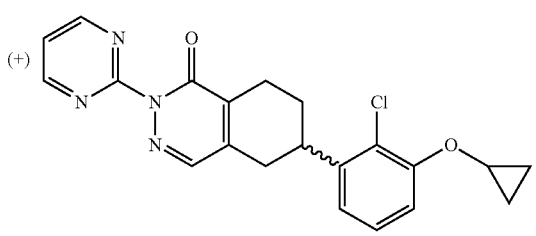

The enantiomers constituting racemic Example 91 (505 mg) were separated by preparative SFC to give (−)-6-(2-chloro-3-cyclopropoxyphenyl)-2-(pyrimidin-2-yl)-5,6,7,8-tetrahydrophthalazin-1(2H)-one Example 130 (187 mg, 37%) with an enantiomeric excess of 99.6%, and (+)-6-(2-chloro-3-cyclopropoxyphenyl)-2-(pyrimidin-2-yl)-5,6,7,8-tetrahydrophthalazin-1(2H)-one Example 131 (187 mg, 37%) with an enantiomeric excess of 99.9%, both as white solid.

Example 130: $^1$H-NMR (400 MHz, CDCl$_3$) δ 8.93 (d, J=4.4 Hz, 2H), 7.70 (s, 1H), 7.42 (t, J=4.8 Hz, 1H), 7.26-7.23 (m, 2H), 6.92-6.87 (m, 1H), 3.83 (tt, J=6.0, 3.2 Hz, 1H), 3.59-3.49 (m, 1H), 3.05-2.92 (m, 2H), 2.76-2.58 (m, 2H), 2.23-2.14 (m, 1H), 1.99-1.85 (m, 1H), 0.90-0.83 (m, 4H).

Example 131: $^1$H-NMR (400 MHz, CDCl$_3$) δ 8.93 (d, J=4.8 Hz, 2H), 7.70 (s, 1H), 7.45-7.39 (m, 1H), 7.26-7.23 (m, 2H), 6.94-6.86 (m, 1H), 3.83 (tt, J=3.2, 6.0 Hz, 1H), 3.63-3.45 (m, 1H), 3.04-2.91 (m, 2H), 2.77-2.57 (m, 2H), 2.23-2.13 (m, 1H), 1.99-1.85 (m, 1H), 0.92-0.79 (m, 4H).

Example 132: (−)-6-(3-cyclopropoxy-2-methylphenyl)-2-(5-methylpyrimidin-2-yl)-5,6,7,8-tetrahydrophthalazin-1(2H)-one and Example 133: (+)-6-(3-cyclopropoxy-2-methylphenyl)-2-(5-methylpyrimidin-2-yl)-5,6,7,8-tetrahydrophthalazin-1(2H)-one Example 132

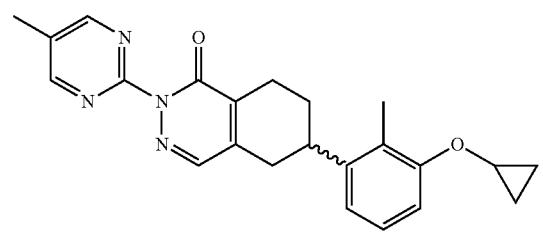

Example 133

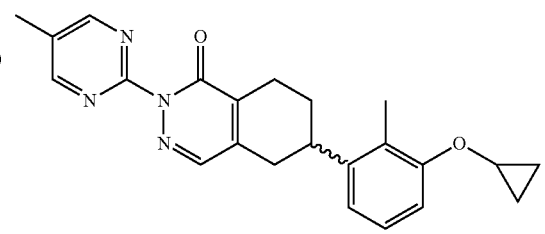

The enantiomers constituting racemic Example 93 (488 mg) were separated by preparative SFC to give (+6-(3-cyclopropoxy-2-methylphenyl)-2-(5-methylpyrimidin-2-yl)-5,6,7,8-tetrahydrophthalazin-1(2H)-one Example 132 (232 mg, 48%) with an enantiomeric excess of 100%, and (+)-6-(3-cyclopropoxy-2-methylphenyl)-2-(5-methylpyrimidin-2-yl)-5,6,7,8-tetrahydrophthalazin-1(2H)-one Example 133 (210 mg, 43%) with an enantiomeric excess of 100%, both as white solid.

Example 132: $^1$H-NMR (400 MHz, CDCl$_3$) δ 8.74 (s, 2H), 7.68 (s, 1H), 7.25-7.15 (m, 2H), 6.85 (d, J=6.4 Hz, 1H), 3.74 (tt, J=6.0, 3.2 Hz, 1H), 3.26-3.17 (m, 1H), 3.05-2.95 (m, 1H), 2.85-2.77 (m, 1H), 2.75-2.60 (m, 2H), 2.43 (s, 3H), 2.18-2.10 (m, 1H), 1.95-1.83 (m, 1H), 0.85-0.78 (m, 4H).

Example 133: $^1$H-NMR (400 MHz, CDCl$_3$) δ 8.74 (s, 2H), 7.68 (s, 1H), 7.23-7.15 (m, 2H), 6.85 (d, J=6.4 Hz, 1H), 3.74 (tt, J=6.0, 3.2 Hz, 1H), 3.25-3.16 (m, 1H), 3.05-2.95 (m, 1H), 2.85-2.77 (m, 1H), 2.75-2.60 (m, 2H), 2.43 (s, 3H), 2.18-2.07 (m, 1H), 1.95-1.83 (m, 1H), 0.83-0.76 (m, 4H).

Example 134: (+6-(2-chloro-3-methoxyphenyl)-2-(5-methylpyrimidin-2-yl)-5,6,7,8-tetrahydrophthalazin-1(2H)-one and EXAMPLE 135: (+)-6-(2-chloro-3-methoxyphenyl)-2-(5-methylpyrimidin-2-yl)-5,6,7,8-tetrahydrophthalazin-1(2H)-one

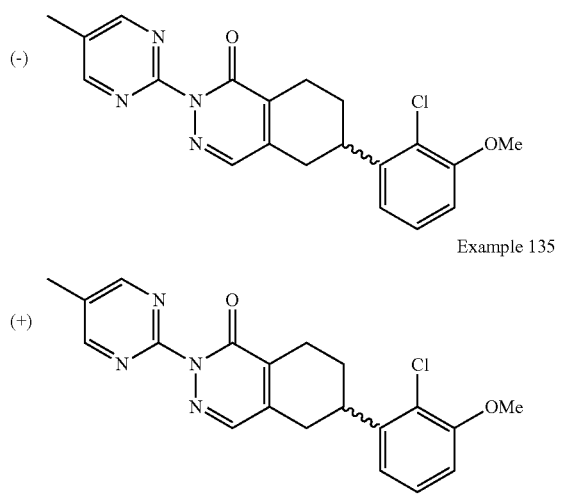

Example 134

Example 135

The enantiomers constituting racemic Example 94 (493 mg) were separated by preparative SFC to give (−)-6-(2-chloro-3-methoxyphenyl)-2-(5-methylpyrimidin-2-yl)-5,6,7,8-tetrahydrophthalazin-1(2H)-one Example 134 (218 mg, 48%) with an enantiomeric excess of 100%, and (+)-6-(2-chloro-3-methoxyphenyl)-2-(5-methylpyrimidin-2-yl)-5,6,7,8-tetrahydrophthalazin-1(2H)-one Example 135 (215 mg, 43%) with an enantiomeric excess of 99.9%, both as white solid.

Example 134: $^1$H NMR (400 MHz, CDCl$_3$) δ 8.73 (s, 2H), 7.69 (s, 1H), 7.30-7.25 (m, 1H), 6.90-6.86 (m, 2H), 3.94 (s, 3H), 3.56-3.53 (m, 1H), 3.04-2.93 (m, 2H), 2.75-2.57 (m, 2H), 2.42 (s, 3H), 2.20-2.15 (m, 1H), 1.93-1.85 (m, 1H).

Example 135: $^1$H NMR (400 MHz, CDCl$_3$) δ 8.73 (s, 2H), 7.69 (s, 1H), 7.27-7.22 (m, 1H), 6.90-6.86 (m, 2H), 3.93 (s, 3H), 3.56-3.53 (m, 1H), 3.04-2.93 (m, 2H), 2.75-2.57 (m, 2H), 2.42 (s, 3H), 2.23-2.15 (m, 1H), 1.93-1.85 (m, 1H).

Example 136: (−)—N-(2-(6-(2,4-dimethylphenyl)-1-oxo-5,6,7,8-tetrahydrophthalazin-2(1H)-yl)pyrimidin-5-yl)acetamide and Example 137: (+)—N-(2-(6-(2,4-dimethylphenyl)-1-oxo-5,6,7,8-tetrahydrophthalazin-2(1H)-yl)pyrimidin-5-yl)acetamide Example 136

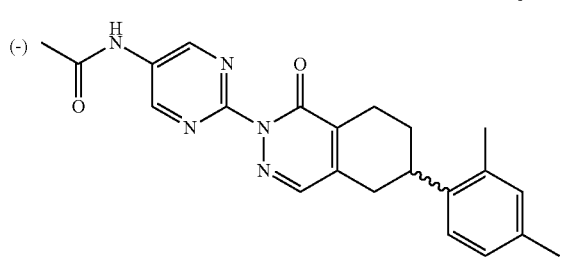

Example 137

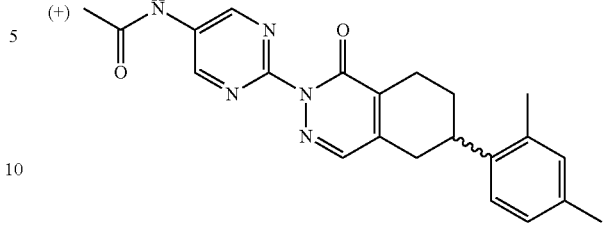

The enantiomers constituting racemic Example 117 (610 mg) were separated by preparative SFC to give (−)—N-(2-(6-(2,4-dimethylphenyl)-1-oxo-5,6,7,8-tetrahydrophthalazin-2(1H)-yl)pyrimidin-5-yl)acetamide Example 136 (187 mg, 31%) with an enantiomeric excess of 99.4%, and (+)—N-(2-(6-(2,4-dimethylphenyl)-1-oxo-5,6,7,8-tetrahydrophthalazin-2(1H)-yl)pyrimidin-5-yl)acetamide Example 137 (218 mg, 36%) with an enantiomeric excess of 100%, both as yellow solid.

Example 136: $^1$H-NMR (400 MHz, CDCl$_3$) δ 8.99 (s, 1H), 7.76 (s, 1H), 7.12-7.05 (m, 3H), 3.17-2.70 (m, 5H), 2.37 (s, 3H), 2.33 (s, 3H), 2.22-2.18 (m, 4H), 1.97-1.90 (m, 1H).

Example 137: $^1$H-NMR (400 MHz, CDCl$_3$) δ=8.90 (s, 1H), 7.76 (s, 1H), 7.04-6.97 (m, 3H), 3.10-2.62 (m, 5H), 2.29 (s, 3H), 2.25 (s, 3H), 2.10-2.09 (m, 4H), 1.87-1.83 (m, 1H).

Example 138: (+)-6-(1-cyclopropyl-1H-indol-4-yl)-2-(pyrimidin-2-yl)-5,6,7,8-tetrahydrophthalazin-1(2H)-one and Example 139: (+6-(1-cyclopropyl-1H-indol-4-yl)-2-(pyrimidin-2-yl)-5,6,7,8-tetrahydrophthalazin-1(2H)-one Example 138

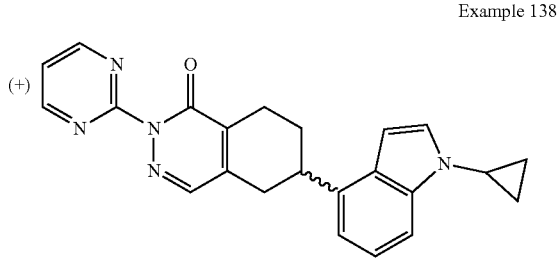

Example 139

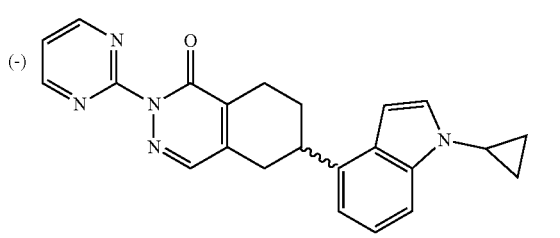

The enantiomers constituting racemic Example 124 (440 mg) were separated by preparative SFC to give (+)-6-(1-cyclopropyl-1H-indol-4-yl)-2-(pyrimidin-2-yl)-5,6,7,8-tetrahydrophthalazin-1(2H)-one Example 138 (140 mg, 32%) with an enantiomeric excess of 99.5%, and (−)-6-(1-cyclopropyl-1H-indol-4-yl)-2-(pyrimidin-2-yl)-5,6,7,8-tetrahydrophthalazin-1(2H)-one Example 139 (155 mg, 35%) with an enantiomeric excess of 98.9%, both as yellow solid.

Example 138: $^1$H-NMR (400 MHz, CDCl$_3$) δ 8.94 (d, J=4.9 Hz, 2H), 7.71 (s, 1H), 7.52 (d, J=8.2 Hz, 1H), 7.42 (t, J=4.8 Hz, 1H), 7.24 (t, J=7.7 Hz, 1H), 7.18 (d, J=3.3 Hz, 1H), 6.99 (d, J=7.2 Hz, 1H), 6.50 (d, J=3.2 Hz, 1H), 3.42-3.37 (m, 2H), 3.04-2.96 (m, 3H), 2.93-2.73 (m, 1H), 2.32 (br d, J=11.7 Hz, 1H), 2.10-2.06 (m, 1H), 1.12-1.02 (m, 4H).

Example 139: $^1$H-NMR (400 MHz, CDCl$_3$) δ 8.94 (d, J=4.9 Hz, 2H), 7.71 (s, 1H), 7.52 (d, J=8.2 Hz, 1H), 7.42 (t, J=4.8 Hz, 1H), 7.24 (t, J=7.7 Hz, 1H), 7.18 (d, J=3.3 Hz, 1H), 6.99 (d, J=7.2 Hz, 1H), 6.50 (s, 1H), 3.50-3.38 (m, 2H), 3.03-2.93 (m, 3H), 2.88-2.73 (m, 1H), 2.30 (br d, J=11.7 Hz, 1H), 2.09-2.03 (m, 1H), 1.10-1.04 (m, 4H).

C. ANALYTICAL PART

Melting Points:

Values are peak values and are obtained with experimental uncertainties that are commonly associated with this analytical method. For a number of compounds, melting points were determined in open capillary tubes on a YRT-3 apparatus. Melting points were measured with a temperature gradient of 1.5° C./minute. Maximum temperature was 270° C. The melting point was read from a digital display. For some compounds, DSC method was used according to the following conditions.

| DSC conditions | |
|---|---|
| Instrument: | NETZSCH DSC214 |
| Crucible | Pan Al, pierced lid |
| Protect flow | N$_2$ 60 mL/min |
| Purge flow | N$_2$ 40 mL/min |
| Gradient Ratio: | 50° C. to 350° C.; 10° C./min |

LCMS Methods:

The High-Performance Liquid Chromatography (HPLC) measurement was performed using a LC pump, a diode-array or a UV detector. Flow from the column was brought to the Mass Spectrometer (MS) which was configured with an atmospheric pressure ion source. It is within the knowledge of the skilled person to set the tune parameters in order to obtain ions allowing the identification of the compound's nominal monoisotopic molecular weight (MW) and/or exact mass monoisotopic molecular weight. Data acquisition was performed with appropriate software. ES MS detector was used, acquiring both in positive and negative ionization modes. Compounds can be described by their molecular ion corresponding to the [M+H] (protonated molecule) and/or [M−H] (deprotonated molecule). For molecules with multiple isotopic patterns (Br, Cl), the reported value is the one obtained for the lowest isotope mass. All results were obtained with experimental uncertainties that are commonly associated with the method used.

NMR:

$^1$H NMR spectra were recorded on a Varian 400 MHz spectrometer. Chemical shifts are expressed in parts per million (ppm, δ units). Splitting patterns describe apparent multiplicities and are designated as s (singlet), d (doublet), t (triplet), q (quadruplet), m (multiplet), br (broad).

SFC-MS:

Preparative Chiral separation were performed using a preparative instrument equipped with Waters 2998 PDA detector. Specific methods used are described herebelow and results are reported in table 1.

| Methods | Method C1 | Method C2 |
|---|---|---|
| Instrument: | Thar SFC80 preparative SFC | MG preparative SFC |
| Column: | Chiralcel OJ 250 * 25 mm i.d. 10 μm | ChiralPak AD, 250 × 30 mm i.d., 5 μm |
| Column temperature: | 40° C. | 38° C. |
| Mobile phase | A for CO2 and B for 2-propanol (0.1% NH$_3$H$_2$O) | A for CO$_2$ and B for ETOH (0.1% NH$_3$H$_2$O) |
| Flow rate: | 70 mL/min | 60 mL/min |
| Gradient | B = 40% | B = 40% |
| Detection: | 220 nm | 220 nm |
| System back pressure | 100 bar | 100 bar |
| Cycle time | 7 min | 4-15 min |

Optical Rotations:

Optical rotations were measured on a Rudolph AUTOPOL V polarimeter using a sodium lamp (589 nm), at a concentration of 10 mg/mL, in methanol or chloroform as solvent, at a temperature of 20° C. The sign of the rotation (+ or −) is given and is reported using degrees in Table 1.

TABLE 1

Analytical data for individual optical isomers.

| Ex. | SFC RT (min) | SFC method | $[\alpha_D]$ (°) | Solvent |
|---|---|---|---|---|
| 4 | 4.94 | C1 | −58.03° | MeOH |
| 5 | 5.80 | C1 | +56.91° | MeOH |
| 128 | 4.11 | C2 | −32.18° | MeOH |
| 129 | 4.62 | C2 | +29.03° | MeOH |
| 130 | 2.24 | C2 | −28.98° | MeOH |
| 131 | 2.56 | C2 | +29.76° | MeOH |
| 132 | 4.74 | C2 | −26.94° | MeOH |
| 133 | 5.59 | C2 | +31.70° | MeOH |
| 134 | 2.20 | C2 | −44.55° | MeOH |
| 135 | 2.53 | C2 | +27.48° | MeOH |
| 136 | 1.24 | C2 | −50.51° | CHCl$_3$ |
| 137 | 1.99 | C2 | +43.53° | CHCl$_3$ |
| 138 | 1.73 | C2 | +7.42° | CHCl$_3$ |
| 139 | 1.86 | C2 | −8.27° | CHCl$_3$ |

In Vitro Pharmacology

Compounds of Formula (I), (II) and (III) are antagonists or negative allosteric modulators of the mGluR7 as they reduce or inhibit the mGluR7 response induced by glutamate or a mGluR7 agonist, such as L-AP4.

The methods described below are suitable for the characterization of such compounds, and more particularly the compounds according to Formula (I), are described below.

Inositol Monophosphate Production Assay (IP1 Assay):

Membrane Preparation and Protocol:

HEK293 cells were transiently transfected with mGluR7 by electroporation and seeded in a poly-ornithine coated 96-well plate at the density of 150 000 cells/well. To allow the monitoring of receptor activity through measurements of inositol monophosphate (IP1) production, mGluR7 was transfected with a chimeric Gq/Gi protein (Gqtop). and was also co-transfected with EAAC1, a glutamate transporter, to avoid influence of extracellular glutamate. Cells were cultured in Dulbecco's Modified Eagle Medium (DMEM, Invitrogen, Cergy Pontoise, France), supplemented with 10% of Fetal Bovine Serum (FBS). Medium was changed by Glutamax™ (Invitrogen, Cergy Pontoise, France) to reduce extracellular glutamate concentration 3 hours before stimulation The HTRF-based assays from CisBio Bioassays allow the measure of different cell signaling pathways, notably those allowing the determination of the production of the second messenger inositol phosphate (IP). IP1 production was determined using the IP-One HTRF kit (CisBio Bioassays), a competitive immunoassay using cryptate-labeled anti-IP1 antibody and d2-labeled IP, according to the manufacturer's recommendations. All points were realized in triplicate.

Data Analysis

Data were analyzed with Prism 6 software (GraphPad-Software, San Diego, CA). Typically, in each experiment, a four-parameter concentration-response curve equation was used to fit data and potency ($IC_{50}$) is estimated as logarithms (log $IC_{50}$). Data were calculated as % of the control mGluR7 agonist L-AP4 response, defined as the response that is generated upon addition of an $EC_{80}$-equivalent concentration of L-AP4.

Results:

The Table 2 below represents the mean $IC_{50}$ obtained from at least two independent experiments.

TABLE 2

Pharmacological activity for compounds according to the invention.

| Example | human mGluR7 $IC_{50}$ (nM)* |
|---|---|
| 1 | +++ |
| 2 | ++ |
| 3 | + |
| 4 | + |
| 5 | +++ |
| 6 | +++ |
| 7 | +++ |
| 8 | +++ |
| 9 | +++ |
| 10 | +++ |
| 11 | +++ |
| 12 | +++ |
| 13 | +++ |
| 14 | +++ |
| 15 | +++ |
| 16 | +++ |
| 17 | +++ |
| 18 | +++ |
| 19 | +++ |
| 20 | +++ |
| 21 | +++ |
| 22 | +++ |
| 23 | +++ |
| 24 | +++ |
| 25 | +++ |
| 26 | +++ |
| 27 | +++ |
| 28 | +++ |
| 29 | +++ |
| 30 | +++ |
| 32 | ++ |
| 33 | +++ |
| 34 | + |
| 35 | +++ |
| 36 | + |
| 37 | +++ |
| 38 | +++ |
| 39 | +++ |
| 40 | +++ |
| 41 | +++ |
| 42 | +++ |
| 43 | +++ |
| 44 | +++ |
| 45 | +++ |
| 46 | +++ |
| 47 | +++ |
| 48 | ++ |
| 49 | +++ |
| 50 | +++ |
| 51 | +++ |
| 52 | +++ |
| 53 | +++ |
| 54 | +++ |
| 55 | +++ |
| 56 | +++ |
| 57 | +++ |
| 58 | +++ |
| 59 | +++ |
| 60 | +++ |
| 61 | +++ |
| 63 | ++ |
| 64 | + |
| 65 | ++ |
| 66 | +++ |
| 67 | ++ |
| 68 | ++ |
| 69 | +++ |
| 70 | ++ |
| 71 | ++ |
| 72 | +++ |
| 73 | + |
| 74 | +++ |
| 75 | +++ |
| 76 | +++ |
| 77 | +++ |
| 78 | +++ |
| 79 | +++ |
| 80 | +++ |
| 81 | ++ |
| 82 | ++ |
| 83 | ++ |
| 84 | +++ |
| 85 | +++ |
| 86 | ++ |
| 87 | +++ |
| 88 | + |
| 89 | +++ |
| 90 | +++ |
| 91 | +++ |
| 92 | +++ |
| 93 | +++ |
| 94 | +++ |
| 95 | +++ |
| 96 | +++ |
| 97 | +++ |
| 98 | +++ |
| 99 | + |
| 100 | +++ |
| 101 | +++ |
| 102 | ++ |
| 103 | + |
| 104 | +++ |
| 105 | + |
| 106 | + |
| 107 | ++ |
| 108 | +++ |
| 109 | +++ |
| 110 | +++ |
| 111 | + |
| 112 | +++ |
| 113 | +++ |
| 114 | +++ |
| 115 | +++ |
| 116 | +++ |
| 117 | +++ |
| 118 | +++ |
| 119 | +++ |
| 120 | + |
| 121 | + |
| 122 | +++ |
| 124 | +++ |
| 125 | +++ |
| 126 | +++ |
| 127 | +++ |

TABLE 2-continued

Pharmacological activity for compounds according to the invention.

| Example | human mGluR7 IC$_{50}$ (nM)* |
|---|---|
| 128 | +++ |
| 129 | ++ |
| 130 | +++ |
| 131 | +++ |
| 132 | +++ |
| 133 | + |
| 134 | +++ |
| 135 | ++ |
| 136 | + |
| 137 | +++ |
| 138 | ++ |
| 139 | +++ |

* Table legend:
(+): 1 µM < IC$_{50}$ < 30 µM
(++): 500 nM < IC$_{50}$ < 1 µM
(+++): IC$_{50}$ < 500 nM In Vivo Pharmacology Compounds of Formula (I), (II) and (III) are antagonists or negative allosteric modulators of the mGluR7 and can exert an in vivo pharmacological activity in disease models associated with glutamate dysfunction.

The pharmacological models suitable for the characterization of the efficacy of such compounds in various indications can be, but are not limited to, the animal models described below. The person skilled in the art will recognize that alternative models for disorders described herein exist and can be used, and that these evolve with medical and scientific progresses.

Elevated-plus-maze (EPM) model of anxiety in rodent: The test can be carried out as described by Pellow et al. (J Neurosci Methods (1985), 149) and File et al. (Psychopharmacol. (1993), 491). The apparatus consists of a gray PVC cross-shaped maze, elevated from the floor. It possesses two opposite open arms and two opposite enclosed arms of the same size, but with walls. The central square formed by the arms is open. The apparatus is placed in a weakly illuminated room. Sixty minutes after the end of the second stress session, each animal is placed in the central square of the plus-maze, facing an enclosed arm. They are then be allowed to freely explore the maze during the 5-min test. The maze is cleaned with water between each animal in order to avoid odor trails left by the animals. During the EPM test, the following parameters are measured: time spent on open arms (TO), time spent in closed arms (TC), number of entries into open arms (EO), number of entries into closed arms (EC). Two parameters are calculated: Time ratio (% of time spent on open arms)=TO/TO+TC; Entries ratio (% entries into open arms)=EO/EO+EC. An entry is defined as all four paws in the arm. Compound of Formula (I), (II) and (III) may be administered 30 min to 2 h (depending of its pharmacokinetic properties) prior to EPM test.

Fear Conditioning Model of Post-Traumatic Stress Disorder in the Rat:

The experiment can take place in one compartment of an active avoidance cage (or shuttle box), with a grid floor controlled by a personal computer and that can deliver foot shocks. The test shall be performed in 2 phases (conditioning and testing) spaced by 24 hours. The Phase 1 (named conditioning) consists of a background white noise (63 dB) produced in the chamber during the entire experiment. The conditioning session lasts 5 minutes and 30 s. The rats is placed in the chamber for a 2-min acclimation, then four 1 s-footshocks (0.5 mA) are delivered with a 60 s interval between shocks. Thirty seconds after the last shock, the rat is removed from the chamber before being placed back in its home cage. The Phase 2 (testing) takes place 24 h after conditioning. The rats are placed back in the chamber and their freezing behaviour is recorded for 5 min. The total time spent by the rat in freezing behaviour, the beginning time and the duration of each episode of freezing during the 5-min testing session are the experimental parameters. Compound of Formula (I), (II) and (III) may be administered 30 min to 2 h (depending of its pharmacokinetic properties) before the test session.

Novel-object recognition test of cognitive deficit in mice: The experiment can be performed according to Nilsson et al. (2007) with minor modifications (Wozniak et al., 2016). Following a 2-day habituation period (10 min/day), a training trial is performed, where mice are allowed to explore two identical objects for 5 min. About 1 h later, a test trial is conducted, where one of the familiar objects is replaced by a novel object. The animals are then allowed to explore the objects for 5 min. Compound of Formula (I), (II) and (III) may be administered 30 min to 2 h (depending of its pharmacokinetic properties) before MK-801 (0.3 mg/kg) which is administered 30 min before the training trial. Time spend exploring (i.e., sniffing or touching) the familiar (Tfamiliar) or novel object (Tnovel) is measured by a trained observer and then the recognition index is calculated for each mouse [(Tnovel−Tfamiliar)/(Tfamiliar+Tnovel)]×100.

Prepulse inhibition (PPI) test of schizophrenia in rodent: The procedure can be performed according to Czyrak et al. (2003). On the day before the experiment, the animals are subjected to a single startle session consisting of two trials, each presented 20 times during the session. During the first trial, a 120 dB, 40 ms pulse is presented, and on the second trial this pulse is preceded by a 75 dB, 20 ms prepulse. On the day of the experiment, the animals are habituated to the background white noise (65 dB) for 5 min (which continued throughout the test), after that the startle session is carried out as described above. Startle response amplitude is defined as the difference between the maximum force detected during a recording window and the force measured immediately before the stimulus onset (the threshold is set at 10 g).

For each animal, the amplitudes are averaged separately for each type of trial. The PPI is calculated as the difference between the amplitudes of the pulse (P) and the prepulse+pulse (PP+P), divided by the amplitude of the pulse alone [([P−(PP+P)]/P)×100]. Compound of Formula (I), (II) and (III) may be administered 30 min to 2 h (depending of its pharmacolkinetic properties) prior to MK-801 (0.3 mg/kg), which was administered 30 min before the habituation phase.

Noise-Induced Hearing Loss Model in the Mice:

Groups of 3-4-month-old CBA/CaJ mice undergo baseline testing (auditory brainstrem response (ABR) audiograms, Distorsion Product of Autoacoustic Emissions (DPOAE)) followed by loud noise exposure comprised of an 8-16 kHz octave band of noise at 110 to 120 dB Sound Pressure Level (SPL) (preferably 110 db SPL) for a period ranging from 30 min to 2 hours (preferably 45 min). Such noise trauma protocol has consistently been shown to produce 25-35 dB threshold shift in CBA mice (Kujawa and Liberman, 2009). Compound of Formula (I), (II) and (III) may be administered 30 min to 2 h (depending of its pharmacokinetic properties) prior to noise exposure, and or after noise exposure. Hearing function is measured at different timepoint, for example 24 hours, 2 and 4 weeks post-acoustic trauma. The experimental groups is compared to the control group through the measure of, for example, ABR Threshold, or ABR Threshold shift.

Colorectal Distension test of visceral pain in rat. The procedure can be performed according to Moloney et al. (Neurobiol of Stress (2015), 28). Animals are fasted overnight (16 h) and on the day of testing, are anaesthetised with isoflurane and a 6 cm latex balloon is inserted into the colorectal cavity, 1 cm from the anus. The animals are allowed to recover for 20 min before colorectal distension commenced. The paradigm used is an ascending phasic distension from 0 mmHg to 80 mmHg over 8 min using a computer-driven electronic barostat. The parameters measured are the threshold pressure (mmHg) that evokes visually identifiable visceral pain behavior, and the total number of pain behaviours. Postures defined as visceral pain behaviours are abdominal retractions and/or abdominal withdrawal reflex. Compound of Formula (I), (II) and (III) may be administered 30 min to 2 h (depending of its pharmacokinetic properties) prior to colorectal distension (T0). Animals undergo the balloon insertion protocol 10 min later (T10) and are allowed to recover until T30. Visceral pain behaviours are assessed at T30 and immediately after, the animals are euthanized.

Formulation Examples

The compounds according to the invention may be provided in an aqueous physiological buffer solution for parenteral administration.

The compounds of the present invention are also capable of being administered in unit dose forms, wherein the expression "unit dose" means a single dose which is capable of being administered to a patient, and which can be readily handled and packaged, remaining as a physically and chemically stable unit dose comprising either the active compound itself, or as a pharmaceutically acceptable composition, as described hereinafter. Compounds provided herein can be formulated into pharmaceutical compositions by mixture with one or more pharmaceutically acceptable excipients. Such unit dose compositions may be prepared for use by oral administration, particularly in the form of tablets, simple capsules or soft gel capsules; or intranasally, particularly in the form of powders, nasal drops, or aerosols; or dermally, for example, topically in ointments, creams, lotions, gels or sprays, or via trans-dermal patches; or by injection into the inner ear and/or into the middle ear (e.g. transtympanic injection), preferably by injection into the middle ear using sustained release system as for example transport enhancers (e.g. hyaluronic acid, DMSO), tixotropic or thermogeling formulation to enable a painless administration and forming a gel or a high viscous composition ensuring prolonged and continuous release of the active ingredient.

The compositions may conveniently be administered in unit dosage form and may be prepared by any of the methods well-known in the pharmaceutical art, for example, as described in *Remington: The Science and Practice of Pharmacy*, 20th ed.; Gennaro, A. R., Ed.; Lippincott Williams & Wilkins: Philadelphia, PA, 2000.

Preferred formulations include pharmaceutical compositions in which a compound of the present invention is formulated for oral or parenteral administration.

For oral administration, tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolved, modified-release or sustained-release preparations and formulations, and wherein such sustained-release formulations are preferably bi-modal. Preferred tablets contain lactose, cornstarch, magnesium silicate, croscarmellose sodium, povidone, magnesium stearate, or talc in any combination.

Liquid preparations for parenteral administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

Typical examples of recipes for the formulation of the invention are as follows:
1. Tablets

| | |
|---|---|
| Active ingredient | 5 to 50 mg |
| Di-calcium phosphate | 20 mg |
| Lactose | 30 mg |

-continued

| | |
|---|---|
| Talcum | 10 mg |
| Magnesium stearate | 5 mg |
| Potato starch | ad 200 mg |

In this Example, active ingredient can be replaced by the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 mL.

3. Injectable

A parenteral composition is prepared by stirring 1.5% by weight of active ingredient of the invention in 10% by volume propylene glycol and water.

4. Ointment

| | |
|---|---|
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the described invention may be varied in many ways by those skilled in the art.

The invention claimed is:
1. A compound of Formula (I):

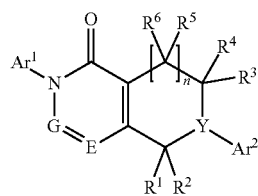

Formula (I)

wherein:
G is N,
E is $CR^8$,
Y is $CR^9$,
$R^1$, $R^2$, $R^3$, $R^4$, $R^5$, $R^6$, $R^8$ and $R^9$, identical or different, are each independently selected from hydrogen, halogen, —CN, —$CF_3$—C(=O)$R^{10}$, —C(=O)$OR^{10}$, —C(=O)$NR^{10}R^{11}$, —$OR^{10}$, —OC(=O)$R^{10}$, —OC(=O)$NR^{10}R^{11}$, —$SR^{10}$, —S(O)$R^{10}$, —S(O)$_2R^{10}$, —S(O)$_2NR^{10}R^{11}$, —$NR^{10}R^{11}$, —$NR^{10}$C(=O)$R^{11}$, —$NR^{10}$C(=O) $OR^{11}$, —$NR^{10}$S(O)$_2R^{11}$, or an optionally substituted radical chosen among: —($C_1$-$C_6$)alkyl, —($C_1$-$C_6$)haloalkyl, —($C_3$-$C_7$)cycloalkyl, —($C_1$-$C_6$)alkylene-($C_3$-$C_7$)cycloalkyl, or —($C_1$-$C_6$)cyanoalkyl,
wherein any two radicals $R^1$ and $R^2$, $R^3$ and $R^4$, and $R^5$ and $R^6$ may be taken together to form an oxo (=O), wherein $R^{10}$ and $R^{11}$, identical or different, are each independently selected from hydrogen, an optionally substituted radical chosen among: —($C_1$-$C_6$)alkyl, —($C_1$-$C_6$)haloalkyl, —($C_1$-$C_6$)cyanoalkyl, —($C_3$-$C_7$)cycloalkyl or —($C_1$-$C_6$)alkylene-($C_3$-$C_7$)cycloalkyl, wherein optionally any two radicals selected from $R^1$, $R^2$, $R^3$, $R^4$, $R^5$, $R^6$, $R^9$, $R^{10}$ and $R^{11}$ may be taken together to form an optionally substituted 3 to 10-membered non-aromatic carbocyclic or heterocyclic ring or a 5 to 10-membered aromatic heterocyclic ring, n is 1, $Ar^1$ represents an aryl or heteroaryl chosen among:

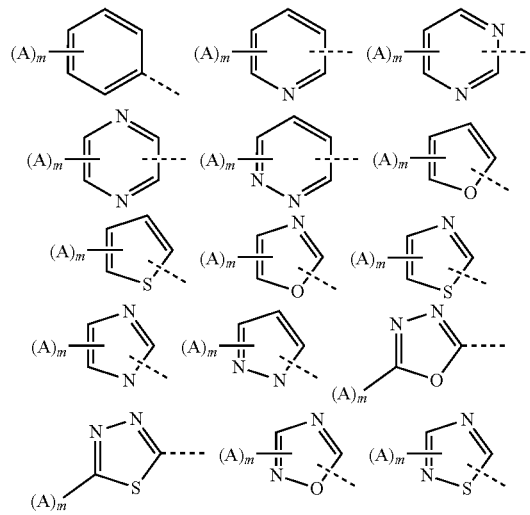

wherein m is the number of substituents A on the cycle and is an integer equal to 0, 1, 2, 3, 4 or 5;

$Ar^2$ represents an aryl or heteroaryl chosen among:

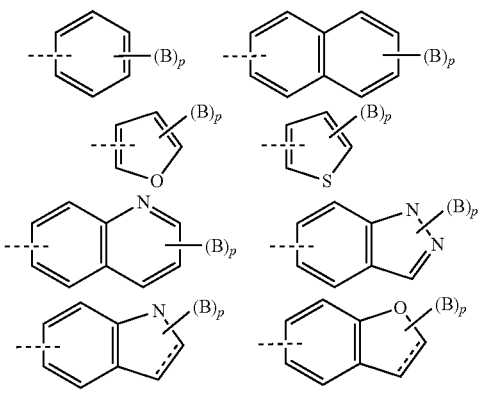

wherein p is the number of substituents B on the cycle and is an integer equal to 0, 1, 2, 3, 4 or 5;

wherein A and B, identical or different, are each independently selected from the group consisting of hydrogen, halogen, —CN, —$NO_2$, —OH, —$NH_2$, —$CF_3$, an optionally substituted radical selected from the group of —($C_1$-$C_6$)alkyl, —($C_1$-$C_6$)haloalkyl, —($C_3$-$C_7$)cycloalkyl, —($C_1$-$C_6$)alkylene-($C_3$-$C_7$)cycloalkyl, —($C_3$-$C_8$)cycloalkenyl, —($C_1$-$C_6$)cyanoalkyl, —($C_1$-$C_6$)alkylene-heteroaryl, —($C_1$-$C_6$)alkylene-aryl, —($C_1$-$C_6$) alkylene-heterocycle, aryl, heteroaryl, heterocycle, —OR$^{13}$, —(C$_1$-C$_6$)alkylene-OR$^{13}$, —O—(C$_2$-C$_6$)alkylene-OR$^{13}$, —NR$^{13}$(C$_2$-C$_6$)alkylene-OR$^{14}$, —(C$_2$-C$_6$)alkenylene-OR$^{13}$, —(C$_2$-C$_6$)alkynylene-OR$^{13}$, —NR$^{13}$R$^{14}$, —(C$_1$-C$_6$)alkylene-NR$^{13}$R$^{14}$, —O—(C$_2$-C$_6$)alkylene-NR$^{13}$R$^{14}$, —NR$^{13}$—(C$_2$-C$_6$)alkylene-NR$^{14}$R$^{15}$, —(C$_2$-C$_6$)alkenylene-NR$^{13}$R$^{14}$, —(C$_2$-C$_6$)alkynylene-NR$^{13}$R$^{14}$, —SR$^{13}$, —(C$_1$-C$_6$)alkylene-SR$^{13}$, —O—(C$_2$-C$_6$)alkylene-SR$^{13}$, —NR$^{13}$—(C$_2$-C$_6$)alkylene-SR$^{14}$, —S(=O)—R$^{13}$, —(C$_1$-C$_6$)alkylene-S(=O)—R$^{13}$, —O—(C$_1$-C$_6$)alkylene-S(=O)—R$^{13}$, —NR$^{13}$—(C$_1$-C$_6$)alkylene-S(=O)—R$^{14}$, —S(=O)$_2$—R$^{13}$, —(C$_1$-C$_6$)alkylene-S(=O)$_2$—R$^{13}$, —O—(C$_1$-C$_6$)alkylene-S(=O)$_2$—R$^{13}$, —NR$^{13}$—(C$_1$-C$_6$)alkylene-S(=O)$_2$—R$^{14}$, —S(=O)$_2$NR$^{13}$R$^{14}$, —(C$_1$-C$_6$)alkylene-S(=O)$_2$NR$^{13}$R$^{14}$, —O—(C$_1$-C$_6$)alkylene-S(=O)$_2$NR$^{13}$R$^{14}$, —NR$^{13}$—(C$_1$-C$_6$)alkylene-S(=O)$_2$NR$^{14}$R$^{15}$, —NR$^{13}$—S(=O)$_2$R$^{14}$, —(C$_1$-C$_6$)alkylene-NR$^{13}$—S(=O)$_2$R$^{14}$, —O—(C$_2$-C$_6$)alkylene-NR$^{13}$—S(=O)$_2$R$^{14}$, —NR$^{13}$—(C$_2$-C$_6$)alkylene-NR$^{14}$—S(=O)$_2$R$^{15}$, —C(=O)—NR$^{13}$R$^{14}$, —(C$_1$-C$_6$)alkylene-C(=O)—NR$^{13}$R$^{14}$, —O—(C$_1$-C$_6$)alkylene-C(=O)—NR$^{13}$R$^{14}$, —NR$^{13}$—(C$_1$-C$_6$)alkylene-C(=O)—NR$^{14}$R$^{15}$, —NR$^{13}$C(=O)—R$^{14}$, —(C$_1$-C$_6$)alkylene-NR$^{13}$C(=O)—R$^{14}$, —O—(C$_2$-C$_6$)alkylene-NR$^{13}$C(=O)—R$^{14}$, —NR$^{13}$—(C$_2$-C$_6$)alkylene-NR$^{14}$C(=O)—R$^{15}$, —C(=O)—R$^{13}$, —(C$_1$-C$_6$)alkylene-C(=O)—R$^{13}$, —O—(C$_1$-C$_6$)alkylene-C(=O)—R$^{13}$, —NR$^{13}$—(C$_1$-C$_6$)alkylene-C(=O)—R$^{14}$, —C(=O)—OR$^{13}$, —(C$_1$-C$_6$)alkylene-C(=O)—OR$^{13}$, —O—(C$_1$-C$_6$)alkylene-C(=O)—OR$^{13}$, —NR$^{13}$—(C$_1$-C$_6$)alkylene-C(=O)—OR$^{14}$, —OC(=O)—R$^{13}$, —(C$_1$-C$_6$)alkylene-OC(=O)—R$^{13}$, —O—(C$_2$-C$_6$)alkylene-OC(=O)—R$^{13}$, —NR$^{13}$—(C$_2$-C$_6$)alkylene-OC(=O)—R$^{14}$, —NR$^{13}$—C(=O)—NR$^{14}$R$^{15}$, —(C$_1$-C$_6$)alkylene-NR$^{13}$—C(=O)—NR$^{14}$R$^{15}$, —O—(C$_2$-C$_6$)alkylene-NR$^{13}$—C(=O)—NR$^{14}$R$^{15}$, —NR$^{13}$—(C$_2$-C$_6$)alkylene-NR$^{14}$—C(=O)—NR$^{15}$R$^{16}$, —NR$^{13}$—C(=O)—OR$^{14}$, —(C$_1$-C$_6$)alkylene-NR$^{13}$—C(=O)—OR$^{14}$, —O—(C$_2$-C$_6$)alkylene-NR$^{13}$—C(=O)—OR$^{14}$, —NR$^{13}$—(C$_2$-C$_6$)alkylene-NR$^{14}$—C(=O)—OR$^{15}$, —O—C(=O)—NR$^{13}$R$^{14}$, —(C$_1$-C$_6$)alkylene-O—C(=O)—NR$^{13}$R$^{14}$, —O—(C$_2$-C$_6$)alkylene-O—C(=O)—NR$^{13}$R$^{14}$, —NR$^{13}$—(C$_2$-C$_6$)alkylene-O—C(=O)—NR$^{14}$R$^{15}$, —C(=O)—(C$_1$-C$_6$)alkylene-NR$^{13}$R$^{14}$, —(C$_1$-C$_6$)alkylene-C(=O)—(C$_1$-C$_6$)alkylene-NR$^{13}$R$^{14}$, —C(=O)—(C$_1$-C$_6$)alkylene-OR$^{13}$, —(C$_1$-C$_6$)alkylene-C(=O)—(C$_1$-C$_6$)alkylene-OR$^{13}$, —NR$^{13}$—C(=S)—NR$^{14}$R$^{15}$, —(C$_1$-C$_6$)alkylene-NR$^{13}$—C(=S)—NR$^{14}$R$^{15}$, —NR$^{13}$_C(=NR$^{14}$)—NR$^{15}$R$^{16}$ or —(C$_1$-C$_6$)alkylene-NR$^{13}$—C(=NR$^{14}$)—NR$^{15}$R$^{16}$;

wherein R$^{13}$, R$^{14}$, R$^{15}$ and R$^{16}$ are each independently selected from hydrogen, an optionally substituted-(C$_1$-C$_6$)haloalkyl, —(C$_1$-C$_6$)alkyl, —(C$_1$-C$_6$)cyanoalkyl, —(C$_3$-C$_7$)cycloalkyl, —(C$_1$-C$_6$)alkylene-(C$_3$-C$_7$)cycloalkyl, heteroaryl, aryl, heterocycle, —(C$_1$-C$_6$)alkylene-heteroaryl, —(C$_1$-C$_6$)alkylene-heterocycle and —(C$_1$-C$_6$)alkylene-aryl;

wherein optionally any two radicals selected from R$^{13}$, R$^{14}$, R$^{15}$ or R$^{16}$ may be taken together to form a 3 to 10-membered carbocycle, heterocycle, aryl or heteroaryl ring; wherein each ring is optionally further substituted with 1 to 5 radicals independently selected from halogen, cyano, nitro, hydroxyl, amino, —(C$_1$-C$_6$)alkyl, —O—(C$_1$-C$_6$)alkyl and —N—((C$_1$-C$_6$)alkyl)$_2$;

wherein any two radicals A and any two radicals B may be combined with the intervening atoms to form a 3 to 10-membered carbocycle, heterocycle, aryl or heteroaryl ring; wherein each ring is optionally further substituted with 1 to 5 radicals independently selected from halogen, —CN, hydroxyl, amino, —(C$_1$-C$_6$)alkyl, —O—(C$_1$-C$_6$)alkyl and —N—((C$_1$-C$_6$)alkyl)$_2$;

wherein the term "heteroaryl" or "aromatic heterocyclic ring", unless otherwise defined, refers to a 5 to 10-membered monocyclic or bicyclic unsaturated aromatic ring system containing from 1 to 3 heteroatoms selected independently from N, O and S;

wherein the term "heterocycle" or "non-aromatic heterocyclic ring", unless otherwise defined, refers to a 5 to 10-membered monocyclic or bicyclic saturated or partially saturated ring system containing from 1 to 3 heteroatoms selected independently from N, O and S;

wherein the term "optionally substituted", unless otherwise defined, refers to an optional substitution with one or more substituents selected from (C$_1$-C$_6$)alkyl, hydroxy, (C$_1$-C$_6$)alkylene-OH, (C$_1$-C$_6$)alkylene-O—(C$_1$-C$_6$)alkyl, mercapto, aryl, heteroaryl, heterocycle, (C$_1$-C$_6$)alkylene-aryl, (C$_1$-C$_6$)alkylene-heterocycle, (C$_1$-C$_6$)alkylene-(C$_3$-C$_7$)cycloalkyl, (C$_1$-C$_6$)alkylene-heteroaryl, halogen, trifluoroalkyl, trifluoroalkoxy, cyano, cyanoalkyl, nitro, amino, carboxyl, carboxamide, —NH—C(=O)O—(C$_1$-C$_6$)alkyl, —S(=O)$_2$—NH$_2$, —C(O)O—(C$_1$-C$_6$)alkyl, and —S(=O)—(C$_1$-C$_6$)alkyl;

or an N-oxide form thereof, a pharmaceutically acceptable salt or solvate thereof, or an optical isomer, racemate, diastereoisomer, enantiomer or tautomer thereof.

2. A compound according to claim 1, which is a compound of Formula (II):

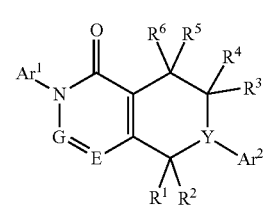

Formula (II)

wherein

Ar$^1$ represents an aryl or heteroaryl chosen among:

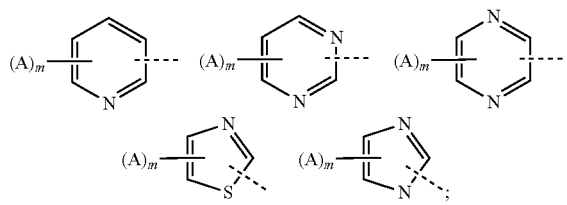

Wherein:
m is the number of substituents A on the cycle and is an integer equal to 0, 1, 2, 3 or 4, A, identical or different, are each independently selected from the group consisting of hydrogen, halogen, —CN, —CF$_3$, —OH, —NH$_2$, an optionally substituted radical selected from the group of —(C$_1$-

C$_6$)alkyl, —(C$_1$-C$_6$)haloalkyl, —(C$_3$-C$_7$)cycloalkyl, —(C$_1$-C$_6$)alkylene-(C$_3$-C$_7$)cycloalkyl, —(C$_1$-C$_6$)alkylene-heterocycle, heterocycle, aryl, heteroaryl, —OR$^{13}$, —(C$_1$-C$_6$)alkylene-OR$^{13}$, —O—(C$_2$-C$_6$)alkylene-OR$^{13}$, —NR$^{13}$ (C$_2$-C$_6$)alkylene-OR$^{14}$, —NR$^{13}$R$^{14}$, —(C$_1$-C$_6$)alkylene-NR$^{13}$R$^{14}$, —O—(C$_2$-C$_6$)alkylene-NR$^{13}$R$^{14}$, —NR$^{13}$—(C$_2$-C$_6$)alkylene-NR$^{14}$R$^{15}$, —SR$^{13}$, —(C$_1$-C$_6$)alkylene-SR$^{13}$, —O—(C$_2$-C$_6$)alkylene-SR$^{13}$, —NR$^{13}$—(C$_2$-C$_6$)alkylene-SR$^{14}$, —S(=O)—R$^{13}$, —S(=O)$_2$—R$^{13}$, —S(=O)$_2$NR$^{13}$R$^{14}$, —(C$_1$-C$_6$)alkylene-S(=O)$_2$NR$^{13}$R$^{14}$, —NR$^{13}$—S(=O)$_2$R$^{14}$, —(C$_1$-C$_6$)alkylene-NR$^{13}$—S(=O)$_2$R$^{14}$, —O—(C$_2$-C$_6$)alkylene-NR$^{13}$—S(=O)$_2$R$^{14}$, —NR$^{13}$—(C$_2$-C$_6$)alkylene-NR$^{14}$—S(=O)$_2$R$^{15}$, —C(=O)—NR$^{13}$R$^{14}$, —(C$_1$-C$_6$)alkylene-C(=O)—NR$^{13}$R$^{14}$, —O—(C$_1$-C$_6$)alkylene-C(=O)—NR$^{13}$R$^{14}$, —NR$^{13}$—(C$_1$-C$_6$)alkylene-C(=O)—NR$^{14}$R$^{15}$, —NR$^{13}$C(=O)—R$^{14}$, —(C$_1$-C$_6$)alkylene-NR$^{13}$C(=O)—R$^{14}$, —O—(C$_2$-C$_6$)alkylene-NR$^{13}$C(=O)—R$^{14}$, —NR$^{13}$—(C$_2$-C$_6$)alkylene-NR$^{14}$C(=O)—R$^{15}$, —C(=O)—R$^{13}$, —C(=O)—OR$^{13}$, —(C$_1$-C$_6$)alkylene-C(=O)—OR$^{13}$, —O—(C$_1$-C$_6$)alkylene-C(=O)—OR$^{13}$, —NR$^{13}$—(C$_1$-C$_6$)alkylene-C(=O)—OR$^{14}$, —OC(=O)—R$^{13}$, —(C$_1$-C$_6$)alkylene-OC(=O)—R$^{13}$, —O—(C$_2$-C$_6$)alkylene-OC(=O)—R$^{13}$, —NR$^{13}$—(C$_2$-C$_6$)alkylene-OC(=O)—R$^{14}$ or —NR$^{13}$—C(=O)—OR$^{14}$;

wherein R$^{13}$, R$^{14}$ and R$^{15}$ are each independently selected from hydrogen, an optionally substituted- (C$_1$-C$_6$)alkyl, —(C$_3$-C$_7$)cycloalkyl, —(C$_1$-C$_6$)alkylene-(C$_3$-C$_7$)cycloalkyl, heteroaryl, aryl, heterocycle, —(C$_1$-C$_6$)alkylene-heteroaryl, —(C$_1$-C$_6$)alkylene-heterocycle and —(C$_1$-C$_6$)alkylene-aryl;

wherein optionally any two radicals selected from R$^{13}$, R$^{14}$ or R$^{15}$ on substituent A may be taken together to form a 3 to 10-membered carbocycle, heterocycle, aryl or heteroaryl ring;

wherein each ring is optionally further substituted with 1 to 5 radicals independently selected from halogen, —CN, —NO$_2$, —OH, —NH$_2$, —(C$_1$-C$_6$)alkyl, —O—(C$_1$-C$_6$)alkyl and —N—((C$_1$-C$_6$)alkyl)$_2$;

wherein any two radicals A may be combined with the intervening atoms to form a 3 to 10-membered carbocycle, heterocycle, aryl or heteroaryl ring; wherein each ring is optionally further substituted with 1 to 5 radicals independently selected from halogen, —CN, —OH, —NH$_2$, —(C$_1$-C$_6$)alkyl, —O—(C$_1$-C$_6$)alkyl and —N—((C$_1$-C$_6$)alkyl)$_2$;

and/or

Ar$^2$ represents an aryl or heteroaryl chosen among:

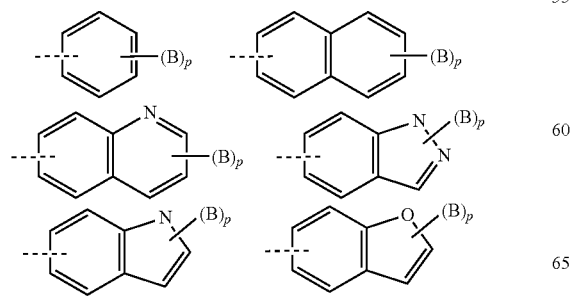

wherein p is the number of substituents B on the cycle and is an integer equal to 0, 1, 2, 3, 4 or 5, B, identical or different, are each independently selected from the group consisting of hydrogen, halogen, —CN, —CF$_3$, an optionally substituted radical selected from the group of (C$_1$-C$_6$)alkyl, —(C$_1$-C$_6$)haloalkyl, —(C$_3$-C$_7$)cycloalkyl, —(C$_1$-C$_6$)alkylene-(C$_3$-C$_7$)cycloalkyl, (C$_1$-C$_6$)alkylene-heterocycle, —(C$_1$-C$_6$)alkylene-aryl, heterocycle, —OR$^{13}$, —(C$_1$-C$_6$)alkylene-OR$^{13}$, —O—(C$_2$-C$_6$)alkylene-OR$^{13}$, —NR$^{13}$ (C$_2$-C$_6$)alkylene-OR$^{14}$, —NR$^{13}$R$^{14}$, —(C$_1$-C$_6$)alkylene-NR$^{13}$R$^{14}$, —O—(C$_2$-C$_6$)alkylene-NR$^{13}$R$^{14}$, —NR$^{13}$—(C$_2$-C$_6$)alkylene-NR$^{14}$R$^{15}$, —SR$^{13}$, —(C$_1$-C$_6$)alkylene-SR$^{13}$, —O—(C$_2$-C$_6$)alkylene-SR$^{13}$, —NR$^{13}$—(C$_2$-C$_6$)alkylene-SR$^{14}$, —S(=O)—R$^{13}$, —(C$_1$-C$_6$)alkylene-S(=O)—R$^{13}$, —O—(C$_1$-C$_6$)alkylene-S(=O)—R$^{13}$, —NR$^{13}$—(C$_1$-C$_6$)alkylene-S(=O)—R$^{14}$, —S(=O)$_2$—R$^{13}$, —(C$_1$-C$_6$)alkylene-S(=O)$_2$—R$^{13}$, —O—(C$_1$-C$_6$)alkylene-S(=O)$_2$—R$^{13}$, —NR$^{13}$—(C$_1$-C$_6$)alkylene-S(=O)$_2$—R$^{14}$, —S(=O)$_2$NR$^{13}$R$^{14}$, —(C$_1$-C$_6$)alkylene-S(=O)$_2$NR$^{13}$R$^{14}$, —O—(C$_1$-C$_6$)alkylene-S(=O)$_2$NR$^{13}$R$^{14}$, —NR$^{13}$—(C$_1$-C$_6$)alkylene-S(=O)$_2$NR$^{14}$R$^{15}$, —NR$^{13}$—S(=O)$_2$R$^{14}$, —(C$_1$-C$_6$)alkylene-NR$^{13}$—S(=O)$_2$R$^{14}$, —O—(C$_2$-C$_6$)alkylene-NR$^{13}$—S(=O)$_2$R$^{14}$, —NR$^{13}$—(C$_2$-C$_6$)alkylene-NR$^{14}$—S(=O)$_2$R$^{15}$, —C(=O)—NR$^{13}$R$^{14}$, —(C$_1$-C$_6$)alkylene-C(=O)—NR$^{13}$R$^{14}$, —O—(C$_1$-C$_6$)alkylene-C(=O)—NR$^{13}$R$^{14}$, —NR$^{13}$—(C$_1$-C$_6$)alkylene-C(=O)—NR$^{14}$R$^{15}$, —NR$^{13}$C(=O)—R$^{14}$, —(C$_1$-C$_6$)alkylene-NR$^{13}$C(=O)—R$^{14}$, —O—(C$_2$-C$_6$)alkylene-NR$^{13}$C(=O)—R$^{14}$, —NR$^{13}$—(C$_2$-C$_6$)alkylene-NR$^{14}$C(=O)—R$^{15}$, —C(=O)—R$^{13}$, —(C$_1$-C$_6$)alkylene-C(=O)—R$^{13}$, —O—(C$_1$-C$_6$)alkylene-C(=O)—R$^{13}$, —NR$^{13}$—(C$_1$-C$_6$)alkylene-C(=O)—R$^{14}$, —C(=O)—OR$^{13}$, —(C$_1$-C$_6$)alkylene-C(=O)—OR$^{13}$, —O—(C$_1$-C$_6$)alkylene-C(=O)—OR$^{13}$, —NR$^{13}$—(C$_1$-C$_6$)alkylene-C(=O)—OR$^{14}$, —OC(=O)—R$^{13}$, —(C$_1$-C$_6$)alkylene-OC(=O)—R$^{13}$, —O—(C$_2$-C$_6$)alkylene-OC(=O)—R$^{13}$, —NR$^{13}$—(C$_2$-C$_6$)alkylene-OC(=O)—R$^{14}$, —(C$_1$-C$_6$)alkylene-NR$^{13}$—C(=O)—NR$^{14}$R$^{15}$, —NR$^{13}$—C(=O)—OR$^{14}$, —(C$_1$-C$_6$)alkylene-NR$^{13}$—C(=O)—OR$^{14}$, —O—(C$_2$-C$_6$)alkylene-NR$^{13}$—C(=O)—OR$^{14}$, —NR$^{13}$—(C$_2$-C$_6$)alkylene-NR$^{14}$—C(=O)—OR$^{15}$, —O—C(=O)—NR$^{13}$R$^{14}$, —(C$_1$-C$_6$)alkylene-O—C(=O)—NR$^{13}$R$^{14}$, —O—(C$_2$-C$_6$)alkylene-O—C(=O)—NR$^{13}$R$^{14}$, —NR$^{13}$—(C$_2$-C$_6$)alkylene-O—C(=O)—NR$^{14}$R$^{15}$, —C(=O)—(C$_1$-C$_6$)alkylene-NR$^{13}$R$^{14}$, —C(=O)—(C$_1$-C$_6$)alkylene-OR$^{13}$;

wherein R$^{13}$, R$^{14}$ and R$^{15}$ are each independently selected from hydrogen, an optionally substituted- (C$_1$-C$_6$)haloalkyl, —(C$_1$-C$_6$)alkyl, —(C$_1$-C$_6$)cyanoalkyl, —(C$_3$-C$_7$)cycloalkyl, —(C$_1$-C$_6$)alkylene-(C$_3$-C$_7$)cycloalkyl, heteroaryl, aryl, heterocycle, —(C$_1$-C$_6$)alkylene-heteroaryl, —(C$_1$-C$_6$)alkylene-heterocycle and —(C$_1$-C$_6$)alkylene-aryl;

wherein optionally any two radicals selected from $R^{13}$, $R^{14}$ or $R^{15}$ on substituent B may be taken together to form a 3 to 10-membered carbocycle, heterocycle, aryl or heteroaryl ring; wherein each ring is optionally further substituted with 1 to 5 radicals independently selected from halogen, —CN, —NO$_2$, —OH, —NH$_2$, —(C$_1$-C$_6$)alkyl, —O—(C$_1$-C$_6$)alkyl and —N—((C$_1$-C$_6$)alkyl)$_2$;

wherein any two radicals B may be combined with the intervening atoms to form a 3 to 10-membered carbocycle, heterocycle, aryl or heteroaryl ring; wherein each ring is optionally further substituted with 1 to 5 radicals independently selected from halogen, —CN, —OH, —NH$_2$, —(C$_1$-C$_6$)alkyl, —O—(C$_1$-C$_6$)alkyl and —N—((C$_1$-C$_6$)alkyl)$_2$.

3. A compound according to claim 1, wherein:

A, identical or different, are each independently selected from the group consisting of hydrogen, halogen, —CN, —CF$_3$, —OH, an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)alkylene-(C$_3$-C$_7$)cycloalkyl, —(C$_1$-C$_6$)alkylene-heterocycle, heterocycle, —OR$^{13}$, —(C$_1$-C$_6$)alkylene-OR$^{13}$, —O—(C$_2$-C$_6$)alkylene-OR$^{13}$, —NR$^{13}$ (C$_2$-C$_6$)alkylene-OR$^{14}$, —O(C$_2$-C$_6$)alkylene-NR$^{13}$R$^{14}$, —NR$^{13}$—(C$_2$-C$_6$)alkylene-NR$^{14}$R$^{15}$, —NR$^{13}$R$^{14}$, —(C$_1$-C$_6$)alkylene-NR$^{13}$R$^{14}$, —NR$^{13}$C(=O)—R$^{14}$, —C(=O)—NR$^{13}$R$^{14}$, S(=O)$_2$NR$^{13}$R$^{14}$ or —NR$^{13}$—S(=O)$_2$R$^{14}$;

wherein $R^{13}$ and $R^{14}$ are each independently selected from hydrogen, an optionally substituted-(C$_1$-C$_3$)alkyl, —(C$_3$-C$_7$)cycloalkyl, —(C$_1$-C$_6$)alkylene-(C$_3$-C$_7$)cycloalkyl, heterocycle and —(C$_1$-C$_6$)alkylene-heterocycle;

wherein optionally radicals $R^{13}$ and $R^{14}$ on substituent A may be taken together to form a 3 to 6-membered carbocycle, heterocycle, aryl or heteroaryl ring; wherein each ring is optionally further substituted with 1 to 5 radicals independently selected from halogen, —CN, —OH, —NH$_2$, —(C$_1$-C$_6$)alkyl, —O—(C$_1$-C$_6$)alkyl and —N—((C$_1$-C$_6$)alkyl)$_2$;

wherein any two radicals A may be combined with the intervening atoms to form a 3 to 10-membered carbocycle, heterocycle, aryl or heteroaryl ring; wherein each ring is optionally further substituted with 1 to 5 radicals independently selected from halogen, —CN, —(C$_1$-C$_6$)alkyl, —O—(C$_1$-C$_6$)alkyl and —N—((C$_1$-C$_6$)alkyl)$_2$; and/or B, identical or different, are each independently selected from the group consisting of hydrogen, halogen, —CF$_3$, —CN, an optionally substituted radical selected from the group of (C$_1$-C$_6$)alkyl, —(C$_1$-C$_6$)haloalkyl, —(C$_3$-C$_7$)cycloalkyl, —(C$_1$-C$_6$)alkylene-(C$_3$-C$_7$)cycloalkyl, (C$_1$-C$_6$)alkylene-aryl, heterocycle, —OR$^{13}$, —(C$_1$-C$_6$)alkylene-OR$^{13}$, —O—(C$_2$-C$_6$)alkylene-OR$^{13}$, —NR$^{13}$ (C$_2$-C$_6$)alkylene-OR$^{14}$, —NR$^{13}$R$^{14}$, —SR$^{13}$, —(C$_1$-C$_6$)alkylene-SR$^{13}$, —S(=O)—R$^{13}$, —S(=O)$_2$—R$^{13}$, —NR$^{13}$C(=O)—R$^{14}$, —C(=O)—NR$^{13}$R$^{14}$, —C(=O)—OR$^{13}$, —OC(=O)—R$^{13}$, —C(=O)—(C$_1$-C$_6$)alkylene-OR$^{13}$ or —C(=O)—R$^{13}$;

wherein $R^{13}$ and $R^{14}$ are each independently selected from hydrogen, an optionally substituted-(C$_1$-C$_6$)alkyl, —(C$_3$-C$_7$)cycloalkyl, —(C$_1$-C$_6$)alkylene-(C$_3$-C$_7$)cycloalkyl, heteroaryl, aryl, heterocycle, —(C$_1$-C$_6$)alkylene-heteroaryl, —(C$_1$-C$_6$)alkylene-heterocycle and —(C$_1$-C$_6$)alkylene-aryl;

wherein optionally any two radicals selected from $R^{13}$ and $R^{14}$ on substituent B may be taken together to form a 3 to 10-membered carbocycle, heterocycle, aryl or heteroaryl ring; wherein each ring is optionally further substituted with 1 to 5 radicals independently selected from halogen, CN, —OH, —NH$_2$, —(C$_1$-C$_6$)alkyl, —O—(C$_1$-C$_6$)alkyl and —N—((C$_1$-C$_6$)alkyl)$_2$;

wherein any two radicals B may be combined with the intervening atoms to form a 3 to 10-membered carbocycle, heterocycle, aryl or heteroaryl ring; wherein each ring is optionally further substituted with 1 to 5 radicals independently selected from halogen, —CN, —OH, —NH$_2$, —(C$_1$-C$_6$)alkyl, —O—(C$_1$-C$_6$)alkyl and —N—((C$_1$-C$_6$)alkyl)$_2$; and/or only of G or E is N.

4. A compound according to claim 1, wherein:

A, identical or different, are each independently selected from the group consisting of hydrogen, halogen, —CN, —CF$_3$, —OH, an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)alkylene-(C$_3$-C$_7$)cycloalkyl, —(C$_1$-C$_6$)alkylene-heterocycle, heterocycle, —O—(C$_1$-C$_6$)alkyl, O—(C$_1$-C$_3$)alkyl-(C$_3$-C$_7$)cycloalkyl, —(C$_1$-C$_6$)alkylene-OR$^{13}$, —O—(C$_2$-C$_6$)alkylene-OR$^{13}$, —NR$^{13}$R$^{14}$, —(C$_1$-C$_6$)alkylene-NR$^{13}$R$^{14}$ or —NR$^{13}$C(=O)—R$^{14}$;

$R^{13}$ and $R^{14}$ are each independently selected from hydrogen, an optionally substituted-(C$_1$-C$_3$)alkyl, —(C$_3$-C$_7$)cycloalkyl, —(C$_1$-C$_6$)alkylene-(C$_3$-C$_7$)cycloalkyl;

optionally radicals $R^{13}$ and $R^{14}$ on substituent A may be taken together to form a 3 to 6-membered carbocycle or heterocycle, wherein each ring is optionally further substituted with 1 to 5 radicals independently selected from halogen, —CN, —OH, —NH$_2$, —(C$_1$-C$_6$)alkyl, —O—(C$_1$-C$_6$)alkyl and —N—((C$_1$-C$_6$)alkyl)$_2$; and any two radicals A may be combined with the intervening atoms to form a 3 to 10-membered carbocycle, heterocycle, aryl or heteroaryl ring; wherein each ring is optionally further substituted with 1 to 5 radicals independently selected from halogen, —CN, —(C$_1$-C$_6$)alkyl, —O—(C$_1$-C$_6$)alkyl and —N—((C$_1$-C$_6$)alkyl)$_2$.

5. A compound according to claim 1, wherein:

B, identical or different, are each independently selected from the group consisting of hydrogen, halogen, —CF$_3$, an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)alkylene-(C$_3$-C$_7$)cycloalkyl, heterocycle, —O—(C$_1$-C$_6$)alkyl, —O—(C$_3$-C$_7$)cycloalkyl, —O—(C$_1$-C$_6$)alkylene-(C$_3$-C$_7$)cycloalkyl, —(C$_1$-C$_6$)alkylene-OR$^{13}$, —O—(C$_1$-C$_6$)alkylene-aryl, —O—(C$_2$-C$_6$)alkylene-O—(C$_1$-C$_6$)alkyl, —NR$^{13}$R$^{14}$ or —C(=O)—R$^{13}$;

$R^{13}$ and $R^{14}$ are each independently selected from hydrogen, an optionally substituted —(C$_1$-C$_6$)alkyl, —(C$_3$-C$_7$)cycloalkyl, —(C$_1$-C$_6$)alkylene-(C$_3$-C$_7$)cycloalkyl;

optionally radicals $R^{13}$ and $R^{14}$ on substituent B may be taken together to form a 3 to 6-membered carbocycle, heterocycle, aryl or heteroaryl ring; wherein each ring is optionally further substituted with 1 to 5 radicals independently selected from halogen, —CN, —OH, —NH$_2$, —(C$_1$-C$_6$)alkyl, —O—(C$_1$-C$_6$)alkyl and —N—((C$_1$-C$_6$)alkyl)$_2$;

any two radicals B may be combined with the intervening atoms to form a 3 to 10-membered carbocycle, heterocycle, aryl or heteroaryl ring; wherein each ring is optionally further substituted with 1 to 5 radicals independently selected from halogen, —CN, —(C$_1$-C$_6$)alkyl, —O—(C$_1$-C$_6$)alkyl and —N—((C$_1$C$_6$)alkyl)$_2$.

6. A compound according to claim 1, wherein:
Ar¹ represents an aryl or heteroaryl chosen among:

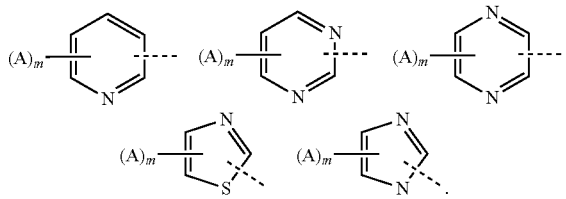

7. A compound according to claim 1, wherein:
Ar² represents an aryl or heteroaryl chosen among:

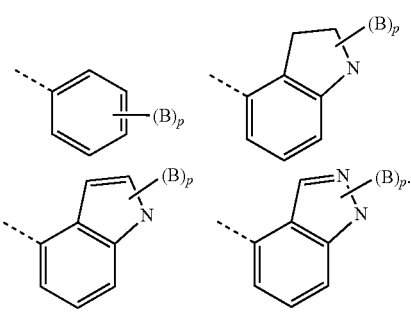

8. A compound according to claim 1, wherein:
$R^1$, $R^2$, $R^3$, $R^4$, $R^5$ and $R^6$ identical or different, are each independently selected from groups consisted of hydrogen, halogen, —$OR^{10}$, —$NR^{10}R^{11}$, an optionally substituted —($C_1$-$C_3$)alkyl,
any two radicals $R^1$ and $R^2$, $R^3$ and $R^4$, and $R^5$ and $R^6$ may be taken together to form an oxo, and
optionally any two radicals selected from $R^1$, $R^2$, $R^3$, $R^4$, $R^5$ and $R^6$ may be taken together to form an optionally substituted 3 to 10-membered non-aromatic carbocyclic or heterocyclic ring.

9. A compound according to claim 1, wherein:
$R^8$ is selected from hydrogen, halogen, —CN, —$OR^{10}$, —$NR^{10}R^{11}$, —$CF_3$, an optionally substituted —($C_1$-$C_3$)alkyl, wherein $R^{10}$ and $R^{11}$, identical or different, are each independently selected from hydrogen, —($C_1$-$C_3$)alkyl or —($C_3$-$C_7$)cycloalkyl, and
optionally the two radicals $R^{10}$ and $R^{11}$ may be taken together to form an optionally substituted 3 to 10-membered non-aromatic carbocyclic or heterocyclic ring.

10. A compound according to claim 1, wherein:
$R^9$ is selected from hydrogen, halogen, —CN, —$OR^{10}$, —$NR^{10}R^{11}$, —$CF_3$, or an optionally substituted —($C_1$-$C_3$)alkyl, wherein $R^{10}$ and $R^{11}$, identical or different, are each independently selected from hydrogen or —($C_1$-$C_3$)alkyl, and
optionally the two radicals $R^{10}$ and $R^{11}$ may be taken together to form an optionally substituted 3 to 10-membered non-aromatic carbocyclic or heterocyclic ring.

11. A compound according to claim 1, wherein $R^1$ to $R^6$ are hydrogen.

12. A compound according to claim 1, wherein $R^8$ is hydrogen, and/or wherein $R^9$ is hydrogen.

13. A compound according to claim 1, which is selected from the following:
6-(2,4-Dimethyl-phenyl)-2-pyridin-2-yl-5,6,7,8-tetrahydro-2H-phthalazin-1-one,
6-(3-methoxyphenyl)-2-(pyridin-2-yl)-5,6,7,8-tetrahydrophthalazin-1(2H)-one,
6-(4-methoxyphenyl)-2-(pyridin-2-yl)-5,6,7,8-tetrahydrophthalazin-1(2H)-one,
(+)-6-(2,4-Dimethyl-phenyl)-2-pyridin-2-yl-5,6,7,8-tetrahydro-2H-phthalazin-1-one,
(−)-6-(2,4-Dimethyl-phenyl)-2-pyridin-2-yl-5,6,7,8-tetrahydro-2H-phthalazin-1-one,
6-(2,4-dimethylphenyl)-2-(5-chloropyridin-2-yl)-5,6,7,8-tetrahydro-phthalazin-1(2H)-one,
2-(4-chloropyridin-2-yl)-6-(2,4-dimethylphenyl)-5,6,7,8-tetrahydrophthalazin-1(2H)-one,
2-(3-chloropyridin-2-yl)-6-(2,4-dimethylphenyl)-5,6,7,8-tetrahydrophthalazin-1(2H)-one,
2-(6-fluoropyridin-2-yl)-6-(2,4-dimethylphenyl)-5,6,7,8-tetrahydrophthalazin-1(2H)-one,
6-(2,4-dimethylphenyl)-2-(5-fluoropyridin-2-yl)-5,6,7,8-tetrahydrophthalazin-1(2H)-one,
6-(2,4-dimethylphenyl)-2-(4-fluoropyridin-2-yl)-5,6,7,8-tetrahydrophthalazin-1(2H)-one,
6-(2,4-dimethylphenyl)-2-(3-fluoropyridin-2-yl)-5,6,7,8-tetrahydrophthalazin-1(2H)-one,
6-(2,4-dimethylphenyl)-2-(6-methoxypyridin-2-yl)-5,6,7,8-tetrahydrophthalazin-1(2H)-one,
6-(2,4-dimethylphenyl)-2-(5-methoxypyridin-2-yl)-5,6,7,8-tetrahydrophthalazin-1(2H)-one,
6-(2,4-dimethylphenyl)-2-(4-methoxypyridin-2-yl)-5,6,7,8-tetrahydrophthalazin-1(2H)-one,
6-(2,4-dimethylphenyl)-2-(3-methoxypyridin-2-yl)-5,6,7,8-tetrahydrophthalazin-1(2H)-one,
6-(2,4-dimethylphenyl)-2-(6-methylpyridin-2-yl)-5,6,7,8-tetrahydrophthalazin-1(2H)-one,
6-(2,4-dimethylphenyl)-2-(5-methylpyridin-2-yl)-5,6,7,8-tetrahydrophthalazin-1(2H)-one,
6-(2,4-dimethylphenyl)-2-(4-methylpyridin-2-yl)-5,6,7,8-tetrahydrophthalazin-1(2H)-one,
6-(2,4-dimethylphenyl)-2-(3-methylpyridin-2-yl)-5,6,7,8-tetrahydrophthalazin-1(2H)-one,
6-(6-(2,4-dimethylphenyl)-1-oxo-5,6,7,8-tetrahydrophthalazin-2 (1H)-yl) picolinonitrile,
6-(6-(2,4-dimethylphenyl)-1-oxo-5,6,7,8-tetrahydrophthalazin-2 (1H)-yl) nicotinonitrile,
2-(6-(2,4-dimethylphenyl)-1-oxo-5,6,7,8-tetrahydrophthalazin-2 (1H)-yl) isonicotinonitrile,
2-(6-(2,4-dimethylphenyl)-1-oxo-5,6,7,8-tetrahydrophthalazin-2 (1H)-yl) nicotinonitrile,
6-(2,4-dimethylphenyl)-2-(5-hydroxypyridin-2-yl)-5,6,7,8-tetrahydrophthalazin-1(2H)-one,
6-(2,4-dimethylphenyl)-2-(4-hydroxypyridin-2-yl)-5,6,7,8-tetrahydrophthalazin-1(2H)-one,
6-(2,4-dimethylphenyl)-2-(5-(methoxymethyl) pyridin-2-yl)-5,6,7,8-tetrahydrophthalazin-1(2H)-one,
6-(2,4-dimethylphenyl)-2-(pyridin-3-yl)-5,6,7,8-tetrahydrophthalazin-1(2H)-one,
6-(2,4-dimethylphenyl)-2-(pyrimidin-2-yl)-5,6,7,8-tetrahydrophthalazin-1(2H)-one,
6-(2,4-dimethylphenyl)-2-(pyrazin-2-yl)-5,6,7,8-tetrahydrophthalazin-1(2H)-one,
6-(2,4-dimethylphenyl)-2-(pyrimidin-5-yl)-5,6,7,8-tetrahydrophthalazin-1(2H)-one,
6-(2,4-dimethylphenyl)-2-(thiazol-2-yl)-5,6,7,8-tetrahydrophthalazin-1(2H)-one,
6-(2,4-dimethylphenyl)-2-(thiazol-4-yl)-5,6,7,8-tetrahydrophthalazin-1(2H)-one,
6-(2,4-dimethylphenyl)-2-(1-methyl-1H-imidazol-4-yl)-5,6,7,8-tetrahydrophthalazin-1(2H)-one, 6-(2,4-dimethylphenyl)-2-(4-methoxypyrimidin-2-yl)-5,6,7,8-tetrahydrophthalazin-1(2H)-one,
6-(2,4-dimethylphenyl)-2-(4,6-dimethylpyrimidin-2-yl)-5,6,7,8-tetrahydrophthalazin-1(2H)-one,
2-(4-cyclopropylpyrimidin-2-yl)-6-(2,4-dimethylphenyl)-5,6,7,8-tetrahydrophthalazin-1(2H)-one,
2-(5-hydroxypyridin-2-yl)-6-(3-methoxy-2-methylphenyl)-5,6,7,8-tetrahydrophthalazin-1(2H)-one,
2-(5-(hydroxymethyl) pyridin-2-yl)-6-(3-methoxy-2-methylphenyl)-5,6,7,8-tetrahydrophthalazin-1(2H)-one,
6-(3-methoxy-2-methylphenyl)-2-(pyrimidin-2-yl)-5,6,7,8-tetrahydrophthalazin-1(2H)-one,
6-(3-methoxy-2-methylphenyl)-2-(5-methylpyrimidin-2-yl)-5,6,7,8-tetrahydrophthalazin-1(2H)-one,
6-(3-methoxy-2-methylphenyl)-2-(4-methoxypyrimidin-2-yl)-5,6,7,8-tetrahydrophthalazin-1(2H)-one,
2-(5-chloropyrimidin-2-yl)-6-(3-methoxy-2-methylphenyl)-5,6,7,8-tetrahydrophthalazin-1(2H)-one,
6-(3-methoxy-2-methylphenyl)-2-(5-methoxypyrazin-2-yl)-5,6,7,8-tetrahydrophthalazin-1(2H)-one,
2-(5-hydroxypyrimidin-2-yl)-6-(3-methoxy-2-methylphenyl)-5,6,7,8-tetrahydrophthalazin-1(2H)-one,
6-(3-methoxy-2-methylphenyl)-2-(4-morpholinopyrimidin-2-yl)-5,6,7,8-tetrahydrophthalazin-1(2H)-one,
6-(5-methoxy-2-methylphenyl)-2-(5-methylpyrimidin-2-yl)-5,6,7,8-tetrahydrophthalazin-1(2H)-one,
6-(5-methoxy-2-methylphenyl)-2-(5-methoxypyrimidin-2-yl)-5,6,7,8-tetrahydrophthalazin-1(2H)-one,
2-(5-chloropyrimidin-2-yl)-6-(5-methoxy-2-methylphenyl)-5,6,7,8-tetrahydrophthalazin-1(2H)-one,
6-(2,4-dimethylphenyl)-2-(pyridin-4-yl)-5,6,7,8-tetrahydrophthalazin-1(2H)-one,
2-(5-chloropyrimidin-2-yl)-6-(2,4-dimethylphenyl)-5,6,7,8-tetrahydro-phthalazin-1(2H)-one,
6-(2,4-dimethylphenyl)-2-(5-methylpyrimidin-2-yl)-5,6,7,8-tetrahydrophthalazin-1(2H)-one,
6-(2,4-dimethylphenyl)-2-(5-methoxypyrimidin-2-yl)-5,6,7,8-tetrahydrophthalazin-1(2H)-one,
6-(2,4-dimethylphenyl)-2-(5-fluoropyrimidin-2-yl)-5,6,7,8-tetrahydrophthalazin-1(2H)-one,
6-(2,4-dimethylphenyl)-2-(5-(trifluoromethyl)pyrimidin-2-yl)-5,6,7,8-tetrahydrophthalazin-1(2H)-one,
6-(2,4-dimethylphenyl)-2-(4-methoxy-5-methylpyrimidin-2-yl)-5,6,7,8-tetrahydrophthalazin-1(2H)-one,
6-(2,4-dimethylphenyl)-2-(5-(morpholinomethyl)pyrimidin-2-yl)-5,6,7,8-tetrahydrophthalazin-1(2H)-one,
6-(2-methoxyphenyl)-2-(pyridin-2-yl)-5,6,7,8-tetrahydrophthalazin-1(2H)-one,
6-(3-(dimethylamino)phenyl)-2-(pyridin-2-yl)-5,6,7,8-tetrahydrophthalazin-1(2H)-one,
6-(3-methoxy-2-methylphenyl)-2-(pyridin-2-yl)-5,6,7,8-tetrahydrophthalazin-1(2H)-one,
6-(5-methoxy-2-methylphenyl)-2-(pyridin-2-yl)-5,6,7,8-tetrahydrophthalazin-1(2H)-one,
2-(pyridin-2-yl)-6-(o-tolyl)-5,6,7,8-tetrahydrophthalazin-1(2H)-one,
6-(3-cyclopropylphenyl)-2-(pyridin-2-yl)-5,6,7,8-tetrahydrophthalazin-1(2H)-one,
6-(3-methoxy-4-methylphenyl)-2-(pyridin-2-yl)-5,6,7,8-tetrahydrophthalazin-1(2H)-one,
6-(3-(1-hydroxyethyl)phenyl)-2-(pyridin-2-yl)-5,6,7,8-tetrahydrophthalazin-1(2H)-one,
6-(3-cyclopropoxyphenyl)-2-(pyridin-2-yl)-5,6,7,8-tetrahydrophthalazin-1(2H)-one,
6-(2-methoxy-4-methylphenyl)-2-(pyridin-2-yl)-5,6,7,8-tetrahydrophthalazin-1(2H)-one,
6-(2-methoxy-3-methylphenyl)-2-(pyridin-2-yl)-5,6,7,8-tetrahydrophthalazin-1(2H)-one,
6-(1-methylindolin-4-yl)-2-(pyridin-2-yl)-5,6,7,8-tetrahydrophthalazin-1(2H)-one,
6-(2-methoxy-4-methylphenyl)-2-(pyrimidin-2-yl)-5,6,7,8-tetrahydrophthalazin-1(2H)-one,
6-(2-methoxy-3-methylphenyl)-2-(pyrimidin-2-yl)-5,6,7,8-tetrahydrophthalazin-1(2H)-one,
6-(2-chloro-3-methoxyphenyl)-2-(pyrimidin-2-yl)-5,6,7,8-tetrahydrophthalazin-1(2H)-one,
6-(5-methoxy-2-(trifluoromethyl)phenyl)-2-(pyrimidin-2-yl)-5,6,7,8-tetrahydrophthalazin-1(2H)-one,
6-(2-fluoro-5-methoxyphenyl)-2-(pyrimidin-2-yl)-5,6,7,8-tetrahydrophthalazin-1(2H)-one,
6-(2-chloro-5-methoxyphenyl)-2-(pyrimidin-2-yl)-5,6,7,8-tetrahydrophthalazin-1(2H)-one,
6-(2-methoxy-5-methylphenyl)-2-(pyrimidin-2-yl)-5,6,7,8-tetrahydrophthalazin-1(2H)-one,
6-(2-methyl-5-(pyrrolidin-1-yl)phenyl)-2-(pyrimidin-2-yl)-5,6,7,8-tetrahydrophthalazin-1(2H)-one,
6-(1-methylindolin-4-yl)-2-(pyrimidin-2-yl)-5,6,7,8-tetrahydrophthalazin-1(2H)-one,
6-(2-fluoro-3-methoxyphenyl)-2-(pyrimidin-2-yl)-5,6,7,8-tetrahydrophthalazin-1(2H)-one,
6-(5-methoxy-2-methylphenyl)-2-(pyrimidin-2-yl)-5,6,7,8-tetrahydrophthalazin-1(2H)-one,
6-(2,5-dimethylphenyl)-2-(pyrimidin-2-yl)-5,6,7,8-tetrahydrophthalazin-1(2H)-one,
6-(2,3-dimethylphenyl)-2-(pyrimidin-2-yl)-5,6,7,8-tetrahydrophthalazin-1(2H)-one,
6-(3-(methoxymethyl)phenyl)-2-(pyrimidin-2-yl)-5,6,7,8-tetrahydrophthalazin-1(2H)-one,
6-(5-cyclopropoxy-2-methylphenyl)-2-(pyrimidin-2-yl)-5,6,7,8-tetrahydrophthalazin-1(2H)-one,
6-(3-cyclopropoxyphenyl)-2-(pyrimidin-2-yl)-5,6,7,8-tetrahydrophthalazin-1(2H)-one,
6-(3-(cyclopentyloxy)phenyl)-2-(pyrimidin-2-yl)-5,6,7,8-tetrahydrophthalazin-1(2H)-one,
6-(4-methoxy-2-methylphenyl)-2-(pyrimidin-2-yl)-5,6,7,8-tetrahydrophthalazin-1(2H)-one,
6-(1,5-dimethyl-1H-indazol-4-yl)-2-(pyrimidin-2-yl)-5,6,7,8-tetrahydrophthalazin-1(2H)-one,
6-mesityl-2-(pyrimidin-2-yl)-5,6,7,8-tetrahydrophthalazin-1(2H)-one,
6-(2,6-difluoro-3-methoxyphenyl)-2-(pyrimidin-2-yl)-5,6,7,8-tetrahydrophthalazin-1(2H)-one,
6-(2-chloro-3-cyclopropoxyphenyl)-2-(pyrimidin-2-yl)-5,6,7,8-tetrahydrophthalazin-1(2H)-one,
6-(1-cyclopropylindolin-4-yl)-2-(pyrimidin-2-yl)-5,6,7,8-tetrahydrophthalazin-1(2H)-one,
6-(3-cyclopropoxy-2-methylphenyl)-2-(5-methylpyrimidin-2-yl)-5,6,7,8-tetrahydrophthalazin-1(2H)-one,
6-(2-chloro-3-methoxyphenyl)-2-(5-methylpyrimidin-2-yl)-5,6,7,8-tetrahydrophthalazin-1(2H)-one
6-(2-methoxyphenyl)-2-(pyridin-2-yl)-5,6,7,8-tetrahydrophthalazin-1(2H)-one,
6-(3-(dimethylamino)-2-methylphenyl)-2-(pyrimidin-2-yl)-5,6,7,8-tetrahydrophthalazin-1(2H)-one,
6-(5-methoxy-2,4-dimethylphenyl)-2-(pyrimidin-2-yl)-5,6,7,8-tetrahydrophthalazin-1(2H)-one,
6-(4-chloro-2-methylphenyl)-2-(pyrimidin-2-yl)-5,6,7,8-tetrahydrophthalazin-1(2H)-one,
6-(4-acetyl-2-methylphenyl)-2-(pyrimidin-2-yl)-5,6,7,8-tetrahydrophthalazin-1(2H)-one,
6-(3-(3-methoxypropoxy)-2-methylphenyl)-2-(pyrimidin-2-yl)-5,6,7,8-tetrahydrophthalazin-1(2H)-one, 6-(3-ethoxy-2-methylphenyl)-2-(pyrimidin-2-yl)-5,6,7,8-tetrahydrophthalazin-1(2H)-one,
6-(3-(cyclopropylmethoxy)-2-methylphenyl)-2-(pyrimidin-2-yl)-5,6,7,8-tetrahydrophthalazin-1(2H)-one,
6-(3-isopropoxy-2-methylphenyl)-2-(pyrimidin-2-yl)-5,6,7,8-tetrahydrophthalazin-1(2H)-one,
6-(3-cyclopropoxy-2-methylphenyl)-2-(pyrimidin-2-yl)-5,6,7,8-tetrahydrophthalazin-1(2H)-one,
6-(3-(2-methoxyethoxy)-2-methylphenyl)-2-(pyrimidin-2-yl)-5,6,7,8-tetrahydrophthalazin-1(2H)-one,
6-(3-(benzyloxy)-2-methylphenyl)-2-(pyrimidin-2-yl)-5,6,7,8-tetrahydrophthalazin-1(2H)-one,
2-(5-cyclopropylpyrimidin-2-yl)-6-(5-methoxy-2-methylphenyl)-5,6,7,8-tetrahydrophthalazin-1(2H)-one,
2-(5-cyclopropylpyrimidin-2-yl)-6-(2,4-dimethylphenyl)-5,6,7,8-tetrahydrophthalazin-1(2H)-one,
2-(5-cyclopropylpyridin-2-yl)-6-(2,4-dimethylphenyl)-5,6,7,8-tetrahydrophthalazin-1(2H)-one,
2-(5-cyclopropylpyridin-2-yl)-6-(3-methoxy-2-methylphenyl)-5,6,7,8-tetrahydrophthalazin-1(2H)-one,
6-(3-methoxy-2-methylphenyl)-2-(5-(pyrrolidin-1-yl)pyrimidin-2-yl)-5,6,7,8-tetrahydrophthalazin-1(2H)-one,
6-(3-methoxy-2-methylphenyl)-2-(5-morpholinopyrimidin-2-yl)-5,6,7,8-tetrahydrophthalazin-1(2H)-one,
6-(2,4-dimethylphenyl)-2-(5-morpholinopyridin-2-yl)-5,6,7,8-tetrahydrophthalazin-1(2H)-one,
6-(2,4-dimethylphenyl)-2-(5-morpholinopyridin-2-yl)-5,6,7,8-tetrahydrophthalazin-1(2H)-one,
6-(2,4-dimethylphenyl)-2-(5-morpholinopyrimidin-2-yl)-5,6,7,8-tetrahydrophthalazin-1(2H)-one,
2-(5-(azetidin-1-yl)pyrimidin-2-yl)-6-(2,4-dimethylphenyl)-5,6,7,8-tetrahydrophthalazin-1(2H)-one,
N-(2-(6-(2,4-dimethylphenyl)-1-oxo-5,6,7,8-tetrahydrophthalazin-2 (1H)-yl)pyrimidin-5-yl) acetamide,
6-(3-methoxy-2-methylphenyl)-2-(5-(2-methoxyethoxy)pyrimidin-2-yl)-5,6,7,8-tetrahydrophthalazin-1(2H)-one,
(2-(5-(2-hydroxyethoxy)-pyrimidin-2-yl)-6-(3-methoxy-2-methylphenyl)-5,6,7,8-tetrahydrophthalazin-1(2H)-one,
6-(3-acetyl-2-methylphenyl)-2-(pyrimidin-2-yl)-5,6,7,8-tetrahydrophthalazin-1(2H)-one,
6-(1-cyclopropyl-1H-indol-4-yl)-2-(pyrimidin-2-yl)-5,6,7,8-tetrahydrophthalazin-1(2H)-one,
2-(5-cyclopropylpyrimidin-2-yl)-6-(3-methoxy-2-methylphenyl)-5,6,7,8-tetrahydrophthalazin-1(2H)-one,
2-(5-bromopyrimidin-2-yl)-6-(3-cyclopropoxy-2-methylphenyl)-5,6,7,8-tetrahydrophthalazin-1(2H)-one,
N-(2-(6-(3-cyclopropoxy-2-methylphenyl)-1-oxo-5,6,7,8-tetrahydrophthalazin-2 (1H)-yl)pyrimidin-5-yl) acetamide,
(−)-6-(3-cyclopropoxy-2-methylphenyl)-2-(pyrimidin-2-yl)-5,6,7,8-tetrahydrophthalazin-1(2H)-one,
(+)-6-(3-cyclopropoxy-2-methylphenyl)-2-(pyrimidin-2-yl)-5,6,7,8-tetrahydrophthalazin-1(2H)-one,
(−)-6-(2-chloro-3-cyclopropoxyphenyl)-2-(pyrimidin-2-yl)-5,6,7,8-tetrahydrophthalazin-1(2H)-one,
(+)-6-(2-chloro-3-cyclopropoxyphenyl)-2-(pyrimidin-2-yl)-5,6,7,8-tetrahydrophthalazin-1(2H)-one,
(−)-6-(3-cyclopropoxy-2-methylphenyl)-2-(5-methylpyrimidin-2-yl)-5,6,7,8-tetrahydrophthalazin-1(2H)-one,
(+)-6-(3-cyclopropoxy-2-methylphenyl)-2-(5-methylpyrimidin-2-yl)-5,6,7,8-tetrahydrophthalazin-1(2H)-one,
(−)-6-(2-chloro-3-methoxyphenyl)-2-(5-methylpyrimidin-2-yl)-5,6,7,8-tetrahydrophthalazin-1(2H)-one,
(+)-6-(2-chloro-3-methoxyphenyl)-2-(5-methylpyrimidin-2-yl)-5,6,7,8-tetrahydrophthalazin-1(2H)-one,
(−)—N-(2-(6-(2,4-dimethylphenyl)-1-oxo-5,6,7,8-tetrahydrophthalazin-2 (1H)-yl)pyrimidin-5-yl) acetamide,
(+)-N-(2-(6-(2,4-dimethylphenyl)-1-oxo-5,6,7,8-tetrahydrophthalazin-2 (1H)-yl)pyrimidin-5-yl) acetamide,
(+)-6-(1-cyclopropyl-1H-indol-4-yl)-2-(pyrimidin-2-yl)-5,6,7,8-tetrahydrophthalazin-1(2H)-one,
(−)-6-(1-cyclopropyl-1H-indol-4-yl)-2-(pyrimidin-2-yl)-5,6,7,8-tetrahydrophthalazin-1(2H)-one,
2-(5-bromopyrimidin-2-yl)-6-(5-methoxy-2-methylphenyl)-5,6,7,8-tetrahydrophthalazin-1(2H)-one,
2-(5-bromopyridin-2-yl)-6-(2,4-dimethylphenyl)-5,6,7,8-tetrahydrophthalazin-1(2H)-one,
2-(5-bromopyrimidin-2-yl)-6-(2,4-dimethylphenyl)-5,6,7,8-tetrahydrophthalazin-1(2H)-one,
2-(5-bromopyridin-2-yl)-6-(3-methoxy-2-methylphenyl)-5,6,7,8-tetrahydrophthalazin-1(2H)-one,
2-(5-bromopyrimidin-2-yl)-6-(3-methoxy-2-methylphenyl)-5,6,7,8-tetrahydrophthalazin-1(2H)-one, and
2-(5-bromo-4-methoxypyrimidin-2-yl)-6-(2,4-dimethylphenyl)-5,6,7,8-tetrahydrophthalazin-1(2H)-one.

14. A compound according to claim 1, in the form of a racemic mixture or in the form of one or both of the individual optical isomers.

15. A pharmaceutical composition comprising a therapeutically effective amount of a compound according to claim 1 and a pharmaceutically acceptable excipient.

* * * * *